(12) United States Patent
Klar et al.

(10) Patent No.: US 7,407,975 B2
(45) Date of Patent: Aug. 5, 2008

(54) EPOTHILONE DERIVATIVES, METHOD FOR PRODUCING SAME AND THEIR PHARMACEUTICAL USE

(75) Inventors: Ulrich Klar, Berlin (DE); Wolfgang Schwede, Berlin (DE); Werner Skuballa, Berlin (DE); Bernd Buchmann, Neuendorr (DE)

(73) Assignee: Bayer Schering Pharma AG, Berlin (DE)

( * ) Notice: Subject to any disclaimer, the term of this patent is extended or adjusted under 35 U.S.C. 154(b) by 0 days.

(21) Appl. No.: 09/485,292

(22) PCT Filed: Aug. 10, 1998

(86) PCT No.: PCT/EP98/05064

§ 371 (c)(1),
(2), (4) Date: May 3, 2000

(87) PCT Pub. No.: WO99/07692

PCT Pub. Date: Feb. 18, 1999

(65) Prior Publication Data

US 2003/0144523 A1    Jul. 31, 2003

(30) Foreign Application Priority Data

| Aug. 9, 1997 | (DE) | 197 35 574 |
| Aug. 9, 1997 | (DE) | 197 35 575 |
| Aug. 9, 1997 | (DE) | 197 35 578 |
| Oct. 24, 1997 | (DE) | 197 48 928 |
| Oct. 31, 1997 | (DE) | 197 49 717 |
| Nov. 13, 1997 | (DE) | 197 51 200 |
| Mar. 20, 1998 | (DE) | 198 13 821 |

(51) Int. Cl.
*A61K 31/335* (2006.01)
*C07D 277/30* (2006.01)

(52) U.S. Cl. .................. 514/365; 548/204; 548/217

(58) Field of Classification Search ............... 548/204, 548/217; 514/365
See application file for complete search history.

(56) References Cited

U.S. PATENT DOCUMENTS

| 5,969,145 | A | 10/1999 | Schinzer et al. | |
| 6,043,372 | A | 3/2000 | Schinzer et al. | |
| 6,156,905 | A | 12/2000 | Schinzer et al. | |
| 6,242,469 | B1 * | 6/2001 | Danishefsky et al. | 514/365 |
| 6,610,736 | B1 * | 8/2003 | Klar et al. | 514/450 |
| 6,730,699 | B2 | 5/2004 | Li et al. | |
| 2002/0058817 | A1 | 5/2002 | Danishefsky | |
| 2004/0012735 | A1 | 1/2004 | Sato et al. | |
| 2004/0019088 | A1 | 1/2004 | Lichtner et al. | |

FOREIGN PATENT DOCUMENTS

| DE | 4138042 | 5/1993 |
| DE | 19636343 | 10/1997 |
| DE | 19701758 | 7/1998 |
| WO | 9719086 | 5/1997 |
| WO | 9808849 | 3/1998 |
| WO | WO 98/25929 | 6/1998 |
| WO | WO 99/01124 | 1/1999 |
| WO | WO 99/02514 | 1/1999 |
| WO | WO 99/07692 | 2/1999 |
| WO | WO 99/67253 | 12/1999 |
| WO | WO 2004/015088 | 2/2004 |

OTHER PUBLICATIONS

CA reference 132:293587, "The Olefin Metathesis Approach to Epothilone A and Its Analogs", Nicolau et al., p. 674, vol. 132, No. 22, year 2000.*

(Continued)

*Primary Examiner*—Celia Chang
(74) *Attorney, Agent, or Firm*—Millen, White, Zelano, Branigan, P.C.

(57) ABSTRACT

This invention relates to the new epothilone derivatives of general formula I,

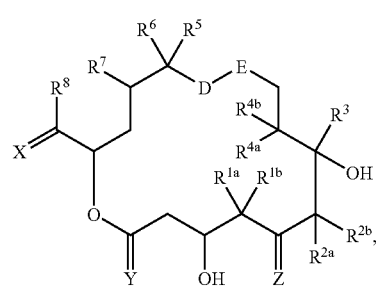

in which substituents Y, Z, $R^{2a}$, $R^{2b}$, $R^3$, $R^{4a}$, $R^{4b}$, D-E, $R^5$, $R^6$, $R^7$, $R^8$ and X have the meanings that are indicated in more detail in the description.

The new compounds interact with tubulin by stabilizing microtubuli that are formed. They are able to influence the cell-splitting in a phase-specific manner and are suitable for treating malignant tumors, for example, ovarian, stomach, colon, adeno-, breast, lung, head and neck carcinomas, malignant melanomas, acute lymphocytic and myelocytic leukemia. In addition, they are suitable for anti-angiogenesis therapy as well as for treatment of chronic inflammatory diseases (psoriasis, arthritis). To avoid uncontrolled proliferation of cells and for better compatibility of medical implants, they can be applied or introduced into polymer materials.

The compounds according to the invention can be used alone or to achieve additive or synergistic actions in combination with other principles and classes of substances that can be used in tumor therapy.

1 Claim, No Drawings

OTHER PUBLICATIONS

Nicolaou et al., "Total Synthesis of Oxazole- and Cyclopropane-Containing Epothilone B Analogues by the Macrolactonization Approach", pp. 1971-1986, Chem. Eur. J. vol. 3, No. 12, 1997.*

Hackh's chemical dictionary, p. 62 (1983).*

W. Clark, Still et al.: Tetrahedron Letters, Bd. 21, 1980, Seiten 1031-4, XP002095727.

K. A. Parker et al.: Journal of Organic Chemistry, Bd. 52, Nr. 19, 1987, Seiten 4369-77, XP002095726.

K. Tamao et al.: Journal of the Chemical Society Chemical Communications,1988, Seiten 795-7, XP002095725.

D. Schinzer et al.: Chemistry—A European Journal, Bd. 2, Nr. 11, 1996, Seiten 1477-82, XP002095724 in der Anmeldung erwaehnt.

K. C. Nicolaou et al.: Angewandte Chemie, Bd. 109, Nr. 19, 1997, Seiten 2181-7, XP002095723 in der Anmeldung erwaehnt.

K. C. Nicolaou et al.: Journal of the American Chemical Society, Bd. 119, Nr. 34, 1997, Seiten 7974-91, XP002095719 in der Anmeldung erwaehnt.

Zhen Yang et al.: Angewandte Chemie, Bd. 109, Nr. 1/2, 1997, Seiten 170-2, XP002095722 in der Anmeldung erwaehnt.

K. C. Nicolaou et al.: Nature, Bd. 387, Nr. 6630, 15. Mai 1997, Seiten 268-72, XP002095721 in der Anmeldung erwaehnt.

D. Schinzer et al.: Angewandte Chemie, Bd. 109, Nr. 5, 1997, Seiten 543-4, XP002095720 in er Anmeldung erwaehnt.

K. C. Nicolaou; Journal of the American Chemical Society, Bd. 119, Nr. 34, 1997, Seiten 7960-73, XP002064442 in der Anmeldung erwaehnt.

U.S. Appl. No. 09/913,163.

U.S. Appl. No. 09/979,939.

K.C. Nicolaou et al.: "Designed Epothilones: Combinatorial Synthesis, Tubulin Assembly Properties, And Cytotoxic Action Against Taxol.Resistant Tumor Cells" Angewandte Chemie. International Edition, DE. Verlag Chemie. Weinheim, vol. 36, No. 19, 1997, pp. 2097-2103, XP002064441.

K.C. Nicolaou et al.: "Chemical Biology of Epothilones" Angewandte Chemie. International Edition, De. Verlag Chemie. Weinheim, vol. 37, No. 15, Aug. 1998 pp. 2014-2045, XP002131418.

K.C. Nicolaou et al.: "Total Synthesis of Oxazole- and Cyclopropane-Containing Epothilone A Analogues by the Olefin Metathesis Approach"—Chem Eur. J. 1997, 3, No. 12, pp. 1957-1970.

K.C. Nicolaou, "Synthesis of Epothilones A and B in Solid and Solution Phase", Nature, vol. 387, (1997), pp. 268-272.

Zhen Yang, et al. "Die Totalsynthese von Epothilon A: der Zugang durch Olefinmetathese " Agnew. Chem (1997), 109, Nr. 112, pp. 170-172.

Dieter Schinzer et al., Totalsynthese von (-)-Epothilon A, Agnew. Chem. 1997, 109. Nr. 5), pp. 543-544.

K.C. Nicolaou et al., The Olefin Metathesis Approach to Epothilone A and Its Analogs and Chemical Abstracts 26-Biomolecules and Their Synthetic Analogs, vol. 132, No. 22 (2000), p. 674.

* cited by examiner

EPOTHILONE DERIVATIVES, METHOD FOR PRODUCING SAME AND THEIR PHARMACEUTICAL USE

Höfle et al. describe the cytotoxic action of the natural products epothilone A (R=hydrogen) and epothilone B (R=methyl)

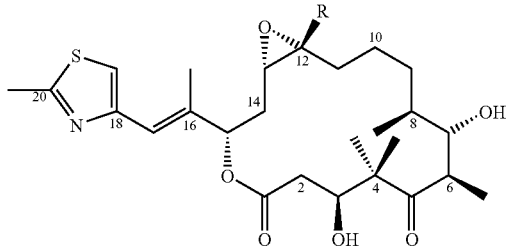

Epothilone A (R=H), Epothilone B (R=CH$_3$) in, e.g., Angew. Chem. [Applied Chem.], 1996, 108, 1671-1673. Because of their in-vitro selectivity for breast cell lines and intestinal cell lines and their significantly higher activity against P-glycoprotein-forming multiresistant tumor lines in comparison to taxol as well as their physical properties that are superior to those of taxol, e.g., a water solubility that is higher by a factor of 30, this novel structural class is especially advantageous for the development of a pharmaceutical agent for treating malignant tumors.

The natural products are not sufficiently stable either chemically or metabolically for the development of pharmaceutical agents. To eliminate these drawbacks, modifications to the natural product are necessary. Such modifications are possible only with a total-synthesis approach and require synthesis strategies that make possible a broad modification of the natural product. The purpose of the structural changes is also to increase the therapeutic range. This can be done by improving the selectivity of the action and/or reducing undesirable toxic side-effects and/or increasing active strength.

The total synthesis of epothilone A is described by Schinzer et al. in Chem. Eur. J. 1996, 2, No. 11, 1477-1482 and in Angew. Chem. 1997, 109, No. 5, pp. 543-544).

Epothilone derivatives were already described by Höfle et al. in WO 97/19086. These derivatives were produced starting from natural epothilone A or B.

Another synthesis of epothilone and epothilone derivatives was described by Nicolaou et al. in Angew. Chem. 1997, 109, No. 1/2, pp. 170-172. The synthesis of epothilone A and B and several epothilone analogues was described in Nature, Vol. 387, 1997, pp. 268-272; and the synthesis of epothilone A and its derivatives was described in J. Am. Chem. Soc., Vol. 119, No. 34, 1997, pp. 7960-7973 as well as the synthesis of epothilone A and B and several epothilone analogues in J. Am. Chem. Soc., Vol. 119, No. 34, 1997, pp. 7974-7991 also by Nicolaou et al.

Nicolaou et al. also describe in Angew. Chem. 1997, 109, No. 19, pp. 2181-2187 the production of epothilone A analogues using combinative solid-phase synthesis. Several epothilone B analogues are also described there.

The object of this invention consists in making available new epothilone derivatives, which are both chemically and metabolically stable enough for the development of pharmaceutical agents and which are superior to natural derivatives in terms of their therapeutic range, their selectivity of action and/or undesirable toxic side-effects and/or their active strength.

This invention describes the new epothilone derivatives of general formula I,

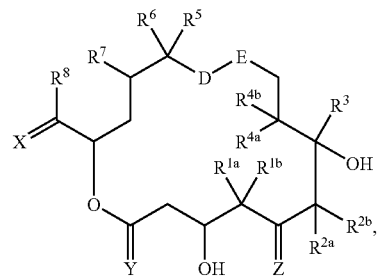

in which
R$^{1a}$, R$^{1b}$ are the same or different and mean hydrogen, C$_1$-C$_{10}$ alkyl, aryl, C$_7$-C$_{20}$ aralkyl, or together a —(CH$_2$)$_m$— group with m=2, 3, 4 or 5, R$^{2a}$, R$^{2b}$ are the same or different and mean hydrogen, C$_1$-C$_{10}$ alkyl, aryl, C$_7$-C$_{20}$ aralkyl or together a —(CH$_2$)$_n$— group with n=2, 3, 4 or 5, whereby, if -D-E-stands for —CH$_2$—CH$_2$— or Y stands for an oxygen atom, R$^{2a}$/R$^{2b}$ cannot be hydrogen/methyl, R$^3$ means hydrogen, C$_1$-C$_{10}$ alkyl, aryl, C$_7$-C$_{20}$ aralkyl, R$^{4a}$, R$^{4b}$ are the same or different and mean hydrogen, C$_1$-C$_{10}$ alkyl, aryl, C$_7$-C$_{20}$ aralkyl or together a —(CH$_2$)$_p$— group with p=2, 3, 4 or 5,

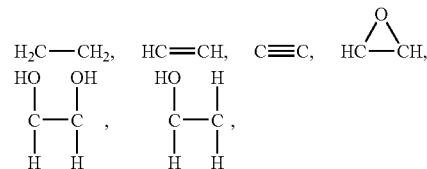

D-E means a group

R$^5$ means hydrogen, C$_1$-C$_{10}$ alkyl, aryl, C$_7$-C$_{20}$ aralkyl,

R$^6$, R$^7$ each mean a hydrogen atom, together an additional bond or an oxygen atom, R$^8$ means hydrogen, C$_1$-C$_{20}$ alkyl, aryl, C$_7$-C$_{20}$ aralkyl, which can all be substituted, X means an oxygen atom, two alkoxy groups OR$^{23}$, a C$_2$-C$_{10}$ alkylene-α,ω-dioxy group, which can be straight-chain or branched, H/OR$^9$ or a grouping CR$^{10}$R$^{11}$, whereby R$^{23}$ stands for a C$_1$-C$_{20}$ alkyl radical, R$^9$ stands for hydrogen or a protective group PG$^x$, R$^{10}$, R$^{11}$ are the same or different and stand for hydrogen, a C$_1$-C$_{20}$ alkyl, aryl, C$_7$-C$_{20}$ aralkyl radical or R$^{10}$ and R$^{11}$ together with the methylene carbon atom together stand for a 5- to 7-membered carbocyclic ring, Y means an oxygen atom or two hydrogen atoms, Z means an oxygen atom or H/OR$^{12}$, whereby R$^{12}$ means hydrogen or a protective group PG$^z$.

The production of the new epothilone derivatives is based on the linkage of three partial fragments A, B and C. The interfaces are as indicated in general formula I'.

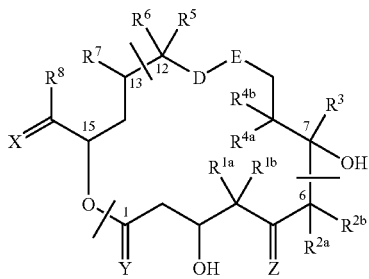

A means a C1-C6 fragment (epothilone numbering system) of general formula

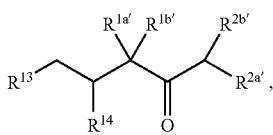

in which $R^{1a'}$, $R^{1b'}$, $R^{2a'}$ and $R^{2b'}$ have the meanings already mentioned for $R^{1a}$, $R^{1b}$, $R^{2a}$ and $R^{2b}$, and $R^{13}$ means $CH_2OR^{13a}$, $CH_2$-Hal, CHO, $CO_2R^{13b}$, COHal, $R^{14}$ means hydrogen, $OR^{14a}$, Hal, $OSO_2R^{14b}$, $R^{13a}$, $R^{14a}$ mean hydrogen, $SO_2$-alkyl, $SO_2$-aryl, $SO_2$-aralkyl or together a —$(CH_2)_o$ group or together a $CR^{15a}R^{15b}$ group, $R^{13b}$, $R^{14b}$ mean hydrogen, $C_1$-$C_{20}$ alkyl, aryl, $C_7$-$C_{20}$ aralkyl, $R^{15a}$, $R^{15b}$ are the same or different and mean hydrogen, $C_1$-$C_{10}$ alkyl, aryl, $C_7$-$C_{20}$ aralkyl or together a —$(CH_2)_q$ group, Hal means halogen, o means 2 to 4, q means 3 to 6, including all stereoisomers as well as their mixtures, and free hydroxyl groups in $R^{13}$ and $R^{14}$ can be etherified or esterified, free carbonyl groups can be ketalized in A and $R^{13}$, converted into an enol ether or reduced, and free acid groups in A can be converted into their salts with bases.

B stands for a C7-C12 fragment (epothilone numbering system) of general formula

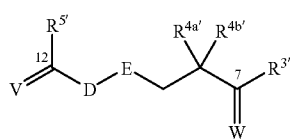

in which $R^{3'}$, $R^{4a'}$, $R^{4b'}$ and $R^{5'}$ have the meanings already mentioned for $R^3$, $R^{4a}$, $R^{4b}$ and $R^5$, V means an oxygen atom, two alkoxy groups $OR^{17}$, a $C_2$-$C_{10}$ alkylene-α,ω-dioxy group, which can be straight-chain or branched or H/$OR^{16}$, W means an oxygen atom, two alkoxy groups $OR^{19}$, a $C_2$-$C_{10}$ alkylene-α,ω-dioxy group, which can be straight-chain or branched or H/$OR^{18}$, $R^{16}$, $R^{18}$, independently of one another, mean hydrogen or a protective group $PG^1$ $R^{17}$, $R^{19}$, independently of one another, mean $C_1$-$C_{20}$ alkyl.

C stands for a C13-C16 fragment (epothilone numbering system) of general formula

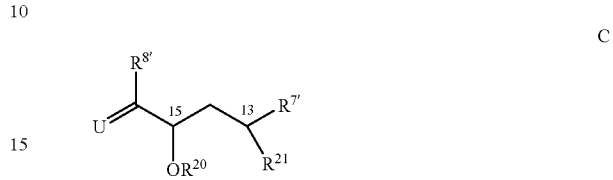

in which $R^{8'}$ has the meaning already mentioned in general formula I for $R^8$, and $R^{7'}$ means a hydrogen atom, $R^{20}$ means a hydrogen atom or a protective group $PG^2$, $R^{21}$ means a hydroxy group, halogen, a protected hydroxy group $OPG^3$, a phosphonium halide radical $PPh_3^+Hal^-$ (Ph=phenyl; Hal=F, Cl, Br, I), a phosphonate radical $P(O)(OQ)_2$ (Q=$C_1$-$C_{10}$ alkyl or phenyl) or a phosphine oxide radical $P(O)Ph_2$ (Ph=phenyl), U means an oxygen atom, two alkoxy groups $OR^{23}$, a $C_2$-$C_{10}$ alkylene-α,ω-dioxy group, which can be straight-chain or branched, H/$OR^9$ or a grouping $CR^{10}R^{11}$, whereby $R^{23}$ stands for a $C_1$-$C_{10}$ alkyl radical, $R^9$ stands for hydrogen or a protective group $PG^3$, $R^{10}$, $R^{11}$ are the same or different and stand for hydrogen, a $C_1$-$C_{20}$ alkyl, aryl, $C_7$-$C_{20}$ aralkyl radical or $R^{10}$ and $R^{11}$ together with the methylene carbon atom together stand for a 5- to 7-membered carbocyclic ring.

As alkyl groups $R^{1a}$, $R^{1b}$, $R^{2a}$, $R^{2b}$, $R^3$, $R^4$, $R^5$, $R^8$, $R^9$, $R^{10}$, $R^{11}$, $R^{12}$, $R^{13b}$, $R^{14b}$, $R^{15a}$, $R^{15b}$, $R^{17}$ and $R^{23}$, straight-chain or branched-chain alkyl groups with 1-20 carbon atoms can be considered, such as, for example, methyl, ethyl, propyl, isopropyl, butyl, isobutyl, tert-butyl, pentyl, isopentyl, neopentyl, heptyl, hexyl, and decyl.

Alkyl groups $R^{1a}$, $R^{1b}$, $R^{2a}$, $R^{2b}$, $R^3$, $R^4$, $R^5$, $R^8$, $R^9$, $R^{10}$, $R^{11}$, $R^{12}$, $R^{13b}$, $R^{14b}$, $R^{15a}$, $R^{15b}$, $R^{17}$ and $R^{23}$ can be perfluorinated or substituted by 1-5 halogen atoms, hydroxy groups, $C_1$-$C_4$ alkoxy groups, $C_6$-$C_{12}$ aryl groups (which can be substituted by 1-3 halogen atoms).

As aryl radicals $R^{1a}$, $R^{1b}$, $R^{2a}$, $R^{2b}$, $R^3$, $R^4$, $R^5$, $R^8$, $R^9$, $R^{10}$, $R^{11}$, $R^{12}$, $R^{13b}$, $R^{14b}$, $R^{15a}$ and $R^{15b}$, substituted and unsubstituted carbocyclic or heterocyclic radicals with one or more heteroatoms, such as, e.g., phenyl, naphthyl, furyl, thienyl, pyridyl, pyrazolyl, pyrimidinyl, oxazolyl, pyridazinyl, pyrazinyl, quinolyl, thiazolyl, which can be substituted in one or more places by halogen, OH, O-alkyl, $CO_2H$, $CO_2$-alkyl, —$NH_2$, —$NO_2$, —$N_3$, —CN, $C_1$-$C_{20}$ alkyl, $C_1$-$C_{20}$ acyl, $C_1$-$C_{20}$ acyloxy groups, are suitable. Heteroatoms in the heteroaryl radicals can be oxidized; thus, for example, the thiazole ring can be present in the form of N-oxide.

The aralkyl groups in $R^{1a}$, $R^{1b}$, $R^{2a}$, $R^{2b}$, $R^3$, $R^4$, $R^5$, $R^8$, $R^9$, $R^{10}$, $R^{11}$, $R^{12}$, $R^{13b}$, $R^{14b}$, $R^{15a}$ and $R^{15b}$ can contain in the ring up to 14 C atoms, preferably 6 to 10, and in the alkyl chain 1 to 8, preferably 1 to 4 atoms. As aralkyl radicals, for example, benzyl, phenylethyl, naphthylmethyl, naphthylethyl, furylmethyl, thienylethyl, and pyridinylpropyl are suitable. The rings can be substituted in one or more places by halogen, OH, O-alkyl, $CO_2H$, $CO_2$-alkyl, $-NO_2$, $-N_3$, $-CN$, $C_1$-$C_{20}$ alkyl, $C_1$-$C_{20}$ acyl, $C_1$-$C_{20}$ acyloxy groups.

The alkoxy groups that are contained in X in general formula I are in each case to contain 1 to 20 carbon atoms, whereby methoxy, ethoxy, propoxy, isopropoxy and t-butyloxy groups are preferred.

As representatives of protective groups PG, alkyl- and/or aryl-substituted silyl, $C_1$-$C_{20}$ alkyl, $C_4$-$C_7$ cycloalkyl, which in addition in the ring can contain an oxygen atom, aryl, $C_7$-$C_{20}$ aralkyl, $C_1$-$C_{20}$ acyl and aroyl can be mentioned.

As alkyl, silyl and acyl radicals for protective groups PG, the radicals that are known to one skilled in the art are suitable. Preferred are alkyl or silyl radicals that can be easily cleaved from the corresponding alkyl and silyl ethers, such as, for example, methoxymethyl, methoxyethyl, ethoxyethyl, tetrahydropyranyl, tetrahydrofuranyl, trimethylsilyl, triethylsilyl, tert-butyldimethylsilyl, tert-butyldiphenylsilyl, tribenzylsilyl, triisopropylsilyl, benzyl, para-nitrobenzyl, para-methoxybenzyl radicals as well as alkylsulfonyl and arylsulfonyl radicals. As acyl radicals, e.g., formyl, acetyl, propionyl, isopropionyl, pivalyl, butyryl or benzoyl, which can be substituted with amino and/or hydroxy groups, are suitable.

Acyl groups $PG^x$ or $PG^z$ in $R^9$ and $R^{12}$ can contain 1 to 20 carbon atoms, whereby formyl, acetyl, propionyl, isopropionyl and pivalyl groups are preferred.

Index m in the alkylene group that is formed from $R^{1a}$ and $R^{1b}$ preferably stands for 2, 3 or 4.

The $C_1$-$C_{10}$ alkylene-α,ω-dioxy group that is possible for X is preferably an ethyleneketal or neopentylketal group.

The substituents can be selected in the compounds of general formula I in such a way that Y, Z, $R^{1a}$, $R^{1b}$, $R^{2a}$ and $R^{2b}$ all can have the meanings that are indicated in general formula I, and the remainder of the molecule is identical to naturally occurring epothilone A or B, or $R^3$, $R^{4a}$, $R^{4b}$, D-E, $R^5$, $R^6$ and $R^7$ all can have the meanings that are indicated in general formula I, and the remainder of the molecule is identical to naturally occurring epothilone A or B, or $R^6$, $R^7$, $R^8$ and X all can have the meanings that are indicated in general formula I, and the remainder of the molecule is identical to naturally occurring epothilone A or B, or Y, Z, $R^{1a}$, $R^{1b}$, $R^{1a}$, $R^{2b}$, $R^3$, $R^{4a}$, $R^{4b}$, D-E, $R^5$, $R^6$ and $R^7$ all can have the meanings that are indicated in general formula I, and the remainder of the molecule is identical to naturally occurring epothilone A or B, or Y, Z, $R^{1a}$, $R^{1b}$, $R^{2a}$, $R^{2b}$, $R^6$, $R^7$, $R^8$ and X all can have the meanings that are indicated in general formula I, and the remainder of the molecule is identical to naturally occurring epothilone A or B, or $R^3$, $R^{4a}$, $R^{4b}$, D-E, $R^5$, $R^6$, $R^7$, $R^8$ and X all can have the meanings that are indicated in general formula I, and the remainder of the molecule is identical to naturally occurring epothilone A or B.

The compounds that are mentioned below are preferred according to the invention:

(4S,7R,8S,9S,13(Z),16S(E))-4,8-Dihydroxy-7-ethyl-16-(1-methyl-2-(2-methyl-4-thiazolyl)ethenyl)-1-oxa-5,5,9,13-tetramethyl-cyclohexadec-13-ene-2,6-dione, and (4S,7R,8S,9S,13E,16S(E))-4,8-dihydroxy-7-ethyl-16-(1-methyl-2-(2-methyl-4-thiazolyl)ethenyl)-1-oxa-5,5,9,13-tetramethyl-cyclohexadec-13-ene-2,6-dione (1S,3S(E),7S,10R,11S,12S,16R)-7,11-Dihydroxy-3-(1-methyl-2-(2-methyl-4-thiazolyl)ethenyl)-10-ethyl-8,8,12,16-tetramethyl-4,17-dioxabicyclo[14.1.0]heptadecane-5,9-dione and (1R,3S(E),7S,10R,11S,12S,16S)-7,11-dihydroxy-3-(1-methyl-2-(2-methyl-4-thiazolyl)ethenyl)-10-ethyl-8,8,12,16-tetramethyl-4,17-dioxabicyclo[14.1.0]heptadecane-5,9-dione (1S,3S(E),7S,10R,11S,12S,16S)-7,11-Dihydroxy-3-(1-methyl-2-(2-methyl-4-thiazoyl)ethenyl)-10-ethyl-8,8,12,16-tetramethyl-4,17-dioxabicyclo[14.1.0]heptadecane-5,9-dione and (1R,3S(E),7S,10R,11S,12S,16R)-7,11-dihydroxy-3-(1-methyl-2-(2-methyl-4-thiazolyl)ethenyl)-10-ethyl-8,8,12,16-tetramethyl-4,17-dioxabicyclo[14.1.0]heptadecane-5,9-dione (4S,7S,8R,9S,13Z,16S(E))-4,8-Dihydroxy-7-ethyl-16-(1-methyl-2-(2-methyl-4-thiazolyl)ethenyl)-1-oxa-5,5,9,13-tetramethyl-cyclohexadec-13-ene-2,6-dione and (4S,7S,8R,9S,13E,16S(E))-4,8-dihydroxy-7-ethyl-16-(1-methyl-2-(2-methyl-4-thiazolyl)ethenyl)-1-oxa-5,5,9,13-tetramethyl-cyclohexadec-13-ene-2,6-dione (1S,3S(E),7S,10S,11R,12S,16R)-7,11-Dihydroxy-3-(1-methyl-2-(2-methyl-4-thiazolyl)ethenyl)-10-ethyl-8,8,12,16-tetramethyl-4,17-dioxabicyclo[14.1.0]heptadecane-5,9-dione, and (1R,3S(E),7S,10S,11R,12S,16S)-7,11-dihydroxy-3-(1-methyl-2-(2-methyl-4-thiazolyl)ethenyl)-10-ethyl-8,8,12,16-tetramethyl-4,17-dioxabicyclo[14.1.0]heptadecane-5,9-dione (1S,3S(E),7S,10S,11R,12S,16S)-7,11-Dihydroxy-3-(1-methyl-2-(2-methyl-4-thiazolyl)ethenyl)-10-ethyl-8,8,12,16-tetramethyl-4,17-dioxabicyclo[14.1.0]heptadecane-5,9-dione, and (1R,3S(E),7S,10S,11R,12S,16S)-7,11-dihydroxy-3-(1-methyl-2-(2-methyl-4-thiazolyl)ethenyl)-10-ethyl-8,8,12,16-tetramethyl-4,17-dioxabicyclo[14.1.0]heptadecane-5,9-dione (4S,7R,8S,9S,13(Z),16S(E))-4,8-Dihydroxy-5,5,7,9,13-pentamethyl-16-((3-pyridyl)ethenyl)-1-oxa-cyclohexadec-13-ene-2,6-dione, and (4S,7R,8S,9S,13E,16S(E))-4,8-dihydroxy-5,5,7,9,13-pentamethyl-16-((3-pyridyl)ethenyl)-1-oxa-cyclohexadec-13-ene-2,6-dione (1S,3S(E),7S,10R,11S,12S,16R)-7,11-Dihydroxy-8,8,10,12,16-pentamethyl-3-((3-pyridyl)ethenyl)-4,17-dioxabicyclo[14.1.0]heptadecane-5,9-dione, and (1S,3S(E),7S,10R,11S,12S,16S)-7,11-dihydroxy-8,8,10,12,16-pentamethyl-3-((3-pyridyl)ethenyl)-4,17-dioxabicyclo[14.1.0]heptadecane-5,9-dione (4S,7R,8S,9S,13(Z),16S(E))-4,8-Dihydroxy-5,5,7,9,13-pentamethyl-16-((4-pyridyl)ethenyl)-1-oxa-cyclohexadec-13-ene-2,6-dione, and (4S,7R,8S,9S,13E,16S(E))-4,8-dihydroxy-5,5,7,9,13-pentamethyl-16-((4-pyridyl)ethenyl)-1-oxa-cyclohexadec-13-ene-2,6-dione (1S,3S(E),7S,10R,11S,12S,16R)-7,11-Dihydroxy-8,8,10,12,16-pentamethyl-3-((4-pyridyl)ethenyl)-4,17-dioxabicyclo[14.1.0]heptadecane-5,9-dione, and (1S,3S(E),7S,10R,11S,12S,16S)-7,11-dihydroxy-8,8,10,12,16-pentamethyl-3-((4-pyridyl)ethenyl)-4,17-dioxabicyclo[14.1.0]heptadecane-5,9-dione (4S,7R,8S,9S,13(E or Z),16S(E))-4,8-Dihydroxy-16-(1-methyl-2-(2-methyl-4-thiazolyl)ethenyl)-1-oxa-7-phenyl-5,5,9,13-tetramethyl-cyclohexadec-13-ene-2,6-dione (1(S or R),3S(E),7S,10R,11S,12S,16R)-7,11-Dihydroxy-3-(1-methyl-2-(2-methyl-4-thiazolyl)ethenyl)-10-phenyl-8,8,12,16-tetramethyl-4,17-dioxabicyclo[14.1.0]heptadecane-5,9-dione (1(R or S),3S(E),7S,10R,11S,12S,16S)-7,11-Dihydroxy-3-(1-methyl-2-(2-methyl-4-thiazolyl)ethenyl)-10-phenyl-8,8,12,16-tetramethyl-4,17-dioxabicyclo[14.1.0]heptadecane-5,9-dione (4S,7R,8S,9S,13(E or Z),16S(E))-7-Benzyl-4,8-dihydroxy-16-(1-methyl-2-(2-methyl-4-thiazolyl)ethenyl)-1-oxa-5,5,9,13-tetramethyl-cyclohexadec-13-ene-2,6-dione (1(S or R),3S(E),7S,10R,11S,12S,16R)-10-Benzyl-7,11-dihydroxy-3-(1-methyl-2-(2-methyl-4-thiazolyl)ethenyl)-8,8,12,16-tetramethyl-4,17-dioxabicyclo[14.1.0]heptadecane-5,9-dione (1(R or S),3S(E),7S,10R,11S,12S,16S)-10-Benzyl-7,11-dihydroxy-3-(1-methyl-2-(2-methyl-4-thiazolyl)ethenyl)-8,8,10,12,16-tetramethyl-4,17-dioxabicyclo[14.1.0]heptadecane-5,9-dione (4S,7R,8S,9S,13(E or Z),16S(E))-4,8-Dihydroxy-16-(1-methyl-2-(2-methyl-4-thiazolyl)ethenyl)-1-oxa-5,5,7,13-tetramethyl-9-trifluoromethyl-cyclohexadec-13-ene-2,6-dione (1(S or R),3S(E),7S,10R,11S,12S,16R)-7,11-Dihydroxy-3-(1-methyl-2-(2-methyl-4-thiazolyl)ethenyl)-8,8,10,16-tetramethyl-12-trifluoromethyl-4,17-dioxabicyclo[14.1.0]heptadecane-5,9-dione (1(R or S),3S(E),7S,10R,11S,12S,16S)-7,11-Dihydroxy-3-(1-methyl-2-(2-methyl-4-thiazolyl)ethenyl)-8,8,10,16-tetramethyl-12-trifluoromethyl-4,17-dioxabicyclo[14.1.0]heptadecane-5,9-dione (4S,7R,8S,9S,11E/Z,13(E or Z),16S(E))-4,8-Dihydroxy-16-(1-methyl-2-(2-methyl-4-thiazolyl)ethenyl)-1-oxa-5,5,7,9,13-pentamethyl-cyclohexadec-11,13-diene-2,6-dione (1(S or R),3S(E),7S,10R,11S,12S,14E/Z,16R)-7,11-Dihydroxy-3-(1-methyl-2-(2-methyl-4-thiazolyl)ethenyl)-8,8,10,12,16-pentamethyl-4,17-dioxabicyclo[14.1.0]heptadec-14-ene-5,9-dione (1(R or S),3S(E),7S,10R,11S,12S,14E/Z,16S)-7,11-Dihydroxy-3-(1-methyl-2-(2-methyl-4-thiazolyl)ethenyl)-8,8,10,12,16-pentamethyl-4,17-dioxabicyclo[14.1.0]heptadec-14-ene-5,9-dione (4S,7R,8S,9S,13(E or Z),16S(E))-4,8-Dihydroxy-16-(1-methyl-2-(2-methyl-4-thiazolyl)ethenyl)-1-oxa-5,5,7,9,13-pentamethyl-cyclohexadec-13-ene-11-ine-2,6-dione (1(S or R),3S(E),7S,10R,11S,12S,16R)-7,11-Dihydroxy-3-(1-methyl-2-(2-methyl-4-thiazolyl)ethenyl)-8,8,10,12,16-pentamethyl-4,17-dioxabicyclo[14.1.0]heptadec-14-ine-5,9-dione (1(R or S),3S(E),7S,10R,11S,12S,16S)-7,11-Dihydroxy-3-(1-methyl-2-(2-methyl-4-thiazolyl)ethenyl)-8,8,10,12,16-pentamethyl-4,17-dioxabicyclo[14.1.0]heptadec-14-ine-5,9-dione (4S,7R,8S,9S,13(E or Z),16S(E))-4,8-Dihydroxy-16-(1-methyl-2-(2-methyl-4-thiazolyl)ethenyl)-1-oxa-5,5,7,9-tetramethyl-13-trifluoromethyl-cyclohexadec-13-ene-2,6-dione (1(S or R),3S(E),7S,10R,11S,12S,16R)-7,11-Dihydroxy-3-(1-methyl-2-(2-methyl-4-thiazolyl)ethenyl)-8,8,10,12-tetramethyl-16-trifluoromethyl-4,17-dioxabicyclo[14.1.0]heptadeca-5,9-dione (1(R or S),3S(E),7S,10R,11S,12S,16S)-7,11-Dihydroxy-3-(1-methyl-2-(2-methyl-4-thiazolyl)ethenyl)-8,8,10,12-tetramethyl-16-trifluoromethyl-4,17-dioxabicyclo[14.1.0]heptadeca-5,9-dione (4S,7R,8S,9S,13(E or Z),16S(E))-4,8-Dihydroxy-16-(1-methyl-2-(2-methyl-4-thiazolyl)ethenyl)-1-oxa-13-pentafluoroethyl-5,5,7,9-tetramethyl-cyclohexadec-13-ene-2,6-dione (1(S or R),3S(E),7S,10R,11S,12S,16R)-7,11-Dihydroxy-3-(1-methyl-2-(2-methyl-4-thiazolyl)ethenyl)-16-pentafluoroethyl-8,8,10,12-tetramethyl-4,17-dioxabicyclo[14.1.0]heptadeca-5,9-dione (1(R or S),3S(E),7S,10R,11S,12S,16S)-7,11-Dihydroxy-3-(1-methyl-2-(2-methyl-4-thiazolyl)ethenyl)-16-pentafluoroethyl-8,8,10,12-tetramethyl-4,17-dioxabicyclo[14.1.0]heptadeca-5,9-dione (4S,7R,8S,9S,13(E or Z),16S(E))-4,8-Dihydroxy-16-(1-methyl-2-(2-methyl-4-thiazolyl)ethenyl)-1-oxa-5,5-(13-triethylene)-7,9,13-trimethyl-cycohexadec-13-ene-2,6-dione (1(S or R),3S(E),7S,10R,11S,12S,16R)-7,11-(Dihydroxy-3-(1-methyl-2-(2-methyl-4-thiazolyl)ethenyl)-8,8-(1,3-trimethylene)-10,12,16-trimethyl-4,17-dioxabicyclo[14.1.0]heptadeca-5,9-dione (1(R or S),3S(E),7S,10R,11S,12S,16S)-7,11-Dihydroxy-3-(1-methyl-2-(2-methyl-4-thiazolyl)ethenyl)-8,8-(1,3-trimethylene)-10,12,16-trimethyl-4,17-dioxabicyclo[14.1.0]heptadeca-5,9-dione (4S,7R,8S,9S,11E/Z,13(E or Z),16S(E))-4,8-Dihydroxy-13-ethyl-16-(1-methyl-2-(2-methyl-4-thiazolyl)ethenyl)-1-oxa-5,5,7,9-tetramethyl-cyclohexadec-11,13-diene-2,6-dione (1(S or R),3S(E),7S,10R,11S,12S,14E/Z,16R)-7,11-Dihydroxy-16-ethyl-3-(1-methyl-2-(2-methyl-4-thiazolyl)ethenyl)-8,8,10,12-tetramethyl-4,17-dioxabicyclo[14.1.0]heptadec-14-ene-5,9-dione (1(R or S),3S(E),7S,10R,11S,12S,14E/Z,16S)-7,11-Dihydroxy-16-ethyl-3-(1-methyl-2-(2-methyl-4-thiazolyl)ethenyl)-8,8,10,12-tetramethyl-4,17-dioxabicyclo[14.1.0]heptadec-14-ene-5,9-dione (4S,7R,8S,9S,11E/Z,13(E or Z),16S(E))-4,8-Dihydroxy-16-(1-methyl-2-(2-methyl-4-thiazolyl)ethenyl)-1-oxa-13-propyl-5,5,7,9-tetramethyl-cyclohexadec-11,13-diene-2,6-dione (1(S or R),3S(E),7S,10R,11S,12S,14E/Z,16R)-7,11-Dihydroxy-3-(1-methyl-2-(2-methyl-4-thiazolyl)ethenyl)-16-propyl-8,8,10,12-tetramethyl-4,17-dioxabicyclo[14.1.0]heptadec-14-ene-5,9-dione (1(R or S),3S(E),7S,10R,11S,12S,14E/Z,16S)-7,11-Dihydroxy-3-(1-methyl-2-(2-methyl-4-thiazolyl)ethenyl)-16-propyl-8,8,10,12-tetramethyl-4,17-dioxabicyclo[14.1.0]heptadec-14-ene-5,9-dione (4S,7R,8S,9S,13(E or Z),16S(E))-4,8-Dihydroxy-16-(1-methyl-2-(2-pyridyl)ethenyl)-1-oxa-5,5,7,9,13-pentamethyl-cyclohexadec-13-ene-2,6-dione (1(S or R),3S(E),7S,10R,11S,12S,16R)-7,11-Dihydroxy-3-(1-methyl-2-(2-pyridyl)ethenyl)-8,8,10,12,16-pentamethyl-4,17-dioxabicyclo[14.1.0]heptadecane-5,9-dione (1(R or S),3S(E),7S,10R,11S,12S,16S)-7,11-Dihydroxy-3-(1-methyl-2-(2-pyridyl)ethenyl)-8,8,10,12,16-pentamethyl-4,17-dioxabicyclo[14.1.0]heptadecane-5,9-dione (4S,7R,8S,9S,13(E or Z),16S(E))-4,8-Dihydroxy-16-(1-methyl-2-(4-pyridyl)ethenyl)-1-oxa-5,5,7,9,13-pentamethyl-cyclohexadec-13-ene-2,6-dione (1(S or R),3S(E),7S,10R,11S,12S,16R)-7,11-Dihydroxy-3-(1-methyl-2-(4-pyridyl)ethenyl)-8,8,10,12,16-pentamethyl-4,17-dioxabicyclo[14.1.0]heptadecane-5,9-dione (1(R or S),3S(E),7S,10R,11S,12S,16S)-7,11-Dihydroxy-3-(1-methyl-2-(4-pyridyl)ethenyl)-8,8,10,12,16-pentamethyl-4,17-dioxabicyclo[14.1.0]heptadecane-5,9-dione (4S,7R,8S,9S,13(E or Z),16S(E))-4,8-Dihydroxy-16-(1-methyl-2-(2-methyl-4-thiazolyl)ethenyl)-5,5,7,9,13-pentamethyl-cyclohexadec-13-en-6-one (1(S or R),3S(E),7S,10R,11S,12S,16R)-7,11-Dihydroxy-3-(1-methyl-2-(2-methyl-4-thiazolyl)ethenyl)-8,8,10,12,16-pentamethyl-4,17-dioxabicyclo[14.1.0]heptadec-9-one (1(R or S),3S(E),7S,10R,11S,12S,16S)-7,11-Dihydroxy-3-(1-methyl-2-(2-methyl-4-thiazolyl)ethenyl)-8,8,10,12,16-pentamethyl-4,17-dioxabicyclo[14.1.0]heptadec-9-one Representation of Partial Fragments A:

It is known that the compound of the following formula

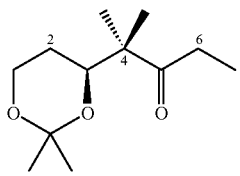

can be used to synthesize the C1-C6 fragment (epothilone numbering system) of epothilone A (Schinzer et al., Chem. Eur. J. 1996, 2, No. 11, pp. 1477-1482; Schinzer et al., Angew. Chem., 1997, 109, No. 5, pp. 543-544).

This way of synthesizing has the drawback that at 10.5% its total yield is very low, that the necessary introduction of the chirality at C-atom 3 requires the synthesis of an expensive, chemically unstable chiral adjuvant that is to be used in equimolar quantities and cannot be recovered, and that at approximately 80% the optical induction that is achieved is incomplete.

For a synthesis that can be used on an industrial scale, however, high yields and high optical purity are required.

In Angew. Chem. 1997, 109, Nos. 1/2, pp. 170-172, a description is given by Nicolaou et al. of the synthesis of a (C1-C6) component with a carboxyl group at C-1 that can be used for the synthesis of epothilone or epothilone derivatives

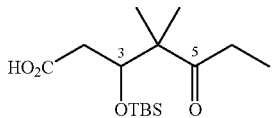

(TBS=tert-butyldimethylsilyl). The stereochemistry at C3 is controlled by the reaction with the Brown reagent allylisopinocamphenylborane (+)-Ipc$_2$B (allyl) that must be inserted into the reaction in an equimolar fashion and that cannot be recovered.

Likewise, the use of this component to synthesize epothilone A and B and some epothilone analogues is described by Nicolaou et al. in Nature, Vol. 387, 1997, pp. 268-272, to synthesize epothilone A and its derivatives in J. Am. Chem. Soc., Vol. 119, No. 34, 1997, pp. 7960-7973, and to synthesize epothilone A and B and some epothilone analogues in J. Am. Chem. Soc., Vol. 119, No. 34, 1997, pp. 7974-7991.

In Angew. Chem. 1997, 109, No. 19, pp. 2181-2187, Nicolaou et al. also describe the production of epothilone A analogues by means of combinatorial solid-phase synthesis. This same citation also mentions epothilone B analogues. The following compounds are used as C1-C6 components:

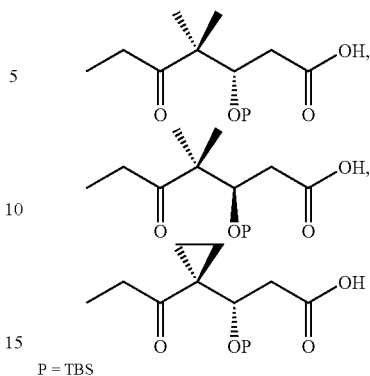

P = TBS

For a synthesis that can be used on an industrial scale, it is advantageous for the synthesis to be carried out without expensive chiral auxiliaries.

The object was therefore to find an appropriate synthesis that provides high yields, produces the desired product at high optical purity, and does not require expensive chiral auxiliaries.

In addition, the new synthesis should make it possible to vary substituents widely in this component and thus, ultimately, in the resulting epothilone derivatives.

The partial fragments (synthesis components) of general formula A can be easily produced as starting products from a) a pantolactone of general formula IIa

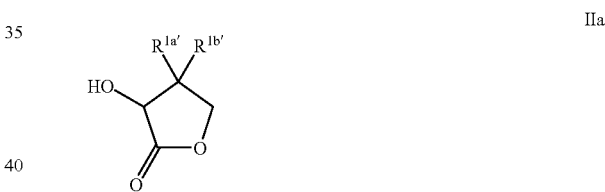

in which $R^{1a'}$, $R^{1b'}$ in each case stand for a methyl group, or b) a malonic acid dialkyl ester of general formula XXVIII

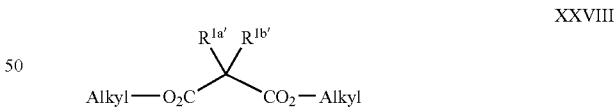

in which $R^{1a'}$, $R^{1b'}$ have the meaning that is indicated in general formula A, and alkyls, independently of one another, mean a $C_1$-$C_{20}$ alkyl, $C_3$-$C_{10}$ cycloalkyl or $C_4$-$C_{20}$ alkylcycloalkyl radical.

Partial fragments A, in which $R^{1a'}=R^{1b'}$=methyl, can be efficiently produced from inexpensive pantolactone with an optical purity of >98%.

The synthesis is described in diagram 1 below in the example of D-(−)-pantolactone. From L-(+)-pantolactone are obtained the corresponding enantiomeric compounds ent-A-II to ent-A-XIV in A-II to A-XIV, and from racemic DL-pantolactone are obtained the corresponding racemic compounds rac-A-II to rac-A-XIV:

Diagram 1

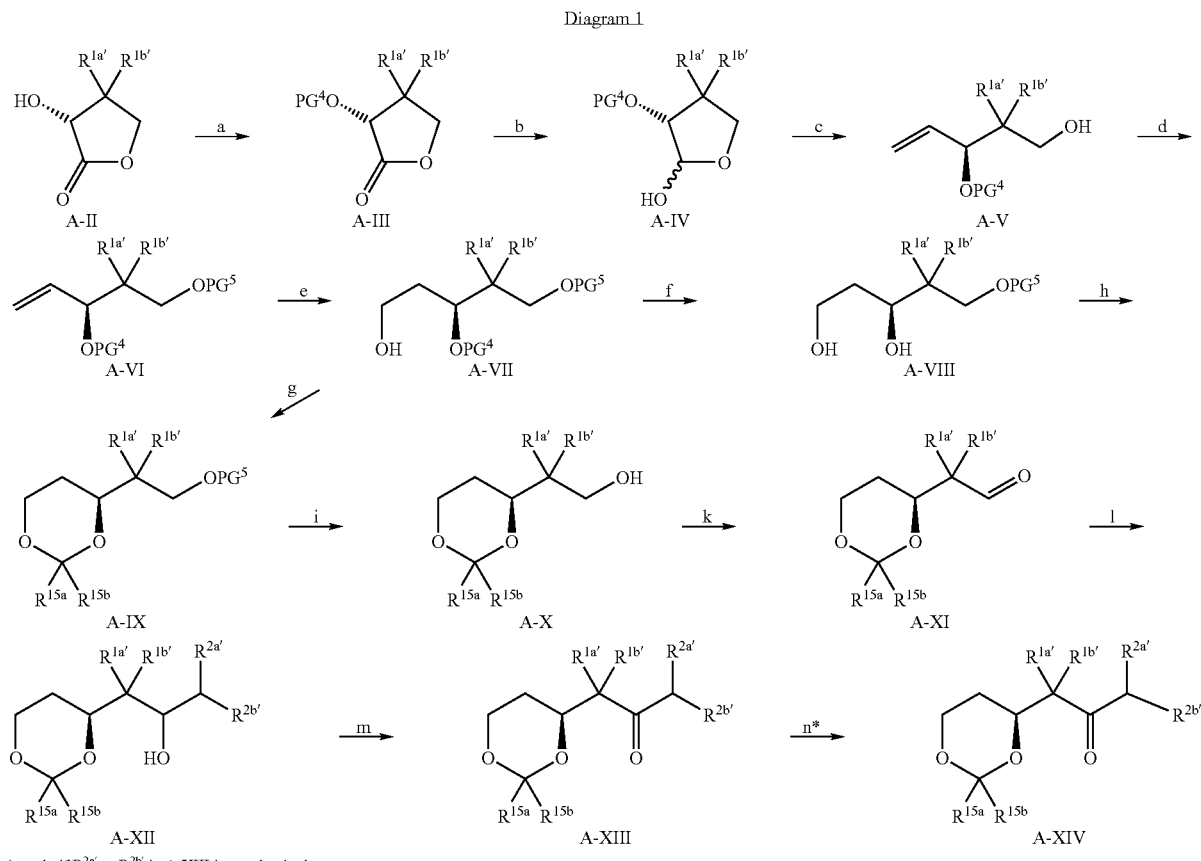

*: only if $R^{2a'}$ or $R^{2b'}$ in A-XIII is equal to hydrogen

Step a (A-II⇒A-III):

The free hydroxy group of pantolactone (A-II) is protected according to the methods that are known to one skilled in the art. As protective group $PG^4$, the protective groups that are known to one skilled in the art, such as, e.g., methoxymethyl, methoxyethyl, ethoxyethyl, tetrahydropyranyl, tetrahydrofuranyl, trimethylsilyl, triethylsilyl, tert-butyldimethylsilyl, tert-butyldiphenylsilyl, tribenzylsilyl, triisopropylsilyl, benzyl, para-nitrobenzyl, para-methoxybenzyl, formyl, acetyl, propionyl, isopropionyl, pivalyl, butyryl or benzoyl radicals, are suitable.

A survey is found in, e.g., "Protective Groups in Organic Synthesis" Theodora W. Green, John Wiley and Sons).

Preferred are those protective groups that can be cleaved under acidic reaction conditions, such as, e.g., methoxymethyl, tetrahydropyranyl, tetrahydrofuranyl, and trimethylsilyl radicals.

Especially preferred is the tetrahydropyranyl radical.

Step b (A-III⇒A-IV):

Protected lactone A-III is reduced to lactol A-IV. As a reducing agent, aluminum hydrides that are modified in their reactivity, such as, e.g., diisobutylaluminum hydride, are suitable. The reaction is carried out in an inert solvent such as, e.g., toluene, preferably at low temperatures.

Step c (A-IV⇒A-V):

Lactol A-IV is opened up to form hydroxyolefin A-V while expanding by one C atom. For this purpose, the methods that are known to one skilled in the art, such as, e.g., olefination according to Tebbe, the Wittig or Wittig/Horner reaction, the addition of an organometallic compound with dehydration, are suitable. Preferred is the Wittig reaction with use of methyltriarylphosphonium halides such as, e.g., methyltriphenylphosphonium bromide with strong bases, such as, e.g., n-butyllithium, potassium-tert-butanolate, sodium ethanolate, sodium hexamethyldisilazane; as a base, n-butyllithium is preferred.

Step d (A-V⇒A-VI):

The free hydroxy group in A-V is protected according to the methods that are known to one skilled in the art. As protective group $PG^5$, the protective groups that are known to one skilled in the art, as were already mentioned above for $PG^4$ in step a (A-II ### A-III), are suitable.

Preferred are those protective groups that can be cleaved under the action of fluoride, such as, e.g., the trimethylsilyl, tert-butyldimethylsilyl, tert-butyldiphenylsilyl, tribenzylsilyl, triisopropylsilyl radical.

Especially preferred is the tert-butyldimethylsilyl, the triisopropylsilyl and the tert-butyldiphenylsilyl radical.

Step e (A-VI⇒A-VII):

Water is added to the double bond in A-VI in an anti-Markovnikov orientation. For this purpose, the processes that are known to one skilled in the art, such as, e.g., reaction with boranes, their subsequent oxidation to the corresponding boric acid esters and their saponification are suitable. As boranes, e.g., the borane-tetrahydrofuran complex, the borane-dimethyl sulfide complex, 9-borabicyclo[3.3.1]

nonane in an inert solvent such as, for example, tetrahydrofuran or diethyl ether, are preferred. As oxidizing agents, preferably hydrogen peroxide is used; for saponification of the boron esters, preferably alkali hydroxides, such as, e.g., sodium hydroxide, are used.

Step f (A-VI⇒A-VII):

Protective group $PG^4$ that is introduced under step a) is now cleaved according to the processes that are known to one skilled in the art. If this is a protective group that can be cleaved acidically, then cleavage can be accomplished with dilute mineral acids in aqueous-alcoholic solutions and with the aid of catalytic quantities of acids, such as, e.g., para-toluenesulfonic acid, para-toluenesulfonic acid-pyridinium salt, camphorsulfonic acid in alcoholic solutions, preferably in ethanol or isopropanol.

Step g (A-VII⇒A-IX):

Common protection of the two alcohol functions of the mono-protected 1,3-diol in A-VII is possible under acid catalysis by direct ketalization with a carbonyl compound of general formula $R^{15a}$—CO—$R^{15b}$ or by reketalization with a ketal of general formulas $R^{15a}$—$C(OC_2H_5)_2$—$R^{15b}$, $R^{15a}$—$C(OC_2H_4)_2$—$R^{15b}$, $R^{15a}$—$C(OCH_2C(C_3)_2CH_2O)$—$R^{15b}$, in which in each case $R^{15a}$ and $R^{15b}$ have the above-indicated meanings. As acids, the acids already mentioned under step f) are suitable; the use of para-toluenesulfonic acid optionally with the addition of copper(II) or cobalt(II) salts, such as, e.g., copper(II) sulfate, is preferred.

Step h (A-VIII⇒A-IX):

Protection of the two alcohol functions of 1,3-diol in A-VIII is possible under acid catalysis by direct ketalization with a carbonyl compound of general formula $R^{15a}$—CO—$R^{15b}$, or by reketalization with a ketal of general formulas $R^{15a}$—$C(OC_2H_5)_2$—$R^{15b}$, $R^{15a}$—$C(OC_2H_4)_2$—$R^{15b}$, $R^{15a}$—$C(OCH_2C(CH_3)_2CH_2O)$—$R^{15b}$, in which in each case $R^{15a}$ and $R^{15b}$ have the above-indicated meanings. Reketalization preferably with 2,2-dimethoxypropane is preferred. As acids, the acids already mentioned under step f) are suitable, and the use of camphorsulfonic acid is preferred.

Step i (A-IX⇒A-X):

Protective group $PG^5$ introduced under step d) is now cleaved according to the process that is known to one skilled in the art. This is a silyl ether, thus suitable for the cleavage are the reaction with fluorides, such as, for example, tetrabutylammonium fluoride, hydrogen fluoride-pyridine complex, potassium fluoride or the use of dilute mineral acids, the use of catalytic quantities of acids, such as, e.g., para-toluenesulfonic acid, para-toluenesulfonic acid-pyridinium salt, camphorsulfonic acid in alcoholic solutions, preferably in ethanol or isopropanol.

Step k (A-X⇒A-XI):

The oxidation of the primary alcohol in A-X to aldehyde is carried out according to the methods that are known to one skilled in the art. For example, oxidation with pyridinium chlorochromate, pyridinium dichromate, chromium trioxide-pyridine complex, oxidation according to Swern or related methods, e.g., with use of oxalyl chloride in dimethyl sulfoxide, the use of Dess-Martin periodinane, the use of nitrogen oxides, such as, e.g., N-methyl-morpholino-N-oxide in the presence of suitable catalysts, such as, e.g., tetrapropylammonium perruthenate in inert solvents, can be mentioned. Preferred is the oxidation according to Swern, as well as with N-methyl-morpholino-N-oxide using tetrapropylammonium perruthenate.

Step l (A-XI⇒A-XII):

The reaction of aldehydes A-XI to alcohols of formula A-XII is carried out with organometallic compounds of general formula $M$-$CHR^{2a'}R^{2b'}$, in which M stands for an alkali metal, preferably lithium or a divalent metal MX, in which X represents a halogen, and radicals $R^{2a'}$ and $R^{2b'}$ in each case have the above-mentioned meanings. As a divalent metal, magnesium and zinc are preferred; as halogen X, chlorine, bromine and iodine are preferred.

Step m (A-XII⇒A-XIII):

Oxidation of the secondary alcohol in A-XII to ketone A-XIII is carried out according to the conditions that are mentioned under step k). Oxidation with N-methyl-morpholino-N-oxide with use of tetrapropylammonium perruthenate is preferred.

Step n (A-XIII⇒A-XIV):

If $R^{2a'}$ in A-XIII is equal to hydrogen, the possibility exists of introducing for this purpose a second radical $R^{2a'}$, which has the above-mentioned meanings, excluding hydrogen. For this purpose, ketone in A-XIII is introduced into the enolate with use of strong bases, such as, e.g., lithium diisopropylamide, and reacted with a compound of general formula $X$-$R^{2a'}$, in which X represents a halogen. As halogen X, chlorine, bromine and iodine are preferred.

The previously described path can also be used to synthesize C1-C6-epothilone components, which on C-1 contain a carboxylic acid or their esters ($R^{13}$=$CO_2R^{13b}$ in A).

The synthesis of component A-XXII is described in Diagram 2 below in the example of intermediate stage A-V that is derived from D-(−)-pantolactone. The corresponding enantiomer compounds ent-A-V to ent-A-XXVII in A-V to A-XXVII are obtained from L-(+)-pantolactone, and the corresponding racemic compounds rac-A-V to rac-A-XXVII are obtained from racemic DL-pantolactone:

Diagram 2

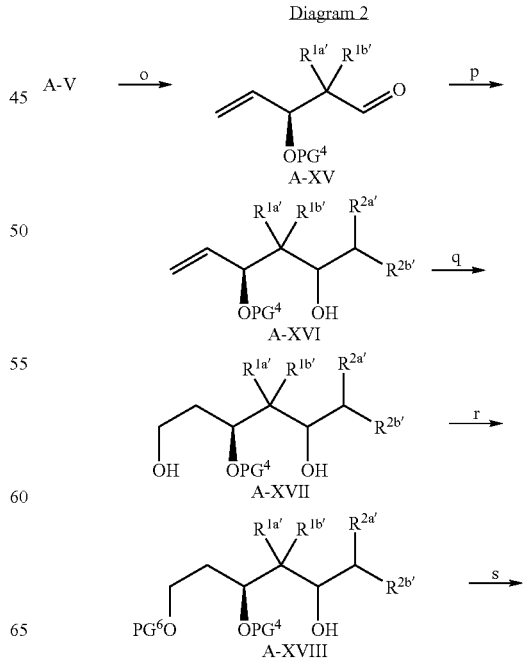

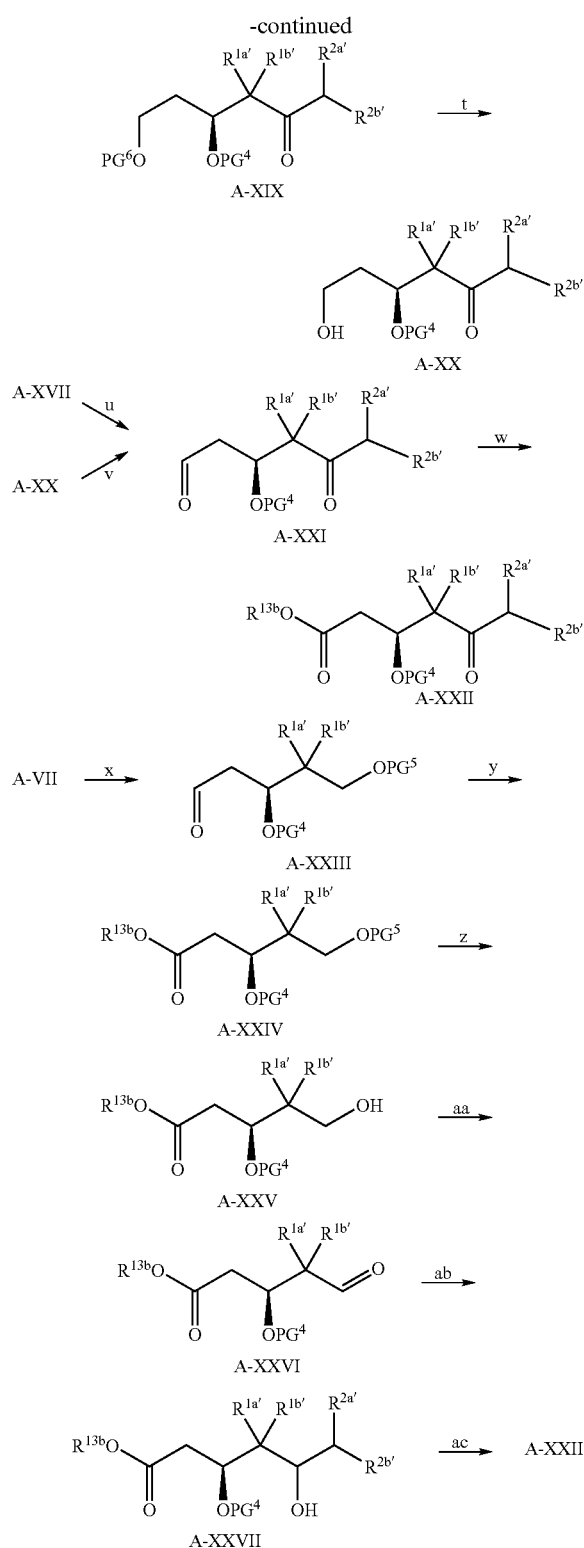

Step o (A-V⇒A-XV):

Oxidation of the primary alcohol in A-V to aldehyde A-XV is carried out according to the conditions that are mentioned under step k). The oxidation process according to Swern is preferred.

Step p (A-XV⇒A-XVI):

The reaction of aldehydes A-XV to alcohols of formula A-XVI is carried out with organometallic compounds of general formula M-CHR$^{2a'}$R$^{2b'}$, in which M stands for an alkali metal, preferably lithium or a divalent metal MX, in which X represents a halogen, and radicals R$^{2a'}$ and R$^{2b'}$ in each case have the above-mentioned meanings. As a divalent metal, magnesium and zinc are preferred; as halogen X, chlorine, bromine and iodine are preferred.

Step q (A-XVI⇒A-XVII):

Water is added to the double bond in A-XVI in an anti-Markovnikov orientation. For this purpose, the processes that are described under e) are suitable.

Step r (A-XVII⇒A-XVIII):

The free hydroxy group in A-XVII is protected according to the methods that are known to one skilled in the art. As protective group PG$^6$, the protective groups that are known to one skilled in the art, as were already mentioned above for PG$^4$ in step a (A-II⇒A-III), are suitable.

Preferred are those protective groups that can be cleaved under basic or hydrogenolytic reaction conditions, such as, e.g., benzyl, para-nitrobenzyl, acetyl, propionyl, butyryl, benzoyl radicals. Especially preferred is the benzoyl radical.

Step s (A-XVIII⇒A-XIX):

Oxidation of the secondary alcohol in A-XVII to ketone A-XIX is carried out according to the conditions that are mentioned under step k). Preferred is oxidation with N-methyl-morpholino-N-oxide with use of tetrapropylammonium perruthenate.

Step t (A-XIX⇒A-XX):

Protective group PG$^6$ in XIX is now selectively cleaved. This is a hydrogenolytically cleavable protective group, thus it is preferably hydrogenated in the presence of palladium or platinum catalysts in inert solvents, such as, for example, ethyl acetate or ethanol. This is a basically cleavable protective group, thus, saponification with carbonates in alcoholic solution, such as, e.g., potassium carbinonate in methanol, saponification with aqueous solutions of alkali hydroxides, such as, e.g., lithium hydroxide or sodium hydroxide, are preferably used while employing organic, water-miscible solvents, such as, e.g., methanol, ethanol, tetrahydrofuran or dioxane.

Step u (A-XVII⇒A-XXI):

Oxidation of alcohols in A-XVII to ketoaldehyde A-XXI is carried out according to the conditions that are mentioned under step k). Preferred is oxidation with N-methyl-morpholino-N-oxide with use of tetrapropylammonium perruthenate and the method according to Swern.

Step v (A-XX⇒A-XXI):

Oxidation of primary alcohol in A-XX to ketoaldehyde A-XXI is carried out according to the conditions that are mentioned under step k). Preferred is oxidation with N-methyl-morpholino-N-oxide with use of tetrapropylammonium perruthenate.

Step w (A-XXI⇒A-XXII):

Oxidation of the aldehyde in A-XXI to carboxylic acid A-XXII (R$^{13b}$=hydrogen) is carried out according to the methods that are known to one skilled in the art. For example, the oxidation according to Jones, oxidation with potassium permanganate, for example in an aqueous system that consists of tert-butanol and sodium dihydrogen phosphate, oxidation with sodium chlorite in aqueous tert-butanol optionally in the presence of a chlorine trap, such as, e.g., 2-methyl-2-butene, can be mentioned.

Oxidation of the aldehyde in A-XXI to ester A-XXII, in which $R^{13b}$ has the above-mentioned meanings and is unequal to hydrogen, can be carried out, for example, with pyridinium dichromate and the desired alcohol HO—$R^{13b}$ in an inert solvent, such as, e.g., dimethylformamide.

Step ac (A-XXVII⇒A-XXII):

Oxidation of the secondary alcohol in A-XXVII to ketone A-XXII is carried out according to the conditions that are mentioned under step k). Preferred is oxidation with N-methyl-morpholino-N-oxide with use of tetrapropylammonium perruthenate.

The compounds of formula A, in which $R^{1a'}$ and $R^{1b'}$ all can have the meanings that are indicated in general formula A can also be produced from inexpensive or readily available malonic acid dialkyl esters in an efficient way with high optical purity.

The synthesis is described in diagram 3 below:

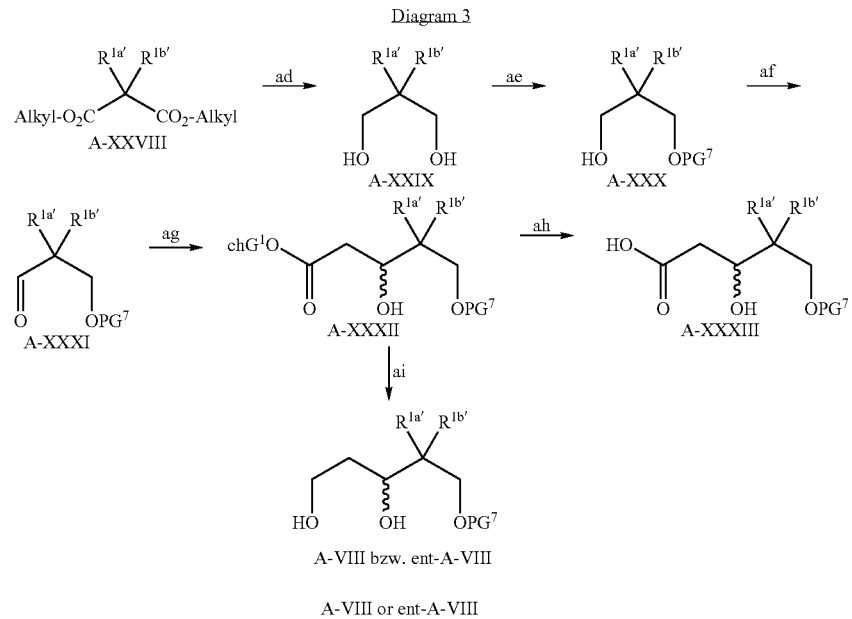

Diagram 3

Step x (A-VII⇒A-XXIII):

Oxidation of the primary alcohol in A-VII to aldehyde A-XXIII is carried out according to the conditions that are mentioned under step k). Preferred is oxidation with N-methyl-morpholino-N-oxide with use of tetrapropylammonium perruthenate as well as the method according to Swern.

Step y (A-XXIII⇒A-XXIV):

Oxidation of aldehyde A-XXIII to carboxylic acid or its esters A-XXIV is carried out according to the conditions already described under w).

Step z (A-XXIV⇒A-XXV):

Protective group $PG^5$ introduced under step d) is cleaved as described under step i.

Step aa (A-XXV⇒A-XXVI):

Oxidation of the primary alcohol in A-XXV to aldehyde A-XXVI is carried out according to the conditions that are mentioned under step k). Preferred is oxidation with N-methyl-morpholino-N-oxide with use of tetrabutylammonium perruthenate as well as the method according to Swern.

Step ab (A-XXVI⇒A-XXVII):

The reaction of aldehyde A-XXVI to alcohols of formula A-XXVII is carried out according to the conditions that are mentioned under step l).

Step ad (A-XXVIII⇒A-XXIX):

Correspondingly substituted malonic acid ester derivatives A-XXVIII, which are either commercially available or can be produced according to the processes that are known to one skilled in the art from malonic acids or their alkyl esters, are reduced to diols A-XXIX. For this purpose, the reducing agents that are known to one skilled in the art, such as, e.g., diisobutylaluminum hydride, and complex metal hydrides, such as, e.g., lithium aluminum hydride, are suitable.

Step ae (A-XXIX⇒A-XXX):

A free hydroxyl group in A-XXIX is selectively protected according to the methods that are known to one skilled in the art. As protective group $PG^7$, the protective groups that are known to one skilled in the art, as were already mentioned above for $PG^4$ in step a (A-II⇒A-III), are suitable.

Preferred are silicon-containing protective groups.

Step af (A-XXX⇒A-XXXI):

Oxidation of the remaining, primary hydroxyl group in A-XXX to aldehyde A-XXXI is carried out according to the conditions that are mentioned under step k).

Preferred is oxidation with N-methyl-morpholino-N-oxide with use of tetrapropylammonium perruthenate, the use of pyridinium chlorochromate, pyridinium dichromate as well as the method according to Swern.

Step ag (A-XXXI⇒A-XXXII):

Aldehydes A-XXXI are reacted with an ester of acetic acid chG¹OC(O)CH₃, in which chG¹ means a chiral auxiliary group, in terms of an aldol reaction. Compounds chG¹OC(O)CH₃ are used in optically pure form in the aldol reaction. The type of chiral auxiliary group determines whether the aldol reaction proceeds with high diastereoselectivity or yields a diastereomer mixture that can be separated with physical methods. A survey on comparable diastereoselective aldol reactions is found in Angew. Chem. 99 (1987), 24-37. As chiral auxiliary groups chG¹-OH, for example, optically pure 2-phenyl-cyclohexanol, pulegol, 2-hydroxy-1,2,2-triphenylethanol, and 8-phenylmenthol are suitable.

Step ah (A-XXXII⇒A-XXXIII):

Diastereomer-pure compounds A-XXXII can then be converted according to the process that is known to one skilled in the art by saponification of the ester unit with simultaneous release of reusable chiral auxiliary component chG¹-OH into enantiomer-pure compounds of type A-XXXIII or ent-A-XXXIII. For saponification, carbonates in alcoholic solution, such as, e.g., potassium carbonate in methanol, aqueous solutions of alkali hydroxides, such as, e.g., lithium hydroxide or sodium hydroxide with use of organic, water-miscible solvents, such as, e.g., methanol, ethanol, tetrahydrofuran or dioxane, are suitable.

Step ai (A-XXXII⇒A-VIII):

As an alternative to step ah, the chiral auxiliary group can also be removed reductively. In this way, the enantiomer-pure compounds of type A-VIII or ent-A-VIII are obtained. The reduction can be carried out according to the processes that are known to one skilled in the art. As a reducing agent, e.g., diisobutylaluminum hydride and complex metal hydrides, such as, e.g., lithium aluminum hydride, are suitable.

Compounds A-VIII or ent-A-VIII can be converted as previously described into compounds of type A-XIII or ent-A-XIII. Correspondingly, compounds of type A-XXXIII or ent-A-XXXIII can be converted into compounds of type A-XXII or ent-A-XXII according to the processes described above.

As an alternative to the above-described method, the sequence can also be carried out without using chiral auxiliary group chG¹. In this way, racemic mixtures of compounds of type rac-A-VIII or rac-A-XXXIII are then obtained via the corresponding, racemic precursors. These mixtures can in turn be separated according to the processes for racemate cleavage, e.g., chromatography on chiral columns, known to one skilled in the art. The continuation of synthesis can also be carried out with racemic mixtures, however.

This invention thus also relates to a process for the production of the compounds of general formula A, which is characterized in that
a) a pantolactone of general formula IIa or
b) a malonic acid dialkyl ester of general formula XXVIII
is used as a starting product.

In addition, this invention thus relates to the new C1-C6-epothilone components of general formula A'

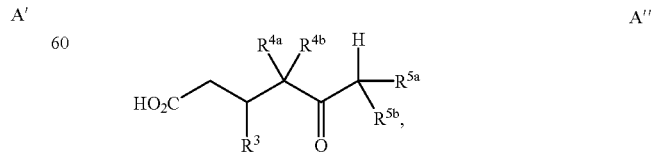

in which $R^2$ means $CH_2OR^{2a}$, CHO, $CO_2R^{2b}$, COX,
$R^{2a}$, $R^{2b}$ mean hydrogen, $C_1$-$C_{20}$ alkyl, aryl, $C_7$-$C_{20}$ aralkyl,
$R^3$ means hydrogen, $OR^{3a}$, X, $OSO_2R^{3b}$,
$R^{3a}$ means hydrogen or together with $R^{2a}$ a —$(CH_2)_n$ group or a $CR^{6a}R^{6b}$ group
$R^{3b}$ means $C_1$-$C_4$ alkyl, aryl,
X means halogen,
n means 2 to 4,
$R^{6a}$, $R^{6b}$ are the same or different and mean $C_1$-$C_8$ alkyl, $C_6$-$C_{10}$ aryl or together a —$(CH_2)_o$ group,
o means 3 to 6,
$R^{6a}$ additionally can assume the meaning of hydrogen,
$R^{4a}$, $R^{4b}$ are the same or different and mean hydrogen, $C_1$-$C_{10}$ alkyl, $C_7$-$C_{20}$ aralkyl or together a —$(CH_2)_m$ group,
m means 2 to 5,
$R^{5a}$, $R^{5b}$ are the same or different and mean hydrogen, $C_1$-$C_{10}$ alkyl, $C_7$-$C_{20}$ aralkyl or together a —$(CH_2)_p$ group,
p means 2 to 5,
$R^{5c}$ means hydrogen,
including all stereoisomers and mixtures thereof, and free hydroxyl groups can be etherified or esterified in $R^2$ and $R^3$, free carbonyl groups can be ketalized in A and $R^2$, converted into an enol ether or reduced, and free acid groups in A can be converted into their salts with bases, excluding the compounds

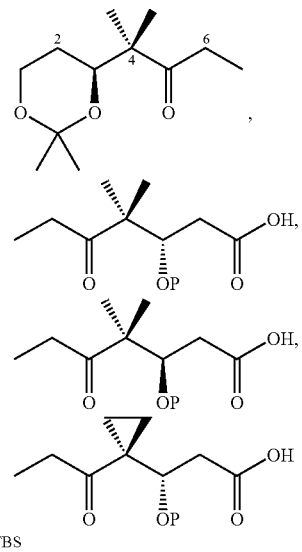

P = TBS

P=TBS

It has also been found that synthesis components of general formula A″

HO₂C— ...

in which $R^3$ means $OR^{3a}$ and $R^{3a}$ means hydrogen or a protective group PG $R^{4a}$, $R^{4b}$ are the same or different and mean hydrogen, $C_1$-$C_{10}$-alkyl, $C_7$-$C_{20}$-aralkyl, or together a —$(CH_2)_m$— group, m means 2-5, $R^{5a}$, $R^{5b}$ are the same or different and mean hydrogen, $C_1$-$C_{10}$-alkyl, $C_7$-$C_{20}$-aralkyl, or together a —$(CH_2)_p$— group, p means 2-5, including all stereoisomers and mixtures thereof, and free carbonyl groups can be ketalized in I, can be produced readily by reaction of a compound of general formula II

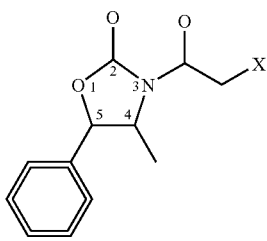

in which

X is a chlorine or bromine atom, and the 2-oxazolidinone ring has either a (4R,5S) or a (4S,5R) conformation, with a compound of general formula III

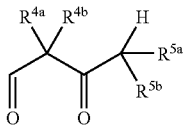

in which $R^{4a}$, $R^{4b}$ are the same or different and mean hydrogen, $C_1$-$C_{10}$-alkyl, $C_7$-$C_{20}$-aralkyl, or together a —$(CH_2)_m$— group, m means 2-5, $R^{5a}$, $R^{5b}$ are the same or different and mean hydrogen, $C_1$-$C_{10}$-alkyl, $C_7$-$C_{20}$-aralkyl, or together a —$(CH_2)_p$— group, p means 2-5, into a compound of general formula IV

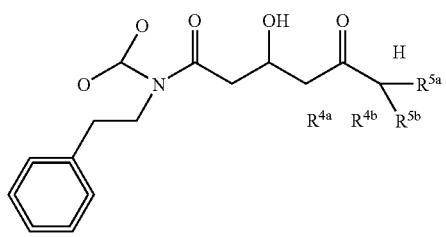

in which the 2-oxazolidinone ring (4R,5S) and the 3'-carbon atom have an R conformation, or the 2-oxazolidinone ring (4S,5R) and the 3'-carbon atom have an S conformation, as well as after the 3'-hydroxy group in IV is protected by a protective group PG, by cleaving the oxazolidinone radical and optionally cleaving protective group PG.

The reaction of a compound of general formula II with a compound of general formula III is accomplished after the compound of general formula II is converted into a metallenolate by insertion of a metal or metal salt into the carbon-halogen bond of the compound of general formula II.

The metals or metal salts that are used generally include all metals or metal salts that are known to one skilled in the art that are suitable for a Reformatzky reaction (see, e.g., A. Furstner, Synthesis 1989, pp. 571-590).

According to the invention, chromium(II) chloride is preferably used.

Upon cleavage, the oxazolidinone ring is recovered from the compounds of general formula IV almost quantitatively and without loss of optical activity.

Alkyl groups $R^{4a}$, $R^{4b}$, $R^{5a}$, and $R^{5b}$ are straight-chain or branched-chain alkyl groups with 1 to a maximum of 10 carbon atoms, such as, for example methyl, ethyl, propyl, isopropyl, butyl, isobutyl, tert-butyl, pentyl, isopentyl, neopentyl, heptyl, hexyl, and decyl.

Alkyl groups $R^{4a}$, $R^{4b}$, $R^{5a}$ and $R^{5b}$ may be perfluorinated or substituted by 1-5 halogen atoms, hydroxy groups, $C_1$-$C_4$ alkoxy groups, and $C_6$-$C_{12}$ aryl groups (which can be substituted by 1-3 halogen atoms).

The aralkyl groups in $R^{4a}$, $R^{4b}$, $R^{5a}$ and $R^{5b}$ can contain up to 14 C atoms, preferably 6-10, in the ring and 1-8, preferably 1-4 atoms in the alkyl chain. The aralkyl radicals that can be considered include, for example, benzyl, phenylethyl, naphthylmethyl, naphthylethyl, furylmethyl, thienylethyl, and pyridylpropyl. The rings can be substituted in one to three places by halogen, OH, O-alkyl, $NH_2$, $CO_2H$, $CO_2$-alkyl, —$NO_2$, —$N_3$, —CN, $C_1$-$C_{20}$-alkyl, $C_1$-$C_{20}$-acyl, and $C_1$-$C_{20}$-acyloxy groups.

Protective groups PG that can be considered include all radicals that are known to one skilled in the art as such protective groups. Preference is given in this case to silyl-containing protective groups, such as, for example the trimethylsilyl, triethylsilyl, tert-butyldimethylsilyl, tert-butyldiphenylsilyl, tribenzylsilyl, and triisopropylsilyl radicals.

A summary of protective groups is given in, e.g., "Protective Groups in Organic Synthesis" by Theodora W. Green, John Wiley and Sons).

Halogen means fluorine, chlorine, bromine, and iodine.

The compounds of general formula II that are required for the process according to the invention can be obtained by acetylation of (4R,5S)- or (4S,5R)-4-methyl-5-phenyl-2-oxazolidinone with bromine or chlorine-acetyl chloride in the presence of a strong base, such as, for example n-butyl-lithium.

The stereochemistry of the hydroxy group in position 3 is controlled later by the selection of the chiral auxiliary.

The compounds of general formula III that are required for the process according to the invention can be obtained commercially or can easily be manufactured.

To the extent that the compounds of general formula III are not available commercially, they can be manufactured using, for example, the methods that are indicated in Schemes 1 and 2.

X = Halogen, PG = protective group
1) In this regard see startng product C, in which $R^{4a} + R^{4b}$ = trimethylene
2) These 1,3-propanediols are available commercially to some extent and can then be incorporated into the synthesis at this point.

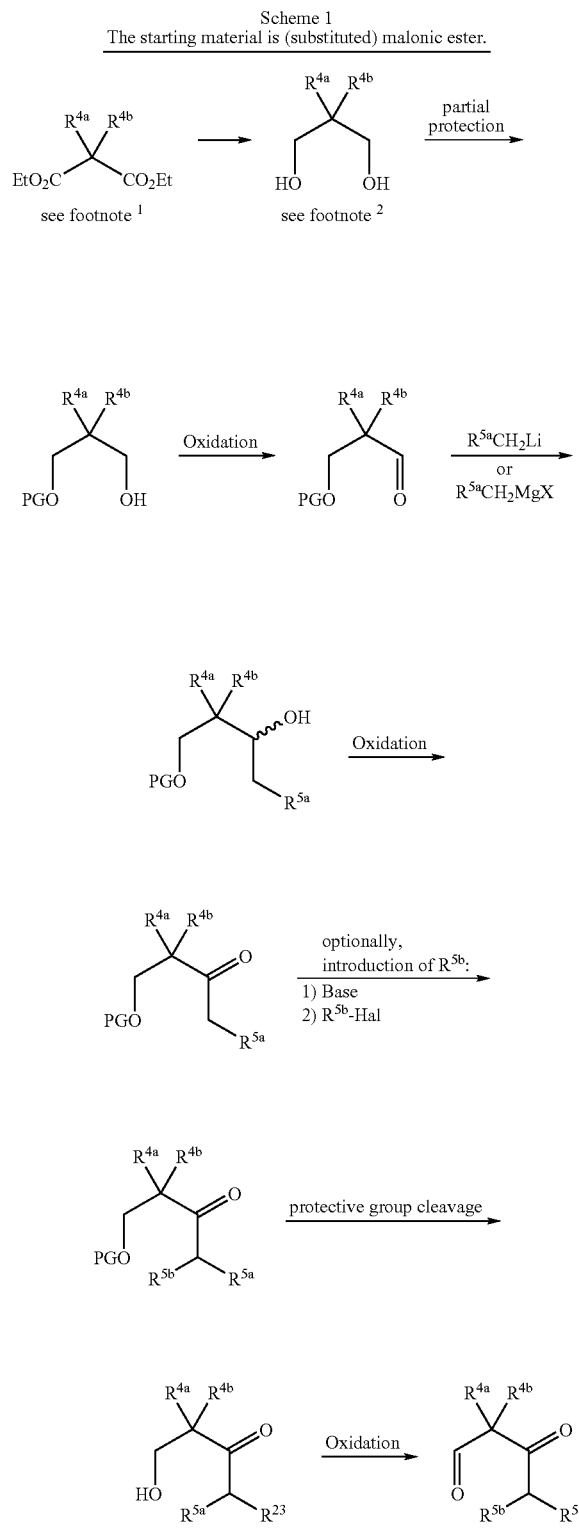

Scheme 1
The starting material is (substituted) malonic ester.

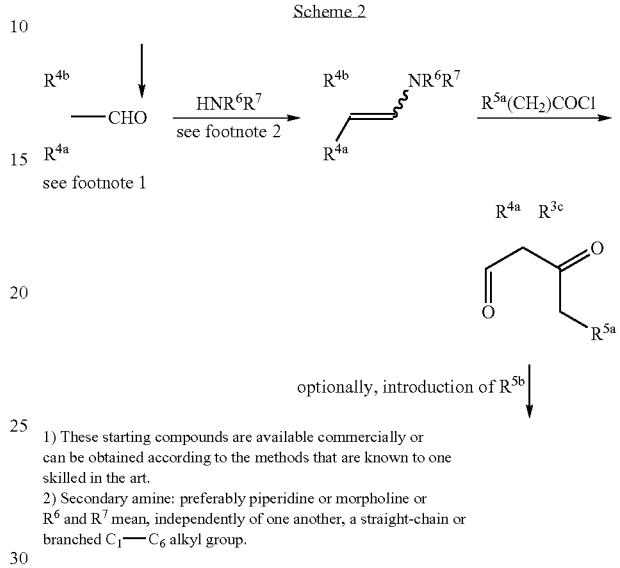

Scheme 2

1) These starting compounds are available commercially or can be obtained according to the methods that are known to one skilled in the art.
2) Secondary amine: preferably piperidine or morpholine or $R^6$ and $R^7$ mean, independently of one another, a straight-chain or branched $C_1$—$C_6$ alkyl group.

By analogy with previously described methods, for instance those cited on page 2 of this application (Schinzer et al., Chem. Eur. J. 1996, 2, No. 11, pp. 1477-1482; Angew. Chem., 1997, 109, No. 5, pp. 543-544; Nicolaou et al.; Angew. Chem. 1997, 109, Nos. 1/2, pp. 170-172; Nature, Vol. 387, 1997, pp. 268-272; J. Am. Chem. Soc., Vol. 119, No. 34, 1997, pp. 7960-7973; J. Am. Chem. Soc., Vol. 119, No. 34, 1997, pp. 7974-7991; Angew. Chem. 1997, 109, No. 19, pp. 2181-2187), the components of general formula I that are produced according to this invention can be used for the synthesis of epothilone A and B, as well as in the $C_1$-$C_6$ section of the epothilone framework that corresponds to modified epothilone derivatives.

The variability of the substituents that was required at the beginning of this document is thus achieved with the compounds of general formula I.

A major advantage of the process according to the invention also lies in the fact that the chiral auxiliary (4R,5S)- or (4S,5R)-4-methyl-5-phenyl-2-oxazolidinone that is used is easy to recover after it is cleaved from the protective compound of general formula IV and can be reinserted into the synthesis process without loss of optical induction.

The components that are obtained in these ways, as well as their enantiomers or mixtures of these enantiomers, are suitable for aldo-condensation with an epothilone component that at C-7 (epothilone numbering system) carries a carbonyl function, as is the case with the above-mentioned total syntheses of epothilone A and epothilone B.

Components A, their enantiomers or mixtures of these enantiomers are also suitable for esterification with an epothilone component which at C-15 (epothilone numbering system) carries a hydroxy function, as is the case with the above-mentioned total syntheses of epothilone A and epothilone B.

Representation of Partial Fragments B:

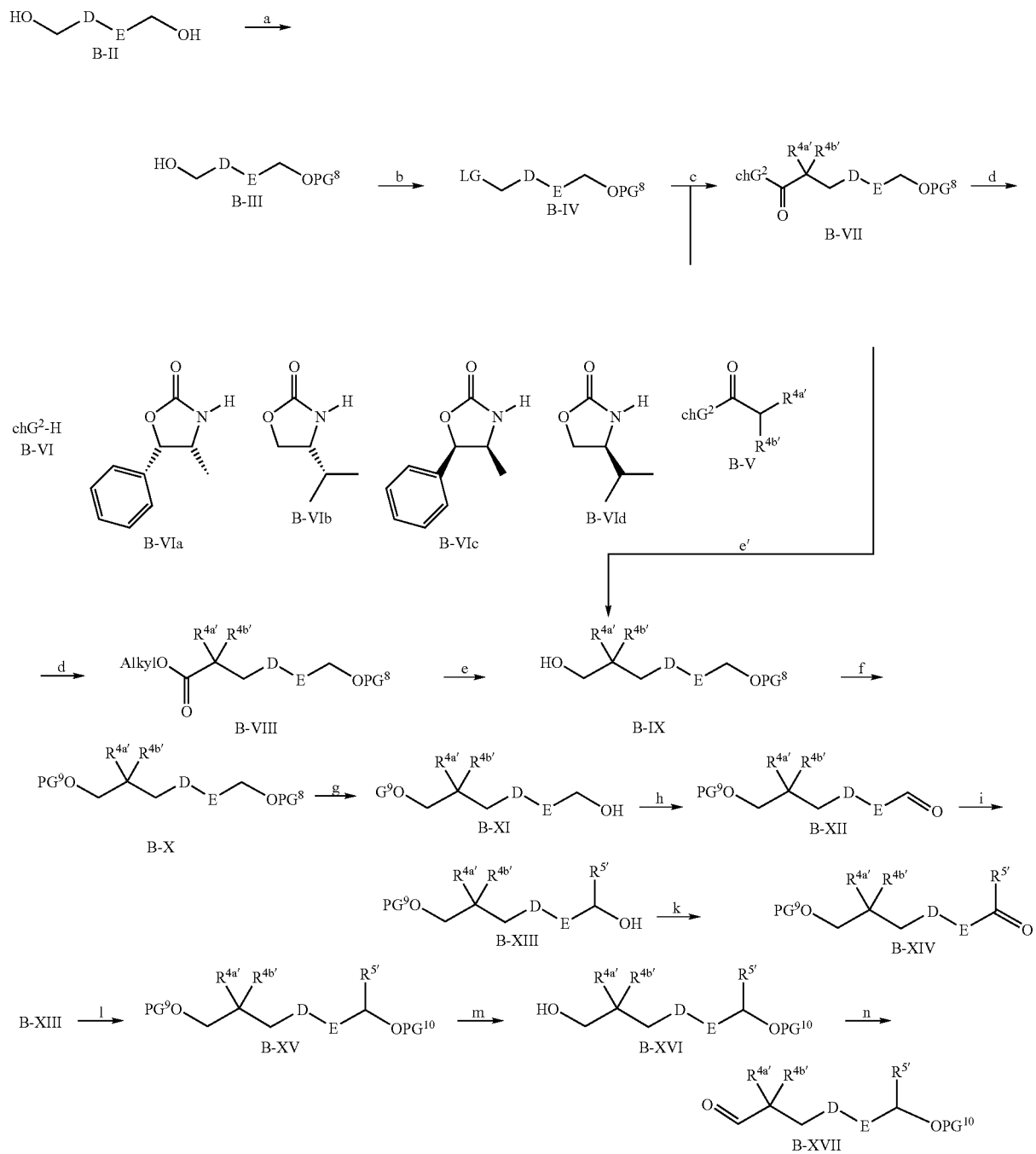

Diagram 4

Step a (B-II⇒B-III):

A hydroxyl group in B-II is protected according to the methods that are known to one skilled in the art. As protective group PG$^8$, the protective groups that are known to one skilled in the art, as were already mentioned above for PG$^4$ in step a (A-II ### A-III), are suitable.

Preferred are silicon-containing protective groups, which can be cleaved under acid reaction conditions or use of fluoride, such as, e.g., trimethylsilyl, triethylsilyl, tert-butyldimethylsilyl, tert-butyldiphenylsilyl, tribenzylsilyl and triisopropylsilyl radicals.

Especially preferred is the tert-butyldimethylsilyl radical.

Step b (B-III⇒B-IV):

The free hydroxyl group in B-III is converted into a leaving group LG according to the methods that are known to one skilled in the art. As leaving group LG, for example, halogens such as, e.g., bromine or iodine or alkyl- or aryl sulfonates, which are produced from the corresponding sulfonic acid halides or sulfonic acid anhydrides according to the methods that are known to one skilled in the art, are suitable.

As leaving group LG, the trifluoromethanesulfonate is preferred.

Step c (B-IV⇒B-VII):

Compound B-IV is alkylated with the enolate of a carbonyl compound of general formula B-V, in which chG$^2$ can be a single alkoxy group or else a chiral auxiliary group according to the methods that are known to one skilled in the art. The enolate is produced by action of stronger bases, such as, e.g., lithium diisopropylamide, lithium hexamethyldisilazane at low temperatures. As chiral auxiliary group chG$^2$-H (B-VI), chiral alcohols that can be produced in an optically pure and inexpensive manner, such as, e.g., pulegol, 2-phenylcyclohexanol, 2-hydroxy-1,2,2-triphenylethanol, 8-phenylmenthol or compounds that contain reactive NH-groups that can be produced in an optically pure and inexpensive manner, such as, e.g., amines, amino acids, lactams or oxazolidinones, are suitable. Preferred are oxazolidinones; especially preferred are the compounds of formulas B-VIa to B-VId. The absolute stereochemistry on the α-carbonylcarbon of the compound of general formula B-VII is set by the selection of the respective antipodes. In this way, the compounds of general formulas B-VII to B-XVII or their respective enantiomers ent-B-VII to ent-B-XVII can be obtained in an enantiomer-pure manner. If an achiral alcohol, such as, e.g., ethanol, is used as chG$^2$-H (B-VI), the racemic compounds rac-B-VII to rac-B-XVII are obtained.

Step d (B-VII⇒B-VIII):

If group chG$^2$ represents one of the chiral auxiliary groups that are mentioned under step c, the latter is recovered by reesterification of B-VII in an alkyl ester of general formula B-VIII. The reesterification is carried out according to the methods that are known to one skilled in the art. Preferred is reesterification with simple alcohols, such as, e.g., methanol or ethanol in the presence of corresponding titanium(IV) alcoholates.

Step e (B-VIII⇒B-IX):

The ester in B-VIII is reduced to alcohol B-IX. As a reducing agent, the reducing agents that are known to one skilled in the art, such as, e.g., aluminum hydrides, such as, e.g., lithium aluminum hydride or diisobutylaluminum hydride, are suitable. The reaction is carried out in an inert solvent, such as, e.g., diethyl ether, tetrahydrofuran, toluene.

Step e' (B-VII⇒B-IX):

As an alternative to steps d) and e), the carbonyl group in B-VII can be reduced immediately to the alcohols of general formula B-IX according to the conditions that are mentioned under step e). Here, the chiral auxiliary component chG$^2$-H can also be recovered.

Step f (B-IX⇒B-X):

The free hydroxyl group in B-IX is protected according to the methods that are known to one skilled in the art. As protective group PG$^9$, the protective groups that are known to one skilled in the art, as were already mentioned above for PG$^4$ in step a (A-II ### A-III), are suitable.

Preferred are those protective groups that can be cleaved under acidic reaction conditions, such as, e.g., the methoxymethyl, tetrahydropyranyl, tetrahydrofuranyl, and trimethylsilyl radical.

Especially preferred is the tetrahydropyranyl radical.

Step g (B-X⇒B-XI):

Protective group PG$^8$, which is introduced under step a), is now cleaved according to the processes that are known to one skilled in the art. If this is a silyl ether, then the reaction with fluorides, such as, for example, tetrabutylammonium fluoride, the hydrogen fluoride-pyridine complex, potassium fluoride or the use of dilute mineral acids, the use of catalytic quantities of acids, such as, e.g., para-toluenesulfonic acid, para-toluenesulfonic acid-pyridinium salt, camphorsulfonic acid in alcoholic solutions, preferably in ethanol or isopropanol, are suitable for the cleavage.

Step h (B-XI⇒B-XII):

Oxidation of the primary alcohol in B-XI to the aldehyde of general formula B-XII is carried out according to the processes that are known to one skilled in the art. For example, oxidation with pyridinium chlorochromate, pyridinium dichromate, chromium trioxide-pyridine complex, oxidation according to Swern or related methods, e.g., with use of oxalyl chloride in dimethyl sulfoxide, the use of Dess-Martin periodinane, the use of nitrogen oxides, such as, e.g., N-methyl-morpholino-N-oxide in the presence of suitable catalysts, such as, e.g., tetrapropylammonium perruthenate in inert solvents, can be mentioned. Preferred is the oxidation according to Swern, as well as with N-methyl-morpholino-N-oxide with use of tetrapropylammonium perruthenate.

Step i (B-XII⇒B-XIII):

The reaction of aldehyde B-XII to alcohols of general formula B-XIII is carried out according to the methods that are known to one skilled in the art with organometallic compounds of general formula M-R$^{5'}$, in which M stands for an alkali metal, preferably lithium or a divalent metal MX, in which X represents a halogen and radical R$^{5'}$ has the above-mentioned meaning. As a divalent metal, magnesium and zinc are preferred; as halogen X, chlorine, bromine and iodine are preferred.

Step k (B-XIII⇒B-XIV):

Oxidation of alcohol B-XIII to the ketone of general formula B-XIV is carried out according to the processes that are mentioned under h). Preferred is oxidation with N-methyl-morpholino-N-oxide with use of tetrapropylammonium perruthenate.

Step l (B-XIII⇒B-XV):

The hydroxyl group in B-XIII can be provided according to the processes that are mentioned under a) with a protective group PG$^{10}$. Preferred are silicon-containing protective groups, which can be cleaved under acidic reaction conditions or use of fluoride, such as, e.g., the trimethylsilyl, triethylsilyl, tert-butyldimethylsilyl, tert-butyldiphenylsilyl, tribenzylsilyl, triisopropylsilyl radical. Especially preferred is the tert-butyldiphenylsilyl radical.

Step m (B-XV⇒B-XVI):

Protective group PG$^9$, which is introduced under step f), is cleaved according to the processes that are described under step g).

Step n (B-XVI⇒B-XVII):

Oxidation of alcohol B-XVI to the aldehyde of general formula B-XVII is carried out according to the processes that are mentioned under h). Preferred is oxidation according to Swern.

As an alternative, the compounds of general formula B-XIII can be produced with the method that is described in Diagram 5.

Diagram 5

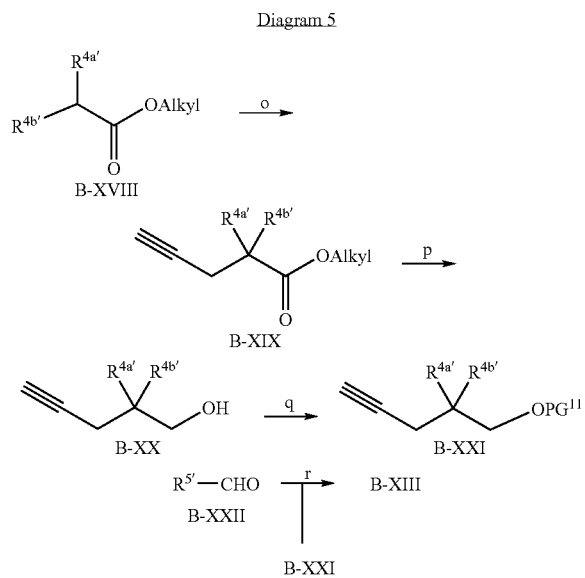

Diagram 6

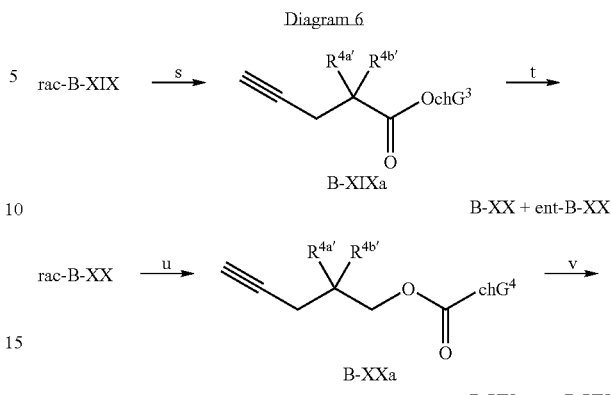

Step s (rac-B-XIX ⇒ B-XIXa):

Racemic compound rac-B-XIX can be reesterified with a chiral alcohol $chG^3$-OH that can be obtained in an optically pure manner according to the methods that are known to one skilled in the art, for example the process that is mentioned under step d), to a mixture of diastereomeric ester B-XIXa and separated with simple, chromatographic methods. As chiral alcohols, for example, pulegol, 2-phenylcyclohexanol, 2-hydroxy-1,2,2-triphenylethanol, 8-phenylmethanol are suitable.

Step t (B-XIXa ⇒ B-XX and ent-B-XX):

Diastereomer-pure esters B-XIXa can be reduced in each case to alcohols B-XX or ent-B-XX according to the process that is described under step e, whereby auxiliary component $chG^3$-OH that is described under step s can be recovered.

Step u (rac-B-XX ⇒ B-XXa):

Racemic compound rac-B-XX can be reacted with a chiral acid $chG^4$-$CO_2$H that can be obtained in an optically pure manner, its esters, anhydride or acid halide, according to the methods that are known to one skilled in the art, to a mixture of the diastereomer ester XXa and separated with simple chromatographic methods. As chiral acids, for example, malic acid, tartaric acid or their derivatives are suitable.

Step v (B-XXa ⇒ B-XX and ent-B-XX):

Diastereomer-pure esters B-XXa can be reduced in each case to alcohols B-XX or ent-B-XX according to the process that is described under step e, or saponified according to the methods that are known to one skilled in the art, whereby in the last-mentioned case, auxiliary component $chG^4$-$CO_2$H that is described under step u can be recovered.

Representation of Partial Fragments C:

It is known that the compound of formula

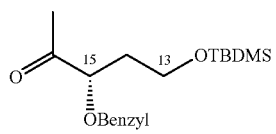

(TBDMS stands for a tert-butyldimethylsilyl radical) can be used for the synthesis of the C13-C16 fragment (epothilone numbering system) of epothilone A (Schinzer et al. Chem. Eur. J. 1996, 2, No. 1, 1477-1482). The synthesis that is

---

Step o (B-XVIII ⇒ B-XIX):

Starting from ethyl acetate derivatives, which can be obtained inexpensively, of general formula B-XVIII, in which $R^{4a'}$ and $R^{4b'}$ have the above-mentioned meanings, the ester enolate is produced by action of strong bases, such as, e.g., lithium diisopropylamide, lithium hexamethyldisilazane at low temperatures and reacted with 3-halogen-1-propine, preferably 3-bromo-1-propine to compounds of general formula B-XIX.

Step p (B-XIX ⇒ B-XX):

The reduction of ester B-XIX to alcohol B-XX is carried out according to the methods that are described under step e), preferably with use of diisobutylaluminum hydride.

Step q (B-XX ⇒ B-XXI):

The hydroxyl group in B-XX can be provided according to the conditions that are mentioned under a) with a protective group $PG^{11}$. Preferred are silicon-containing protective groups, which can be cleaved under acidic reaction conditions or use of fluoride, such as, e.g., the trimethylsilyl, triethylsilyl, tert-butyldimethylsilyl, tert-butyldiphenylsilyl, tribenzylsilyl-triisopropylsilyl radical. Especially preferred is the tert-butyldimethylsilyl radical.

Step r (B-XXI ⇒ B-XIII):

Acetylene B-XXI can be deprotonated according to the processes that are known to one skilled in the art, and the acetylide that is obtained can be reacted with carbonyl compounds of general formula B-XXII, in which $R^{5'}$ has the above-mentioned meaning, to an alcohol of general formula XIII. For deprotonation, alkyl alkali compounds, such as, e.g., butyllithium or other strong bases, such as, e.g., alkali hexamethyldisilazane or lithium diisopropylamide, are suitable. Preferred is n-butyllithium.

In the process that is described in Diagram 5, first the racemic compounds rac-B-XIII are obtained. Optionally, steps rac-B-XIX or rac-B-XX that are passed through according to Diagram 6 offer the possibility for chemical racemate cleavage and thus also access to enantiomer-pure compounds B-XX or ent-B-XX, if $R^{4a'}$ is not identical to $R^{4b'}$.

described by Schinzer et al. introduces the required chirality via a kinetic racemate cleavage according to Sharpless. A necessary chromatographic separation, an inadequate enantiomer excess (80%) and a small overall yield disqualify this method for an industrial synthesis, which requires high yields and high optical purity of the synthesis products.

It is further known that the above-mentioned synthesis component can be converted with the phosphonate of formula

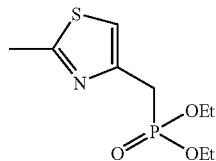

by Wittig reaction into a compound of formula

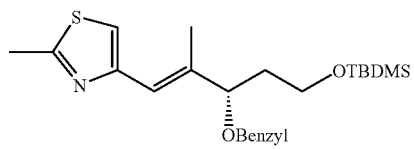

which can then be used for the introduction of the C13-C20 fragment for epothilone synthesis.

Partial fragments of formula C can be produced from malic acid, which can be obtained in an inexpensive, reasonably-priced manner, in an efficient way with high optical purity (>99.5%).

The synthesis is described in Diagram 7 below in the example of L-(−)-malic acid (C-I). Starting from D(+)-malic acid (ent-C-I), the corresponding enantiomeric compounds (ent-C-II to ent-C-XI) are obtained, and starting from racemic malic acid (rac-C-I), the corresponding racemic compounds (rac-C-II to rac-C-XI) are obtained).

Diagram 7

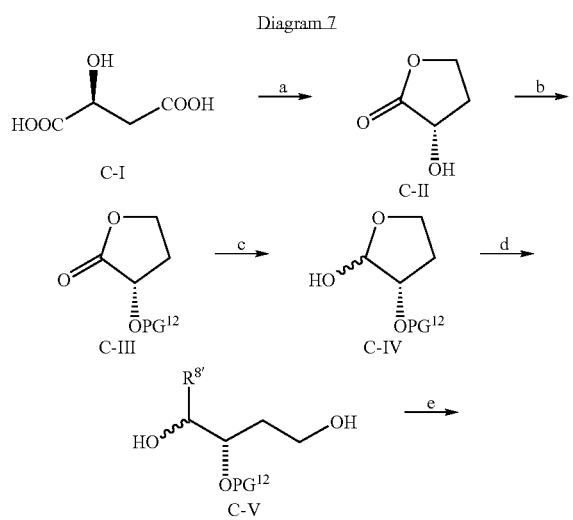

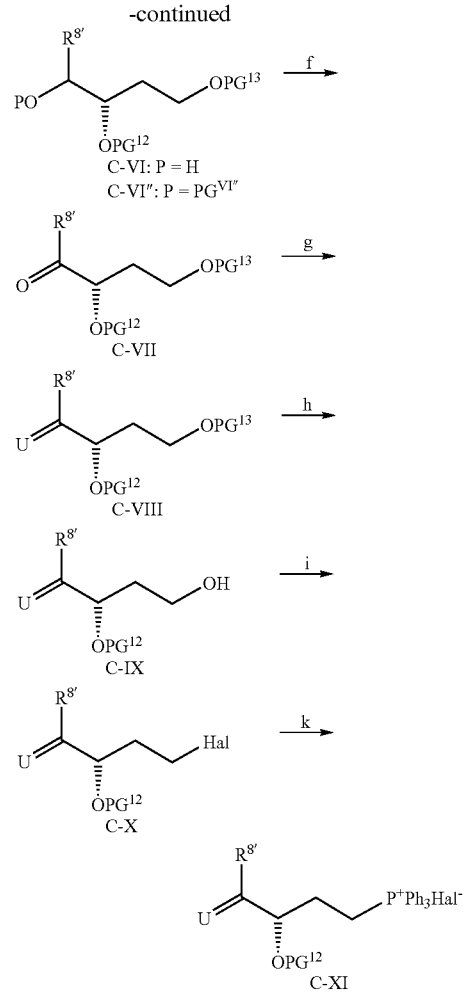

Step a (malic acid C-I⇒C-II):

L-(−)-Malic acid is converted into hydroxylactone C-II according to a process that is known in the literature (Liebigs Ann. Chem. 1993, 1273-1278).

Step b (C-II⇒C-III):

The free hydroxy group in compound C-II is protected according to the methods that are known to one skilled in the art. As protective group $PG^{12}$, the protective groups that are known to one skilled in the art, as were already mentioned above for $PG^4$ in step a (A-II ### A-III), are suitable.

Preferred are those protective groups that can be cleaved under the action of fluoride, but are stable under weakly acid reaction conditions, such as, e.g., the tert-butyldiphenylsilyl, tert-butyldimethylsilyl or triisopropylsilyl radical.

Especially preferred are the tert-butyldiphenylsilyl radical and the tert-butyldimethylsilyl radical.

Step c (C-III⇒C-IV):

Lactone C-III is reduced to lactol C-IV according to the methods that are known to one skilled in the art. As reducing agents, aluminum hydrides that are modified in their reactivity, such as, e.g., diisobutylaluminum hydride, are suitable. The reaction is carried out in an inert solvent, such as, e.g., toluene, preferably at low temperatures (−20 to −100° C.).

Step d (C-IV⇒C-V):

The reaction of lactol C-IV to compounds of formula C-V is carried out with organometallic compounds of general formula M-R$^{8'}$, in which M stands for an alkali metal, preferably lithium, or a divalent metal MX, in which X represents a halogen, and R$^{8'}$ has the above-mentioned meanings. As a divalent metal, magnesium and zinc are preferred, and as halogen X, chlorine, bromine and iodine are preferred.

Step e (C-V⇒C-VI):

The primary hydroxyl group in compound C-V is protected in a selective manner relative to the secondary hydroxyl group according to the methods that are known to one skilled in the art.

The secondary hydroxy group is optionally then protected also according to the methods that are familiar to one skilled in the art.

As protective groups PG$^{13}$ and PG$^{VI''}$, the protective groups that are known to one skilled in the art, as were already mentioned above for PG$^4$ in step a (A-II ### A-III), are suitable.

Preferred are those protective groups that can be cleaved under weakly acidic reaction conditions in a selective manner in the presence of protective group PG10, which is introduced from component A into the synthesis of the compounds of general formula I, such as, e.g., the trimethylsilyl, triethylsilyl, tert-butyldimethylsilyl radical.

Especially preferred is the tert-butyldimethylsilyl radical.

Step f (C-VI⇒C-VII):

Oxidation of the secondary alcohol in C-VI to ketone C-VII is carried out according to the methods that are known to one skilled in the art. For example, oxidation with pyridinium chlorochromate, pyridinium dichromate, chromium trioxide-pyridine complex, oxidation according to Swern or related methods, e.g., with use of oxalyl chloride in dimethyl sulfoxide, the use of Dess-Martin periodinane, the use of nitrogen oxides, such as, e.g., N-methyl-morpholino-N-oxide in the presence of suitable catalysts, such as, e.g., tetrapropylammonium perruthenate in inert solvents, can be mentioned. Preferred is oxidation according to Swern.

Step g (C-VII⇒C-VIII):

For compounds in which U is equal to CR10'R11', this grouping is established according to the processes that are known to one skilled in the art. For this purpose, methods such as, e.g., the Wittig or Wittig/Horner reaction, the addition of an organometallic compound MCHR10'R11' with dehydration, are suitable. Preferred is the Wittig and Wittig/Horner reaction with use of phosphonium halides of type CR10'R11'P(Ph)3$^+$Hal$^-$ or phosphonates of type CR10'R11'P(O)(Oalkyl)2 with Ph equal to phenyl, R10', R11' and halogen in the already mentioned conditions with strong bases, such as, e.g., n-butyllithium, potassium-tert-butanolate, sodium ethanolate, sodium hexamethyldisilazane; n-butyllithium is preferred as a base.

For compounds in which U represents two alkoxy groups OR$^{23}$ or a C$_2$-C$_{10}$ alkylene-α,ω-dioxy group, the ketone is ketalized under acid catalysis according to the methods that are known to one skilled in the art, for example, with use of an alcohol HOR$^{23}$ or a C$_2$-C$_{10}$ alkylene-α,ω-diol.

Step h (C-VIII⇒C-IX):

Protective group PG$^{13}$ that is introduced under e is now selectively cleaved in the presence of PG$^{12}$ according to the processes that are known to one skilled in the art. If this a protective group that can be cleaved acidically, then cleavage is carried out preferably under weakly acidic conditions, such as, e.g., by reaction with dilute organic acids in inert solvent. Preferred is acetic acid.

Step i (C-IX⇒C-X):

The free primary hydroxyl group is optionally converted into a halide according to the processes that are known to one skilled in the art. Preferred halides are chlorine, but especially bromine and iodine. The substitution of the hydroxyl group for a bromine can be carried out using, e.g., triphenylphosphine/tetrabromomethane, but also according to any other process that is known to one skilled in the art. The establishment of an iodine atom can be done from the bromide by substitution, e.g., according to Finkelstein with sodium iodide in acetone. Direct conversion of the hydroxyl group into iodide is also possible, e.g., with use of elementary iodine, imidazole and triphenylphosphine in dichloromethane.

If U ultimately is to stand for H/OR$^9$ with R$^9$ in the meaning of a hydrogen atom, the conversion of the primary hydroxy group into a halogen atom is performed in the stage of compound C-VI' according to selective reaction of the primary hydroxy group.

Step k (C-X⇒C-XI):

If the linkage of the C13-C16 unit with the 12-position of the epothilone radical or of the epothilone fragments, e.g., a C7-C12 unit, is to be carried out by Wittig reaction, as described in, e.g., Nature Vol. 387, 268-272 (1997), the triphenyl-phosphonium-halides (R$^{21}$=P(Ph)$_3$$^+$Hal$^-$), alkyl or aryl phosphonates (R$^{21}$=P(O)(OQ)$_2$) or phosphine oxides (R$^{21}$=P(O)Ph$_2$) of type C-XI are produced starting from halides C-X according to the processes that are known to one skilled in the art. In this case, Ph means phenyl; Hal stands for F, Cl, Br or I, and Q is a C$_1$-C$_{10}$ alkyl or phenyl radical.

For the production of phosphonium salts, e.g., the reaction of the corresponding halides with triphenylphosphine in solvents such as toluene or benzene is suitable.

The production of phosphonates can be carried out, e.g;, by reaction of halides C-X with a metallized dialkylphosphite. The metallization is usually carried out with strong bases, such as, e.g., butyllithium.

The production of the phosphine oxides can be carried out, e.g., by reaction of halides C-X with metallized diphenylphosphine and subsequent oxidation. For metallization, strong bases such as butyllithium are also suitable. The subsequent oxidation to phosphine oxide can then be carried out with, e.g., dilute aqueous hydrogen peroxide solution.

It has been found that, surprisingly enough, compounds of formula C' can be produced from enantiomer-pure malic acid, which can be obtained in an inexpensive, reasonably-priced manner, in an efficient way with high optical purity (>99.5%), although basically the possibility for complete or partial racemization would exist in the described process according to the invention.

As mentioned above, the known process supplies those compounds in which R$^1$ is a methyl group, R$^2$ is a tert-butyldimethylsilyl or benzyl radical, R$^3$ is an O-tert-butyldimethylsilyl radical and X is an oxygen atom or a (2-methylthiazol-4-yl)methylene radical, only in an optical purity of about 80%.

In addition, the chemical yields of the process according to the invention are considerably higher than the yields that are indicated in the processes that are described by Schinzer et al. For example, the yield of (3S)-5-[[dimethyl(1,1-dimethylethyl)silyl]oxy]-3-[[(1,1-dimethylethyl)diphenylsilyl]oxy]-2-pentanone, produced according to the process of the-invention and starting from L-(−)-malic acid with 26.5% is almost twice as high as the yield that is indicated by Schinzer et al. in the production of (3S)-3-benzyloxy-5-[[dimethyl(1,1-dimethylethyl)silyl]oxy]-2-pentanone (14.35%; Chem. Eur. J. 1996, 2, No. 11, 1477-1482) or achieved in the production of (3S)-3-[[dimethyl(1,1-dimethylethyl)silyl]oxy]-5-[[dimethyl(1,1-dimethylethyl)silyl]oxy]-2-pentanone (20.58%; Angew. Chem. 1997, 109, No. 5, 543-544).

This comparison is based on the yields that are indicated in the above-mentioned bibliographic references, whereby—as already mentioned above—it is to be taken into consideration that the compounds that are obtained according to the known processes do not accumulate in an enantiomer-pure manner, such that the actual yield of the enantiomer-pure compound i question is lower, and an additional purification step in this or a later process stage is necessary for obtaining an enantiomer-pure compound.

Moreover, the process according to the invention makes possible a very wide variation of substituents in this C13-C16 component.

This invention thus relates to a process for the production of the compounds of general formula C', which is characterized in that L-(−)-malic acid, D-(+)-malic acid or racemic malic acid is used as a starting product.

Optically pure D-(+)- or L-(−)-malic acid is preferably used.

The invention also relates to the intermediate compounds of general formulas V, VI and VI' (combined below as VI") that occur in the process

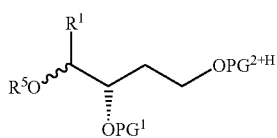

in which
R$^1$, PG$^1$ and R$^5$ have the meaning that is indicated in general formula C' and
PG$^{2+H}$ stands for a hydrogen atom or a protective group PG$^2$.

These compounds are produced according to the invention in that an organometal compound of general formula

R$^1$Y in which
R$^1$ has the meaning that is indicated in general formula C', and
Y stands for an alkali metal atom or MZ, whereby M is a divalent metal atom and Z is a halogen atom, is added to a compound of general Formula IV

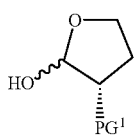

in which
PG$^1$ has the meaning that is indicated in general Formula C, while the lactol ring is opened.

Lithium is preferred as an alkali atom.

In the case of MZ, magnesium and zinc are preferred for the divalent metal atom; as a halogen atom, primarily chlorine, bromine and iodine are considered.

In addition, this invention relates to the new C13-C16 epothilone components of general formula C

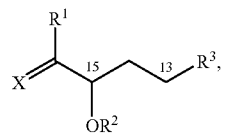

in which
R$^1$ means hydrogen, C$_1$-C$_{20}$ alkyl, aryl, C$_7$-C$_{20}$ aralkyl, which can all be substituted,
R$^2$ means hydrogen or a protective group PG$^1$,
R$^3$ means a hydroxy group, halogen, a protected hydroxy group OPG$^2$, a phosphonium halide radical PPh$_3^+$Hal$^-$ (Ph=phenyl; Hal=F, Cl, Br, I), a phosphonate radical P(O)(OQ)$_2$ (Q=C$_1$-C$_{10}$ alkyl or phenyl) or a phosphine oxide radical P(O)Ph$_2$ (Ph=phenyl),
X means an oxygen atom, two alkoxy groups OR$^4$, a C$_2$-C$_{10}$ alkylene-α,ω-dioxy group, which can be straight-chain or branched, H/OR$^5$ or a grouping CR$^6$R$^7$, whereby
R$^4$ stands for a C$_1$-C$_{20}$ alkyl radical,
R$^5$ stands for hydrogen or a protective group PG$^3$,
R$^6$, R$^7$ are the same or different and stand for hydrogen, a C$_1$-C$_{20}$ alkyl, aryl, C$_7$-C$_{20}$ aralkyl radical or R$^6$ and R$^7$ together with the methylene carbon atom together stand for a 5- to 7-membered carbocyclic ring, whereby not simultaneously
R$^1$ can be a methyl group, R$^2$ can be a tert-butyldimethylsilyl or benzyl radical, R$^3$ can be an O-tert-butyldimethylsilyl radical and X can be a (2-methylthiazol-4-yl)methylene radical or R$^1$ can be a methyl group, R$^2$ can be a tert-butyldimethylsilyl radical, R$^3$ can be a triphenylphosphonium iodide radical and X can be a (2-methylthiazol-4-yl)methylene radical.

The first disclaimer excludes those compounds that were already produced by Schinzer et al. according to a process different from the process according to the invention (Chem. Eur. J. 1996, 2, No. 11, 1477-1482 and Angew. Chem. 1997, 109, No. 5, 543-544).

The second disclaimer takes into consideration the (5E, 3S)-[3-[[(1,1-dimethylethyl)-dimethylsilyl]oxy]-4-methyl-5-(2-methylthiazol-4-yl)-pent-4-en-1-yl]-triphenylphosphonium iodide that is mentioned by K. C. Nicolaou et al. in Nature, Vol. 387, 1997, 268-272.

For the more detailed explanation of substituents R$^1$, R$^4$, R$^6$, R$^7$, PG$^1$, PG$^2$ and PG$^3$ that occur in the compounds of general formula C, the statements that are made above for the substituents of general formula C' hold true.

According to the invention, those compounds of general formula C are preferred, in which
R$^1$ stands for a hydrogen atom, an optionally substituted C$_1$-C$_4$ alkyl radical, a phenyl radical that is optionally substituted with 1 to 3 radicals, selected from the group of substituents halogen, free hydroxy group or protected hydroxy group OPG$^4$, C$_1$-C$_4$ alkyl, azido, nitro, nitrile and amino (NH$_2$), and/or X stands for an oxygen atom, and/or the aryl radical that stands for $R^6$ and/or $R^7$ stands for a phenyl radical that is optionally substituted with 1 to 3 radicals, selected from the group of substituents halogen, free hydroxy group or protected hydroxy group $OPG^5$, $CO_2H$, $CO_2$-alkyl, $C_1$-$C_4$ alkyl, azido, nitro, nitrile, amino ($NH_2$), or for a 5- or 6-membered heteroaryl radical that is optionally substituted with 1 to 2 $C_1$-$C_4$ alkyl radicals, especially for a substituent that is selected from the group 2-, 3-furanyl; 2-, 3-, 4-pyridinyl; 2-, 4-, 5-thiazolyl; 2-, 4- and 5-imidazolyl radical, which optionally is substituted by 1 or 2 $C_1$-$C_4$ alkyl radicals, and/or $PG^1$, $PG^2$ and $PG^3$ are selected from the group of substituents methoxymethyl, methoxyethyl, ethoxyethyl, tetrahydropyranyl, tetrahydrofuranyl, trimethylsilyl, triethylsilyl, tert-butyldimethylsilyl, tert-butyldiphenylsilyl, tribenzylsilyl, triisopropylsilyl, benzyl, para-nitrobenzyl, para-methoxybenzyl, acetyl, propionyl, butyryl and benzoyl radicals, in particular $PG^1$ is a tert-butyldiphenylsilyl, tert-butyldimethylsilyl or triisopropylsilyl radical, and in particular $PG^2$ is a tert-butyldimethylsilyl, acetyl, benzoyl, benzyl, tetrahydropyranyl radical.

As protective groups $PG^4$ and $PG^5$, all protective groups that are indicated above for $PG^1$, $PG^2$ and $PG^3$ are suitable.

Representation of partial fragments ABC and their cyclization to I:

Partial fragments of general formula AB

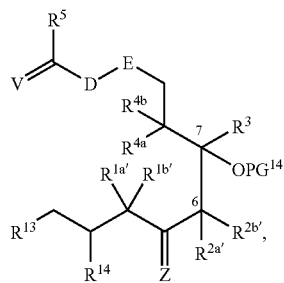

in which $R^{1a'}$, $R^{1b'}$, $R^{2a'}$, $R^{2b'}$, $R^3$, $R^{4a}$, $R^{4b}$, $R^5$, $R^{13}$, $R^{14}$, D, E, V and Z have the meanings already mentioned, and $PG^{14}$ represents a hydrogen atom or a protective group PG, are obtained from previously described fragments A and B according to the process that is shown in Diagram 8.

Diagram 8

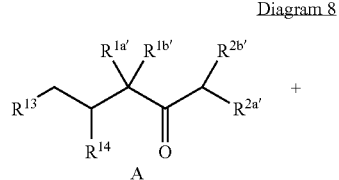

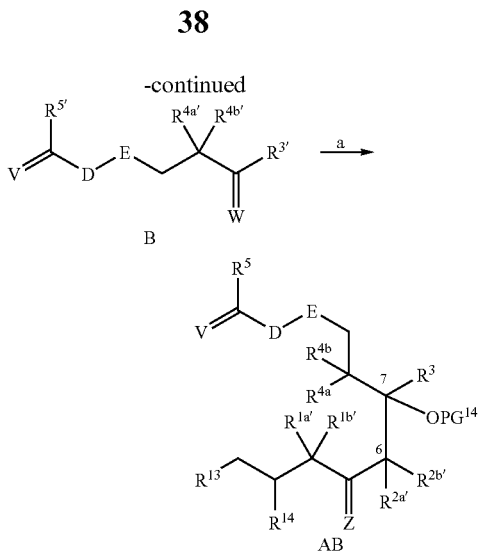

Step a (A+B⇒AB):

Compound B, in which W has the meaning of an oxygen atom and optionally present additional carbonyl groups are protected, is alkylated with the enolate of a carbonyl compound of general formula A. The enolate is produced by action of strong bases, such as, e.g., lithium diisopropylamide, lithium hexamethyldisilazane, at low temperatures.

Partial fragments of general formula ABC

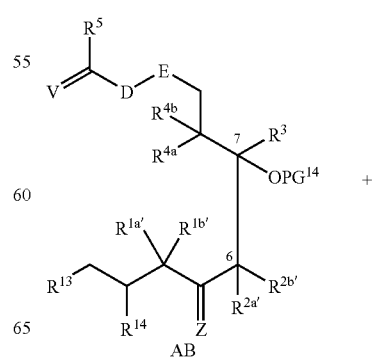

in which $R^{1a'}$, $R^{1b'}$, $R^{2a'}$, $R^{2b'}$, $R^3$, $R^{4a}$, $R^{4b}$, $R^5$, $R^6$, $R^7$, $R^8$, $R^{13}$, $R^{14}$, D, E, U and Z have the already mentioned meanings, are obtained from previously described fragments AB and C according to the process that is shown in Diagram 9.

Diagram 9

-continued

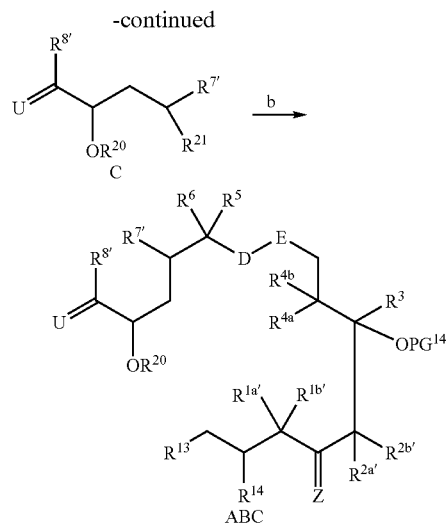

Step b (AB+C⇒ABC):

Compound C, in which $R^{21}$ has the meaning of a Wittig salt, and optionally present additional carbonyl groups are protected, is deprotonated by a suitable base, such as, e.g., n-butyllithium, lithium diisopropyl amide, potassium tert-butanolate, sodium or lithium-hexamethyldisilazide and reacted with a compound AB, in which V has the meaning of an oxygen atom.

Step c (ABC⇒1):

Compounds ABC, in which $R^{13}$ represents a carboxylic acid $CO_2H$ and $R^{20}$ represents a hydrogen atom, are reacted according to the methods that are known to one skilled in the art for the formation of large macrolides to compounds of formula I, in which Y has the meaning of an oxygen atom. Preferred is the method that is described in "Reagents for Organic Synthesis, Vol. 16, p. 353" with use of 2,4,6-trichlorobenzoic acid chloride and suitable bases, such as, e.g., triethylamine, 4-dimethylaminopyridine, sodium hydride.

Step d (ABC⇒1):

Compounds ABC, in which $R^{13}$ represents a group $CH_2OH$ and $R^{20}$ represents a hydrogen atom, can be reacted preferably with use of triphenylphosphine and azodiesters, such as, for example, azodicarboxylic acid diethyl ester, to compounds of formula I, in which Y has the meaning of two hydrogen atoms.

Compounds ABC, in which $R^{13}$ represents a group $CH_2OSO_2$ alkyl or $CH_2OSO_2$ aryl or $CH_2OSO_2$ aralkyl and $R^{20}$ represents a hydrogen atom, can be cyclized to compounds of formula I, in which Y has the meaning of two hydrogen atoms, after deprotonation with suitable bases, such as, for example, sodium hydride, n-butyllithium, 4-dimethylaminopyridine, Hunig base, alkylhexamethyldisilazanes.

The flexible functionalization of described components A, B, and C also ensures a linkage sequence that deviates from the above-described process and that leads to components ABC. These processes are listed in the following table:

| Possible Linkages | Linkage Methods a to e | Prerequisites |
|---|---|---|
| A + B → A - B | a: Aldol (see Diagram 8) | Z = W = oxygen |
| B + C → B - C | b: Wittig (analogously to Diagram 9) e: McMurry | U = oxygen and $R^{21}$ = Wittig salt or phosphine oxide or phosphonate U = V = oxygen |
| A + C → A - C | c: Esterification (e.g., 2,4,6-trichlorobenzoyl chloride/4-dimethylamino-pyridine) d: etherification (e.g., Mitsunobu) | $R^{13} = CO_2R^{13b}$ or COHal and $R^{20}$ = hydrogen $R^{13} = CH_2OH$ and $R^{20}$ = hydrogen or $SO_2$-alkyl or $SO_2$-aryl or $SO_2$-aralkyl |

According to these processes, components A, B and C, as indicated in Diagram 10, can be linked:

Diagram 10

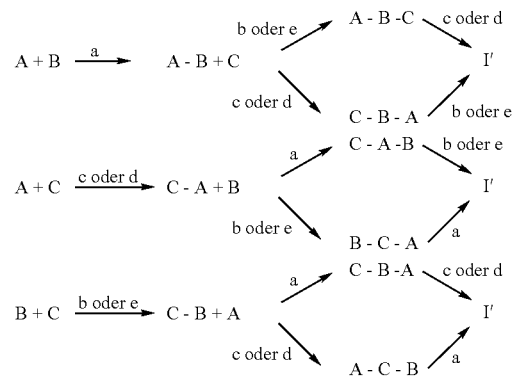

[oder = or]

Free hydroxyl groups in I, A, B, C, AB, ABC can be further functionally modified by etherification or esterification, free carbonyl groups by ketalization, enol ether formation or reduction.

The invention relates to all stereoisomers of these compounds and also their mixtures.

Biological Actions and Applications of the New Derivatives:

The new compounds of formula I are valuable pharmaceutical agents. They interact with tubulin by stabilizing microtubuli that are formed and are thus able to influence the cell-splitting in a phase-specific manner. This relates mainly to quick-growing, neoplastic cells, whose growth is largely unaffected by intercellular regulating mechanisms. Active ingredients of this type are in principle suitable for treating malignant tumors. As applications, there can be mentioned, for example, the treatment of ovarian, stomach, colon, adeno-, breast, lung, head and neck carcinomas, malignant melanoma, acute lymphocytic and myelocytic leukemia. The compounds according to the invention are suitable owing to their properties basically for anti-angiogenesis therapy as well as for treatment of chronic inflammatory diseases, such as, for example, psoriasis or arthritis. To avoid uncontrolled proliferation of cells and for better compatibility of medical implants, they can basically be applied or introduced into the polymer materials that are used for this purpose. The compounds according to the invention can be used alone or to achieve additive or synergistic actions in combination with other principles and classes of substances that can be used in tumor therapy.

As examples, there can be mentioned the combination with
Platinum complexes, such as, e.g., cis-platinum, carboplatinum,
intercalating substances, e.g., from the class of anthracyclines, such as, e.g., doxorubicin or from the class of anthrapyrazoles, such as, e.g., Cl-941,
substances that interact with tubulin, e.g., from the class of vinca-alkaloids, such as, e.g., vincristine, vinblastine or from the class of taxanes, such as, e.g., taxol, taxotere or from the class of macrolides, such as, e.g., rhizoxin or other compounds, such as, e.g., colchicine, combretastatin A-4,
DNA topoisomerase inhibitors, such as, e.g., camptothecin, etoposide, topotecan, teniposide,
folate- or pyrimidine-antimetabolites, such as, e.g., lometrexol, gemcitubin,
DNA-alkylating compounds, such as, e.g., adozelesin, dystamycin A,
inhibitors of growth factors (e.g., of PDGF, EGF, TGFb, EGF), such as, e.g., somatostatin, suramin, bombesin antagonists,
inhibitors of protein tyrosine kinases or protein kinases A or C, such as, e.g., erbstatin, genistein, staurosporine, ilmofosine, 8-Cl-cAMP,
antihormones from the class of antigestagens, such as, e.g., mifepristone, onapristone or from the class of antiestrogens, such as, e.g., tamoxifen or from the class of antiandrogens, such as, e.g., cyproterone acetate,
metastases-inhibiting compounds, e.g., from the class of eicosanoids, such as, e.g., $PGl_2$, $PGE_1$, $6$-oxo-$PGE_1$ as well as their more stable derivatives (e.g., iloprost, cicaprost, misoprostol),
inhibitory, oncogenic RAS proteins, which influence the mitotic signal transduction, such as, for example, inhibitors of the farnesyl-protein-transferase,
natural or synthetically produced antibodies, which are directed against factors or their receptors, which promote tumor growth, such as, for example, the erbB2 antibodies.

The invention also relates to pharmaceutical agents that are based on pharmaceutically compatible compounds, i.e., compounds of general formula I that are nontoxic in the doses used, optionally together with commonly used adjuvants and vehicles.

According to methods of galenicals that are known in the art, the compounds according to the invention can be processed into pharmaceutical preparations for enteral, percutaneous, parenteral or local administration. They can be administered in the form of tablets, coated tablets, gel capsules, granulates, suppositories, implants, injectable, sterile, aqueous or oily solutions, suspensions or emulsions, ointments, creams and gels.

In this case, the active ingredient or ingredients can be mixed with the adjuvants that are commonly used in galenicals, such as, e.g., gum arabic, talc, starch, mannitol, methyl cellulose, lactose, surfactants such as Tweens or Myrj, magnesium stearate, aqueous or non-aqueous vehicles, paraffin derivatives, cleaning agents, dispersing agents, emulsifiers, preservatives and flavoring substances for taste correction (e.g., ethereal oils).

The invention thus also relates to pharmaceutical compositions, which as active ingredients contain at least one compound according to the invention. A dosage unit contains about 0.1-100 mg of active ingredient(s). In humans, the dosage of the compounds according to the invention is approximately 0.1-1000 mg per day.

The examples below are used for a more detailed explanation of the invention, without intending that it be limited to these examples:

Production of the Components of General Formula a from Pantolactone or from Malonic Acid Dialkyl Esters:

EXAMPLE 1

(3S)-1-Oxa-2-oxo-3-(tetrahydropyran-2(RS)-yloxy)-4,4-dimethyl-cyclopentane

The solution of 74.1 g (569 mmol) of D-(−)-pantolactone in 1 l of anhydrous dichloromethane is mixed with 102 ml of 3,4-dihydro-2H-pyran, 2 g of p-toluenesulfonic acid-pyridinium salt under an atmosphere of dry argon, and it is stirred for 16 hours at 23° C. It is poured into a saturated sodium bicarbonate solution, the organic phase is separated and dried on sodium sulfate. After filtration and removal of the solvent, the residue is chromatographed on about 5 kg of fine silica gel with a mixture of n-hexane and ethyl acetate. 119.6 g (558 mmol, 98%) of the title compound is isolated as a colorless oil.

$^1$H-NMR (CDCl$_3$): δ=1.13 (3H), 1.22 (3H), 1.46-1.91 (6H), 3.50-3.61 (1H), 3.86 (1H), 3.92 (1H), 4.01 (1H), 4.16 (1H), 5.16 (1H) ppm.

EXAMPLE 2

(2RS,3S)-1-Oxa-2-hydroxy-3-(tetrahydropyran-2(RS)-yloxy)-4,4-dimethyl-cyclopentane The solution of 117.5 g (548 mmol) of the compound, presented according to Example 1, in 2.4 l of anhydrous toluene is cooled under an atmosphere of dry argon to −70° C., mixed within 1 hour with 540 ml of a 1.2 molar solution of diisobutylaluminum hydride in toluene, and it is stirred for 3 more hours at −70° C. It is allowed to heat to −20° C., mixed with saturated ammonium chloride solution, water, and the precipitated aluminum salts are separated by filtration on Celite. The filtrate is washed with water and saturated sodium chloride solution and dried on magnesium sulfate. After filtration and removal of the solvent, 111.4 g (515 mmol, 94%) of the title compound is isolated as a colorless oil, which is further reacted without purification.

IR(CHCl$_3$): 3480, 3013, 2950, 2874, 1262, 1133, 1074, 1026 and 808 cm$^{-1}$.

EXAMPLE 3

(3S)-2,2-Dimethyl-3-(tetrahydropyran-2(R)-yloxy)-pent-4-en-1-ol and (3S)-2,2-dimethyl-3-(tetrahydropyran-2(S)-yloxy)-pent-4-en-1-ol The suspension of 295 g of methyl-triphenylphosphonium bromide in 2.5 l of anhydrous tetrahydrofuran is mixed under an atmosphere of dry argon at −60° C. with 313 ml of a 2.4 molar solution of n-butyllithium in n-hexane, allowed to heat to 23° C., stirred for one more hour and cooled to 0° C. It is mixed with the solution of 66.2 g (306 mmol) of the compound, presented according to Example 2, in 250 ml of tetrahydrofuran, allowed to heat to 23° C. and stirred for 18 hours. It is poured into a saturated sodium bicarbonate solution, extracted several times with dichloromethane, and the combined organic extracts are dried on sodium sulfate. After filtration and removal of the solvent, the residue is chromatographed on about 5 l of fine silica gel with a gradient system that consists of n-hexane and ethyl acetate. 36.5 g (170 mmol, 56%) of the nonpolar THP-isomers of the title compound, 14.4 g (67.3 mmol, 22%) of the polar THP-isomers of the title compound, as well as 7.2 g (33.3 mmol; 11%) of the starting material are isolated in each case as a colorless oil.

$^1$H-NMR (CDCl$_3$), nonpolar isomer: δ=0.78 (3H), 0.92 (3H), 1.41-1.58 (4H), 1.63-1.87 (2H), 3.18 (1H), 3.41 (1H), 3.48 (1H), 3.68 (1H), 3.94 (1H), 4.00 (1H), 4.43 (1H), 5.19 (1H), 5.27 (1H), 5.75 (1H) ppm.

$^1$H-NMR (CDCl$_3$), polar isomer: δ=0.83 (3H), 0.93 (3H), 1.42-1.87 (6H), 2.76 (1H), 3.30 (1H), 3.45 (1H), 3.58 (1H), 3.83 (1H), 3.89 (1H), 4.65 (1H), 5.12-5.27 (2H), 5.92 (1H) ppm.

EXAMPLE 4

(3S)-1-(tert-Butyldiphenylsilyloxy)-2,2-dimethyl-pentane-3-(tetrahydropyran-2-yloxy)-pent-4-ene The solution of 59.3 g (277 mmol) of the THP-isomer-mixture, presented according to Example 3, in 1000 ml of anhydrous dimethylformamide is mixed under an atmosphere of dry argon with 28 g of imidazole, 85 ml of tert-butyldiphenylchlorosilane and stirred for 16 hours at 23° C. It is poured into water, extracted several times with dichloromethane, the combined organic extracts are washed with water and dried on sodium sulfate. After filtration and removal of the solvent, the residue is chromatographed on fine silica gel with a gradient system that consists of n-hexane and ethyl acetate. 106.7 g (236 mmol, 85%) of the title compound is isolated as a colorless oil.

$^1$H-NMR (CDCl$_3$): δ=0.89 (3H), 0.99 (3H), 1.08 (9H), 1.34-1.82 (6H), 3.40 (1H), 3.51 (2H), 3.76 (1H), 4.02 (1H), 4.67 (1H), 5.18 (1H), 5.23 (1H), 5.68 (1H), 7.30-7.48 (6H), 7.60-7.73 (4H) ppm.

EXAMPLE 5

(3S)-1-(tert-Butyldiphenylsilyloxy)-2,2-dimethyl-3-(tetrahydropyran-2-yloxy)-pentan-5-ol The solution of 3.09 g (6.83 mmol) of the compound, presented according to Example 4, in 82 ml of tetrahydrofuran is mixed with 13.1 ml of a 1 molar solution of borane in tetrahydrofuran under an atmosphere of dry argon at 23° C., and it is allowed to react for 1 hour. Then, while being cooled with ice, it is mixed with 16.4 ml of a 5% sodium hydroxide solution as well as 8.2 ml of a 30% hydrogen peroxide solution, and it is stirred for another 30 minutes. It is poured into water, extracted several times with ethyl acetate, the combined organic extracts are washed with water, saturated sodium chloride solution and dried on magnesium sulfate. The residue that is obtained after filtration and removal of the solvent is purified by chromatography on fine silica gel with a gradient system that consists of n-hexane and ethyl acetate. 1.78 g (3.78 mmol, 55%) of the title compound is isolated as a chromatographically separable mixture of the two THP-epimeres, as well as 0.44 g (1.14 mmol, 17%) of the title compound of Example 6 in each case as a colorless oil.

$^1$H-NMR (CDCl$_3$), nonpolar THP-isomer: δ=0.80 (3H), 0.88 (3H), 1.10 (9H), 1.18-1.80 (9H), 3.27 (1H), 3.39 (1H), 3.48 (1H), 3.64 (1H), 3.83 (1H), 3.90-4.08 (2H), 4.49 (1H), 7.31-7.50 (6H), 7.58-7.73 (4H) ppm.

$^1$H-NMR (CDCl$_3$), polar THP-isomer: δ=0.89 (3H), 0.98 (3H), 1.08 (9H), 1.36-1.60 (4H), 1.62-1.79 (3H), 1.88 (1H), 2.03 (1H), 3.37 (1H), 3.50 (1H), 3.57 (1H), 3.62-3.83 (4H), 4.70 (1H), 7.30-7.48 (6H), 7.61-7.73 (4H) ppm.

EXAMPLE 6

(3S)-1-(tert-Butyldiphenylsilyloxy)-2,2-dimethyl-pentane-3,5-diol

Analogously to Example 5, the solution of 570 mg (1.55 mmol) of the compound that is presented according to Example 12 is reacted, and after working-up and purification, 410 mg (1.06 mmol, 68%) of the title compound is isolated as a colorless oil.

$^1$H-NMR (CDCl$_3$): δ=0.82 (3H), 0.93 (3H), 1.08 (9H), 1.56-1.79 (2H), 3.11 (1H), 3.50 (2H), 3.78-3.92 (3H), 4.02 (1H), 7.34-7.51 (6H), 7.61-7.71 (4H) ppm.

EXAMPLE 7

Variant I

4(S)-[2-Methyl-1-(tert-butyldiphenylsilyloxy)-prop-2-yl]-2,2-dimethyl-[1,3]dioxane The solution of 100 mg (0.212 mmol) of the compounds, presented according to Example 5, in 2.6 ml of anhydrous acetone is mixed with 78.9 mg of copper(II) sulfate, a spatula tip full of p-toluenesulfonic acid-monohydrate under an atmosphere of dry argon, and it is stirred for 16 hours at 23° C. It is mixed with saturated sodium bicarbonate solution, extracted several times with diethyl ether, washed with saturated sodium chloride solution and dried on sodium sulfate. The residue that is obtained after filtration and removal of the solvent is purified by chromatography on fine silica gel with a gradient system that consists of n-hexane and ethyl acetate. 24 mg (56 μmol, 27%) of the title compound is isolated as a colorless oil.

$^1$H-NMR (CDCl$_3$): δ=0.83 (3H), 0.89 (3H), 1.07 (9H), 1.30 (1H), 1.36 (3H), 1.44 (3H), 1.71 (1H), 3.24 (1H), 3.62 (1H), 3.86 (1H), 3.91-4.03 (2H), 7.31-7.48 (6H), 7.61-7.74 (4H) ppm.

Variant II

Analogously to Example 7, 320 mg (0.88 mmol) of the compound that is presented according to Example 6 is reacted; variant 1, and after working-up and purification, 234 mg (0.548 mmol, 62%) of the title compound is isolated.

Variant III

The solution of 5.60 g (14.5 mmol) of the compound, presented according to Example 6, in 250 ml of anhydrous dichloromethane, is mixed with 10 ml of 2,2-dimethoxypropane, 145 mg of camphor-10-sulfonic acid under an atmosphere of dry argon, and it is stirred for 6 hours at 23° C. It is mixed with triethylamine, diluted with ethyl acetate, washed with saturated sodium bicarbonate solution and dried on sodium sulfate. After filtration and removal of the solvent, the residue is chromatographed on fine silica gel with a mixture of n-hexane and ethyl acetate. 5.52 g (12.9 mmol, 89%) of the title compound is isolated as a colorless oil.

EXAMPLE 8

(4S)-4-(2-Methyl-1-hydroxy-prop-2-yl)-2,2-dimethyl-[1,3]dioxane

The solution of 5.6 g (13.1 mmol) of the compound, presented according to Example 7, in 75 ml of anhydrous tetrahydrofuran is mixed with 39 ml of a 1 molar solution of tetrabutylammonium fluoride in tetrahydrofuran under an atmosphere of dry argon, and it is heated for 16 hours to 50° C. It is mixed with saturated sodium bicarbonate solution, extracted several times with ethyl acetate, washed with saturated sodium chloride solution and dried on sodium sulfate. The residue that is obtained after filtration and removal of the solvent is purified by chromatography on fine silica gel with a gradient system that consists of n-hexane and ethyl acetate. 2.43 g (12.9 mmol, 99%) of the title compound is isolated as a colorless oil.

$^1$H-NMR (CDCl$_3$): δ=0.87 (3H), 0.90 (3H), 1.35 (1H), 1.37 (3H), 1.43 (3H), 1.77 (1H), 2.93 (1H), 3.36 (1H), 3.53 (1H), 3.79 (1H), 3.87 (1H), 3.96 (1H) ppm.

EXAMPLE 9

(4S)-4-(2-Methyl-1-oxo-prop-2-yl)-2,2-dimethyl-[1,3]dioxane

The solution of 0.13 ml of oxalyl chloride in 5.7 ml of anhydrous dichloromethane is cooled under an atmosphere of dry argon to −70° C., mixed with 0.21 ml of dimethyl sulfoxide, the solution of 200 mg (1.06 mmol) of the compound, presented according to Example 8, in 5.7 ml of anhydrous dichloromethane, and it is stirred for 0.5 hour. Then, it is mixed with 0.65 ml of triethylamine, allowed to react for 1 hour at −30° C. and mixed with n-hexane and saturated sodium bicarbonate solution. The organic phase is separated, the aqueous phase is extracted once more with n-hexane, the combined organic extracts are washed with water and dried on magnesium sulfate. The residue that is obtained after filtration and removal of the solvent is further reacted without purification.

EXAMPLE 10

(4S)-4-(2-methyl-3(RS)-hydroxy-pent-2-yl)-2,2-dimethyl-[1,3]dioxane

The solution of 900 mg (4.83 mmol) of the compound, presented according to Example 9, in 14 ml of anhydrous diethyl ether is mixed with 2.42 ml of a 2.4 molar solution of ethylmagnesium bromide in diethyl ether under an atmosphere of dry argon at 0° C., allowed to heat to 23° C. and stirred for 16 hours. It is mixed with saturated ammonium chloride solution, the organic phase is separated and dried on sodium sulfate. The residue that is obtained after filtration and removal of the solvent is purified by chromatography on fine silica gel with a gradient system that consists of n-hexane and ethyl acetate. 321 mg (1.48 mmol, 31%) of the nonpolar 3R- or 3S-epimeres of the title compound, 542 mg (2.51 mmol, 52%) of the polar 3S- or 3R-epimeres of the title compound and 77 mg of the title compound that is described in Example 8 are isolated in each case as a colorless oil.

$^1$H-NMR (CDCl$_3$) nonpolar isomer: δ=0.86 (3H), 0.89 (3H), 1.03 (3H), 1.25-1.37 (2H), 1.37 (3H), 1.46 (3H), 1.49 (1H), 1.84 (1H), 3.35 (1H), 3.55 (1H), 3.81-4.02 (3H) ppm.

$^1$H-NMR (CDCl$_3$) polar isomer: δ=0.72 (3H), 0.91 (3H), 0.99 (3H), 1.25-1.44 (2H), 1.38 (3H), 1.43-1.60 (1H), 1.49 (3H), 1.76 (1H), 3.39 (1H), 3.63 (1H), 3.79-4.03 (3H) ppm.

EXAMPLE 11

(4S)-4-(2-Methyl-3-oxo-pent-2-yl)-2,2-dimethyl-[1,3]dioxane

The solution of 850 mg (3.93 mmol) of a mixture of the compound, presented according to Example 10, in 63 ml of anhydrous dichloromethane is mixed with molecular sieve (4A, about 80 spheres), 690 mg of n-methylmorpholino-N-oxide, and 70 mg of tetrapropylammonium perruthenate, and it is stirred for 16 hours at 23° C. under an atmosphere of dry argon. It is concentrated by evaporation, and the crude product that is obtained is purified by chromatography on about 200 ml of fine silica gel with a gradient system that consists of n-hexane and ethyl acetate. 728 mg (3.39 mmol, 86%) of the title compound is isolated as a colorless oil.

$^1$H-NMR (CDCl$_3$): δ=1.00 (3H), 1.07 (3H), 1.11 (3H), 1.31 (1H), 1.32 (3H), 1.41 (3H), 1.62 (1H), 2.52 (2H), 3.86 (1H), 3.97 (1H), 4.05 (1H) ppm.

EXAMPLE 12

(3S)-1-(tert-Butyldiphenylsilyloxy)-2,2-dimethyl-3-hydroxy-pent-4-ene

The solution of 106.7 g (236 mmol) of the compound, presented according to Example 4, in 1.5 l of anhydrous ethanol is mixed with 5.9 g of pyridinium-p-toluenesulfonate under an atmosphere of dry argon, and it is heated for 6 hours to 50° C. After removal of the solvent, the residue is chromatographed on fine silica gel with a mixture of n-hexane and ethyl acetate. 82.6 g (224 mmol, 95%) of the title compound is isolated as a colorless oil, in which in addition about 5 g of ethoxy-tetrahydropyran is contained.

$^1$H-NMR (CDCl$_3$) of an analytic sample: δ=0.89 (6H), 1.08 (9H), 3.45 (1H), 3.49 (1H), 3.58 (1H), 4.09 (1H), 5.21 (1H), 5.33 (1H), 5.93 (1H), 7.34-7.51 (6H), 7.63-7.73 (4H) ppm.

EXAMPLE 13

(4S)-4-((2RS)-3-Methyl-2-hydroxy-prop-3-yl)-2,2-dimethyl-[1,3]dioxane

Analogously to Example 10, 450 mg (2.42 mmol) of the compound that is presented according to Example 9 is reacted with use of methylmagnesium bromide. After working-up and purification, 431 mg (2.13 mmol, 88%) of a chromatographically separable mixture of the epimeric title compounds is isolated as a colorless oil.

EXAMPLE 14

(4S)-4-(3-Methyl-2-oxo-prop-3-yl)-2,2-dimethyl-[1,3]dioxane 420 mg (2.08 mmol) of the compound that is presented according to Example 13 is reacted analogously to Example 11. After working-up and purification, 388 mg (1.94 mmol, 93%) of the title compound is isolated as a colorless oil.

$^1$H-NMR (CDCl$_3$): δ=1.08 (3H), 1.12 (3H), 1.33 (3H), 1.35 (1H), 1.42 (3H), 1.63 (1H), 2.17 (3H), 3.87 (1H), 3.98 (1H), 4.04 (1H) ppm.

EXAMPLE 15

(4S)-4-((3RS)-2-Methyl-3-hydroxy-hex-2-yl)-2,2-dimethyl-[1,3]dioxane

Analogously to Example 10, 450 mg (2.42 mmol) of the compound that is presented according to Example 9 is reacted with use of n-propylmagnesium bromide. After working-up and purification, a total of 244 mg (1.06 mmol, 44%) of a separable mixture of epimeric title compounds as well as 191 mg of the title compound that is described in Example 8 are isolated in each case as a colorless oil.

$^1$H-NMR (CDCl$_3$) nonpolar isomer: δ=0.87 (3H), 0.89 (3H), 0.94 (3H), 1.25-1.52 (4H), 1.38 (3H), 1.45 (3H), 1.66 (1H), 1.85 (1H), 3.46 (1H), 3.80-4.02 (4H) ppm.

$^1$H-NMR (CDCl$_3$) polar isomer: δ=0.73 (3H), 0.92 (3H), 0.95 (3H), 1.19-1.84 (6H), 1.37 (3H), 1.49 (3H), 3.49 (1H), 3.60 (1H), 3.80-4.03 (3H) ppm.

EXAMPLE 16

(4S)-4-(2-Methyl-3-oxo-hex-2-yl)-2,2-dimethyl-[1,3]dioxane 230 mg (1.00 mmol) of the compounds presented according to Example 15 are reacted analogously to Example 11. After working-up and purification, 185 mg (0.81 mmol, 81%) of the title compound is isolated as a colorless oil.

$^1$H-NMR (CDCl$_3$): δ=0.88 (3H), 1.04 (3H), 1.12 (3H), 1.22-1.37 (1H), 1.31 (3H), 1.40 (3H), 1.48-1.71 (3H), 2.46 (2H), 3.83 (1H), 3.96 (1H), 4.04 (1H) ppm.

EXAMPLE 17

(4R)-4-(2-Methyl-3-oxo-pent-2-yl)-2,2-dimethyl-[1,3]-dioxane

Starting from L-(+)-pantolactone, the title compound is produced analogously to the processes that are described in Examples 1 to 9 and 12 via the respective enantiomer intermediate stages.

$^1$H-NMR (CDCl$_3$): δ=1.00 (3H), 1.07 (3H), 1.12 (3H), 1.24-1.37 (1H), 1.31 (3H), 1.40 (3H), 1.61 (1H), 2.50 (2H), 3.84 (1H), 3.95 (1H), 4.03 (1H) ppm.

EXAMPLE 18

(4R)-4-(3-Methyl-2-oxo-prop-3-yl)-2,2-dimethyl-[1,3]dioxane

Starting from L-(+)-pantolactone, the title compound is produced analogously to the processes that are described in Examples 1 to 9 and 12 to 14 via the respective enantiomer intermediate stages.

$^1$H-NMR (CDCl$_3$): δ=1.07 (3H), 1.12 (3H), 1.30-1.39 (1H), 1.33 (3H), 1.43 (3H), 1.62 (1H), 2.17 (3H), 3.86 (1H), 3.96 (1H), 4.03 (1H) ppm.

EXAMPLE 19

(4R)-4-(2-Methyl-3-oxo-hex-2-yl)-2,2-dimethyl-[1,3]dioxane

Starting from L-(+)-pantolactone, the title compound is produced analogously to the processes that are described in Examples 1 to 9, 12, 15 and 16 via the respective enantiomer intermediate stages.

$^1$H-NMR (CDCl$_3$): δ=0.88 (3H), 1.04 (3H), 1.12 (3H), 1.22-1.37 (1H), 1.31 (3H), 1.41 (3H), 1.48-1.72 (3H), 2.47 (2H), 3.84 (1H), 3.96 (1H), 4.05 (1H) ppm.

EXAMPLE 20

(2S,4S)-2-(2-Cyanophenyl)-4-[2-methyl-1-(tert-butyldiphenylsilyloxy)-prop-2-yl]-[1,3]dioxane The solution of 1.00 g (2.59 mmol) of the compound, presented according to Example 6, in 50 ml of benzene is mixed with 850 mg of 2-cyanobenzaldehyde, a spatula tip full of p-toluenesulfonic acid-monohydrate, and it is refluxed for 16 hours in a water separator under an atmosphere of dry argon. It is mixed with 0.5 ml of triethylamine, diluted with ethyl acetate, washed with saturated sodium bicarbonate solution and dried on sodium sulfate. After filtration and removal of the solvent, the residue is chromatographed on fine silica gel with a mixture of n-hexane and ethyl acetate. 1.22 g (2.44 mmol, 94%) of the title compound is isolated as a colorless oil.

$^1$H-NMR (CDCl$_3$): δ=0.99 (6H), 1.05 (9H), 1.47 (1H), 1.98 (1H), 3.34 (1H), 3.63 (1H), 3.96-4.09 (2H), 4.31 (1H), 5.75 (1H), 7.17 (2H), 7.24-7.51 (5H), 7.51-7.74 (7H) ppm.

EXAMPLE 21

(2S,4S)-2-(2-Cyanophenyl)-4-(2-methyl-1-hydroxy-prop-2-yl)-[1,3]dioxane

Analogously to Example 8, 1.22 g (2.44 mmol) of the compound that is presented according to Example 20 is reacted, and after working-up and purification, 593 mg (2.27 mmol, 93%) of the title compound is isolated as a colorless oil.

$^1$H-NMR (CDCl$_3$): δ=0.89 (3H), 0.97 (3H), 1.51 (1H), 2.01 (1H), 2.42 (1H), 3.31 (1H), 3.72 (1H), 3.97 (1H), 4.02 (1H), 4.39 (1H), 5.78 (1H), 7.46 (1H), 7.63 (1H), 7.69 (1H), 7.75 (1H) ppm.

EXAMPLE 22

(2S,4S)-2-(2-Cyanophenyl)-4-(2-methyl-1-oxo-prop-2-yl)-[1,3]-dioxane

Analogously to Example 9, 570 mg (2.18 mmol) of the compound that is presented according to Example 21 is reacted, and after working-up, 780 mg of the title compound is isolated as a yellow oil, which is further reacted without purification.

EXAMPLE 23

(2S,4S)-2-(2-Cyanophenyl)-4-((3RS)-2-methyl-3-hydroxy-pent-2-yl)-[1,3]-dioxane

Analogously to Example 10, 780 mg (max. 2.18 mmol) of the crude product that is presented according to Example 22 is reacted, and after working-up and purification, 468 mg (1.62 mmol, 74%) of the epimeric title compounds is isolated as a colorless oil.

$^1$H-NMR (CDCl$_3$): δ=0.81-1.09 (9H), 1.22-1.43 (1H), 1.43-1.70 (2H), 2.04 (1H), 2.35 (0.55H), 2.89 (0.45H), 3.41-3.59 (1H), 3.89-4.13 (2H), 4.36 (1H), 5.78 (0.45H), 5.81 (0.55H), 7.45 (1H), 7.54-7.78 (3H) ppm.

EXAMPLE 24

(2S,4S)-2-(2-Cyanophenyl)-4-(2-methyl-3-oxo-pent-2-yl)-[1,3]dioxane

Analogously to Example 11, 463 mg (1.60 mmol) of the compound that is presented according to Example 23 is reacted, and after working-up and purification, 420 mg (1.46 mmol, 91%) of the title compound is isolated as a colorless oil.
$^1$H-NMR (CDCl$_3$): δ=1.00 (3H), 1.19 (3H), 1.24 (3H), 1.49 (1H), 1.92 (1H), 2.56 (2H), 4.3 (1H), 4.16 (1H), 4.32 (1H), 5.78 (1H), 7.44 (1H), 7.60 (1H), 7.64-7.72 (2H) ppm.

EXAMPLE 25

(4S,2S)-4-[2-Methyl-1-(tert-butyldiphenylsilyloxy)-prop-2-yl]-2-phenyl-[1,3]dioxane Analogously to Example 20, 1.00 g (2.59 mmol) of the compound, presented according to Example 6, in 50 ml of toluene is reacted with use of benzaldehyde, and after working-up and purification, 1.2 g (2.53 mmol, 98%) of the title compound is isolated as a colorless oil.
$^1$H-NMR (CDCl$_3$): δ=0.93 (3H), 1.00 (3H), 1.07 (9H), 1.43 (1H), 1.92 (1H), 3.30 (1H), 3.72 (1H), 3.95 (1H), 4.00 (1H), 4.30 (1H), 5.53 (1H), 7.18 (2H), 7.29-7.49 (9H), 7.61 (2H), 7.67 (2H) ppm.

EXAMPLE 26

(4S,2S)-4-(2-Methyl-1-hydroxy-prop-2-yl)-2-phenyl-[1,3]dioxane

Analogously to Example 8, 1.20 g (2.53 mmol) of the compound that is presented according to Example 25 is reacted, and after working-up and purification, 518 mg (2.19 mmol, 87%) of the title compound is isolated as a colorless oil.
$^1$H-NMR (CDCl$_3$) δ=0.98 (6H), 1.49 (1H), 2.00 (1H), 2.49 (1H), 3.46 (1H), 3.62 (1H), 3.81 (1H), 3.98 (1H), 4.33 (1H), 5.51 (1H), 7.30-7.41 (3H), 7.41-7.51 (2H) ppm.

EXAMPLE 27

(2S,4S)-4-(2-Methyl-1-oxo-prop-2-yl)-2-phenyl-[1,3]dioxane

Analogously to Example 9, 500 mg (2.12 mmol) of the compound that is presented according to Example 26 is reacted, and after working-up, 715 mg of the title compound is isolated as a yellow oil, which is further reacted without purification.

EXAMPLE 28

(2S,4S)-4-((3RS)-2-Methyl-3-hydroxy-pent-2-yl)-2-phenyl-[1,3]dioxane

Analogously to Example 10, 715 mg (max. 2.12 mmol) of the crude product that is presented according to Example 27 is reacted, and after working-up and purification, 440 mg (1.66 mmol, 79%) of the epimeric title compounds is isolated as a colorless oil.
$^1$H-NMR (CDCl$_3$): δ=0.80-1.10 (9H), 1.23-1.42 (1H), 1.42-1.70 (2H), 1.90-2.16 (1H), 2.92 (0.6H), 3.07 (0.4H), 3.40-3.53 (1H), 3.86 (1H), 3.98 (1H), 4.32 (1H), 5.49 (0.4H), 5.55 (0.6H), 7.28-7.40 (3H), 7.40-7.51 (2H) ppm.

EXAMPLE 29

(2S,4S)-4-(2-Methyl-3-oxo-pent-2-yl)-2-phenyl-[1,3]dioxane

Analogously to Example 11, 435 mg 91.65 mol) of the compound that is presented according to Example 28 is reacted, and after working-up and purification, 410 mg (1.56 mmol, 95%) of the title compound is isolated as a colorless oil.
$^1$H-NMR (CDCl$_3$): δ=1.02 (3H), 1.17 (3H), 1.23 (3H), 1.44 (1H), 1.84 (1H), 2.58 (2H), 3.97 (1H), 4.06 (1H), 4.30 (1H), 5.50 (1H), 7.28-7.49 (5H) ppm.

EXAMPLE 30

(4S)-4-[2-Methyl-1-(tert-butyldiphenylsilyloxy)-prop-2-yl]-2,2-pentamethylene-[1,3]dioxane Analogously to Example 20, 1.00 g (2.59 mmol) of the compound, presented according to Example 6, in 50 mol of toluene is reacted with use of cyclohexanone, and after working-up and purification, 1.09 g (2.34 mmol, 90%) of the title compound is isolated as a colorless oil.
$^1$H-NMR (CDCl$_3$): δ=0.84 (3H), 0.89 (3H), 0.97-1.10 (10H), 1.20-1.64 (9H), 1.71 (1H), 2.13 (1H), 3.33 (1H), 3.56 (1H), 3.81 (1H), 3.89 (1H), 3.99 (1H), 7.32-7.49 (6H), 7.60-7.74 (4H) ppm.

EXAMPLE 31

(4S)-4-(2-Methyl-1-hydroxy-prop-2-yl)-2,2-pentamethylene-[1,3]dioxane

Analogously to Example 8, 1.09 g (2.34 mmol) of the compound that is presented according to Example 30 is reacted, and after working-up and purification, 470 mg (2.06 mmol, 88%) of the title compound is isolated as a colorless oil.
$^1$H-NMR (CDCl$_3$): δ=0.88 (3H), 0.94 (3H), 1.24-1.71 (10H), 1.81 (1H), 2.18 (1H), 3.09 (1H), 3.39 (1H), 3.60 (1H), 3.80 (1H), 3.87 (1H), 4.02 (1H) ppm.

EXAMPLE 32

(4S)-4-(2-Methyl-1-oxo-prop-2-yl)-2,2-pentamethylene-[1,3]dioxane

Analogously to Example 9, 450 mg (1.97 mmol) of the compound that is presented according to Example 31 is reacted, and after working-up, 678 mg of the title compound is isolated as a yellow oil, which is further reacted without purification.

EXAMPLE 33

(4S)-4-(2-Methyl-3-hydroxy-pent-2-yl)-2,2-pentamethylene-[1,3]dioxane

Analogously to Example 10, 678 mg (max. 1.97 mmol) of the crude product that is presented according to Example 32 is reacted, and after working-up and purification, 391 mg (1.54 mmol, 77%) of the epimeric title compounds is isolated as a colorless oil.

¹H-NMR (CDCl₃): δ=0.70-1.08 (9H), 1.23-1.98 (13H), 2.01-2.13 (1H), 3.37-3.50 (1H), 3.61 (0.5H), 3.80-4.06 (3.5H) ppm.

EXAMPLE 34

(4S)-(2-Methyl-3-oxo-pent-2-yl)-2,2-pentamethylene-[1,3]dioxane

Analogously to Example 11, 386 mg (1.51 mmol) of the compound that is presented according to Example 33 is reacted, and after working-up and purification, 376 mg (1.48 mmol, 98%) of the title compound is isolated as a colorless oil.
¹H-NMR (CDCl₃): δ=1.01 (3H), 1.09 (3H), 1.17 (3H), 1.22-1.38 (3H), 1.40-1.72 (8H), 2.15 (1H), 2.57 (2H), 3.81 (1H), 3.92-4.07 (2H) ppm.

EXAMPLE 35

(4S)-4-[2-Methyl-1-(tert-butyldiphenylsilyloxy)-prop-2-yl]-2,2-tetramethylene-[1,3]dioxane Analogously to Example 20, 1.00 g (2.59 mmol) of the compound, presented according to Example 6, in 50 ml of toluene is reacted with use of cyclopentanone, and after working-up and purification, 997 mg (2.20 mmol, 85%) of the title compound is isolated as a colorless oil.
¹H-NMR (CDCl₃): δ=0.84 (3H), 0.88 (3H), 0.99-1.10 (10H), 1.30 (1H), 1.50-1.99 (8H), 3.23 (1H), 3.60 (1H), 3.80-3.98 (3H), 7.31-7.49 (6H), 7.61-7.73 (4H) ppm.

EXAMPLE 36

(4S)-4-(2-Methyl-1-hydroxy-prop-2-yl)-2,2-tetramethylene-[1,3]dioxane

Analogously to Example 8, 997 mg (2.20 mmol) of the compound that is presented according to Example 35 is reacted, and after working-up and purification, 415 mg (1.94 mmol, 88%) of the title compound is isolated as a colorless oil.
¹H-NMR (CDCl₃):δ=0.90 (6H), 1.36 (1H), 1.53-2.02 (9H), 2.93 (1H), 3.39 (1H), 3.55 (1H), 3.70 (1H), 3.87 (1H), 3.96 (1H) ppm.

EXAMPLE 37

(4S)-4-(2-Methyl-1-oxo-prop-2-yl)-2,2-tetramethylene-[1,3]dioxane

Analogously to Example 9, 400 mg (1.87 mmol) of the compound that is presented according to Example 36 is reacted, and after working-up, 611 mg of the title compound is isolated as a yellow oil, which is further reacted without purification.

EXAMPLE 38

(4S)-4-(2-Methyl-3-hydroxy-pent-2-yl)-2,2-tetramethylene-[1,3]dioxane

Analogously to Example 10, 611 mg (max. 1.87 mmol) of the compound that is presented according to Example 37 is reacted, and after working-up and purification, 353 mg (1.46 mmol, 78%) of the epimeric title compounds is isolated as a colorless oil.

¹H-NMR (CDCl₃): δ=0.71-1.09 (9H), 1.20-1.44 (2H), 1.44-1.78 (5H), 1.78-2.02 (5H), 3.32-3.44 (1H), 3.51-3.60 (1H), 3.76 (1H), 3.80-4.02 (2H) ppm.

EXAMPLE 39

(4S)-4-(2-Methyl-3-oxo-pent-2-yl)-2,2-tetramethylene-[1,3]dioxane

Analogously to Example 11, 348 mg (1.44 mmol) of the compound that is presented according to Example 38 is reacted, and after working-up and purification, 332 mg (1.38 mmol, 96%) of the title compound is isolated as a colorless oil.
¹H-NMR (CDCl₃): δ=1.00 (3H), 1.07 (3H), 1.17 (3H), 1.31 (1H), 1.50-2.00 (9H), 2.52 (2H), 3.84 (1H), 3.88-3.99 (2H) ppm.

EXAMPLE 40

1,1-Cyclobutanedimethanol 170 ml of a 1.2 molar solution of diisobutylaluminium hydride is added in drops to a solution of 20 g (99.9 mmol) of 1,1-cyclobutanedicarboxylic acid diethyl ester in 200 ml of absolute tetrahydrofuran at 0° C. It is allowed to stir for one more hour at 0° C., and then 30 ml of water is added. It is filtered on Celite. The filtrate is dried with sodium sulfate and concentrated by evaporation in a vacuum. The crude product that is obtained (9.9 g, 85.2 mmol, 85%) is used without purification in the next step.

EXAMPLE 41

1-[[[Dimethyl(1,1-dimethylethyl)silyl]oxy]-methyl] cyclobutanemethanol

A solution of 9.9 g (85 mmol) of the compound, presented according to Example 40, in 100 ml of absolute tetrahydrofuran is added to a suspension of 3.4 g of sodium hydride (60% in oil) in 35 ml of absolute tetrahydrofuran at 0° C. It is allowed to stir for 30 more minutes, and then a solution of 12.8 g of tert-butyldimethylsilyl chloride in 50 ml of tetrahydrofuran is added. It is allowed to stir for one more hour at 25° C., and then the reaction mixture is poured onto saturated aqueous sodium bicarbonate solution. It is extracted with ethyl acetate. The organic phase is washed with saturated sodium chloride solution and dried on sodium sulfate. After the solvent is drawn off in a vacuum, the crude product that is obtained is purified by column chromatography on silica gel with a mixture of hexane/ethyl acetate. 13.5 g (58.6 mmol, 69%) of the title compound is obtained.
¹H-NMR (CDCl₃): δ=0.04 (6H), 0.90 (9H), 1.70-2.00 (6H), 3.70 (4H) ppm.

EXAMPLE 42

1-[[[Dimethyl(1,1-dimethylethyl)silyl]oxy]-methyl] cyclobutanecarbaldehyde 8 ml of oxalyl chloride is dissolved in 100 ml of dichloromethane. It is cooled to –78° C., and 13 ml of dimethyl sulfoxide is added. It is allowed to stir for 3 more minutes, and then a solution of 13.5 g (58.6 mmol) of the compound, presented according to Example 41, in 80 ml of dichloromethane is added. After another 15 minutes of stirring time, 58 ml of triethylamine is added in drops. Then, it is allowed to heat to 0° C. Then, the reaction mixture is poured onto saturated sodium bicarbonate solution. It is extracted with dichloromethane, the organic phase is washed with saturated sodium chloride solution, dried on sodium sulfate and concentrated by evaporation in a vacuum. After chromatography of the crude product on silica gel with a mixture of hexane/ethyl acetate, 7.7 g (33.7 mmol, 58%) of the title compound is obtained.

$^1$H-NMR (CDCl$_3$): δ=9.70 s (1H), 3.83 s (2H), 2.20-2.30 m (2H), 1.85-2.00 m (4H), 0.90 s (9H), 0.03 s (6H) ppm.

EXAMPLE 43

[1R-[1α(R*)2β]]-2-Phenylcyclohexyl 3-[1-[[[dimethyl(1,1-dimethylethyl)silyl]oxy]methyl]cyclobutyl]-3-hydroxypropanoate (A) and [1R-[1α(S*)2β]]-2-phenylcyclohexyl 3-[1-[[[dimethyl(1,1-dimethylethyl)silyl]oxy]methyl]cyclobutyl]-3-hydroxypropanoate (B)

Lithium diisopropylamide is produced in absolute tetrahydrofuran from 7.2 ml of diisopropylamine and butyllithium (32 ml of a 1.6 molar solution in hexane). Then, a solution of 11.2 g (1R-trans)-2-phenylcyclohexyl acetate in 100 ml of absolute tetrahydrofuran is added at −78° C., and it is allowed to stir for 30 more minutes at this temperature. Then, a solution of 7.7 g (33.7 mmol) of the compound, presented according to Example 42, in 50 ml of tetrahydrofuran is added. It is allowed to stir for 1.5 more hours at −78° C., and then the reaction mixture is poured onto saturated aqueous ammonium chloride solution. It is extracted with ethyl acetate, the organic phase is washed with saturated sodium chloride solution, dried on sodium sulfate and concentrated by evaporation in a vacuum. After column chromatography of the crude product on silica gel with a mixture of hexane/ethyl acetate, 6.34 g (14.2 mmol, 42%) of title compound A and 4.22 g (9.4 mmol, 28%) of title compound B are obtained.

$^1$H-NMR (CDCl$_3$) of A: δ=0.04 (6H), 0.98 (9H), 2.69 (1H), 3.08 (1H), 3.60 (1H), 3.67 (1H), 3.78-3.84 (1H), 4.97 (1H), 7.15-7.30 (5H) ppm.

$^1$H-NMR (CDCl$_3$) of B: δ=0.03 (6H), 0.90 (9H), 2.68 (1H), 2.80 (1H), 3.56 (2H), 3.68-3.72 (1H), 4.99 (1H), 7.18-7.30 m (5H) ppm.

EXAMPLE 44

(S)-1-[1-[[[Dimethyl(1,1-dimethylethyl)silyl]oxy]methyl]cyclobutyl]-1,3-propanediol 4 ml of a 1.2 molar solution of diisobutylaluminum hydride in toluene is added in drops to a solution of 1 g (2.24 mmol) of compound A, presented according to Example 43, in 10 ml of absolute toluene at 0° C. It is allowed to stir for 1.5 more hours at 0° C., and then 5 ml of water is added. It is filtered on Celite. The filtrate is dried on sodium sulfate and concentrated by evaporation in a vacuum. After column chromatography of the crude product on silica gel with a mixture of hexane/ethyl acetate, 370 mg (1.35 mmol, 60%) of the title compound is obtained.

$^1$H-NMR (CDCl$_3$): δ=0.05 (6H), 0.90 (9H), 1.55-1.60 (2H), 1.80 (2H), 1.90 (3H), 2.10 (1H), 3.75 (1H), 3.85-3.95 (4H) ppm.

EXAMPLE 45

(S)-2,2-Dimethyl-4-[1-[[[dimethyl(1,1-dimethylethyl)silyl]oxy]methyl]cyclobutyl]-1,3-dioxane 370 mg (1.35 mmol) of the compound that is presented according to Example 44 is dissolved in 10 ml of acetone. A spatula tip full of p-toluenesulfonic acid is added, and it is allowed to stir for 2 more hours at 25° C. Then, the reaction mixture is poured onto saturated sodium bicarbonate solution. It is extracted with ethyl acetate, the organic phase is washed with saturated sodium chloride solution, dried on sodium sulfate and concentrated by evaporation in a vacuum. After column chromatography on silica gel with a mixture of hexane/ethyl acetate, 338 mg (1.07 mmol, 79%) of the title compound is obtained.

$^1$H-NMR (CDCl$_3$): δ=0.03 (6H), 0.88 (9H), 1.38 (3H), 1.42 (3H), 1.50-1.80 (4H), 2.00 (1H), 3.52 (1H), 3.62 (1H), 3.85-4.00 (3H) ppm.

EXAMPLE 46

(R)-1-[1-[[[Dimethyl(1,1-dimethylethyl)silyl]oxy]methyl]-cyclobutyl]-1,3-propanediol Analogously to Example 44, 700 mg (1.57 mmol) of compound B that is presented according to Example 43 is reacted, and after working-up and purification, 250 mg (0.91 mmol, 58%) of the title compound is isolated.

The coverage of the $^1$H-NMR spectrum is identical to that described in Example 44.

EXAMPLE 47

(R)-2,2-Dimethyl-4-[1-[[[dimethyl(1,1-dimethylethyl)silyl[oxy]methyl]cyclobutyl]-1,3-dioxane Analogously to Example 45, 250 mg (0.91 mmol) of the compound that is presented according to Example 46 is reacted, and after working-up and purification, 228 mg (0.72 mmol, 60%) of the title compound is isolated.

The coverage of the $^1$H-NMR spectrum is identical to that described in Example 45.

EXAMPLE 48

1-[1-[[[Dimethyl(1,1-dimethylethyl)silyl]oxy]methyl]cyclobutyl]-1,3-propanediol

Analogously to Example 44, 500 g (1.12 mmol) of a mixture of compounds A and B that are produced according to Example 43 is reacted, and after working-up and purification, 190 mg (0.69 mmol, 62%) of the title compound is isolated.

The coverage of the $^1$H-NMR spectrum is identical to that described in Example 44.

EXAMPLE 49

2,2-Dimethyl-4-[1-[[[dimethyl(1,1-dimethylethyl)silyl]oxy]methyl]cyclobutyl]-1,3-dioxane Analogously to Example 45, 190 mg (0.69 mmol) of the compound that is produced according to Example 48 is reacted, and after working-up and purification, 171 mg (0.54 mmol, 79%) of the title compound is isolated.

The coverage of the $^1$H-NMR spectrum is identical to that described in Example 45.

EXAMPLE 50

[1R-[1α(3S*),2β]]-2-Phenylcyclohexyl 3-[1-[[[dimethyl(1,1-dimethylethyl)silyl]oxy]methyl]cyclobutyl]-3-[(tetrahydro-2H-pyran-2-yl)oxy]propanoate Analogously to Example 1, 460 mg (1.03 mmol) of the compound that is presented according to Example 43 is reacted, and after working-up and purification, 398 mg (0.75 mmol, 73%) of the title compound is isolated as a colorless oil.

$^1$H-NMR (CDCl$_3$): δ=0.01 (6H), 0.89 (9H), 1.24-1.97 (19H), 2.15-2.27 (3H), 2.66 (1H), 3.12 (1H), 3.50 (2H), 3.58 (1H), 3.98 (1H), 4.52 (1H), 4.87 (1H), 7.09-7.27 (5H) ppm.

EXAMPLE 51

(S)-3-[1-[[[Dimethyl(1,1-dimethylethyl)silyl]oxy]methyl]cyclobutyl]-3-[(tetrahydro-2H-pyran-2-yl)oxy]propanoic acid 420 mg (3.75 mmol) of potassium tert-butylate is suspended in 5 ml of diethyl ether. 16 μl of water is added, and it is allowed to stir for 5 more minutes. Then, a solution of 398 mg (0.75 mmol) of the compound, presented according to Example 50, in 5 ml of diethyl ether is added. It is allowed to stir for 3 more hours. Then, the reaction solution is diluted with water and neutralized with 10% hydrochloric acid. It is extracted with dichloromethane, the organic phase is washed with saturated aqueous sodium chloride solution, dried on sodium sulfate and concentrated by evaporation in a vacuum. Column chromatography of the crude product on silica gel with a mixture of hexane/ethyl acetate yields 112 mg (0.3 mmol).

$^1$H-NMR (CDCl$_3$): δ=0.01 (6H), 0.90 (9H), 1.30-2.25 (10H), 3.12 (1H), 3.50 (2H), 3.58 (1H), 3.98 (1H), 4.45 (1H) ppm.

After the silyl protective group is cleaved by oxidation, the reaction product can be converted into aldehyde analogously to Example 9, brought to reaction with an organometallic compound such as, e.g., XMgCHR$^{5a}$R$^{5b}$, for example with ethylmagnesium bromide, analogously to Example 10, and converted by subsequent oxidation of the alcohol mixture that is obtained to compounds according to claim 1 analogously to Example 11.

If the starting material 1,1-cyclobutanedicarboxylic acid diethyl ester is replaced in Example 40 by other 2-substituted or 2,2-disubstituted malonic ester derivatives, for example the following compounds can be produced analogously to Examples 9, 10 and 40-51:

| R$^{4a}$ | R$^{4b}$ | R$^{5a}$ | R$^{5b}$ |
|---|---|---|---|
| —(CH$_2$)$_2$— | | H | CH$_3$ |
| —(CH$_2$)$_2$— | | H | CH$_2$—CH$_3$ |
| —(CH$_2$)$_2$— | | H | (CH$_2$)$_2$—CH$_3$ |
| —(CH$_2$)$_2$— | | H | CH$_2$—C$_6$H$_5$ |
| —(CH$_2$)$_2$— | | H | (CH$_2$)$_2$—C$_6$H$_5$ |
| —(CH$_2$)$_2$— | | CH$_3$ | CH$_3$ |
| —(CH$_2$)$_2$— | | CH$_3$ | CH$_2$—C$_{3H}$ |
| —(CH$_2$)$_3$— | | H | CH$_3$ |
| —(CH$_2$)$_3$— | | H | CH$_2$—CH$_3$ |
| —(CH$_2$)$_3$— | | H | (CH$_2$)$_2$—CH$_3$ |
| —(CH$_2$)$_3$— | | H | CH$_2$—C$_6$H$_5$ |
| —(CH$_2$)$_3$— | | H | (CH$_2$)$_2$—C$_6$H$_5$ |
| —(CH$_2$)$_3$— | | CH$_3$ | CH$_3$ |
| —(CH$_2$)$_3$— | | CH$_3$ | CH$_2$—CH$_3$ |
| —(CH$_2$)$_4$— | | H | CH$_3$ |
| —(CH$_2$)$_4$— | | H | CH$_2$—CH$_3$ |
| —(CH$_2$)$_4$— | | H | (CH$_2$)$_2$—CH$_3$ |
| —(CH$_2$)$_4$— | | H | CH$_2$—C$_6$H$_5$ |
| —(CH$_2$)$_4$— | | H | (CH$_2$)$_2$—C$_6$H$_5$ |
| —(CH$_2$)$_4$— | | CH$_3$ | CH$_3$ |
| —(CH$_2$)$_4$— | | CH$_3$ | CH$_2$—CH$_3$ |
| CH$_3$ | CH$_3$ | H | CH$_3$ |
| CH$_3$ | CH$_3$ | CH$_2$—CH$_3$ | CH$_2$—CH$_3$ |
| CH$_3$ | CH$_3$ | H | (CH$_2$)$_2$—CH$_3$ |
| CH$_3$ | CH$_3$ | H | CH$_2$—C$_6$H$_5$ |
| CH$_3$ | CH$_3$ | H | (CH$_2$)$_2$—C$_6$H$_5$ |
| CH$_2$—CH$_3$ | CH$_2$—CH$_3$ | H | CH$_3$ |
| CH$_2$—CH$_3$ | CH$_2$—CH$_3$ | H | CH$_2$—CH$_3$ |
| CH$_2$—CH$_3$ | CH$_2$—CH$_3$ | H | (CH$_2$)$_2$—CH$_3$ |
| CH$_2$—CH$_3$ | CH$_2$—CH$_3$ | H | CH$_2$—C$_6$H$_5$ |
| CH$_2$—CH$_3$ | CH$_2$—CH$_3$ | H | (CH$_2$)$_2$—C$_6$H$_5$ |
| CH$_3$ | CH$_2$—CH$_3$ | H | CH$_3$ |
| CH$_3$ | CH$_2$—CH$_3$ | H | CH$_2$—CH$_3$ |
| CH$_3$ | CH$_2$—CH$_3$ | H | (CH$_2$)$_2$—CH$_3$ |
| CH$_3$ | CH$_2$—CH$_3$ | H | CH$_2$—C$_6$H$_5$ |
| CH$_3$ | CH$_2$—CH$_3$ | H | (CH$_2$)$_2$—C$_6$H$_5$ |

EXAMPLE 52

(3S)-4,4-Dimethyl-5-oxo-3-(tetrahydropyran-2-yloxy)-pent-1-ene

Analogously to Example 9, 5.0 g (23.3 mmol) of the compound that is presented according to Example 3 is reacted, and after working-up, 6.1 g of the title compound is isolated as a colorless oil, which is further reacted without purification.

EXAMPLE 53

(3S,5RS)-4,4-Dimethyl-5-hydroxy-3-(tetrahydropyran-2-yloxy)-hept-1-ene

Analogously to Example 10, 6.1 g (max. 23.3 mmol) of the crude product that is presented according to Example 52 is reacted, and after working-up and purification, 1.59 g (6.56 mmol, 28%) of the nonpolar diastereomer and 1.67 g (6.89 mmol, 30%) of the polar diastereomer are isolated in each case as a colorless oil.

$^1$H-NMR (CDCl$_3$) nonpolar isomer: δ=0.79 (3H), 0.84 (3H), 1.03 (3H), 1.23-1.62 (6H), 1.62-1.88 (2H), 3.41-3.58 (2H), 3.88-4.01 (2H), 4.08 (1H), 4.47 (1H), 5.20 (1H), 5.29 (1H), 5.78 (1H) ppm.

$^1$H-NMR (CDCl$_3$) polar isomer: δ=0.78 (3H), 0.93 (3H), 1.01 (3H), 1.38 (1H), 1.47-1.85 (7H), 3.39-3.57 (3H), 3.90 (1H), 4.04 (1H), 4.62 (1H), 5.21 (1H), 5.32 (1H), 5.69 (1H) ppm.

EXAMPLE 54

(3S,5S)-4,4-Dimethyl-3-(tetrahydropyran-2-yloxy)-heptane-1,5-diol and/or (3S,5S)-4,4-dimethyl-3-(tetrahydropyran-2-yloxy)-heptane-1,5-diol Analogously to Example 5, 1.59 g (6.56 mmol) of the nonpolar alcohol that is presented according to Example 53 is reacted, and after working-up, 1.14 g (4.38 mmol, 67%) of the title compound is isolated as a colorless oil.

$^1$H-NMR (CDCl$_3$): δ=0.78 (6H), 1.01 (3H), 1.28 (1H), 1.36-1.64 (6H), 1.64-1.93 (4H), 3.41-3.55 (2H), 3.61-3.82 (2H), 387 (1H), 3.99 (1H), 4.28 (1H), 4.56 (1H) ppm.

EXAMPLE 55

(3S,5R or 5S)-1-Benzoyloxy-4,4-dimethyl-3-(tetrahydropyran-2-yloxy)-heptan-5-ol

The solution of 1.04 g (3.99 mmol) of the compound, presented according to Example 54, in 20 ml of anhydrous pyridine is mixed under an atmosphere of dry argon with 476 μl of benzoyl chloride, and it is stirred for 16 hours at 23° C. It is poured into a saturated sodium bicarbonate solution, extracted with dichloromethane and dried on sodium sulfate. The residue that is obtained after filtration and removal of the solvent is purified by chromatography on about 300 ml of fine silica gel with a gradient system that consists of n-hexane and ethyl acetate. 785 mg (2.15 mmol, 54%) of the title compound is isolated as a colorless oil as well as 352 mg of starting material.

$^1$H-NMR (CDCl$_3$): δ=0.83 (6H), 1.04 (3H), 1.31 (1H), 1.38-1.58 (5H), 1.74-1.99 (3H), 2.12 (1H), 3.40 (1H), 3.52 (1H), 3.90-4.03 (2H), 4.28-4.56 (4H), 7.45 (2H), 7.58 (1H), 8.05 (2H) ppm.

EXAMPLE 56

(3S)-1-Benzoyloxy-4,4-dimethyl-3-(tetrahydropyran-2-yloxy)-heptan-5-one.

Analogously to Example 11, 780 mg (2.14 mmol) of the compound that is presented according to Example 55 is reacted, and after working-up and purification, 641 mg (1.77 mmol, 83%) of the title compound is isolated as a colorless oil.

$^1$H-NMR (CDCl$_3$): δ=1.02 (3H), 1.11 (3H), 1.23 (3H), 1.40-1.56 (4H), 1.65-1.87 (3H), 1.93 (1H), 2.59 (2H), 3.36 (1H), 3.80 (1H), 4.13 (1H), 4.32 (1H), 4.45 (1H), 4.53 (1H), 7.45 (2H), 7.58 (1H), 8.05 (2H) ppm.

EXAMPLE 57

(3S)-1-Hydroxy-4,4-dimethyl-3-(tetrahydropyran-2-yloxy)-heptan-5-one

The solution of 636 mg (1.75 mmol) of the compound, presented according to Example 56, in 25 ml of methanol is mixed with 738 mg of potassium carbonate and stirred for 2 hours at 23° C. It is mixed with dichloromethane, filtered off, washed with water, and the organic phase is dried on sodium sulfate. The residue that is obtained after filtration and removal of the solvent is purified by chromatography on about 100 ml of fine silica gel with a gradient system that consists of n-hexane and ethyl acetate. 311 mg (1.20 mmol, 69%) of the title compound is isolated as a colorless oil.

$^1$H-NMR (CDCl$_3$): δ=0.98 (3H), 1.07 (3H), 1.18 (3H), 1.44-1.90 (10H), 2.00 (1H), 3.50-3.68 (2H), 3.74 (1H), 3.83-4.06 (2H), 4.79 (1H) ppm.

Production of the Components of General Formula A" with the 2-Oxazolidinone Auxiliary Group Starting Products A) 2.2-Dimethyl-3-oxopentanal Aa) 4-(2-Methylprop-1-enyl)morpholine 43.6 g of morpholine is placed in a 250 ml round-bottom three-neck flask. While being cooled in an ice bath, 46 ml of isobutylaldehyde is added in drops at a temperature of 5° C. over a period of 20 minutes. In this case, a sharp rise in temperature was noted (a strongly exothermic reaction). Once the addition process had been completed, the feedstock is refluxed via a water separator for a period of four hours. The volume of the water separator is filled with isobutylaldehyde. 7.5 ml of H$_2$O is separated. Once the reaction has taken place, the reaction mixture is distilled in a vacuum.
    Oil bath temperature: 85°-90° C.
    Main fraction m=58.37 g 82.03%
    Boiling point: 59° C. at 11 mbar
    Yield: 58.37 g 82.03% Aa).

A) 2,2-Dimethyl-3-oxopentanal

The solution of 77.14 g of propionic acid chloride in 200 ml of ether p.a. is placed in a 1000 ml round-bottom three-neck flask. While being cooled in an ice bath, a solution of 117.73 g of the compound obtained under Aa) in 200 ml of ether p.A. is added in drops within 30 minutes at a reaction temperature of 6° C. Precipitation, a white precipitate appears. Once the addition process is completed, the feedstock is boiled for 5 hours under reflux and then stirred overnight at room temperature. The white precipitate that is produced, which is sensitive to moisture, is suctioned off, washed with ether, and dried in the oil pump.
    Crude product: m=65.26 g of hydrochloride
    Post-precipitation can be observed in the filtrate.
    Crude product m=35.49 g, total: m=100.75 g.
    The 100.75 g of hydrochloride is dissolved in 150 ml of H$_2$O. Then, the aqueous phase is adjusted to pH 0 5 overall with NaHCO$_3$ and then extracted four times with 150 ml of ether in each case. The organic phase is washed once with brine and then dried on Na$_2$SO$_4$. The ether is distilled off at normal pressure, and the residue is distilled in a vacuum on a small Vigreux column (6 plates).
    Main fraction: m=29.65 g 27.75%
    Boiling point: 62° C. at 15 mbar
    Yield: 29.65 g 27.75% A)

B) 2,2-Dimethyl-3-oxo-butanal
    Execution analogous to A).
    Feedstock: 58.37 g=413.36 mmol of Aa), M=141.21 g/mol
        100 ml of diethyl ether p.A.
    32.45 g=413.38 mmol of acetyl chloride, M=0 78.5 g/mol=1.104 g/ml
    100 ml of diethyl ether p.A. is stirred over the weekend at room temperature.
    Crude product m=72.07 g of hydrochloride
    For working-up see Ab)
    Oil bath temperature: 75° C. to 80° C.
    Main fraction: m=18.75 g 39.74%
    Boiling point: 50° C. at 11 mbar
    Yield m=18.7 g 39.6% B)

C) 1-(1-Oxopropyl)cyclobutanecarbaldehyde

Ca) 1,1-Cyclobutanedimethanol 170 ml of a 1.2 molar solution of diisobutylaluminum hydride is added in drops to a solution of 20 g (100 mmol) of 1,1-cyclobutanedicarboxylic acid diethyl ester in 200 ml of absolute tetrahydrofuran at 0° C. It is allowed to stir for one more hour at 0° C., and then 30 ml of water is added. It is filtered on Celite. The filtrate is dried with sodium sulfate and concentrated by evaporation in a vacuum. The crude product that is obtained (9.9 g) is used without purification in the next step.

Cb) 1-[[[Dimethyl(1,1-dimethylethyl)silyl]oxy]methyl]cyclobutanemethanol

A solution of 9.9 g of Ca) (85 mmol) in 100 ml of absolute tetrahydrofuran is added to a suspension of 3.4 g of sodium hydride (60% in oil, 85 mmol)) in 35 ml of absolute tetrahydrofuran at 0° C. It is allowed to stir for 30 more minutes, and then a solution of 12.8 g of tert-butyldimethylsilyl chloride (85 mmol) in 50 ml of tetrahydrofuran is added. It is allowed to stir for one more hour at 25° C., and then the reaction mixture is poured onto saturated aqueous sodium bicarbonate solution. It is extracted with ethyl acetate. The organic phase is washed with saturated sodium chloride solution and dried on sodium sulfate. After the solvent is drawn off in a vacuum, the crude product that is obtained is purified by column chromatography on silica gel with a mixture of hexane/ethyl acetate. 13.5 g (69%) of the title compound is obtained.

$^1$H-NMR (CDCl$_3$): δ=0.04 (6H), 0.90 (9H), 1.70-2.00 (6H), 3.70 (4H) ppm.

Cc) 1-[[[Dimethyl(1,1-dimethylethyl)silyl]oxy]methyl]cyclobutanecarbaldehyde 8 ml of oxalyl chloride is dissolved in 100 ml of dichloromethane. It is cooled to −78° C., and 13 ml of dimethyl sulfoxide is added. It is allowed to stir for 3 more minutes, and then a solution of 13.5 g of Cb) (58.6 mmol) in 80 ml of dichloromethane is added. After 15 more minutes of stirring time, 58 ml of triethylamine is added in drops. Then, it is allowed to heat to 0° C. Then, the reaction mixture is poured onto saturated sodium bicarbonate solution. It is extracted with dichloromethane, the organic phase is washed with saturated sodium chloride solution, dried on sodium sulfate and concentrated by evaporation in a vacuum. After chromatography of the crude product on silica gel with a mixture of hexane/ethyl acetate, 7.7 g (58%) of the title compound is obtained.

$^1$H-NMR (CDCl$_3$): δ=0.03 (6H), 0.90 (9H), 1.85-2.00 (4H), 2.20-2.30 (2H), 3.83 (2H), 9.70 (1H) ppm.

Cd) 1-[[[Dimethyl(1,1-dimethylethyl)silyl]oxy]methyl]-α-ethylcyclobutanemethanol A solution of 7.7 g (33.7 mmol) of the compound, described under Cc), in 80 ml of tetrahydrofuran is added in drops at 0° C. to 20 ml of a 2 molar solution of ethylmagnesium chloride (40 mmol) in tetrahydrofuran. It is allowed to stir for 30 more minutes at 0° C., and then the reaction mixture is poured onto saturated ammonium chloride solution. It is extracted with ethyl acetate. The organic phase is washed with saturated sodium chloride solution and dried on sodium sulfate. After the solvent is drawn off, the crude product that is obtained is purified by column chromatography on silica gel. 7.93 g (91.5%) of the title compound is obtained.

$^1$H-NMR (CDCl$_3$): δ=0.09 s (6H), 0.90 s (9H), 1.05 (3H), 1.30-1.50 (3H), 1.70-1.90 (4H), 2.09 (1H), 3.19 (1H), 3.46 (1H), 3.72 (1H), 3.85 (1H) ppm.

Ce) 1-[1-[[[Dimethyl(1,1-dimethylethyl)silyl]oxy]-methyl]cyclobut-1-yl]-1-propanone 6 ml (85.7 mmol) of dimethyl sulfoxide is added to 3.76 ml (43.8 mmol) of oxalyl chloride in 80 ml of dichloromethane at −78° C. It is allowed to stir for 3 more minutes, and then a solution of 7.93 g (30.7 mmol) of the compound, described under Cd), in 80 ml of dichloromethane is added. it is stirred for 15 more minutes at −78° C. Then, a mixture of 19 ml (136 mmol) of triethylamine and 40 ml of dichloromethane is added in drops. It is allowed to heat to −25° C. and stirred at this temperature for 30 more minutes. Then, the reaction mixture is poured onto saturated ice-cooled sodium bicarbonate solution. It is extracted with dichloromethane. The organic phase is washed with saturated sodium chloride solution and dried on sodium sulfate. After the solvent is drawn off, the crude product that is obtained is filtered on silica gel. 7.87 g (100%) of the title compound is obtained.

$^1$H-NMR (CDCl$_3$): δ=0.05 (6H), 0.88 (9H), 1.04 (3H), 1.82-1.95 (4H), 2.33-2.47 (2H), 2.45-2.54 (2H), 3.81 (2H) ppm.

Cf) 1-[1-(Hydroxymethyl)cyclobut-1-yl]-1-propanone 7.87 g (30.7 mmol) of the compound that is described under Ce) is dissolved in 100 ml of tetrahydrofuran. 15 ml of a 1 molar solution of tetrabutylammonium fluoride is added, and it is allowed to stir for 12 more hours at 25° C. Then, the reaction mixture is poured onto saturated sodium bicarbonate solution. It is extracted with ethyl acetate. The organic phase is washed with saturated sodium chloride solution and dried on sodium sulfate. After the solvent is drawn off, the crude product that is obtained is purified by column chromatography on silica gel. 3.19 g (73.4%) of the title compound is obtained.

$^1$H-NMR (CDCl$_3$): δ=1.07 (3H), 1.86-2.08 (4H), 2.32-2.40 (2H), 2.55-2.65 (2H), 3.88 (2H) ppm.

C) 1-(1-Oxopropyl)cyclobutanecarbaldehyde

Analogously to Example Ce), 3.14 g (100%) of the title compound is obtained by oxidation from 3.19 g (22.4 mmol) of the compound that is described under Cf).

$^1$H-NMR (CDCl$_3$): δ=1.07 (3H), 1.85-2.00 (2H), 2.40-2.53 (6H), 9.70 (1H) ppm.

EXAMPLE 1

(R)-4,4-Dimethyl-3-[3-[[dimethyl(1,1-dimethylethyl)silyl]oxy]-5-oxo-heptanoic acid 0.17 ml of a 30% hydrogen peroxide solution is added at 0° C. to a solution of 190 mg of the silyl ether, produced under Example 1c), in 2.5 ml of a mixture of tetrahydrofuran and water at a 4:1 ratio. After 5 minutes of stirring, a solution of 15.8 mg of lithium hydroxide in 0.83 ml of water is then added, and the reaction mixture is stirred for 3 hours at 25° C. Then, it is mixed with a solution of 208 mg of sodium sulfite in 1.24 ml of water and extracted with 10 ml of methylene chloride. The aqueous phase is set at pH=1 with 5N hydrochloric acid and extracted three times with 10 ml of ethyl acetate each. After drying on sodium sulfate and filtration, it is concentrated by evaporation in a vacuum. In addition, the above-mentioned methylene chloride phase is washed with 5N hydrochloric acid, and then this aqueous phase is extracted three times with 10 ml of ethyl acetate each. After drying on sodium sulfate and filtration, it is concentrated by evaporation in a vacuum, and an additional amount of crude product is obtained. The combined residues that are thus obtained are purified by chromatography on silica gel. In addition to 70 mg of (4R,5S)-4-methyl-5-phenyloxazolidin-2-one, 93 mg of the title compound is obtained with hexane/0-50% ethyl acetate as a colorless oil. [α]$_D$=+15.5° (CHCl$_3$)

$^1$H-NMR (CDCl$_3$): d=0.03-0.08 (6H), 0.86 (9H), 1.01 (3H), 1.10 (3H), 1.15 (3H), 2.35 (1H), 2.4-2.7 (3H), 4.48 (1H) ppm.

1a) (4R,5S)-3-(Bromoacetyl)-4-methyl-5-phenyloxazolidin-2-one 117 ml of a 1.6 molar solution of butyllithium in hexane is added to a solution of 30.1 g of (4R,5S)-4-methyl-5-phenyloxazolidin-2-one in 500 ml of tetrahydrofuran within 30 minutes at −70° C. under nitrogen. Then, a solution of 26.8 g of bromoacetyl chloride in 250 ml of tetrahydrofuran is added in drops in such a way that the temperature does not exceed −65° C. After 1.75 hours of stirring at −70° C., a saturated ammonium chloride solution is added, followed by 60 ml of a saturated sodium bicarbonate solution, and it is allowed to come to 25° C. After the phases are separated, the aqueous phase is extracted twice with 100 ml of ether each. The combined organic phases are washed with semiconcentrated sodium chloride solution, dried on sodium sulfate and concentrated by evaporation in a vacuum after filtration. The residue that is thus obtained is purified by chromatography on silica gel. With hexane/0-50% ether, 34.8 g of the title compound is obtained as a colorless oil.

$^1$H-NMR (CDCl$_3$): δ=0.95 (3H), 4.57 (2H), 4.80 (2H), 5.76 (2H), 7.2-7.5 (5H) ppm.

1b) [4R-[3(R*),4α,5α]]-3-[4,4-Dimethyl-1,5-dioxo-3-hydroxyheptyl]-4-methyl-5-phenyl-oxazolidin-2-one 218 mg of lithium iodide is added to a suspension of 5.0 g of anhydrous chromium(II) chloride in 60 ml of tetrahydrofuran under argon. Then, a mixture of 2.09 g of the 2,2-dimethyl-3-oxo-pentanol that is known in the literature (see under "Starting Products" Ab) and 5.34 g of the above-produced bromine compound in 10 ml of tetrahydrofuran are added. After 2 hours of reaction time, it is mixed with 30 ml of saturated sodium chloride solution and stirred for 15 minutes. The aqueous phase is extracted three times with 200 ml of ether each. The combined organic phases are washed with semiconcentrated sodium chloride solution, dried on sodium sulfate and concentrated by evaporation in a vacuum after filtration. The residue that is thus obtained is purified by chromatography on silica gel. With hexane/0-30% ethyl acetate, 1.55 g of the title compound is obtained as a colorless oil.

$^1$H-NMR (CDCl$_3$): δ=0.92 (3H), 1.06 (3H), 1.18 (3H), 1.23 (3H), 2.58 (2H), 3.07 (2H), 3.28 (1H), 4.35 (1H), 4.79 (1H), 5.70 (2H), 7.2-7.5 (5H) ppm.

1c) [4R-[3(R*),4α,5α]]-3-[4,4-Dimethyl-3-[[dimethyl(1,1-dimethylethyl)silyl]oxy]-1,5-dioxoheptyl]-4-methyl-5-phenyloxazolidin-2-one 150 mg of 2,6-lutidine is added to a solution of 347 mg of the above-produced alcohol in 3 ml of methylene chloride under argon at −70° C. After 5 minutes of stirring, 344 mg of tert-butyldimethylsilyltrifluoromethane sulfonate is added, and it is stirred for another 45 minutes at −70° C. It is mixed with 1 ml of saturated sodium chloride solution and allowed to come to 25° C. Then, it is diluted with ether, and the organic phase is washed with saturated sodium chloride solution. After drying on sodium sulfate and filtration, it is concentrated by evaporation in a vacuum. The residue that is thus obtained is purified by chromatography on silica gel. With hexane/0-30% ethyl acetate, 192 mg of the title compound is obtained as a colorless crystalline compound with a melting point of 111-112° C.

$^1$H-NMR (CDCl$_3$): δ=0.01-0.12 (6H), 0.86 (9H), 0.90 (3H), 1.00 (3H), 1.13 (3H), 1.17 (3H), 2.56 (2H), 3.05 (2H), 4.65-4.80 (2H), 5.68 (1H), 7.2-7.5 (5H) ppm.

EXAMPLE 2

(S)-4,4-Dimethyl-3-[3-[[dimethyl(1,1-dimethylethyl)silyl]oxy]-5-oxo-heptanoic acid The compound is produced analogously to Example 1. As a starting product, (4S,5R)-4-methyl-5-phenyloxazolidin-2-one is used. The coverage of NMR is identical to Example 1. [α]$_D$ =−15.7° (CHCl$_3$)

2a) (4S,5R)-3-(Bromoacetyl)-4-methyl-5-phenyloxazolidin-2-one

Production is carried out analogously to Example 1a) starting from (4S,5R)-4-methyl-5-phenyloxazolidin-2-one. The coverage of NMR is identical to 1a).

EXAMPLE 3

(S)-3-[3-[[Dimethyl(1,1-dimethyl)silyl]oxy]-3-[1-(1-oxopropyl)cyclobut-1-yl]propanoic Acid 1.49 g (80%) of the title compound and 941 mg of recovered (4S,5R)-4-methyl-5-phenyloxazolidin-2-one are obtained analogously to Example 1 from 2.79 g (5.9 mmol) of the compound that is described under 3b). The title compound and the recovered chiral auxiliary can be separated by chromatography (analogously to Example 1) or else fractionated crystallization and then optionally purified by chromatography.

$^1$H-NMR (CDCl$_3$): δ=0.09 (3H), 0.19 (3H), 0.90 (9H), 1.08 (3H), 1.70-2.00 (3H), 2.20-2.40 (4H), 2.47 (1H), 2.50-2.70 (2H), 4.45 (1H) ppm.

3a) [4S-[3(R*),4α,5α]]-3-[3-Hydroxy-1-oxo-3-[1-(1-oxopropyl)cyclobut-1-yl]propyl]-4-methyl-5-phenyloxazolidin-2-one Analogously to Example 1b), 3.0 g (37.4%) of the title compound is obtained as a colorless oil from 3.14 g (22.4 mmol) of the compound that is described under C), 9.7 g (78.8 mmol) of anhydrous chromium(II) chloride, 9.69 g (32.5 mmol) of 2a) and 300 mg (2.2 mmol) of anhydrous lithium iodide in tetrahydrofuran after column chromatography on silica gel.

$^1$H-NMR (CDCl$_3$): δ=0.93 (3H), 1.10 (3H), 1.80-2.03 (2H), 2.10-2.21 (1H), 2.26-2.35 (3H), 2.54-2.70 (2H), 3.03-3.08 (2H), 3.34 (1H), 4.39 (1H), 4.74-4.85 (1H), 5.69 (1H), 7.27-7.34 (2H), 7.36-7.49 (3H) ppm.

3b) [4S-[3(R*),4α,5α]]-3-[[Dimethyl(1,1-dimethylethyl)silyl]oxy]-1-oxo-3-[1-(1-oxopropyl)cyclobut-1-yl]propyl]-4-methyl-5-phenyloxazolidin-2-one Analogously to Example 1c), 2.79 g (70.6%) of the title compound is obtained from 3.0 g (8.35 mmol) of the compound that is described under Example 3a), tert-butyldimethylsilyl-trifluoromethane sulfonate and 2,6-lutidine after recrystallization from diisopropyl ether.

$^1$H-NMR (CDCl$_3$): δ=0.10 (3H), 0.21 (3H), 0.92 (3H), 0.95 (9H), 1.10 (3H), 1.70-1.92 (2H), 2.02-2.16 (1H), 2.20-2.40 (3H), 2.50-2.72 (2H), 2.98-3.10 (2H), 4.63-4.75 (1H), 5.69 (1H), 7.28-7.35 (2H), 7.36-7.48 (3H) ppm.

EXAMPLE 4

(R)-3-[3-[[Dimethyl(1,1-dimethyl)silyl]oxy]-3-[1-(1-oxopropyl)cyclobut-1-yl]propanoic Acid The compound is produced analogously to Example 3. As a starting product, (4R,5S)-3-(bromoacetyl)-4-methyl-5-phenyloxazolidin-2-one is used.

The coverage of the NMR spectrum is identical to Example 3.

The stereochemistry in 3-position can be controlled by the selection of the stereochemistry at C4 and C5 of the chiral auxiliary 4-methyl-5-phenyl-2-oxazolidone.

The structure of intermediate product 1b) was confirmed by an x-ray structural analysis.

EXAMPLES OF THE PRODUCTION OF COMPONENT C

EXAMPLE 1

(S)-Dihydro-3-hydroxy-2(3H)-furanone 10 g of L-(−)-malic acid is stirred in 45 ml of trifluoroacetic acid anhydride for 2 hours at 25° C. Then, it is concentrated by evaporation in a vacuum, 7 ml of methanol is added to the residue, and it is allowed to stir for 12 more hours. Then, it is concentrated by evaporation in a vacuum. The residue that is obtained is dissolved in 150 ml of absolute tetrahydrofuran. It is cooled to 0° C., and 150 ml of borane-tetrahydrofuran complex is added and allowed to stir for 2.5 hours at 0° C. Then, 150 ml of methanol is added. It is allowed to stir for one more hour at room temperature and then concentrated by evaporation in a vacuum. The crude product that is obtained is dissolved in 80 ml of toluene. 5 g of Dowex® (activated, acidic) is added and refluxed for one hour. Then, Dowex® is filtered off, and the filtrate is concentrated by evaporation in a vacuum. The crude product that is obtained (7.61 g, 99.9%) is used without purification in the next step.

EXAMPLE 2

(S)-Dihydro-3-[[(1,1-dimethylethyl)diphenylsilyl] oxy]-2(3H)-furanone 24 ml of tert-butyldiphenylsilyl chloride is added to a solution of 7.61 g of the substance that is described under Example 1 and 10 g of imidazole in 100 ml of N,N-dimethylformamide. It is allowed to stir for two more hours at 25° C., and then the reaction mixture is poured onto ice-cold saturated sodium bicarbonate solution. It is extracted with ethyl acetate, the organic phase is washed with saturated sodium chloride solution, dried on sodium sulfate and concentrated by evaporation in a vacuum. After column chromatography of the crude product on silica gel with a mixture of hexane/ethyl acetate, 13.4 g (52.8%) of the title compound is obtained.

$^1$H-NMR (CDCl$_3$): δ=7.72 (2H), 7.70 (2H), 7.40-7.50 (6H), 4.30-4.42 (2H), 4.01 (1H), 2.10-2.30 (2H), 1.11 (9H) ppm.

EXAMPLE 3

(2RS,3S)-3-[[(1,1-Dimethylethyl)diphenylsilyl]oxy] tetrahydro-2-furanol 80 ml of a 1 molar solution of diisobutylaluminum hydride in hexane is added at −78° C. to a solution of 13.4 g of the substance, described under Example 2, in 150 ml of absolute tetrahydrofuran. It is stirred for 45 more minutes at −78° C. and then quenched with water. It is extracted with ethyl acetate, the organic phase is washed with saturated sodium chloride solution, dried on sodium sulfate and concentrated by evaporation in a vacuum. 13.46 g (99.4%) of the title compound, which is used without purification in the next step, is obtained.

EXAMPLE 4

(2RS,3S)-3-[[(1,1-Dimethylethyl)diphenylsilyl]oxy]-1,4-pentanediol

A solution of 13.46 g of the substance, described under Example 3, in 150 ml of absolute tetrahydrofuran is added in drops to 20 ml of a 3 molar solution of methylmagnesium chloride in tetrahydrofuran at 0° C. It is allowed to stir for one more hour at 0° C. and then poured onto saturated aqueous ammonium chloride solution. It is extracted with ethyl acetate, the organic phase is washed with saturated sodium chloride solution, dried on sodium sulfate and concentrated by evaporation in a vacuum. After column chromatography of the crude product on silica gel with a mixture of hexane/ethyl acetate, 11.42 g (81.6%) of the title compound is obtained.

$^1$H-NMR (CDCl$_3$): δ=7.65-7.75 (4H), 7.40-7.55 (6H), 5.20 (1H), 4.30 (2H), 3.70 (1H), 1.80 (2H), 1.05 (9H) ppm.

EXAMPLE 5

(2RS,3S)-5-[[Dimethyl(1,1-dimethylethyl)silyl]oxy]-3-[[(1,1-dimethylethyl)diphenylsilyl]oxy]-2-pentanol 4.9 g of tert-butyldimethylsilyl chloride is added to a solution of 11.42 g of the substance that is described under Example 1ac, and 3.25 g of 1H-imidazole in 120 ml of N,N-dimethylformamide. It is allowed to stir for 2 more hours at 25° C., and then the reaction mixture is poured onto ice-cold, saturated sodium bicarbonate solution. It is extracted with ethyl acetate, the organic phase is washed with saturated sodium chloride solution, dried on sodium sulfate and concentrated by evaporation in a vacuum. After column chromatography of the crude product on silica gel with a mixture of hexane/ethyl acetate, 10.64 g (70.5%) of the title compound is obtained.

$^1$H-NMR (CDCl$_3$): δ=7.60-7.70 (4H), 7.30-7.45 (6H), 3.70-3.80 (2H), 3.40 (1H), 3.00 (1H), 1.80 (1H), 1.60 (1H), 1.05-1.12 (12H), 0.82 (9H), 0.02 (6H) ppm.

EXAMPLE 6

(3S)-5-[[Dimethyl(1,1-dimethylethyl)silyl]oxy]-3-[[(1,1-dimethylethyl)diphenylsilyl]oxy]-2-pentanone 13 ml of dimethyl sulfoxide is added to 7.37 ml of oxalyl chloride in 80 ml of dichloromethane at −78° C. It is allowed to stir for 3 more minutes, and then 10.46 g of the substance, described under Example 5, in 100 ml of dichloromethane, is added. After another 15 minutes of stirring time, 52 ml of triethylamine is added in drops. Then, it is allowed to heat to 0° C. Then, the reaction mixture is poured onto saturated sodium bicarbonate solution. It is extracted with dichloromethane, the organic phase is washed with saturated sodium chloride solution, dried on sodium sulfate and concentrated by evaporation in a vacuum. After column chromatography of the crude product on silica gel with a mixture of hexane/ethyl acetate, 9.3 g (26.5% relative to the malic acid that is used) of the title compound is obtained.

$^1$H-NMR (CDCl$_3$): δ=7.60-7.70 (4H), 7.32-7.50 (6H), 4.25 (1H), 3.72 (1H), 3.58 (1H), 2.05 (3H), 1.90 (1H), 1.75 (1H), 1.13 (9H), 0.89 (9H), 0.01 (6H) ppm.

EXAMPLE 7

(R)-Dihydro-3-hydroxy-2(3H)-furanone 10 g of D-(+)-malic acid is reacted analogously to Example 1. 7.26 g of the title compound is obtained. The coverage of the $^1$H-NMR spectrum is identical to 1.

EXAMPLE 8

(R)-Dihydro-3-[[(1,1-dimethylethyl)diphenylsilyl]oxy]-2(3H)-furanone

Analogously to Example 2, 12.9 g of the title compound is obtained from 7.26 g of the substance that is described under Example 7. The coverage of the 1H-NMR spectrum is identical to 2.

EXAMPLE 9

(2RS,3R)-3-[[(1,1-Dimethylethyl)diphenylsilyl]oxy]tetrahydro-2-furanol

Analogously to Example 3, 12.95 g of the title compound is obtained from 12.9 g of the substance that is described under Example 8. The coverage of the $^1$H-NMR spectrum is identical to 3.

EXAMPLE 10

(2RS,3R)-3-[[(1,1-Dimethylethyl)diphenylsilyl]oxy]-1,4-pentanediol

Analogously to Example 4, 11 g of the title compound is obtained from 12.95 g of the substance that is described under Example 9. The coverage of the $^1$H-NMR spectrum is identical to 4.

EXAMPLE 11

(2RS,3R)-5-[[Dimethyl(1,1-dimethylethyl)silyl]oxy]-3-[[(1,1-dimethylethyl)diphenylsilyl]oxy]-2-pentanol Analogously to Example 5, 10.11 g of the title compound is obtained from 11 g of the substance that is described under Example 10. The coverage of the $^1$H-NMR spectrum is identical to 5.

EXAMPLE 12

(R)-5-[[Dimethyl(1,1-dimethylethyl)silyl]oxy]-3-[[(1,1-dimethylethyl)diphenylsilyl]oxy]-2-pentanone Analogously to Example 6, 8.85 g of the title compound is obtained from 10.11 g of the substance that is described under Example 11. The coverage of the $^1$H-NMR spectrum is identical to 6.

EXAMPLE 13

(3RS)-Dihydro-3-hydroxy-2(3H)-furanone 5 g of racemic malic acid is reacted analogously to Example 1. 3.68 g of the title compound is obtained. The coverage of the $^1$H-NMR spectrum is identical to 1.

EXAMPLE 14

(3RS)-Dihydro-3-[[(1,1-dimethylethyl)diphenylsilyl]oxy]-2(3H)-furanone

Analogously to Example 2, 6.5 g of the title compound is obtained from 3.68 g of the substance that is described under Example 13. The coverage of the $^1$H-NMR spectrum is identical to 2.

EXAMPLE 15

(2RS,3RS)-3-[[(1,1-Dimethylethyl)diphenylsilyl]oxy]tetrahydro-2-furanol

Analogously to Example 3, 6.51 g of the title compound is obtained from 6.5 g of the substance that is described under Example 14. The coverage of the $^1$H-NMR spectrum is identical to 15.

EXAMPLE 16

(2RS,3RS)-3-[[(1,1-dimethylethyl)diphenylsilyl]oxy]-1,4-pentanediol

Analogously to Example 4, 5.5 g of the title compound is obtained from 6.51 g of the substance that is described under Example 15. The coverage of the $^1$H-NMR spectrum is identical to 4.

EXAMPLE 17

(2RS,3RS)-5-[[Dimethyl(1,1-diethylethyl)silyl]oxy]-3-[[(1,1-dimethylethyl)diphenylsilyl]oxy]-2-pentanol Analogously to Example 5, 5.05 g of the title compound is obtained from 5.5 g of the substance that is described under Example 16. The coverage of the $^1$H-NMR spectrum is identical to 5.

EXAMPLE 18

(3RS)-5-[[Dimethyl(1,1-dimethylethyl)silyl]oxy]-3-[[(1,1-dimethylethyl)diphenylsilyl]oxy]-2-pentanone Analogously to Example 6, 4.3 g of the title compound is obtained from 5.05 g of the substance that is described under Example 17. The coverage of the $^1$H-NMR spectrum is identical to 6.

EXAMPLE 19

(E,3S)-1-[[Dimethyl(1,1-dimethylethyl)silyl]oxy]-3-[[(1,1-dimethylethyl)diphenylsilyl]oxy]-4-methyl-5-(2-methylthiazol-4-yl)-pent-4-ene The solution of 6.82 g of diethyl(2-methylthiazol-4-yl)methanephosphonate in 300 ml of anhydrous tetrahydrofuran is cooled under an atmosphere of dry argon to −5° C., mixed with 16.2 ml of a 1.6 molar solution of n-butyllithium in n-hexane, allowed to heat to 23° C. and stirred for 2 hours. Then, it is cooled to −78° C., the solution of 6.44 g (13.68 mmol) of the compound, presented according to Example 6, in 150 ml of tetrahydrofuran is added in drops, allowed to heat to 23° C. and stirred for 16 hours. It is poured into saturated ammonium chloride solution, extracted several times with ethyl acetate, the combined organic extracts are washed with saturated sodium chloride solution and dried on sodium sulfate. The residue that is obtained after filtration and removal of the solvent is purified by chromatography on fine silica gel with a gradient system that consists of n-hexane and ethyl acetate. 6.46 g (11.4 mmol, 83%; yield relative to the malic acid that is used: 22%) of the title compound is isolated as a colorless oil.

$^1$H-NMR (CDCl$_3$): δ=−0.04 (6H), 0.83 (9H), 1.10 (9H), 1.79 (1H), 1.90 (1H), 1.97 (3H), 2.51 (3H), 3.51 (2H), 4.38 (1H), 6.22 (1H), 6.74 (1H), 7.23-7.47 (6H), 7.63 (2H), 7.70 (2H) ppm.

EXAMPLE 20

(E,3S)-3-[[(1,1-Dimethylethyl)diphenylsilyl]oxy]-4-methyl-5-(2-methylthiazol-4-yl)-pent-4-en-1-ol The solution of 4.79 g (8.46 mmol) of the compound, presented according to Example 19, in 48 ml of tetrahydrofuran is mixed with 48 ml of a 65:35:10 mixture of glacial acetic acid/water/tetrahydrofuran, and it is stirred for 2.5 days at 23° C. It is poured into saturated sodium carbonate solution, extracted several times with ethyl acetate, the combined organic extracts are washed with saturated sodium chloride solution and dried on sodium sulfate. The residue that is obtained after filtration and removal of the solvent is purified by chromatography on fine silica gel with a gradient system that consists of n-hexane and ethyl acetate. 3.42 g (7.57 mmol, 90%) of the title compound is isolated as a colorless oil.

$^1$H-NMR (CDCl$_3$): δ=1.10 (9H), 1.53 (1H), 1.81 (2H), 1.96 (3H), 2.71 (3H), 3.59 (2H), 4.41 (1H), 6.38 (1H), 6.78 (1H), 7.26-7.49 (6H), 7.65 (2H), 7.72 (2H) ppm.

EXAMPLE 21

(E,3S)-1-Bromo-3-[[(1,1-dimethylethyl)diphenylsilyl]oxy]-4-methyl-5-(2-methylthiazol-4-yl)-pent-4-ene The solution of 378 mg (0.84 mmol) of the compound, presented according to Example 20, in 9 ml of dichloromethane is mixed at 0° C. under an atmosphere of dry argon with 90 µl of pyridine, 439 mg of triphenylphosphine, and 556 mg of tetrabromomethane, and it is stirred for 1 hour at 0° C. The solution is chromatographed on fine silica gel with a gradient system that consists of n-hexane and ethyl acetate. 362 mg (0.70 mmol, 84%) of the title compound is isolated as a colorless oil.

$^1$H-NMR (CDCl$_3$): δ=1.09 (9H), 1.95 (3H), 2.01-2.23 (2H), 2.71 (3H), 3.15-3.35 (2H), 4.35 (1H), 6.30 (1H), 6.79 (1H), 7.25-7.49 (6H), 7.63 (2H), 7.69 (2H) ppm.

EXAMPLE 22

(E,3S)-1-Iodo-3-[[(1,1-dimethylethyl)diphenylsilyl]oxy]-4-methyl-5-(2-methylthiazol-4-yl)-pent-4-ene The solution of 8.41 g of triphenylphosphine in 120 ml of dichloromethane is mixed at 23° C. under an atmosphere of dry argon with 2.19 g of imidazole and 8.14 g of iodine, the solution of 12.2 g (27.0 mmol) of the compound, presented according to Example 20, in 30 ml of dichloromethane is added in drops and stirred for 0.5 hour. The solution is chromatographed on fine silica gel with a gradient system that consists of n-hexane and ethyl acetate. 12.15 g (21.6 mmol, 80%) of the title compound is isolated as a colorless oil.

$^1$H-NMR (CDCl$_3$): δ=1.08 (9H), 1.96 (3H), 2.10 (2H), 2.70 (3H), 2.87-3.08 (2H), 4.24 (1H), 6.32 (1H), 6.79 (1H), 7.28-7.48 (6H), 7.60-7.72 (4H) ppm.

EXAMPLE 23

(5E,3S)-[3-[[(1,1-Dimethylethyl)diphenylsilyl]oxy]-4-methyl-5-(2-methylthiazol-4-yl)-pent-4-en-1-yl]-triphenylphosphonium iodide The suspension of 12.55 g (22.3 mmol) of the compound that is presented according to Example 22, 85 g of triphenylphosphine and 11.6 ml of N-ethyldiisopropylamine is stirred under an atmosphere of dry argon for 16 hours at 80° C. After cooling, it is mixed with diethyl ether, filtered, and the residue is rewashed several times with diethyl ether and recrystallized from ethyl acetate. 15.7 g (19.1 mmol, 74%) of the title compound is isolated as a crystalline solid.

$^1$H-NMR (CDCl$_3$): δ=1.07 (9H), 1.68-1.92 (2H), 1.98 (3H), 2.70 (3H), 2.93 (1H), 3.30 (1H), 4.53 (1H), 6.62 (1H), 7.03 (1H), 7.23-7.47 (6H), 7.48-7.72 (16H), 7.73-7.85 (3H) ppm.

EXAMPLE 24

(E,3R)-1-[[Dimethyl(1,1-dimethylethyl)silyl]oxy]-3-[[(1,1-dimethylethyl)diphenylsilyl]oxy]-4-methyl-5-(2-methylthiazol-4-yl)-pent-4-ene Analogously to Example 19, 8.56 g (80%) of the title compound is obtained from 8.85 g of the compound that is described under Example 12. The coverage of $^1$H-NMR is identical to 19.

EXAMPLE 25

(E,3R)-3-[[(1,1-Dimethylethyl)diphenylsilyl]oxy]-4-methyl-5-(2-methylthiazol-4-yl)-pent-4-en-1-ol Analogously to Example 20, 6.25 g (92%) of the title compound is obtained from 8.56 g of the compound that is described under Example 24. The coverage of $^1$H-NMR is identical to 20.

EXAMPLE 26

(E,3R)-1-Iodo-3-[[(1,1-dimethylethyl)diphenylsilyl]oxy]-4-methyl-5-(2-methylthiazol-4-yl)-pent-4-ene Analogously to Example 22, 6.22 g (80%) of the title compound is obtained from 6.25 g of the compound that is described under Example 25. The coverage of the $^1$H-NMR spectrum is identical to 22.

EXAMPLE 27

(5E,3R)-[3-[[(1,1-Dimethylethyl)-diphenylsilyl]oxy]-4-methyl-5-(2-methylthiazol-4-yl)-pent-4-en-1-yl]-triphenylphosphonium Iodide Analogously to Example 23, 7.36 g (70%) of the title compound is obtained from 6.22 g of the compound that is described under Example 26. The coverage of the $^1$H-NMR spectrum is identical to 23.

EXAMPLE 28

(E,3RS)-1-[[Dimethyl(1,1-dimethylethyl)silyl]oxy]-3-[[(1,1-dimethylethyl)diphenylsilyl]oxy]-4-methyl-5-(2-methylthiazol-4-yl)-pent-4-ene Analogously to Example 19, 4.52 g (87%) of the title compound is obtained from 4.3 g of the compound that is described under Example 18. The coverage of the $^1$H-NMR spectrum is identical to 19.

EXAMPLE 29

(E,3RS)-3-[[(1,1-Dimethylethyl)diphenylsilyl]oxy]-4-methyl-5-(2-methylthiazol-4-yl)-pent-4-en-1-ol Analogously to Example 20, 3.16 g (88%) of the title compound is obtained from 4.52 g of the compound that is described under Example 28. The coverage of the $^1$H-NMR spectrum is identical to 20.

EXAMPLE 30

(E,3RS)-1-Iodo-3-[[(1,1-dimethylethyl)diphenylsilyl]oxy]-4-methyl-5-(2-methylthiazol-4-yl)-pent-4-ene Analogously to Example 22, 3.34 g (85%) of the title compound is obtained from 3.16 g of the compound that is described under Example 25. The coverage of the $^1$H-NMR spectrum is identical to 22.

EXAMPLE 31

(5E,3RS)-[3-[[(1,1-Dimethylethyl)diphenylsilyl]oxy]-4-methyl-5-(2-methylthiazol-4-yl)-pent-4-en-1-yl]-triphenylphosphonium Iodide Analogously to Example 23, 4.35 g (77%) of the title compound is obtained from 3.34 g of the compound that is described under Example 26. The coverage of the $^1$H-NMR spectrum is identical to 23.

EXAMPLE 32

(E,3S)-1-[[Dimethyl(1,1-dimethylethyl)silyl]oxy]-3-[[(1,1-dimethylethyl)diphenylsilyl]oxy]-4-methyl-5-(2-pyridyl)-pent-4-ene Analogously to Example 19, 2 g (4.23 mmol) of the compound that is presented according to Example 6 is reacted with use of diethyl(2-pyridyl)methanephosphonate, and after working-up and purification, 2 g (3.68 mmol, 87%) of the title compound is isolated as a colorless oil.

$^1$H-NMR (CDCl$_3$): δ=−0.06 (6H), 0.80 (9H), 1.09 (9H), 1.81 (1H), 1.90 (1H), 2.00 (3H), 3.53 (2H), 4.40 (1H), 6.22 (1H), 6.99 (1H), 7.06 (1H), 7.25-7.45 (6H), 7.58 (1H), 7.65-7.77 (4H), 8.58 (1H) ppm.

EXAMPLE 33

(E,3S)-3-[[(1,1-Dimethylethyl)diphenylsilyl]oxy]-4-methyl-5-(2-pyridyl)-pent-4-en-1-ol Analogously to Example 20, 2 g (3.68 mmol) of the compound that is produced under Example 32 is reacted with a 65:35:10 mixture of glacial acetic acid/water/tetrahydrofuran. After working-up, 1.38 g (3.20 mmol, 87%) of the title compound is obtained.

$^1$H-NMR (CDCl$_3$): δ=1.12 (9H), 1.85 (2H), 2.00 (3H), 3.62 (2H), 4.5 (1H), 6.44 (1H), 7.03 (1H), 7.08 (1H), 7.25-7.48 (6H), 7.59 (1H), 7.65-7.77 (4H), 8.58 (1H) ppm.

EXAMPLE 34

(Z,3S)-1-[[Dimethyl(1,1-dimethylethyl)silyl]oxy]-3-[[(1,1-dimethylethyl)diphenylsilyl]oxy]-4-methyl-5-(3-pyridyl)-pent-4-ene (A) and (E,3S)-1-[[dimethyl(1,1-dimethylethyl)silyl]oxy]-3-[[(1,1-dimethylethyl)diphenylsilyl]oxy]-4-methyl-5-(3-pyridyl)-pent-4-ene (B)

Analogously to Example 19, 4.8 g (10.2 mmol) of the compound that is presented according to Example 6 is reacted with use of diethyl(3-pyridyl)methanephosphonate, and after working-up and purification, 448 mg (0.82 mmol, 8%) of title compound A and 3.5 g (6.41 mmol, 63%) of title compound B are isolated in each case as a colorless oil.

$^1$H-NMR (CDCl$_3$) of A: δ=−0.06 (6H), 0.81 (9H), 1.01 (9H), 1.75 (1H), 1.97 (4H), 3.48 (2H), 4.83 (1H), 6.11 (1H), 6.97 (1H), 7.11-7.30 (5H), 7.30-7.39 (2H), 7.39-7.50 (4H), 8.08 (1H), 8.33 (1H) ppm.

$^1$H-NMR (CDCl$_3$) of B: δ=−0.01 (6H), 0.85 (9H), 1.11 (9H), 1.78 (3H), 1.83 (1H), 1.97 (1H), 3.58 (2H), 4.42 (1H), 6.03 (1H), 7.21 (1H), 7.28-7.50 (7H), 7.62-7.75 (4H), 8.29 (1H), 8.41 (1H) ppm.

EXAMPLE 35

(E,3S)-3-[[(1,1-Dimethylethyl)diphenylsilyl]oxy]-4-methyl-5-(3-pyridyl)-pent-4-en-1-ol Analogously to Example 20, 3.5 g (6.41 mmol) of the compound that is produced under Example 34B is reacted with a 65:35:10 mixture of glacial acetic acid/water/tetrahydrofuran. After purification, 2.1 g (4.86 mmol, 76%) is obtained.

$^1$H-NMR (CDCl$_3$): δ=1.12 (9H), 1.75 (3H), 1.88 (2H), 3.65 (2H), 4.45 (1H), 6.25 (1H), 7.21 (1H), 7.28-7.50 (7H), 7.60-7.75 (4H), 8.30 (1H), 8.44 (1H) ppm.

EXAMPLE 36

Analogously to Example 22, 1.98 g (75%) of the title compound is obtained from 2.1 g of the compound that is described under Example 35.

$^1$H-NMR (CDCl$_3$): δ=1.11 (9H), 1.78 (3H), 2.17 (2H), 3.03 (2H), 4.29 (1H), 6.19 (1H), 7.22 (1H), 7.30-7.50 (7H), 7.63-7.75 (4H), 8.32 (1H), 8.44 (1H) ppm.

EXAMPLE 37

Analogously to Example 23, 2.35 g (80%) of the title compound is obtained from 1.98 g of the compound that is described under Example 36.

$^1$H-NMR (CDCl$_3$): δ=1.08 (9H), 1.80 (3H), 3.27 (1H), 3.56 (1H), 4.66 (1H), 6.52 (1H), 7.25-7.90 (27H), 8.35 (1H), 8.46 (1H) ppm.

EXAMPLE 38

(Z,3S)-1-[[Dimethyl(1,1-dimethylethyl)silyl]oxy]-3-[[(1,1-dimethylethyl)diphenylsilyl]oxy]-4-methyl-5-(4-pyridyl)-pent-4-ene (A) and (E,3S)-1-[[dimethyl(1,1-dimethylethyl)silyl]oxy]-3-[[(1,1-dimethylethyl)diphenylsilyl]oxy]-4-methyl-5-(4-pyridyl)-pent-4-ene (B)

Analogously to Example 19, 4.59 g (9.75 mmol) of the compound that is produced according to Example 6 is reacted with use of diethyl(4-pyridyl)methanephosphonate, and after working-up and purification, 605 mg (1.11 mmol, 11%) of title compound A and 4.34 g (7.95 mmol, 82%) of title compound B are isolated in each case as a colorless oil.

$^1$H-NMR (CDCl$_3$) of A: δ=−0.05 (6H), 0.82 (9H), 1.02 (9H), 1.78 (1H), 1.96 (3H), 3.48 (2H), 4.92 (1H), 6.08 (1H), 6.73 (2H), 7.20-7.30 (4H), 7.32-7.40 (2H), 7.41-7.49 (4H), 8.30 (2H) ppm.

$^1$H-NMR (CDCl$_3$) of B: δ=−0.04 (6H), 0.80 (9H), 1.08 (9H), 1.78 (3H), 1.91 (1H), 3.55 (2H), 4.39 (1H), 6.02 (1H), 6.93 (2H), 7.26-7.48 (6H), 7.60-7.72 (4H), 8.50 (2H) ppm.

EXAMPLE 39

(E,3S)-3-[[(1,1-Dimethylethyl)diphenylsilyl]oxy]-4-methyl-5-(4-pyridyl)-pent-4-en-1-ol Analogously to Example 20, 4.34 g (7.95 mmol) of the compound that is produced under Example 38B is reacted with a 65:35:10 mixture of glacial acetic acid/water/tetrahydrofuran. After purification, 2.92 g (6.76 mmol, 85%) of the title compound is obtained.

$^1$H-NMR (CDCl$_3$): δ=1.12 (9H), 1.78 (3H), 1.87 (2H), 3.65 (2H), 4.42 (1H), 6.26 (1H), 6.97 (2H), 7.26-7.48 (6H), 7.60-7.72 (4H), 8.52 (2H) ppm.

EXAMPLE 40

Analogously to Example 22, 2.82 g (77%) of the title compound is obtained from 2.92 g (6.76 mmol) of the compound that is described under Example 39.

$^1$H-NMR (CDCl$_3$): δ=1.08 (6H), 1.78 (3H), 2.15 (2H), 3.00 (2H), 4.26 (1H), 6.17 (1H), 6.95 (2H), 7.30-7.50 (6H), 7.60-7.70 (4H), 8.50 (2H) ppm.

EXAMPLE 41

Analogously to Example 23, 3.27 g (4.06 mmol, 78%) of the title compound is obtained from 2.82 g (5.21 mmol) of the compound that is described under Example 40.

$^1$H-NMR (CDCl$_3$): δ=1.09 (6H), 1.82 (3H), 3.15 (1H), 3.50 (1H), 4.65 (1H), 6.53 (1H), 7.05 (2H), 7.25-7.48 (6H), 7.50-7.70 (4H), 8.50 (2H) ppm.

Production of the Epothilone Derivatives of General Formula I:

EXAMPLE 1

(4S,7R,8S,9S,13(Z),16S(E))-4,8-Dihydroxy-7-ethyl-16-(1-methyl-2-(2-methyl-4-thiazolyl)ethenyl)-1-oxa-5,5,9,13-tetramethyl-cyclohexadec-13-ene-2,6-dione

EXAMPLE 1a (3S)-1-Oxa-2-oxo-3-(tetrahydropyran-2(RS)-yloxy)-4,4-dimethyl-cyclopentane The solution of 74.1 g (569 mmol) of D-(−)-pantolactone in 1 l of anhydrous dichloromethane is mixed with 102 ml of 3,4-dihydro-2H-pyran and 2 g of p-toluenesulfonic acid-pyridinium salt under an atmosphere of dry argon, and it is stirred for 16 hours at 23° C. It is poured into a saturated sodium bicarbonate solution, and the organic phase is separated and dried on sodium sulfate. After filtration and removal of the solvent, the residue is chromatographed on about 5 kg of fine silica gel with a mixture of n-hexane and ethyl acetate. 119.6 g (558 mmol, 98%) of the title compound is isolated as a colorless oil.

$^1$H-NMR (CDCl$_3$) δ=1.13 (3H), 1.22 (3H), 1.46-1.91 (6H), 3.50-3.61 (1H), 3.86 (1H), 3.92 (1H), 4.01 (1H), 4.16 (1H), 5.16 (1H) ppm.

EXAMPLE 1b (2RS,3S)-1-Oxa-2-hydroxy-3-(tetrahydropyran-2(RS)-yloxy)-4,4-dimethyl-cyclopentane The solution of 117.5 g (548 mmol) of the compound, presented according to Example 1a, in 2.4 l of anhydrous toluene is cooled under an atmosphere of dry argon to −70° C., mixed within 1 hour with 540 ml of a 1.2 molar solution of diisobutyl aluminum hydride in toluene, and it is stirred for another 3 hours at −70° C. It is allowed to heat to −20° C., mixed with saturated ammonium chloride solution and water, and the precipitated aluminum salts are separated by filtration on Celite. The filtrate is washed with water and saturated sodium chloride solution and dried on magnesium sulfate. After filtration and removal of the solvent, 111.4 g (515 mmol, 94%) of the title compound is isolated as a colorless oil, which is further reacted without purification.

IR(CHCl$_3$): 3480, 3013, 2950, 2874, 1262, 1133, 1074, 1026 and 808 cm$^{-1}$.

EXAMPLE 1c (3S)-2,2-Dimethyl-3-(tetrahydropyran-2(R)-yloxy)-pent-4-en-1-ol and (3S)-2,2-dimethyl-3-(tetrahydropyran-2(S)-yloxy)-pent-4-en-1-ol The suspension of 295 g of methyl-triphenylphosphonium bromide in 2.5 l of anhydrous tetrahydrofuran is mixed under an atmosphere of dry argon at −60° C. with 313 ml of a 2.4 molar solution of n-butyllithium in n-hexane, allowed to heat to 23° C., stirred for one more hour and cooled to 0° C. It is mixed with the solution of 66.2 g (306 mmol) of the compound, presented according to Example 1b, in 250 ml of tetrahydrofuran, allowed to heat to 23° C. and stirred for 18 hours. It is poured into a saturated sodium bicarbonate solution, extracted several times with dichloromethane, and the combined organic extracts are dried on sodium sulfate. After filtration and removal of the solvent, the residue is chromatographed on about 5 l of fine silica gel with a gradient system that consists of n-hexane and ethyl acetate. 36.5 g (170 mmol, 56%) of the nonpolar THP-isomer of the title compound, 14.4 g (67.3 mmol, 22%) of the polar THP-isomer of the title compound, and 7.2 g (33.3 mmol; 11%) of the starting material are isolated in each case as a colorless oil.

$^1$H-NMR (CDCl$_3$), nonpolar isomer: δ=0.78 (3H), 0.92 (3H), 1.41-1.58 (4H), 1.63-1.87 (2H), 3.18 (1H), 3.41 (1H), 3.48 (1H), 3.68 (1H), 3.94 (1H), 4.00 (1H), 4.43 (1H), 5.19 (1H), 5.27 (1H), 5.75 (1H) ppm.

$^1$H-NMR (CDCl$_3$), polar isomer: δ=0.83 (3H), 0.93 (3H), 1.42-1.87 (6H), 2.76 (1H), 3.30 (1H), 3.45 (1H), 3.58 (1H), 3.83 (1H), 3.89 (1H), 4.65 (1H), 5.12-5.27 (2H), 5.92 (1H) ppm.

EXAMPLE 1d (3S)-1-(tert-Butyldiphenylsilyloxy)-2,2-dimethyl-pentane-3-(tetrahydropyran-2-yloxy)-pent-4-ene The solution of 59.3 g (277 mmol) of the THP-isomer mixture, presented according to Example 1c, in 1000 ml of anhydrous dimethylformamide is mixed under an atmosphere of dry argon with 28 g of imidazole, 85 ml of tert-butyldiphenylchlorosilane, and it is stirred for 16 hours at 23° C. It is poured into water, extracted several times with dichloromethane, the combined organic extracts are washed with water and dried on sodium sulfate. After filtration and removal of the solvent, the residue is chromatographed on fine silica gel with a gradient system that consists of n-hexane and ethyl acetate. 106.7 g (236 mmol, 85%) of the title compound is isolated as a colorless oil.

$^1$H-NMR (CDCl$_3$): δ=0.89 (3H), 0.99 (3H), 1.08 (9H), 1.34-1.82 (6H), 3.40 (1H), 3.51 (2H), 3.76 (1H), 4.02 (1H), 4.67 (1H), 5.18 (1H), 5.23 (1H), 5.68 (1H), 7.30-7.48 (6H), 7.60-7.73 (4H) ppm.

EXAMPLE 1e (3S)-1-(tert-Butyldiphenylsilyloxy)-2,2-dimethyl-3-(tetrahydropyran-2-yloxy)-pentan-5-ol The solution of 3.09 g (6.83 mmol) of the compound, presented according to Example 1d, in 82 ml of tetrahydrofuran is mixed with 13.1 ml of a 1 molar solution of borane in tetrahydrofuran under an atmosphere of dry argon at 23° C., and it is allowed to react for 1 hour. Then, while being cooled with ice, it is mixed with 16.4 ml of a 5% sodium hydroxide solution as well as 8.2 ml of a 30% hydrogen peroxide solution, and it is stirred for another 30 minutes. It is poured into water, extracted several times with ethyl acetate, the combined organic extracts are washed with water and saturated sodium chloride solution and dried on magnesium sulfate. The residue that is obtained after filtration and removal of the solvent is purified by chromatography on fine silica gel with a gradient system that consists of n-hexane and ethyl acetate. 1.78 g (3.78 mmol, 55%) of the title compound is isolated as a chromatographically separable mixture of the two THP-epimeres, as well as 0.44 g (1.14 mmol, 17%) of the title compound of Example 6 in each case as a colorless oil.

$^1$H-NMR (CDCl$_3$), nonpolar THP-isomer: δ=0.80 (3H), 0.88 (3H), 1.10 (9H), 1.18-1.80 (9H), 3.27 (1H), 3.39 (1H), 3.48 (1H), 3.64 (1H), 3.83 (1H), 3.90-4.08 (2H), 4.49 (1H), 7.31-7.50 (6H), 7.58-7.73 (4H) ppm.

$^1$H-NMR (CDCl$_3$), polar THP-isomer: δ=0.89 (3H), 0.98 (3H), 1.08 (9H), 1.36-1.60 (4H), 1.62-1.79 (3H), 1.88 (1H), 2.03 (1H), 3.37 (1H), 3.50 (1H), 3.57 (1H), 3.62-3.83 (4H), 4.70 (1H), 7.30-7.48 (6H), 7.61-7.73 (4H) ppm.

EXAMPLE 1f (3S)-1-(tert-Butyldiphenylsilyloxy)-2,2-dimethyl-3-hydroxy-pent-4-ene The solution of 106.7 g (236 mmol) of the compound, presented according to Example 1d, in 1.5 l of anhydrous ethanol is mixed with 5.9 g of pyridinium-p-toluenesulfonate under an atmosphere of dry argon, and it is heated for 6 hours to 50° C. After removal of the solvent, the residue is chromatographed on fine silica gel with a mixture of n-hexane and ethyl acetate. 82.6 g (224 mmol, 95%) of the title compound is isolated as a colorless oil, in which in addition about 5 g of ethoxy-tetrahydropyran is contained.

$^1$H-NMR (CDCl$_3$) of an analytic sample: δ=0.89 (6H), 1.08 (9H), 3.45 (1H), 3.49 (1H), 3.58 (1H), 4.09 (1H), 5.21 (1H), 5.33 (1H), 5.93 (1H), 7.34-7.51 (6H), 7.63-7.73 (4H) ppm.

EXAMPLE 1g (3S)-1-(tert-Butyldiphenylsilyloxy)-2,2-dimethyl-pentane-3,5-diol

Analogously to Example 1e, the solution of 570 mg (1.55 mmol) of the compound that is presented according to Example 1f is reacted, and after working-up and purification, 410 mg (1.06 mmol, 68%) of the title compound is isolated as a colorless oil.

$^1$H-NMR (CDCl$_3$): δ=0.82 (3H), 0.93 (3H), 1.08 (9H), 1.56-1.79 (2H), 3.11 (1H), 3.50 (2H), 3.78-3.92 (3H), 4.02 (1H), 7.34-7.51 (6H), 7.61-7.71 (4H) ppm.

EXAMPLE 1h

4(S)-[2-Methyl-1-(tert-butyldiphenylsilyloxy)-prop-2-yl]-2,2-dimethyl-[1,3]dioxane The solution of 100 mg (0.212 mmol) of the compounds, presented according to Example 1e, in 2.6 ml of anhydrous acetone is mixed with 78.9 mg of copper(II) sulfate, a spatula tip full of p-toluenesulfonic acid-monohydrate under an atmosphere of dry argon, and it is stirred for 16 hours at 23° C. It is mixed with saturated sodium bicarbonate solution, extracted several times with diethyl ether, washed with saturated sodium chloride solution and dried on sodium sulfate. The residue that is obtained after filtration and removal of the solvent is purified by chromatography on fine silica gel with a gradient system that consists of n-hexane and ethyl acetate. 24 mg (56 µmol, 27%) of the title compound is isolated as a colorless oil.

$^1$H-NMR (CDCl$_3$): δ=0.83 (3H), 0.89 (3H), 1.07 (9H), 1.30 (1H), 1.36 (3H), 1.44 (3H), 1.71 (1H), 3.24 (1H), 3.62 (1H), 3.86 (1H), 3.91-4.03 (2H), 7.31-7.48 (6H), 7.61-7.74 (4H) ppm.

Variant II

Analogously to Example 1h, 320 mg (0.88 mmol) of the compound that is presented according to Example 1g is reacted; variant 1, and after working-up and purification, 234 mg (0.548 mmol, 62%) of the title compound is isolated.

Variant III

The solution of 5.60 g (14.5 mmol) of the compound, presented according to Example 1g, in 250 ml of anhydrous dichloromethane, is mixed with 10 ml of 2,2-dimethoxypropane and 145 mg of camphor-10-sulfonic acid under an atmosphere of dry argon, and it is stirred for 6 hours at 23° C. It is mixed with triethylamine, diluted with ethyl acetate, washed with saturated sodium bicarbonate solution and dried on sodium sulfate. After filtration and removal of the solvent, the residue is chromatographed on fine silica gel with a mixture of n-hexane and ethyl acetate. 5.52 g (12.9 mmol, 89%) of the title compound is isolated as a colorless oil.

EXAMPLE 1i (4S)-4-(2-Methyl-1-hydroxy-prop-2-yl)-2,2-dimethyl-[1,3]dioxane

The solution of 5.6 g (13.1 mmol) of the compound, presented according to Example 1h, in 75 ml of anhydrous tetrahydrofuran is mixed with 39 ml of a 1 molar solution of tetrabutylammonium fluoride in tetrahydrofuran under an atmosphere of dry argon, and it is heated for 16 hours to 50° C. It is mixed with saturated sodium bicarbonate solution, extracted several times with ethyl acetate, washed with saturated sodium chloride solution and dried on sodium sulfate. The residue that is obtained after filtration and removal of the solvent is purified by chromatography on fine silica gel with a gradient system that consists of n-hexane and ethyl acetate. 2.43 g (12.9 mmol, 99%) of the title compound is isolated as a colorless oil.

$^1$H-NMR (CDCl$_3$): δ=0.87 (3H), 0.90 (3H), 1.35 (1H), 1.37 (3H), 1.43 (3H), 1.77 (1H), 2.93 (1H), 3.36 (1H), 3.53 (1H), 3.79 (1H), 3.87 (1H), 3.96 (1H) ppm.

EXAMPLE 1k (4S)-4-(2-Methyl-1-oxo-prop-2-yl)-2,2-dimethyl-[1,3]dioxane

The solution of 0.13 ml of oxalyl chloride in 5.7 ml of anhydrous dichloromethane is cooled under an atmosphere of dry argon to −70° C., mixed with 0.21 ml of dimethyl sulfoxide, the solution of 200 mg (1.06 mmol) of the compound, presented according to Example 1i, in 5.7 ml of anhydrous dichloromethane, and it is stirred for 0.5 hour. Then, it is mixed with 0.65 ml of triethylamine, allowed to react for 1 hour at −30° C. and mixed with n-hexane and saturated sodium bicarbonate solution. The organic phase is separated, the aqueous phase is extracted once more with n-hexane, the combined organic extracts are washed with water and dried on magnesium sulfate. The residue that is obtained after filtration and removal of the solvent is further reacted without purification.

EXAMPLE 1l (4S)-4-((3RS)-2-Methyl-3-hydroxy-hex-2-yl)-2,2-dimethyl-[1,3]dioxane

The solution of 450 mg (2.42 mmol) of the compound, presented according to Example 1k, in 7 ml of anhydrous diethyl ether is mixed with 1.21 ml of a 2.4 molar solution of propylmagnesium bromide in diethyl ether under an atmosphere of dry argon at 0° C., allowed to heat to 23° C. and stirred for 16 hours. It is mixed with saturated ammonium chloride solution, the organic phase is separated and dried on sodium sulfate. The residue that is obtained after filtration and removal of the solvent is purified by chromatography on fine silica gel with a gradient system that consists of n-hexane and ethyl acetate. 244 mg (1.06 mmol, 44%) of the chromatographically separable 3R- and 3S-epimeres of the title compound as well as 191 mg of the title compound that is described in Example 1i are isolated in each case as a colorless oil.

$^1$H-NMR (CDCl$_3$) nonpolar isomer: δ=0.87 (3H), 0.89 (3H), 0.94 (3H), 1.25-1.52 (4H), 1.38 (3H), 1.45 (3H), 1.66 (1H), 1.85 (1H), 3.46 (1H), 3.80-4.02 (4H) ppm.

$^1$H-NMR (CDCl$_3$) polar isomer: δ=0.73 (3H), 0.92 (3H), 0.95 (3H), 1.19-1.84 (6H), 1.37 (3H), 1.49 (3H), 3.49 (1H), 3.60 (1H), 3.80-4.03 (3H) ppm.

EXAMPLE 1m (4S)-4-(2-Methyl-3-oxo-hex-2-yl)-2,2-dimethyl-[1,3]dioxane

The solution of 207 mg (0.90 mmol) of a mixture of the compound, presented according to Example 1l, in 18 ml of anhydrous dichloromethane is mixed with molecular sieve (4A, about 20 spheres), 176 mg of N-methylmorpholino-N-oxide and 18 mg of tetrapropylammonium perruthenate, and it is stirred for 16 hours at 23° C. under an atmosphere of dry argon. It is concentrated by evaporation, and the crude product that is obtained is purified by chromatography on about 100 ml of fine silica gel with a gradient system that consists of n-hexane and ethyl acetate. 185 mg (0.81 mmol, 90%) of the title compound is isolated as a colorless oil.

$^1$H-NMR (CDCl$_3$): δ=0.88 (3H), 1.04 (3H), 1.12 (3H), 1.22-1.37 (1H), 1.31 (3H), 1.40 (3H), 1.48-1.71 (3H), 2.46 (2H), 3.83 (1H), 3.96 (1H), 4.04 (1H) ppm.

EXAMPLE 1n

4-Tert-butyldimethylsilyloxy-but-2-in-1-ol

A solution of 175 g of tert-butyldimethylsilyl chloride in 100 ml of a 1:1 mixture of hexane and dimethylformamide is slowly added in drops to a solution of 100 g of 2-butin-1-ol and 158 g of imidazole in 300 ml of dimethylformamide at 0° C. under nitrogen, and it is stirred for 2 hours at 0° C. and for 16 hours at 22° C. The reaction mixture is diluted with 2.5 l of ether, washed once with water, once with 5% sulfuric acid, once with water, once with saturated sodium bicarbonate solution and washed neutral with semi-saturated sodium chloride solution. After drying on sodium sulfate and filtration, it is concentrated by evaporation in a vacuum. The residue that is thus obtained is purified by chromatography on silica gel. 74.3 g of the title compound is obtained with hexane/0-40% ether as a colorless oil.

IR (film): 3357, 2929, 2858, 1472, 1362, 1255, 1132, 1083, 1015, 837, 778 cm$^{-1}$.

EXAMPLE 1o (4R,5S,2'S)-4-Methyl-5-phenyl-3-[1-oxo-2-methyl-6-(tert-butyldimethylsilyloxy)-hex-4-in-1-yl]-2-oxazolidinone 11.3 ml of lutidine is added to 21 g of a solution of silyl ether, produced according to Example 1n, in 125 ml of toluene under nitrogen. Then, it is cooled to −40° C., and 17.7 ml of trifluoromethanesulfonic acid anhydride is added in drops at this temperature. Then, it is diluted with 100 ml of hexane and stirred for 10 minutes. Under nitrogen via a reversing frit, this solution is added to a solution that was produced from 17.8 g of hexamethyldisilazane in 140 ml of tetrahydrofuran with 73.5 ml of a 1.6 M solution of butyllithium in hexane at −60° C. (10 more minutes of stirring time) and 23.3 g of (4R,5S)-4-methyl-5-phenyl-3-propionyl-2-oxazolidinone in 62 ml of tetrahydrofuran (30 more minutes of stirring time). It is allowed to stir for one more hour at −60° C., then mixed with 6 ml of acetic acid in 5 ml of tetrahydrofuran, and the reaction mixture is allowed to heat to 22° C. It is added to 80 ml of water and extracted three times with ether. The combined organic phases are washed twice with saturated sodium chloride solution and dried on sodium sulfate. After filtration, it is concentrated by evaporation in a vacuum. The residue that is thus obtained is purified by chromatography on silica gel. With hexane/0-20% ether, 16.0 g of the title compound is obtained as a colorless oil.

$^1$H-NMR (CDCl$_3$): δ=0.10 (6H), 0.90 (9H), 0.92 (3H), 1.28 (3H), 2.47 (1H), 2.61 (1H), 3.96 (1H), 4.26 (2H), 4.78 (1H), 5.68 (1H), 7.31 (1H), 7.3-7.5 (3H) ppm.

EXAMPLE 1p (2S)-2-Methyl-6-(tert-butyldimethylsilyloxy)-4-hexinoic Acid Ethyl Ester 9.0 ml of titanium(IV)ethylate is added to a solution of 39.3 g of the alkylating product, produced according to Example 1o, in 120 ml of ethanol under nitrogen, and it is refluxed for 4 hours. The reaction mixture is concentrated by evaporation in a vacuum, and the residue is dissolved in 100 ml of ethyl acetate. 3 ml of water is added, stirred for 20 minutes, precipitate is suctioned out, and it is rewashed well with ethyl acetate. The filtrate is concentrated by evaporation, mixed with 200 ml of hexane, and precipitate is filtered out. The precipitate is washed well with hexane. The filtrate is concentrated by evaporation in a vacuum, and the residue that is thus obtained is purified by chromatography on silica gel. With hexane/0-20% ether, 25.4 g of the title compound is obtained as a colorless oil.

$^1$H-NMR (CD$_2$Cl$_2$): δ=0.10 (3H), 0.90 (9H), 1.2-1.3 (6H), 2.37 (1H), 2.54 (1H), 2.60 (1H), 4.12 (2H), 4.27 (2H) ppm.

EXAMPLE 1q (2S)-2-Methyl-6-(tert-butyldimethylsilyloxy)-hexanoic Acid Ethyl Ester A solution of 10.5 g of the ester, produced according to Example 1p, in 200 ml of ethyl acetate is mixed with 1 g of 10% palladium on carbon, and it is stirred for 3 hours at 22° C. in a hydrogen atmosphere. Then, catalyst is filtered out, it is rewashed well with ethyl acetate, and the filtrate is concentrated by evaporation in a vacuum. The residue that is thus obtained is purified by chromatography on silica gel. With hexane/0-10% ether, 9.95 g of the title compound is obtained as a colorless oil.

$^1$H-NMR (CD$_2$Cl$_2$): δ=0.01 (6H), 0.84 (9H), 1.07 (3H), 1.18 (3H), 1.2-1.7 (6H), 2.38 (1H), 3.57 (2H), 4.05 (2H) ppm.

EXAMPLE 1r (2S)-2-Methyl-6-(tert-butyldimethylsilyloxy)-hexan-1-ol 63 ml of a 1.2 M solution of diisobutylaluminum hydride in toluene is added to a solution of 9.94 g of the ester, produced according to Example 1q, in 130 ml of toluene at −40° C. under nitrogen, and it is stirred for 1 hour at this temperature. Then, 15 ml of isopropanol is carefully added, and after 10 minutes, 30 ml of water is added, allowed to come to 22° C., and it is stirred at this temperature for 2 hours. Precipitate is filtered out, it is rewashed well with ethyl acetate, and the filtrate is concentrated by evaporation in a vacuum. The residue that is thus obtained is purified by chromatography on silica gel. With hexane/0-30% ether, 7.9 g of the title compound is obtained as a colorless oil. [α]$_D$−8.1° (c=0.97, CHCl$_3$)

$^1$H-NMR (CDCl$_3$): δ=0.07 (3H), 0.89 (9H), 0.91 (3H), 1.0-1.7 (7H), 3.48 (2H), 3.52 (2H) ppm.

EXAMPLE 1s (2S)-2-Methyl-6-(tert-butyldimethylsilyloxy)-1-(tetrahydro-2H-pyran-2-yloxy)-hexane 3.52 ml of dihydropyran, followed by 49 mg of p-toluenesulfonic acid-monohydrate, is added to 6.4 g of the alcohol, produced according to Example 1r, in 26 ml of methylene chloride at 0° C. under argon. After 1.5 hours of stirring at 0° C., it is mixed with 10 ml of saturated sodium bicarbonate solution and diluted with ether. The organic phase is washed twice with semi-saturated sodium chloride solution and dried on sodium sulfate. After filtration, it is concentrated by evaporation in a vacuum, and the residue that is thus obtained is purified by chromatography on silica gel. With hexane/0-5% ether, 4.75 g of the title compound is obtained as a colorless oil.

$^1$H-NMR (CDCl$_3$): δ=0.05 (6H), 0.89 (9H), 0.92 (3H), 1.0-1.9 (13H), 3.19 (1H), 3.50 (1H), 3.55-3.65 (3H), 4.87 (1H), 4.57 (1H) ppm.

EXAMPLE 1t (5S)-5-Methyl-6-(tetrahydro-2H-pyran-2-yloxy)-hexan-1-ol 13.5 g of tetrabutylammonium fluoride trihydrate is added to a solution of 4.7 g of the THP-ether, produced according to Example 1s, in 170 ml of tetrahydrofuran, under nitrogen, and it is stirred for 3 hours. Then, the reaction mixture is diluted with 800 ml of ether, and it is washed three times each with 20 ml of semi-saturated sodium chloride solution and dried on sodium sulfate. After filtration, it is concentrated by evaporation in a vacuum, and the residue that is thus obtained is purified by chromatography on silica gel. With hexane/0-50% ethyl acetate, 2.88 g of the title compound is obtained as a colorless oil.

$^1$H-NMR (CD$_2$Cl$_2$): δ=0.90/0.92 (3H), 1.1-1.9 (13H), 3.18 (1H), 3.40-3.65 (4H), 3.82 (1H), 4.53 (1H) ppm.

EXAMPLE 1u (5S)-5-Methyl-6-(tetrahydro-2H-pyran-2-yloxy)-hexanal 1.9 ml of dimethyl sulfoxide, dissolved in 7 ml of methylene chloride, is carefully added in drops to 1.08 ml of oxalyl chloride, dissolved in 10 ml of methylene chloride, under nitrogen at −70° C., and it is stirred for 10 minutes at this temperature. Then, a solution of 2.0 g of the alcohol, produced according to Example 1t, in 7 ml of methylene chloride is added in drops, and it is stirred for 2 hours between −60° C. and −70° C. Then, 3.86 ml of triethylamine is added, and after 1 hour of stirring at −60° C., the reaction mixture is added to 30 ml of water. After phase separation, the aqueous phase is extracted twice with 30 ml of methylene chloride each. The combined organic phases are washed three times with saturated sodium chloride solution. After drying on sodium sulfate and filtration, it is concentrated by evaporation in a vacuum. 1.99 g of the aldehyde, which is used without further purification, is obtained.

EXAMPLE 1v (2RS,6S)-6-Methyl-7-(tetrahydro-2H-pyran-2-yloxy)-heptan-2-ol 6.16 ml of a 3 M methylmagnesium bromide solution in ether is slowly added in drops to a solution of 1.98 g of the aldehyde, produced according to Example 1u, in 30 ml of ether under nitrogen at 0° C. After 60 minutes, it is slowly poured onto 50 ml of ice-cold saturated ammonium chloride solution and extracted three times with ether. The combined organic phases are washed once with water, and twice with saturated sodium chloride solution and dried on sodium sulfate. After filtration, it is concentrated by evaporation in a vacuum, and the residue that is thus obtained is purified by chromatography on silica gel. With hexane/0-60% ether, 1.57 g of the title compound is obtained as a colorless oil.

$^1$H-NMR (CD$_2$Cl$_2$): δ=0.90/0.93 (3H), 1.15 (3H), 1.0-1.9 (13H), 3.18 (1H), 3.4-3.6 (2H), 3.7-3.9 (2H), 4.53 (1H) ppm.

EXAMPLE 1w (2S,6RS)-2-Methyl-6-(tert-butyl-diphenylsilyloxy)-1-(tetrahydro-2H-pyran-2-yloxy)-heptane 2.13 ml of tert-butyldiphenylsilyl chloride is added to a solution of 1.57 g of alcohol, produced according to Example 1v, and 1.11 g of imidazole in 20 ml of dimethylformamide at 0° C. under nitrogen, and it is stirred for 15 minutes at 0° C. and for 16 hours at 22° C. The reaction mixture is diluted with 200 ml of ether, washed once with water, once with 10% sulfuric acid, once with saturated sodium bicarbonate solution and washed neutral with saturated sodium chloride solution. After drying on sodium sulfate and filtration, it is concentrated by evaporation in a vacuum. The residue that is thus obtained is purified by chromatography on silica gel. With hexane/0-10% ether, 2.87 g of the title compound is obtained as a colorless oil.

$^1$H-NMR (CDCl$_3$): δ=0.87/0.89 (3H), 1.04 (9H), 0.9-1.9 (16H), 3.15 (1H), 3.4-3.6 (2H), 3.8-3.9 (2H), 4.56 (1H), 7.3-7.5 (6H), 7.69 (4H) ppm.

EXAMPLE 1x (2S,6RS)-2-Methyl-6-(tert-butyl-diphenylsilyloxy)-heptan-1-ol 131 mg of pyridinium-p-toluenesulfonate is added to a solution of 2.3 g of silyl ether, produced according to Example 1w, in 100 ml of ethanol, and it is stirred for 4 hours at 40° C. Then, it is concentrated by evaporation in a vacuum, and the residue that is thus obtained is purified by chromatography on silica gel. With hexane/20% ether, 1.68 g of the title compound is obtained as a colorless oil.

EXAMPLE 1y (2S,6RS)-2-Methyl-6-(tert-butyl-diphenylsilyloxy)-heptanal

Analogously to Example 1u, 2.13 g of the alcohol that is presented under Example 1x is oxidized, and after working-up and chromatographic purification, 2.10 g of the title compound is isolated as a colorless oil.

$^1$H-NMR (CDCl$_3$): δ=1.00-1.12 (15H), 1.18-1.63 (6H), 2.22 (1H), 3.83 (1H), 7.32-7.47 (6H), 7.61-7.72 (4H), 9.54 (1H) ppm.

EXAMPLE 1z (S)-Dihydro-3-hydroxy-2(3H)-furanone 10 g of L-(-)-malic acid is stirred in 45 ml of trifluoroacetic acid anhydride for 2 hours at 25° C. Then, it is concentrated by evaporation in a vacuum, 7 ml of methanol is added to the residue and allowed to stir for 12 more hours. Then, it is concentrated by evaporation in a vacuum. The residue that is obtained is dissolved in 150 ml of absolute tetrahydrofuran. It is cooled to 0° C., and 150 ml of borane-tetrahydrofuran complex is added and allowed to stir for 2.5 hours at 0° C. Then, 150 ml of methanol is added. It is allowed to stir for one more hour at room temperature and then concentrated by evaporation in a vacuum. The crude product that is obtained is dissolved in 80 ml of toluene. 5 g of Dowex### (activated, acidic) is added and refluxed for one hour. Then, Dowex### is filtered off, and the filtrate is concentrated by evaporation in a vacuum. The crude product that is obtained (7.61 g) is used without purification in the next step.

EXAMPLE 1aa (S)-Dihydro-3-[[(1,1-dimethylethyl)diphenylsilyl]oxy]-2(3H)-furanone 24 ml of tert-butyldiphenylsilyl chloride is added to a solution of 7.61 g of the substance that is described under Example 1z and 10 g of imidazole in 100 ml of N,N-dimethylformamide. It is allowed to stir for two more hours at 25° C., and then the reaction mixture is poured onto ice-cold saturated sodium bicarbonate solution. It is extracted with ethyl acetate, the organic phase is washed with saturated sodium chloride solution, dried on sodium sulfate and concentrated by evaporation in a vacuum. After column chromatography of the crude product on silica gel with a mixture of hexane/ethyl acetate, 13.4 g of the title compound is obtained.

$^1$H-NMR (CDCl$_3$): δ=7.72 (2H), 7.70 (2H), 7.40-7.50 (6H), 4.30-4.42 (2H), 4.01 (1H), 2.10-2.30 (2H), 1.11 (9H) ppm.

EXAMPLE 1ab (2RS,3S)-3-[[(1,1-Dimethylethyl)diphenylsilyl]oxy]tetrahydro-2-furanol 80 ml of a 1 molar solution of diisobutylaluminum hydride in hexane is added at -78° C. to a solution of 13.4 g of the substance, described under Example 1aa, in 150 ml of absolute tetrahydrofuran. It is stirred for 45 more minutes at -78° C. and then quenched with water. It is extracted with ethyl acetate, the organic phase is washed with saturated sodium chloride solution, dried on sodium sulfate and concentrated by evaporation in a vacuum. 13.46 g of the title compound, which is used without purification in the next step, is obtained.

EXAMPLE 1ac (2RS,3S)-3-[[(1,1-Dimethylethyl)diphenylsilyl]oxy]-1,4-pentanediol A solution of 13.46 g of the substance, described under Example 1ab, in 150 ml of absolute tetrahydrofuran is added in drops to 20 ml of a 3 molar solution of methylmagnesium chloride in tetrahydrofuran at 0° C. It is allowed to stir for one more hour at 0° C. and then poured onto saturated aqueous ammonium chloride solution. It is extracted with ethyl acetate, the organic phase is washed with saturated sodium chloride solution, dried on sodium sulfate and concentrated by evaporation in a vacuum. After column chromatography of the crude product on silica gel with a mixture of hexane/ethyl acetate, 11.42 g of the title compound is obtained.

$^1$H-NMR (CDCl$_3$): δ=7.65-7.75 (4H), 7.40-7.55 (6H), 5.20 (1H), 4.30 (2H), 3.70 (1H), 1.80 (2H), 1.05 (9H) ppm.

EXAMPLE 1ad (2RS,3S)-5-[[Dimethyl(1,1-dimethylethyl)silyl]oxy]-3-[[(1,1-dimethylethyl)diphenylsilyl]oxy]-2-pentanol 4.9 g of tert-butyldimethylsilyl chloride is added to a solution of 11.42 g of the substance that is described under Example 1ac, and 3.25 g of 1H-imidazole in 120 ml of N,N-dimethylformamide. It is allowed to stir for 2 more hours at 25° C., and then the reaction mixture is poured onto ice-cold, saturated sodium bicarbonate solution. It is extracted with ethyl acetate, the organic phase is washed with saturated sodium chloride solution, dried on sodium sulfate and concentrated by evaporation in a vacuum. After column chromatography of the crude product on silica gel with a mixture of hexane/ethyl acetate, 10.64 g of the title compound is obtained.

$^1$H-NMR (CDCl$_3$): δ=7.60-7.70 (4H), 7.30-7.45 (6H), 3.70-3.80 (2H), 3.40 (1H), 3.00 (1H), 1.80 (1H), 1.60 (1H), 1.05-1.12 (12H), 0.82 (9H), 0.02 (6H) ppm.

EXAMPLE 1ae (3S)-5-[[Dimethyl(1,1-dimethylethyl)silyl]oxy]-3-[[(1,1-dimethylethyl)diphenylsilyl]oxy]-2-pentanone 13 ml of dimethyl sulfoxide is added to 7.37 ml of oxalyl chloride in 80 ml of dichloromethane at −78° C. It is allowed to stir for 3 more minutes, and then 10.46 g of the substance, described under Example 1ad, in 100 ml of dichloromethane, is added. After another 15 minutes of stirring time, 52 ml of triethylamine is added in drops. Then, it is allowed to heat to 0° C. Then, the reaction mixture is poured onto saturated sodium bicarbonate solution. It is extracted with dichloromethane, the organic phase is washed with saturated sodium chloride solution, dried on sodium sulfate and concentrated by evaporation in a vacuum. After column chromatography of the crude product on silica gel with a mixture of hexane/ethyl acetate, 9.3 g of the title compound is obtained.

$^1$H-NMR (CDCl$_3$): δ=7.60-7.70 (4H), 7.32-7.50 (6H), 4.25 (1H), 3.72 (1H), 3.58 (1H), 2.05 (3H), 1.90 (1H), 1.75 (1H), 1.13 (9H), 0.89 (9H), 0.01 (6H) ppm.

EXAMPLE 1af (E,3S)-1-[[Dimethyl(1,1-dimethylethyl)silyl]oxy]-3-[[(1,1-dimethylethyl)diphenylsilyl]oxy]-4-methyl-5-(2-methylthiazol-4-yl)-pent-4-ene The solution of 6.82 g of diethyl(2-methylthiazol-4-yl)methanephosphonate in 300 ml of anhydrous tetrahydrofuran is cooled under an atmosphere of dry argon to −5° C., mixed with 16.2 ml of a 1.6 molar solution of n-butyllithium in n-hexane, allowed to heat to 23° C. and stirred for 2 hours. Then, it is cooled to −78° C., the solution of 6.44 g (13.68 mmol) of the compound, presented according to Example 1ae, in 150 ml of tetrahydrofuran is added in drops, allowed to heat to 23° C. and stirred for 16 hours. It is poured into saturated ammonium chloride solution, extracted several times with ethyl acetate, the combined organic extracts are washed with saturated sodium chloride solution and dried on sodium sulfate. The residue that is obtained after filtration and removal of the solvent is purified by chromatography on fine silica gel with a gradient system that consists of n-hexane and ethyl acetate. 6.46 g (11.4 mmol, 83%) of the title compound is isolated as a colorless oil.

$^1$H-NMR (CDCl$_3$): δ=−0.04 (6H), 0.83 (9H), 1.10 (9H), 1.79 (1H), 1.90 (1H), 1.97 (3H), 2.51 (3H), 3.51 (2H), 4.38 (1H), 6.22 (1H), 6.74 (1H), 7.23-7.47 (6H), 7.63 (2H), 7.70 (2H) ppm.

EXAMPLE 1ag (E,3S)-3-[[(1,1-Dimethylethyl)diphenylsilyl]oxy]-4-methyl-5-(2-methylthiazol-4-yl)-pent-4-en-1-ol The solution of 4.79 g (8.46 mmol) of the compound, presented according to Example 1af, in 48 ml of tetrahydrofuran is mixed with 48 ml of a 65:35:10 mixture of glacial acetic acid/water/tetrahydrofuran and stirred for 2.5 days at 23° C. It is poured into saturated sodium carbonate solution, extracted several times with ethyl acetate, the combined organic extracts are washed with saturated sodium chloride solution and dried on sodium sulfate. The residue that is obtained after filtration and removal of the solvent is purified by chromatography on fine silica gel with a gradient system that consists of n-hexane and ethyl acetate. 3.42 g (7.57 mmol, 90%) of the title compound is isolated as a colorless oil.

$^1$H-NMR (CDCl$_3$) δ=1.10 (9H), 1.53 (1H), 1.81 (2H), 1.96 (3H), 2.71 (3H), 3.59 (2H), 4.41 (1H), 6.38 (1H), 6.78 (1H), 7.26-7.49 (6H), 7.65 (2H), 7.72 (2H) ppm.

EXAMPLE 1ah (E,3S)-1-Iodo-3-[[(1,1-dimethylethyl)diphenylsilyl]oxy]-4-methyl-5-(2-methylthiazol-4-yl)-pent-4-ene The solution of 8.41 g of triphenylphosphine in 120 ml of dichloromethane is mixed at 23° C. under an atmosphere of dry argon with 2.19 g of imidazole, 8.14 g of iodine, the solution of 12.2 g (27.0 mmol) of the compound, presented according to Example 1ag, in 30 ml of dichloromethane is added in drops and stirred for 0.5 hour. The solution is chromatographed on fine silica gel with a gradient system that consists of n-hexane and ethyl acetate. 12.15 g (21.6 mmol, 80%) of the title compound is isolated as a colorless oil.

$^1$H-NMR (CDCl$_3$) δ=1.08 (9H), 1.96 (3H), 2.10 (2H), 2.70 (3H), 2.87-3.08 (2H), 4.24 (1H), 6.32 (1H), 6.79 (1H), 7.28-7.48 (6H), 7.60-7.72 (4H) ppm.

EXAMPLE 1ai (5E,3S)-[3-[[(1,1-Dimethylethyl)diphenylsilyl]oxy]-4-methyl-5-(2-methylthiazol-4-yl)-pent-4-en-1-yl]-triphenylphosphonium iodide The suspension of 12.55 g (22.3 mmol) of the compound that is presented according to Example 1ah, 85 g of triphenylphosphine and 11.6 ml of N-ethyldiisopropylamine is stirred under an atmosphere of dry argon for 16 hours at 80° C. After cooling, it is mixed with diethyl ether, filtered, and the residue is rewashed several times with diethyl ether and recrystallized from ethyl acetate. 15.7 g (19.1 mmol, 74%) of the title compound is isolated as a crystalline solid.

$^1$H-NMR (CDCl$_3$): δ=1.07 (9H), 1.68-1.92 (2H), 1.98 (3H), 2.70 (3H), 2.93 (1H), 3.30 (1H), 4.53 (1H), 6.62 (1H), 7.03 (1H), 7.23-7.47 (6H), 7.48-7.72 (16H), 7.73-7.85 (3H) ppm.

EXAMPLE 1ak (4S(4R,5S,6S,10RS))-4-(2,6-Dimethyl-10-[[(1,1-dimethylethyl)diphenylsilyl]oxy]-4-ethyl-5-hydroxy-3-oxo-undec-2-yl)-2,2-dimethyl-[1,3]dioxane (A) and (4S(4S,5R,6S,10RS))-4-(2,6-dimethyl-10-[[(1,1-dimethylethyl)diphenylsilyl]oxy]-4-ethyl-5-hydroxy-3-oxo-undec-2-yl)-2,2-dimethyl-[1,3]dioxane (B)

The solution of 1.96 ml of diisopropylamine in 44 ml of anhydrous tetrahydrofuran is cooled under an atmosphere of dry argon to −30° C., mixed with 6.28 ml of a 2.4 molar solution of n-butyllithium in n-hexane and stirred for 15 more minutes. At −78° C., the solution of 3.08 g (13.47 mmol) of the compound, presented according to Example 1m, in 44 ml of tetrahydrofuran is added in drops, and it is allowed to react for 1 hour. Then, it is mixed with the solution of 5.77 g (15.1 mmol) of the compound, presented according to Example 1y, in 44 ml of tetrahydrofuran and poured after 45 minutes into saturated ammonium chloride solution. It is diluted with water, extracted several times with ethyl acetate, the combined organic extracts are washed with saturated sodium chloride solution, dried on sodium sulfate and concentrated by evaporation in a vacuum. After column chromatography on silica gel with a gradient system that consists of n-hexane and ethyl acetate, in addition to 13% starting material, 4.03 g (5.92 mmol, 44%) of title compound A and 1.58 g (2.32 mmol, 17%) of a diastereomer B are obtained.

$^1$H-NMR (CDCl$_3$) of A: δ=0.79 (3H) 0.85 (3H), 0.90-1.10 (16H), 1.19-1.79 (10H), 1.26 (3H), 1.32 (3H), 1.38 (3H), 2.79 (1H), 3.18 (1H), 3.42 (1H), 3.78-3.92 (2H), 3.98 (1H), 4.17 (1H), 7.30-7.46 (6H), 7.62-7.72 (4H) ppm.

$^1$H-NMR (CDCl$_3$) of B: δ=0.83 (3H), 0.91 (3H), 0.94-1.12 (16H), 1.19 (3H), 1.15-1.80 (10H), 1.31 (3H), 1.41 (3H), 2.54 (1H), 3.18 (1H), 3.47 (1H), 3.78-3.91 (2H), 3.97 (1H), 4.14 (1H), 7.31-7.47 (6H), 7.62-7.73 (4H) ppm.

EXAMPLE 1al (4S(4R,5S,6S,10RS))-4-(2,6-Dimethyl-10-[[(1,1-dimethylethyl)diphenylsilyl]oxy]-4-ethyl-3-oxo-5-(tetrahydropyran-2-yloxy)-undec-2-yl)-2,2-dimethyl-[1,3]dioxane Analogously to Example 1a, the solution of 4.02 g (6.58 mmol) of the compound that is presented according to Example 1ak is reacted, and after working-up and purification, 4.26 g (6.13 mmol, 93%) of the title compound is isolated as a colorless oil.

$^1$H-NMR (CDCl$_3$): δ=0.67-1.97 (47H), 3.02+3.12 (1H), 3.38 (1H), 3.48-4.04 (5H), 4.18+4.26 (1H), 4.42+4.50 (1H), 7.30-7.46 (6H), 7.61-7.72 (4H) ppm.

EXAMPLE 1am (4S(4R,5S,6S,10RS))-4-(2,6-Dimethyl-4-ethyl-10-hydroxy-3-oxo-5-(tetrahydropyran-2-yloxy)-undec-2-yl)-2,2-dimethyl-[1,3]dioxane Analogously to Example 1i, the solution of 4.26 g (6.13 mmol) of the compound that is presented according to Example 1al is reacted, and after working-up and purification, 2.38 g (5.21 mmol, 85%) of the title compound is isolated as a colorless oil.

$^1$H-NMR (CDCl$_3$): δ=0.78+0.84 (3H), 0.92-1.10 (6H), 1.13-1.98 (29H), 2.43 (1H), 3.06+3.18 (1H), 3.42 (1H), 3.60-4.04 (5H), 4.21+4.28 (1H), 4.42+4.54 (1H) ppm.

EXAMPLE 1an (4S(4R,5S,6S))-4-(3,10-Dioxo-2,6-dimethyl-4-ethyl-5-(tetrahydropyran-2-yloxy)-undec-2-yl)-2,2-dimethyl-[1,3]dioxane Analogously to Example 1m, the solution of 2.49 g (5.45 mmol) of the compound that is presented according to Example 1am is reacted, and after working-up and purification, 2.24 g (4.93 mmol, 90%) of the title compound is isolated as a colorless oil.

$^1$H-NMR (CDCl$_3$): δ=0.78+0.86 (3H), 0.90-1.37 (15H), 1.37-1.95 (15H), 2.13 (3H), 2.42 (2H), 3.07+3.18 (1H), 3.42 (1H), 3.60-4.04 (4H), 4.22+4.27 (1H), 4.41+4.53 (1H) ppm.

EXAMPLE 1ao (4S(4R,5S,6S,10E/Z,13S,14E))-4-(13-[[(1,1-Dimethylethyl)dimethylsilyl]oxy]-4-ethyl-15-(2-methyl-4-thiazolyl)-3-oxo-5-(tetrahydropyran-2-yloxy)-2,6,10,14-tetramethyl-pentadeca-10,14-dien-2-yl)-2,2-dimethyl-[1,3]dioxane The suspension of 4.92 g (5.97 mmol) of the compound (5E,3S)-[3-[[(1,1-dimethylethyl)dimethylsilyl]oxy]-4-methyl-5-(2-methyl-thiazol-4-yl)-pent-4-en-1-yl]-triphenylphosphonium iodide, presented analogously to Example 1ai, in 14 ml of anhydrous tetrahydrofuran is mixed at 0° C. under an atmosphere of dry argon with 5.96 ml of a 1 M solution of sodium-bis-(trimethylsilyl)-amide in tetrahydrofuran and allowed to heat to 23° C. The solution of 877 mg (1.93 mmol) of the compound, presented according to Example 1an, in 14 ml of tetrahydrofuran is added in drops to the red solution, allowed to stir for 2 hours, poured onto saturated ammonium chloride solution and extracted several times with ethyl acetate. The combined organic extracts are dried on sodium sulfate and concentrated by evaporation in a vacuum. After column chromatography on silica gel with a gradient system that consists of n-hexane and ethyl acetate, in addition to 29% starting material, 732 mg (0.98 mmol, 51%) of the title compound is obtained.

$^1$H-NMR (CDCl$_3$): δ=0.01 (3H), 0.05 (3H), 0.79 (3H), 0.81-1.02 (6H), 0.90 (9H), 1.04-1.38 (11H), 1.38-2.08 (19H), 1.60 (3H), 2.01 (3H), 2.16-2.34 (2H), 2.72 (3H), 3.06+3.17 (1H), 3.42 (1H), 3.68 (1H), 3.80-4.03 (3H), 4.03-4.32 (2H), 4.46+4.54 (1H), 5.13 (1H), 6.45 (1H), 6.92 (1H) ppm.

EXAMPLE 1ap (3S,6R,7S,8S,12E/Z,15S,16E)-6-Ethyl-17-(2-methyl-4-thiazolyl)-5-oxo-4,4,8,12,16-pentamethyl-heptadeca-12,16-diene-1,3,7,15-tetraol (A) and (3S,6R,7S,8S,12E/Z,15S,16E)-15-[[(1,1-dimethylethyl)dimethylsilyl]oxy]-6-ethyl-17-(2-methyl-4-thiazolyl)-5-oxo-4,4,8,12,16-pentamethyl-heptadeca-12,16-diene-1,3,7-triol (B)

Analogously to Example 1f, the solution of 732 mg (0.98 mmol) of the compound that is presented according to Example 1ao is reacted, and after working-up and purification, 98 mg (0.19 mmol, 20%) of title compound A and 380 mg (0.61 mmol, 62%) of title compound B are isolated in each case as a colorless oil.

$^1$H-NMR (CDCl$_3$) of A: δ=0.79-0.95 (6H), 0.98-1.19 (4H), 1.21-1.86 (15H), 1.92-2.17 (5H), 2.33 (2H), 2.74 (3H), 2.87-3.23 (3H), 3.31-3.50 (1H), 3.65-3.92 (3H), 4.05-4.20 (2H), 5.10-5.25 (1H), 6.53 (1H), 6.96 (1H) ppm.

$^1$H-NMR (CDCl$_3$) of B: δ=0.01+0.05 (6H), 0.80-0.96 (15H), 1.01-1.17 (4H), 1.20-1.68 (4H), 1.68-1.90 (10H), 1.90-2.16 (5H), 2.25 (2H), 2.73+2.77 (3H), 2.91 (1H), 3.19

(1H), 3.42 (1H), 3.61 (1H), 3.79-3.93 (3H), 3.99-4.19 (2H), 5.10+5.20 (1H), 6.42 (1H), 6.94 (1H) ppm.

EXAMPLE 1aq (3S,6R,7S,8S,12E/Z,15S,16E)-6-Ethyl-17-(2-methyl-4-thiazolyl)-4,4,8,12,16-pentamethyl-1,3,7,15-tetrakis-[[dimethyl(1,1-dimethylethyl)silyl]oxy]-heptadeca-12,16-dien-5-one The solution of 520 mg (about 0.86 mmol) of a mixture of compounds A and B, presented according to Example 1ap, in 25 ml of anhydrous dichloromethane is cooled under an atmosphere of dry argon to −78° C., mixed with 2.6 ml of 2,6-lutidine and 2.57 ml of trifluoromethanesulfonic acid-tert-butyldimethylsilyl ester and stirred for 16 hours. It is poured into saturated sodium bicarbonate solution and extracted several times with dichloromethane. The combined organic extracts are dried on sodium sulfate and concentrated by evaporation in a vacuum. After column chromatography on silica gel with a gradient system that consists of n-hexane and ethyl acetate, 1.14 g (max. 0.86 mmol, max. 100%) of the title compound, which also contains silanol, is isolated.

$^1$H-NMR (CDCl$_3$) of an analytically purified sample: $^1$H-NMR (CDCl$_3$) δ=−0.04-0.11 (24H), 0.78-0.96 (42H), 1.13 (3H), 1.20 (3H), 1.02-1.65 (6H), 1.58+1.68 (3H), 1.72 (1H), 1.88-2.07 (2H), 2.00 (3H), 2.23 (2H), 2.71 (3H), 3.01 (1H), 3.52-3.73 (2H), 3.82 (1H), 3.91 (1H), 4.09 (1H), 5.13 (1H), 6.45 (1H), 6.91 (1H) ppm.

EXAMPLE 1ar (3S,6R,7S,8S,12E/Z,15S,16E)-3,7,15-6-Ethyl-tris-[[dimethyl(1,1-dimethylethyl)silyl]oxy]-1-hydroxy-17-(2-methyl-4-thiazolyl)-4,4,8,12,16-pentamethyl-heptadeca-12,16-dien-5-one The solution of 1.14 g (max. 0.86 mmol) of the compound, presented according to Example 1aq, in a mixture of 8 ml of dichloromethane and 8 ml of methanol is mixed at 0° C. under an atmosphere of dry argon with 204 mg of camphor-10-sulfonic acid, allowed to heat to 23° C. and stirred for 1.5 more hours. It is mixed with triethylamine, poured into a saturated sodium bicarbonate solution and extracted several times with dichloromethane. The combined organic extracts are dried on sodium sulfate and concentrated by evaporation in a vacuum. After column chromatography on fine silica gel with a gradient system that consists of n-hexane and ethyl acetate, 618 mg (0.78 mmol, 90%) of the title compound is isolated.

$^1$H-NMR (CDCl$_3$): δ=−0.02-0.13 (18H), 0.77-0.98 (33H), 1.01-1.80 (10H), 1.08 (3H), 1.19 (3H), 1.55+1.66 (3H), 1.74-2.05 (2H), 2.00 (3H), 2.25 (2H), 2.70 (3H), 3.00 (1H), 3.68 (2H), 3.85 (1H), 4.08 (2H), 5.14 (1H), 6.44 (1H), 6.90 (1H) ppm.

EXAMPLE 1as (3S,6R,7S,8S,12E/Z,15S,16E)-6-Ethyl-3,7,15-tris-[[dimethyl(1,1-dimethylethyl)silyl]oxy]-4,4,8,12,16-pentamethyl-17-(2-methyl-4-thiazolyl)-5-oxo-heptadeca-12,16-dienal Analogously to Example 1k, 510 mg (0.64 mmol) of the compound that is presented according to Example 1ar is reacted, and after working-up, 545 mg (max. 0.64 mmol) of the title compound is isolated as a crude product, which is further reacted without purification.

EXAMPLE 1at (3S,6R,7S,8S,12E/Z,15S,16E)-6-Ethyl-3,7,15-tris-[[dimethyl(1,1-dimethylethyl)silyl]oxy]-4,4,8,12,16-pentamethyl-17-(2-methyl-4-thiazolyl)-5-oxo-heptadeca-12,16-dienoic acid The solution of 545 mg (max. 0.64 mmol) of the compound, presented according to Example 1as, in 15 ml of acetone is cooled to −30° C., mixed with 460 µl of a standardized, 8N chromosulfuric acid solution and stirred for 1 hour. It is poured into a mixture of water and diethyl ether, the organic phase is washed with saturated sodium chloride solution and dried on sodium sulfate. After filtration and removal of the solvent, 410 mg (0.47 mmol, 74% relative to the educt in Example 1as) of the title compounds, which can be chromatographically separated, is isolated as a pale yellow oil.

$^1$H-NMR (CDCl$_3$) of the Z-isomer: δ=−0.02-0.15 (18H), 0.80-0.95 (33H), 1.03-2.28 (12H), 1.17 (3H), 1.18 (3H), 1.69 (3H), 1.96 (3H), 2.35 (1H), 2.54 (1H), 2.71 (3H), 3.03 (1H), 3.81 (1H), 4.16 (1H), 4.41 (1H), 5.20 (1H), 6.53 (1H), 6.94 (1H) ppm.

$^1$H-NMR (CDCl$_3$) of the E-isomer: δ=−0.03-0.16 (18H), 0.79-0.95 (33H), 0.99-2.06 (10H), 1.17 (3H), 1.19 (3H), 1.57 (3H), 1.97 (3H), 2.26 (2H), 2.32 (1H), 2.61 (1H), 2.70 (3H), 3.09 (1H), 3.85 (1H), 4.09 (1H), 4.36 (1H), 5.12 (1H), 6.48 (1H), 6.94 (1H) ppm.

EXAMPLE 1au (3S,6R,7S,8S,12E/Z,15S,16E)-3,7-Bis-[[dimethyl(1,1-dimethylethyl)silyl]oxy]-15-hydroxy-6-ethyl-17-(2-methyl-4-thiazolyl)-5-oxo-4,4,8,12,16-pentamethyl-heptadeca-12,16-dienoic Acid Variant I:
The solution of 310 mg (0.36 mmol) of the acid, presented according to Example 1at, in 30 ml of anhydrous tetrahydrofuran, is mixed under an atmosphere of dry argon with 500 µl of a hydrogen fluoride-pyridine complex and 7.1 ml of a 1.1 M solution of tetrabutylammonium fluoride in tetrahydrofuran, and it is stirred for 3 days at 50° C. It is poured into a saturated ammonium chloride solution, extracted several times with ethyl acetate, the combined organic extracts are washed with saturated sodium chloride solution and dried on sodium sulfate. After filtration and removal of the solvent, the residue is purified by chromatography on about 200 ml of fine silica gel with a gradient system that consists of dichloromethane and methanol. 125 mg (max. 0.24 mmol, max. 66%), which also contains tetrabutylammonium salts, is isolated.

Variant II:
Analogously to Example 1t, 32 mg (37 µmol) of the acid that is presented according to Example 1at is reacted, and after working-up and purification, 16 mg (31 µmol, 83%) of the title compound is isolated as a colorless oil.

$^1$H-NMR (CDCl$_3$) of the Z-isomer: δ=0.01-0.14 (12H), 0.80-0.99 (24H), 1.02-1.67 (7H), 1.18 (3H), 1.19 (3H), 1.70 (1H), 1.73 (3H), 1.97 (1H), 2.01 (3H), 2.14 (1H), 2.27-2.40 (3H), 2.53 (1H), 2.71 (3H), 2.81 (1H), 3.01 (1H), 3.82 (1H), 4.17 (1H), 4.48 (1H), 5.19 (1H), 6.69 (1H), 6.95 (1H) ppm.

$^1$H-NMR (CDCl$_3$) of the E-isomer: δ=−0.02-0.11 (12H), 0.73-0.95 (24H), 1.00-1.63 (7H), 1.12 (3H), 1.17 (3H), 1.60 (3H), 1.71 (1H), 1.89-2.06 (2H), 2.00 (3H), 2.22-2.39 (3H), 2.53 (1H), 2.69 (3H), 2.79 (1H), 3.02 (1H), 3.79 (1H), 4.15 (1H), 4.34 (1H), 5.15 (1H), 6.56 (1H), 6.92 (1H) ppm.

EXAMPLE 1aw (4S,7R,8S,9S,13E/Z,16S(E))-4,8-Bis-[[dimethyl(1,1-dimethylethyl)silyl]oxy]-7-ethyl-16-(1-methyl-2-(2-methyl-4-thiazolyl)ethenyl)-1-oxa-5,5,9,13-tetramethyl-cyclohexadec-13-ene-2,6-dione The solution of 55 mg (73 µmol) of the compound, presented according to Example 1au, in 0.8 ml of anhydrous tetrahydrofuran is mixed with 46 µl of triethylamine and 44 µl of 2,4,6-trichlorobenzoyl chloride under an atmosphere of dry argon, and it is stirred for 20 minutes. It is diluted with 20 ml of tetrahydrofuran, mixed with 68 mg of 4-dimethylaminopyridine and stirred for 30 minutes at 23° C. It is concentrated by evaporation, taken up in a little dichloromethane and purified by chromatography on 100 ml of fine silica gel with a gradient system that consists of n-hexane and ethyl acetate. 49 mg (65 µmol, 89%) of the title compound is isolated as a colorless oil.

$^1$H-NMR (CDCl$_3$) of the Z-isomer: δ=–0.12 (3H), 0.08 (3H), 0.10 (3H), 0.13 (3H), 0.73 (3H), 0.79-1.78 (7H), 0.85 (9H), 0.93 (9H), 0.99 (3H), 1.10 (3H), 1.18 (3H), 1.67 (3H), 1.88 (1H), 2.05 (1H), 2.09 (3H), 2.45 (1H), 2.54-2.74 (2H), 2.69 (3H), 2.77 (1H), 3.08 (1H), 4.00 (2H), 4.56 (1H), 5.16 (1H), 6.56 (1H), 6.95 (1H) ppm.

$^1$H-NMR (CDCl$_3$) of the E-isomer: δ=0.02-0.16 (12H), 0.78-1.00 (24H), 1.09 (3H), 1.14-1.93 (8H), 1.20 (3H), 1.59 (3H), 2.09-2.21 (1H), 2.13 (3H), 2.39 (1H), 2.43-2.64 (3H), 2.70 (3H), 2.98 (1H), 3.95 (1H), 4.40 (1H), 5.21 (1H), 5.29 (1H), 6.51 (1H), 6.92 (1H) ppm.

EXAMPLE 1

(4S,7R,8S,9S,13Z,16S(E))-4,8-Dihydroxy-7-ethyl-16-(1-methyl-2-(2-methyl-4-thiazolyl)ethenyl)-1-oxa-5,5,9,13-tetramethyl-cyclohexadec-13-ene-2,6-dione (A) and (4S,7R,8S,9S,13E,16S(E))-4,8-dihydroxy-7-ethyl-16-(1-methyl-2-(2-methyl-4-thiazolyl)ethenyl)-1-oxa-5,5,9,13-tetramethyl-cyclohexadec-13-ene-2,6-dione (B)

The solution of 48 mg (64 µmol) of the compound, presented according to Example 1aw, in 3 ml of anhydrous dichloromethane, is mixed at –20° C. under an atmosphere of dry argon with 220 µl of an approximately 20% trifluoroacetic acid, and it is stirred for 1 hour. It is poured into a saturated sodium bicarbonate solution, extracted with dichloromethane, and the organic phase is dried on sodium sulfate. After filtration and removal of the solvent, the residue is purified by repeated chromatography on analytical thin-layer plates. As a mobile solvent, a mixture of n-hexane and ethyl acetate is used; as an eluant, ethyl acetate is used. 13 mg (25 µmol, 39%) of title compound A and 12 mg (23 µmol, 36%) of title compound B are isolated in each case as a colorless oil.

$^1$H-NMR (CDCl$_3$) of A: δ=0.89 (3H), 1.04 (3H), 1.09 (3H), 1.19-1.94 (8H), 1.33 (3H), 1.70 (3H), 2.07 (3H), 2.15-2.33 (2H), 2.38 (1H), 2.44-2.74 (3H), 2.70 (3H), 3.23 (1H), 3.62 (1H), 3.72 (1H), 4.24 (1H), 5.12 (1H), 5.22 (1H), 6.57 (1H), 6.95 (1H) ppm.

$^1$H-NMR (CDCl$_3$) of B: δ=0.84 (3H), 1.01 (6H), 1.29 (3H), 1.38-2.00 (8H), 1.61 (3H), 2.07 (3H), 2.20 (1H), 2.22-2.50 (3H), 2.58 (1H), 2.70 (3H), 3.37 (1H), 3.73 (1H), 4.02 (1H), 4.12 (1H), 4.41 (1H), 5.05 (1H), 5.38 (1H), 6.57 (1H), 6.99 (1H) ppm.

EXAMPLE 2

(1S,3S(E),7S,10R,11S,12S,16R)-7,11-Dihydroxy-3-(1-methyl-2-(2-methyl-4-thiazolyl)ethenyl)-10-ethyl-8,8,12,16-tetramethyl-4,17-dioxabicyclor[14.1.0]heptadecane-5,9-dione (A) and (1R,3S(E),7S,10R,11S,12S,16S)-7,11-dihydroxy-3-(1-methyl-2-(2-methyl-4-thiazolyl)ethenyl)-10-ethyl-8,8,12,16-tetramethyl-4,17-dioxabicyclo[14.1.0]heptadecane-5,9-dione (B)

The solution of 10 mg (19 µmol) of compound A, presented according to Example 1, in 1 ml of dichloromethane is mixed under an atmosphere of dry argon at –10° C. with 10 mg of an approximately 80% meta-chloroperbenzoic acid, and it is stirred for 4 hours at 0° C. It is poured into a saturated sodium bicarbonate solution, extracted with dichloromethane, and the organic phase is dried on sodium sulfate. After filtration and removal of the solvent, the residue is purified by repeated chromatography on analytic thin-layer plates. As a mobile solvent, mixtures of n-hexane and ethyl acetate as well as dichloromethane and methanol are used; as an eluant, ethyl acetate is used. 4.5 mg (8.4 µmol, 44%) of title compound A and 1 mg (1.9 µmol, 10%) of title compound B are used as colorless foams.

$^1$H-NMR (CDCl$_3$) of A: δ=0.86 (3H), 1.00 (3H), 1.05 (3H), 1.28 (3H), 1.33-2.12 (10H), 1.38 (3H), 2.11 (3H), 2.41 (1H), 2.57 (1H), 2.70 (3H), 2.77-2.85 (2H), 3.38 (1H), 3.49 (1H), 3.67 (1H), 4.27 (1H), 4.56 (1H), 5.46 (1H), 6.57 (1H), 6.97 (1H) ppm.

$^1$H-NMR (CDCl$_3$) of B: δ=0.85 (3H), 0.95 (3H), 1.03 (3H), 1.22-1.73 (10H), 1.30 (3H), 1.38 (3H), 2.08 (1H), 2.61 (3H), 2.41-2.59 (2H), 2.71 (3H), 2.91 (1H), 2.99 (1H), 3.24 (1H), 3.43 (1H), 3.96 (1H), 4.30 (1H), 5.60 (1H), 6.60 (1H), 6.98 (1H) ppm.

EXAMPLE 3

(1R,3S(E),7S,10R,11S,12S,16R)-7,11-Dihydroxy-3-(1-methyl-2-(2-methyl-4-thiazolyl)ethenyl)-10-ethyl-8,8,12,16-tetramethyl-4,17-dioxabicyclo[14.1.0]heptadecane-5,9-dione (A) and (1S,3S(E),7S,10R,11S,12S,16S)-7,11-dihydroxy-3-(1-methyl-2-(2-methyl-4-thiazolyl)ethenyl)-10-ethyl-8,8,12,16-tetramethyl-4,17-dioxabicyclor[4.1.0]heptadecane-5,9-dione (B)

Analogously to Example 2, 10 mg (19 µmol) of compound B that is presented according to Example 1 is reacted, and after working-up and purification, 6 mg (11 µmol, 59%) of a mixture of the two title compounds is isolated as a colorless foam.

$^1$H-NMR (CDCl$_3$) of A or B: δ=0.86 (3H), 0.96 (3H), 1.03 (3H), 1.06-2.08 (1H), 1.28 (3H), 1.38 (3H), 2.09 (3H), 2.46-2.59 (2H), 2.70 (3H), 2.87 (1H), 3.02 (1H), 3.33 (1H), 3.79 (1H), 4.22 (1H), 4.34 (1H), 5.49 (1H), 6.65 (1H), 7.00 (1H) ppm.

$^1$H-NMR (CDCl$_3$) of B or A: δ=0.86 (3H), 0.96 (3H), 1.09 (3H), 1.21-1.94 (9H), 1.25 (3H), 1.37 (3H), 2.03 (2H), 2.09 (3H), 2.50-2.61 (2H), 2.71 (3H), 2.87 (1H), 2.94 (1H), 3.28 (1H), 3.67 (1H), 3.72 (1H), 4.27 (1H), 5.46 (1H), 6.59 (1H), 6.97 (1H) ppm.

EXAMPLE 4

(4S,7S,8R,9S,13Z,16S(E))-4,8-Dihydroxy-7-ethyl-16-(1-methyl-2-(2-methyl-4-thiazolyl)ethenyl)-1-oxa-5,5,9,13-tetramethyl-cyclohexadec-13-ene-2,6-dione (A) and (4S,7S,8R,9S,13E,16S(E))-4,8-dihydroxy-7-ethyl-16-(1-methyl-2-(2-methyl-4-thiazolyl)ethenyl)-1-oxa-5,5,9,13-tetramethyl-cyclohexadec-13-ene-2,6-dione (B)

Diastereomeric compound B that is produced according to Example 1ak is reacted analogously to Examples 1al to 1aw and 1 to title compounds A and B.

EXAMPLE 5

(1S,3S(E),7S,10S,11R,12S,16R)-7,11-Dihydroxy-3-(1-methyl-2-(2-methyl-4-thiazolyl)ethenyl)-10-ethyl-8,8,12,16-tetramethyl-4,17-dioxabicyclo[14.1.0]heptadecane-5,9-dione (A) and (1R,3S(E),7S,10S,11R,12S,16S)-7,11-dihydroxy-3-(1-methyl-2-(2-methyl-4-thiazolyl)ethenyl)-10-ethyl-8,8,12,16-tetramethyl-4,17-dioxabicyclo[14.1.0]heptadecane-5,9-dione (B)

Analogously to Example 2, Compound A that is produced according to Example 4 is reacted to separable title compounds A and B.

EXAMPLE 6

(1S,3S(E),7S,10,S,11R,12S,16R)-7,11-Dihydroxy-3-(1-methyl-2-(2-methyl-4-thiazolyl)ethenyl)-10-ethyl-8,8,12,16-tetramethyl-4,17-dioxabicyclo[14.1.0]heptadecane-5,9-dione and (1R,3S(E),7S,10S,11R,12S,16S)-7,11-dihydroxy-3-(1-methyl-2-(2-methyl-4-thiazolyl)ethenyl)-10-ethyl-8,8,12,16-tetramethyl-4,17-dioxabicyclo[14.1.0]heptadecane-5,9-dione Compound B that is produced according to Example 4 is reacted analogously to Example 2 in a mixture of title compounds.

EXAMPLE 7

(4S,7R,8S,9S,13(Z),16S(E))-4,8-Dihydroxy-5,5,7,9,13-pentamethyl-16-((3-pyridyl)ethenyl)-1-oxa-cyclohexadec-13-ene-2,6-dione (A) and (4S,7R,8S,9S,13E,16S(E))-4,8-dihydroxy-5,5,7,9,13-pentamethyl-16-((3-pyridyl)ethenyl)-1-oxa-cyclohexadec-13-ene-2,6-dione (B)

EXAMPLE 7a (Z,3S)-1-[[Dimethyl(1,1-dimethylethyl)silyl]oxy]-3-[[(1,1-dimethylethyl)diphenylsilyl]oxy]-4-methyl-5-(3-pyridyl)-pent-4-ene (A) and (E,3S)-1-[[dimethyl(1,1-dimethylethyl)silyl]oxy]-3-[[(1,1-dimethylethyl)diphenylsilyl]oxy]-4-methyl-5-(3-pyridyl)-pent-4-ene (B)

Analogously to Example 1af, 4.8 g (10.2 mmol) of the compound that is presented according to Example 1ae is reacted with use of diethyl(3-pyridyl)methanephosphonate, and after working-up and purification, 448 mg (0.82 mmol, 8%) of title compound A and 3.5 g (6.41 mmol, 63%) of title compound B are isolated in each case as a colorless oil.

$^1$H-NMR (CDCl$_3$) of A: δ=−0.06 (6H), 0.81 (9H), 1.01 (9H), 1.75 (1H), 1.97 (4H), 3.48 (2H), 4.83 (1H), 6.11 (1H), 6.97 (1H), 7.11-7.30 (5H), 7.30-7.39 (2H), 7.39-7.50 (4H), 8.08 (1H), 8.33 (1H) ppm.
$^1$H-NMR (CDCl$_3$) of B: δ=−0.01 (6H), 0.85 (9H), 1.11 (9H), 1.78 (3H), 1.83 (1H), 1.97 (1H), 3.58 (2H), 4.42 (1H), 6.03 (1H), 7.21 (1H), 7.28-7.50 (7H), 7.62-7.75 (4H), 8.29 (1H), 8.41 (1H) ppm.

EXAMPLE 7b (E,3S)-3-[[(1,1-Dimethylethyl)diphenylsilyl]oxy]-4-methyl-5-(3-pyridyl)-pent-4-en-1-ol Analogously to Example 1ag, 3.5 g (6.41 mmol) of the compound that is produced under Example 7aB is reacted with a 65:35:10 mixture of glacial acetic acid/water/tetrahydrofuran. After purification, 2.1 g (4.86 mmol, 76%) is obtained.

$^1$H-NMR (CDCl$_3$): δ=1.12 (9H), 1.75 (3H), 1.88 (2H), 3.65 (2H), 4.45 (1H), 6.25 (1H), 7.21 (1H), 7.28-7.50 (7H), 7.60-7.75 (4H), 8.30 (1H), 8.44 (1H) ppm.

EXAMPLE 7c (E,3S)-1-Iodo-3-[[(1,1-Dimethylethyl)diphenylsilyl]oxy]-4-methyl-5-(3-pyridyl)-pent-4-ene Analogously to Example 1ah, 1.98 g (3.66 mmol, 75%) of the title compound is obtained from 2.1 g (4.86 mmol) of the compound that is described under Example 7b.

$^1$H-NMR (CDCl$_3$): δ=1.11 (9H), 1.78 (3H), 2.17 (2H), 3.03 (2H), 4.29 (1H), 6.19 (1H), 7.22 (1H), 7.30-7.50 (7H), 7.63-7.75 (4H), 8.32 (1H), 8.44 (1H) ppm.

EXAMPLE 7d (5E,3S)-[3-[[(1,1-Dimethylethyl)diphenylsilyl]oxy]-4-methyl-5-(3-pyridyl)-pent-4-en-1-yl]-triphgenylphosphonium Iodide Analogously to Example 1ai, 2.35 g (2.93 mmol, 80%) of the title compound is obtained from 1.98 g (3.66 mmol) of the compound that is described under Example 7c.

$^1$H-NMR (CDCl$_3$): δ=1.08 (9H), 1.80 (3H), 3.27 (1H), 3.56 (1H), 4.66 (1H), 6.52 (1H), 7.25-7.90 (27H), 8.35 (1H), 8.46 (1H) ppm.

EXAMPLE 7e (4S(4R,5S,6S,10E/Z,13S,14E))-4-(13-[[(1,1-Dimethylethyl)diphenylsilyl]oxy]-2,4,6,10,14-pentamethyl-15-(3-pyridyl)-3-oxo-5-(tetrahydropyran-2-yloxy)-pentadeca-10,14-dien-2-yl)-2,2-dimethyl-[1,3]dioxane Analogously to Example 1ao, 800 mg (1.76 mmol) of the compound (4S(4R,5S,6S))-4-(3,10-dioxo-2,4,6-trimethyl-5-(tetrahydropyran-2-yloxy)-undec-2-yl)-2,2-dimethyl-[1,3]dioxane that is produced analogously to Examples 11 (reaction with ethylmagnesium bromide) to 1an is reacted with 4.24 g (5.28 mmol) of the compound that is described under Example 7d, and 5.44 ml of a 1 M solution of sodium-bis-(trimethylsilyl)-amide in tetrahydrofuran. 684 mg (0.79 mmol, 45%) of the title compound is obtained.

$^1$H-NMR (CDCl$_3$): δ=0.86-0.98 (3H), 0.98-1.94 (45H), 2.20-2.42 (2H), 3.22 (1H), 3.42 (1H), 3.58-4.02 (4H), 4.08-

4.22 (2H), 4.46+4.52 (1H), 5.00 (1H), 6.03 (1H), 7.19 (1H), 7.24-7.47 (7H), 7.60-7.73 (4H), 8.28+8.40 (2H) ppm.

EXAMPLE 7f (3S,6R,7S,8S,12E/Z,15S,16E)-15-[[(1,1-Dimethylethyl)diphenylsilyl]oxy]-4,4,6,8,12,16-hexamethyl-17-(3-pyridyl)-5-oxo-heptadeca-12,16-diene-1,3,7-triol Analogously to Example 1ap, 542 mg (0.73 mmol, 92%) of the title compound is obtained from 684 mg (0.79 mmol) of the compound that is described under Example 7e.

EXAMPLE 7g (3S,6R,7S,8S,12E/Z,15S,16E)-15-[[(1,1-Dimethylethyl)-diphenylsilyl]oxy]-4,4,6,8,12,16-hexamethyl-17-(3-pyridyl)-1,3,7-tris-[[dimethyl(1,1-dimethylethyl)silyl]oxy]-heptadeca-12,16-dien-5-one Analogously to Example 1aq, 995 mg (max. 0.73 mmol, max. 100%) of the title compound, which is contaminated with silanol, is obtained from 542 mg (0.73 mmol) of the compound that is described under Example 7f.

EXAMPLE 7h (3S,6R,7S,8S,12E/Z,15S,16E)-3,7-Bis-[[dimethyl(1,1-dimethylethyl)silyl]oxy]-15-[[(1,1-dimethylethyl)-diphenylsilyl]oxy]-1-hydroxy-4,4,6,8,12,16-hexamethyl-17-(3-pyridyl)-heptadeca-12,16-dien-5-one Analogously to Example 1ar, 604 mg (0.62 mmol, 85%) of the title compound is obtained from 995 mg (max. 0.73 mmol) of the compound that is described under Example 7g.

EXAMPLE 7i (3S,6R,7S,8S,12E/Z,15S,16E)-3,7-Bis-[[dimethyl(1,1-dimethylethyl)silyl]oxy]-15-[[(1,1-dimethylethyl)diphenylsilyl]oxy]-4,4,6,8,12,16-hexamethyl-17-(3-pyridyl)-5-oxo-heptadeca-12,16-dienoic acid Analogously to Examples 1as and 1at, 550 mg (0.56 mmol, 90%) of the title compound is obtained from 604 mg (0.62 mmol) of the compound that is described under Example 7h.

EXAMPLE 7k (3S,6R,7S,8S,12E/Z,15S,16E)-4,4,6,8,12,16-Hexamethyl-17-(3-pyridyl)-5-oxo-3,7,15-trihydroxy-heptadeca-12,16-dienoic acid Analogously to Example 1au, 269 mg (0.49 mmol, 88%) of the title compound is obtained from 550 mg (0.56 mmol) of the compound that is described under Example 7i.

EXAMPLE 7l (3s,6R,8s,12E/Z,15S,16E)-3,7-Bis[[dimethyl(1,1-dimethylethyl)silyl]oxy]-4,4,6,8,12,16-hexamethyl-15-hydroxy-17-(3-pyridyl)-5-oxy-heptadeca-12,16-dienoic acid Analogously to Example 1av, 127 mg (0.17 mmol, 35%) of the title compound is obtained from 269 mg (0.49 mmol) of the compound that is described under Example 7k.

Alternative Production of 7l over 7n to 7r:

EXAMPLE 7n (4S(4R,5S,6S,10E/Z,13S,14E))-4-(13-Hydroxy-2,4,6,10,14-pentamethyl-15-(3-pyridinyl)-3-oxo-5-(tetrahydropyran-2-yloxy)-pentadeca-10,14-dien-2-yl)-2,2-dimethyl-[1,3]dioxane Analogously to Example 1i, 486 mg (0.81 mmol, 95%) of the title compound is obtained from 710 mg (0.85 mmol) of the compound that is described under 7e.

$^1$H-NMR (CDCl$_3$): δ=0.90-1.00 (3H), 1.05-1.90 (36H), 2.38 (2H), 3.27 (1H), 3.46 (1H), 3.63+3.80-4.00 (4H), 4.10-4.20 (2H) 4.46+4.55 (1H), 5.15 (1H), 6.49 (1H), 7.24 (1H), 7.57 (1H), 8.47 (1H), 8.54 (1H) ppm.

EXAMPLE 7o (3S,6R,7S,8S,12E/Z,15S,16E)-4,4,6,8,12,16-Hexamethyl-17-(3-pyridyl)-1,3,7,15-tetra-hydroxy-heptadeca-12,16-dien-5-one Analogously to Example 1f, 335 mg (0.71 mmol, 87%) of the title compound is obtained from 486 mg (0.81 mmol) of the compound that is described under 7n.

$^1$H-NMR (CDCl$_3$): δ=0.82+0.86 (3H), 1.08+1.10 (3H), 1.13 (3H), 1.22 (3H), 1.68+1.72 (3H), 1.90 (3H), 2.40 (2H), 3.30 (1H), 3.35-3.48 (2H), 3.85-3.96 (2H), 4.17 (1H), 4.20 (1H), 5.05 (1H), 6.50 (1H), 7.25 (1H), 7.61 (1H), 8.45 (1H), 8.53 (1H) ppm.

EXAMPLE 7p (3S,6R,7S,8S,12E/Z,15S,16E)-3,7,15-Tris-[[dimethyl(1,1-dimethylethyl)silyl]oxy]-1-hydroxy-4,4,6,8,12,16-hexamethyl-17-(3-pyridyl)-heptadeca-12,16-dien-5-one Analogously to Example 1aq, 730 mg (max. 0.71 mmol, max. 100%) of the title compound, which is contaminated with silanol, is obtained from 335 mg (0.71 mmol) of the compound that is described under 7o.

$^1$H-NMR (CDCl$_3$): δ=0.05-1.16 (24H), 0.85-0.97 (39H), 1.02+1.04+1.07 (6H), 1.22 (3H), 1.60 (3H), 1.70+1.83 (3H), 2.29 (1H), 3.13 (1H), 3.05-3.80 (2H), 3.76 (1H), 3.89 (1H), 4.11 (1H), 5.13 (1H), 6.46 (1H), 7.23 (1H), 7.54 (1H), 8.42 (1H), 8.50 (1H) ppm.

EXAMPLE 7q (3S,6R,7S,8S,12E/Z,15S,16E)-3,7,15-Tris-[[dimethyl(1,1-dimethylethyl)silyl]oxy]-1-hydroxy-4,4,6,8,12,16-hexamethyl-17-(3-pyridyl)-heptadeca-12,16-dien-5-one Analogously to Example 1ar, 441 mg (0.54 mmol, 76%) of the title compound is obtained from 730 mg (max. 0.71 mmol) of the compound that is described under 7p.

$^1$H-NMR (CDCl$_3$): δ=0.05-0.18 (18H), 0.90-1.10 (30H), 1.11 (6H), 1.25 (3H), 1.62+1.70 (3H), 1.82 (3H), 2.38 (1H), 3.13 (1H), 3.63 (2H), 3.81 (1H), 4.05-4.15 (2H), 5.17 (1H), 6.38 (1H), 7.22 (1H), 7.53 (1H), 8.45 (1H), 8.52 (1H) ppm.

EXAMPLE 7r (3S,6R,7S,8S,12E/Z,15S,16E)-3,7,15-Tris-[[dimethyl(1,1-dimethylethyl)silyl]oxy]-4,4,6,8,12,16-hexamethyl-17-(3-pyridyl)-5-oxo-heptadeca-12,16-dienoic Acid Analogously to Examples 1as and 1at, 316 mg (0.38 mmol, 70%) of the title compound is obtained from 441 mg (0.38 mmol) of the compound that is described under 7q.

$^1$H-NMR (CDCl$_3$): δ=0.00-0.18 (18H), 0.90-1.00 (30H), 1.12 (3H), 1.13+1.14 (3H), 1.19 (3H), 1.62+1.70 (3H), 1.79+1.80 (3H), 3.18 (1H), 3.75+3.80 (1H), 4.19 (1H), 4.44+4.48 (1H), 5.12+5.14 (1H), 6.32+6.35 (1H), 7.30 (1H), 7.60+7.62 (1H), 8.38+8.40 (1H), 8.58 ppm.

EXAMPLE 7l (3S,6R,8S,12E/Z,15S,16E)-3,7-Bis[[dimethyl(1,1-dimethylethyl)silyl]oxy]-4,4,6,8,12,16-hexamethyl-15-hydroxy-17-(3-pyridyl)-5-oxy-heptadeca-12,16-dienoic Acid Analogously to Example 1i, 295 mg (max. 0.38 mmol, max. 100%) of the title compound is obtained from 316 mg (0.38 mmol) of the compound that is described under 7r.

$^1$H-NMR (CDCl$_3$): δ=0.00-0.18 (12H), 0.88-1.00 (21H), 1.10 (3H), 1.15 (3H), 1.18 (3H), 1.63+1.70 (3H), 1.84+1.86 (3H), 2.30-2.50 (3H), 3.10 (1H), 3.75+3.78 (1H), 4.20+4.25 (1H), 4.45 (1H), 5.14 (1H), 6.49 (1H), 7.33 (1H), 7.68 (1H), 8.41 (1H), 8.60 (1H) ppm.

EXAMPLE 7m (4S,7R,8S,13E/Z,16S(E))-4,8-Bis-[[dimethyl(1,1-dimethylethyl)silyl]oxy]-4,4,6,8,12,16-hexamethyl-16-((3-prydiyl)ethenyl)1-oxa-cyclohexadec-13-ene-2,6-dione Analogously to Example 1aw, 104 mg (0.14 mmol, 85%) of the title compound is obtained from 127 mg (0.17 mmol) of the compound that is described under Example 7l.

$^1$H-NMR (CDCl$_3$): δ=−0.05-0.13 (12H), 0.82-1.00 (21H), 1.12 (3H), 1.15 (3H), 1.23 (3H), 1.60+1.69 (3H), 1.90+1.92 (3H), 2.40-2.60 (4H), 3.02 (1H), 3.88+3.90 (1H), 4.10 (1H), 4.48 (1H), 5.07+5.14 (1H), 5.18+5.25 (1H), 6.47+6.50 (1H), 7.25 (1H), 7.55+7.60 (1H), 8.45 (1H), 8.50+8.53 (1H) ppm.

EXAMPLE 7

(4S,7R,8S,9S,13Z,16S(E))-4,8-Dihydroxy-5,5,7,9,13-pentamethyl-16-((3-pyridyl)ethenyl)-1-oxa-cyclohexadec-13-ene-2,6-dione (A) and (4S,7R,8S,9S,13E,16S(E))-4,8-dihydroxy-5,5,7,9,13-pentamethyl-16-((3-pyridyl)ethenyl)-1-oxa-cyclohexadec-13-ene-2,6-dione (B)

Analogously to Example 1, 24 mg (48 μmol, 34%) of title compound A and 25 mg (50 μmol, 36%) of title compound B are obtained from 104 mg (0.14 mmol) of the compound that is described under Example 7m.

$^1$H-NMR (CDCl$_3$) Compound A: δ=1.03 (3H), 1.10 (3H), 1.21 (3H), 1.32 (3H), 1.62 (3H), 1.92 (3H), 2.18-2.80 (6H), 3.14 (1H), 3.73 (1H), 4.16 (1H), 5.17 (1H), 5.29 (1H), 6.51 (1H), 7.25 (1H) 7.58 (1H), 8.47 (1H), 8.53 (1H) ppm.

Compound A: δ=1.00 (3H), 1.05 (3H), 1.16 (3H), 1.30 (3H), 1.63 (3H), 1.91 (3H), 2.18-2.65 (6H), 3.22 (1H), 3.65 (1H), 4.20 (1H), 5.11 (1H), 5.43 (1H), 6.49 (1H), 7.27 (1H), 7.59 (1H), 8.49 (1H), 8.52 (1H) ppm.

EXAMPLE 8

(1S,3S(E),7S,10R,11S,12S,16R)-7,11-Dihydroxy-8,8,10,12,16-pentamethyl-3-((3-pyridyl)ethenyl)-4,17-dioxabicyclo[14.1.0]heptadecane-5,9-dione (A) and (1S,3S(E),7S,11R,11S,12S,16S)-7,11-dihydroxy-8,8,10,12,16-pentamethyl-3-((3-pyridyl)ethenyl)-4,17-dioxabicyclo[14.1.0]heptadecane-5,9-dione (B) and (1S,3S(E),7S,10R,11S,12S,16R)-7,11-dihydroxy-8,8,10,12,16-pentamethyl-3-((3-N-oxypyridyl)ethenyl)-4,17-dioxabicyclor[14.1.0]heptadecane-5,9-dione (C) and (1S,3S(E),7S,10R,11S,12S,16S)-7,11-dihydroxy-8,8,10,12,16-pentamethyl-3-((3-N-oxypyridyl)ethenyl)-4,17-dioxabicyclor[14.1.0]heptadecane-5,9-dione (D)

Analogously to Example 2, 7.4 mg (14 μmol, 46%) of title compound A, 1.6 mg (3 μmol, 10%) of title compound B, 2.4 mg of title compound C and 0.9 mg (4.4 mmol, 15%) of title compound D (1.7 mg, 6%) are obtained from 15 mg (30 μmol) of the compound that is described under Example 7.

$^1$H-NMR (CDCl$_3$): Compound C: δ=1.03 (3H), 1.10 (3H), 1.17 (3H), 1.28 (3H), 1.22 (3H), 1.91 (3H), 2.40-2.63 (3H), 2.79 (1H), 3.33 (1H), 3.68 (1H), 3.77 (1H), 4.12 (3H), 5.46 (1H), 6.46 (1H), 7.18 (1H), 7.25 (1H), 8.11 (1H), 8.18 (1H) ppm.

Compound D: δ=0.97 (3H), 1.10 (3H), 1.13 (3H), 1.28 (3H), 1.40 (3H), 1.95 (3H), 2.50 (1H), 3.12 (1H), 3.34 (1H), 3.80 (1H), 4.08 (1H), 4.16 (1H), 5.69 (1H), 6.47 (1H), 7.17 (1H), 7.26 (1H), 8.11 (1H), 8.18 (1H) ppm.

EXAMPLE 9

(4S,7R,8S,9S,13(Z),16S(E))-4,8-Dihydroxy-5,5,7,9,13-pentamethyl-16-((4-pyridyl)ethenyl)-1-oxa-cyclohexadec-13-ene-2,6-dione (A) and (4S,7R,8S,9S,13E,16S(E))-4,8-dihydroxy-5,5,7,9,13-pentamethyl-16-((4-pyridyl)ethenyl)-1-oxa-cyclohexadec-13-ene-2,6-dione (B)

EXAMPLE 9a (4S(4R,5S,6S,10E/Z,13S,14E))-4-(13-[[(1,1-Dimethylethyl)diphenylsilyl]oxy]-2,4,6,10,14-pentamethyl-15-(4-pyridyl)-3-oxo-5-(tetrahydropyran-2-yloxy)-pentadeca-10,14-dien-2-yl)-2,2-dimethyl-[1,3]dioxane Analogously to Example 7e, 2.08 g (4.70 mmol) of the compound (4S(4R,5S,6S))-4-(3,10-dioxo-2,4,6-trimethyl-5-(tetrahydropyran-2-yloxy)-undec-2-yl)-2,2-dimethyl-[1,3]dioxane that is produced analogously to Examples 1l (reaction with ethylmagnesium bromide) to 1an is reacted with 11.4 g (14.2 mmol) of (5E,3S)-[3-[[(1,1-dimethylethyl)diphenylsilyl]oxy]-4-methyl-5-(4-pyridyl)-pent-4-en-1-yl]-triphenylphosphonium iodide, which has been produced analogously to Examples 7a to 7d using diethyl(4-pyridyl)methanephosphonate. After working-up and purification, 2.10 g (2.5 mmol, 53%) of the title compound is isolated.

$^1$H-NMR (CDCl$_3$): δ=0.81-1.95 (49H), 2.20-2.42 (2H), 3.23 (1H), 3.42 (1H), 3.58-4.02 (3H), 4.06-4.21 (2H), 4.46+4.52 (1H), 4.99 (1H), 6.03 (1H), 6.94 (2H), 7.22-7.48 (6H), 7.59-7.73 (4H), 8.49 (2H) ppm.

EXAMPLE 9b (4S(4R,5S,6S,10E/Z,13S,14E))-4-(13-Hydroxy-2,4,6,10,14-pentamethyl-15-(4-pyridyl)-3-oxo-5-(tetrahydropyran-2-yloxy)-pentadeca-10,14-dien-2-yl)-2,2-dimethyl-[1,3]dioxane Analogously to Example 1i, 550 mg (0.91 mmol, 98%) of the title compound is obtained from 780 mg (0.93 mmol) of the compound that is described under Example 9a.

$^1$H-NMR (CDCl$_3$): δ=0.80-1.85 (33H), 1.91 (3H), 1.94-2.11 (5H), 2.36 (2H), 3.27 (1H), 3.43 (1H), 3.61-4.01 (3H), 4.08-4.21 (2H), 4.46+4.54 (1H), 5.16 (1H), 6.48 (1H), 7.18 (2H), 8.55 (2H) ppm.

EXAMPLE 9c (3S,6R,7S,8S,12E/Z,15S,16E)-4,4,6,8,12,16-Hexamethyl-17-(4-pyridyl)-1,3,7,15-tetra-hydroxy-heptadeca-12,16-dien-5-one Analogously to Example 1f, 340 mg (0.71 mmmol, 71%) of the title compound is obtained from 600 mg (1.00 mmol) of the compound that is described under Example 9b with use of p-toluenesulfonic acid.

$^1$H-NMR (CDCl$_3$): δ=0.82 (3H), 1.06 (3H), 1.12 (3H), 1.22 (3H), 1.73 (3H), 0.90-1.83 (9H), 1.91 (3H), 1.95-2.13 (3H), 2.30-2.47 (2H), 3.19-3.35 (2H), 3.42 (1H), 3.81-3.97 (2H), 4.04 (1H), 4.19 (1H), 5.18 (1H), 6.46 (1H), 7.18 (2H), 8.52 (2H) ppm.

EXAMPLE 9d (3S,6R,7S,8S,12E/Z,15S,16E)-3,7,15-Tris-[[dimethyl(1,1-dimethylethyl)silyl]oxy]-1-hydroxy-4,4,6,8,12,16-hexamethyl-17-(4-pyridyl)-heptadeca-12,16-dien-5-one Analogously to Example 1aq, 435 mg (0.47 mmol, 74%) of the title compound is obtained from 300 mg (0.63 mmol) of the compound that is described under Example 9c.

$^1$H-NMR (CDCl$_3$): δ=−0.01-0.14 (24H), 0.82-0.97 (37H), 1.02 (3H), 1.04 (3H), 1.21 (3H), 0.98-1.70 (12H), 1.87 (3H), 1.90-2.03 (2H), 2.25 (2H), 3.13 (1H), 3.51-3.71 (2H), 3.76 (1H), 3.88 (1H), 4.03-4.14 (1H), 5.13 (1H), 6.34 (1H), 7.13 (2H), 8.52 (2H) ppm.

EXAMPLE 9e (3S,6R,7S,8S,12E/Z,15S,16E)-3,7,15-Tris-[[dimethyl(1,1-dimethylethyl)silyl]oxy]-1-hydroxy-4,4,6,8,12,16-hexamethyl-17-(4-pyridyl)-heptadeca-12,16-dien-5-one Analogously to Example 1ar, 339 mg (0.41 mmol, 94%) of the title compound is obtained from 410 mg (0.44 mmol) of the compound that is described under Example 9d.

$^1$H-NMR (CDCl$_3$): δ=−0.01-0.14 (18H), 0.80-0.95 (31H), 0.97-1.70 (7H), 1.06 (6H), 1.21 (3H), 1.59+1.69 (3H), 1.87 (3H), 1.90-2.06 (2H), 2.26 (2H), 3.12 (1H), 3.65 (2H), 3.80 (1H), 4.09 (2H), 5.14 (1H), 6.36 (1H), 7.13 (2H), 8.53 (2H) ppm.

EXAMPLE 9f (3S,6R,7S,8S,12E/Z,15S,16E)-3,7,15-Tris-[[dimethyl(1,1-dimethylethyl)silyl]oxy]-4,4,6,8,12,16-hexamethyl-17-(4-pyridyl)-5-oxo-heptadeca-12,16-dienoic Acid Analogously to Examples 1as and 1at, 204 mg (0.25 mmol, 72%) of the title compound is obtained from 280 mg (0.34 mmol) of the compound that is described under Example 9e.

$^1$H-NMR (CDCl$_3$): δ=0.00-0.14 (18H), 0.78-0.98 (30H), 1.06 (3H), 1.08 (3H), 1.24 (3H), 1.05-1.55 (5H), 1.60+1.69 (3H), 1.87 (3H), 1.98 (2H), 2.20-2.37 (3H), 2.10-3.10 (1H), 2.51 (1H), 3.14 (1H), 3.79 (1H), 4.11 (1H), 4.40 (1H), 5.13 (1H), 6.36 (1H), 7.17 (2H), 8.53 (2H) ppm.

EXAMPLE 9g (3S,6R,8S,12E/Z,15S,16E)-3,7-Bis[[dimethyl(1,1-dimethylethyl)silyl]oxy]-4,4,6,8,12,16-hexamethyl-15-hydroxy-17-(4-pyridyl)-5-oxy-heptadeca-12,16-dienoic Acid Analogously to Example 1av, 132 mg (0.18 mmol, 77%) of the title compound is obtained from 198 mg (0.24 mmol) of the compound that is described under Example 9f.

$^1$H-NMR (CDCl$_3$): δ=0.00-0.15 (12H), 0.85-1.00 (18H), 1.10-1.18 (6H), 1.20-1.28 (6H), 1.62+1.73 (3H), 2.05 (1H), 2.20-2.50 (4H), 2.85 (1H), 3.15 (1H), 3.79 (1H), 4.18 (1H), 4.42 (1H), 5.18 (1H), 6.50 (1H), 7.15-7.25 (2H), 8.50-8.60 (2H) ppm.

EXAMPLE 9h (4S,7R,8S,13E/Z,16S(E))-4,8-Bis-[[dimethyl(1,1-dimethylethyl)silyl]oxy]-4,4,6,8,12,16-hexamethyl-16-((4-pyridyl)ethenyl)l-oxa-cyclohexadec-13-ene-2,6-dione Analogously to Example 1aw, 98 mg (0.14 mmol, 76%) of the title compound is obtained from 130 mg (0.18 mmol) of the compound that is described under Example 9g.

EXAMPLE 9

(4S,7R,8S,9S,13Z,16S(E))-4,8-Dihydroxy-5,5,7,9,13-pentamethyl-16-((4-pyridyl)ethenyl)-1-oxa-cyclohexadec-13-ene-2,6-dione (A) and (4S,7R,8S,9S,13E,16S(E)))-4,8dihydroxy-5,5,7,9,13-pentamethyl-16-((4-pyridyl)ethenyl)-1-oxa-cyclohexadec-13-ene-2,6-dione (B)

Analogously to Example 1, 24 mg (49 μmol, 35%) of title compound A and 21 mg (43 μmol, 31%) of title compound B are obtained from 98 mg (0.14 mmol) of the compound that is described under Example 9h.

EXAMPLE 10

(1S,3S(E),7S,10R,11S,12S,16R)-7,11-Dihydroxy-8,8,10,12,16-pentamethyl-3-((4-pyridyl)ethenyl)-4,17-dioxabicyclo[14.1.0]heptadecane-5,9-dione (A) and (1S,3S(E),7S,10R,11S,12S,16S)-7,11-dihydroxy-8,8,10,12,16-pentamethyl-3-((4-pyridyl)ethenyl)-4,17-dioxabicyclo[14.1.0]heptadecane-5,9-dione (B)

Analogously to Example 2, 11 mg (22 μmol, 59%) of title compound A is obtained from 18 mg (37 μmol) of compound A that is described under Example 9, or 9 mg (18 µmol, 58%) of title compound B is obtained from 15 mg (31 µmol) of compound B.

EXAMPLE 11

(1S,3S(E),7S,10R,11S,12S,16R)-7,11-Dihydroxy-3-(1-methyl-2-(3-N-oxido-2-methyl-4-thiazolyl)ethenyl)-10-ethyl-8,8,12,16-tetramethyl-4,17-dioxabicyclo[14.1.0]heptadecane-5,9-dione Analogously to Example 2, 10 mg (19 µmol) of compound A that is presented according to Example 2 is reacted at 23° C., and after working-up and purification, 3.5 mg (6.5 µmol, 34%) of the title compound is isolated as a colorless oil.

$^1$H-NMR (CDCl$_3$): δ=0.90 (3H), 1.03 (3H), 1.07 (3H), 1.10-2.03 (9H), 1.31 (3H), 1.43 (3H), 2.03 (1H), 2.09 (3H), 2.19-2.26 (2H), 2.52 (1H), 2.61 (3H), 2.68-2.81 (2H), 3.34 (1H), 3.65 (1H), 4.59 (1H), 5.39 (1H), 6.61 (1H), 6.81 (1H), 7.08 (1H) ppm.

EXAMPLE 12

(4S,7R,8S,9S,13Z,16S(E))-4,8-Dihydroxy-7-benzyl-16-(1-methyl-2-(2-methyl-4-thiazolyl)ethenyl)-1-oxa-5,5,9,13-tetramethyl-cyclohexadec-13-ene-2,6-dione

EXAMPLE 12a (4S)-4-((3RS)-2-Methyl-3-hydroxy-5-phenyl-pent-2-yl)-2,2-dimethyl-[1,3]dioxane Analogously to Example 11, 2.97 g (15.9 mmol) of the compound that is presented according to Example 1k is reacted with use of phenethylmagnesium bromide, and after working-up and purification, 3.27 g (11.2 mmol, 70%) of the title compound is isolated as a colorless oil.

$^1$H-NMR (CDCl$_3$): δ=0.72+0.88 (3H), 0.89+0.93 (3H), 1.33 (1H), 1.39+1.42 (3H), 1.47+1.50 (3H), 1.58-1.93 (3H), 2.61 (1H), 3.00 (1H), 3.48-3.60 (1H), 3.72-4.03 (4H), 7.13-7.35 (5H) ppm.

EXAMPLE 12b (4S)-4-(2-Methyl-3-oxo-5-phenyl-pent-2-yl)-2,2-dimethyl-[1,3]dioxane Analogously to Example 1m, 2.71 g (9.3 mmol) of the compound that is presented according to Example 12a is reacted, and after working-up and purification, 2.35 g (8.1 mmol, 87%) of the title compound is isolated as a colorless oil.

$^1$H-NMR (CDCl$_3$): δ=1.03 (3H), 1.12 (3H), 1.28 (1H), 1.31 (3H), 1.38 (3H), 1.60 (1H), 2.77-2.92 (4H), 3.83 (1H), 3.93 (1H), 4.02 (1H), 7.12-7.22 (3H), 7.22-7.32 (2H) ppm.

EXAMPLE 12c (4S(4R,5S,6S,10RS))-4-(2,6-Dimethyl-10-[[(1,1-dimethylethyl)diphenylsilyl]oxy]-4-benzyl-5-hydroxy-3-oxo-undec-2-yl)-2,2-dimethyl-[1,3]dioxane (A) and (4S(4S,5R,6S,10RS))-4-(2,6-Dimethyl-10-[[(1,1-dimethylethyl)diphenylsilyl]oxy]-4-benzyl-5-hydroxy-3-oxo-undec-2-yl)-2,2-dimethyl-[1,3]dioxane (B)

Analogously to Example 1ak, 2.34 g (8.06 mmol) of the compound that is presented according to Example 12b is reacted, and after working-up and purification, 2.91 g (4.32 mmol, 54%) of title compound A and 1.72 g (2.55 mmol, 32%) of title compound B are isolated in each case as a colorless oil.

$^1$H-NMR (CDCl$_3$) of A: δ=0.38 (3H), 0.83-1.82 (31H), 2.66-3.02 (3H), 3.47 (1H), 3.58 (1H), 3.74-3.94 (4H), 7.05-7.28 (5H), 7.31-7.46 (6H), 7.61-7.72 (4H) ppm.

$^1$H-NMR (CDCl$_3$) of B: δ=0.78 (3H), 0.82-1.66 (21H), 0.98 (3H), 1.29 (3H), 1.36 (3H), 2.78 (1H), 2.94 (1H), 3.05 (1H), 3.44 (1H), 3.54 (1H), 3.72-3.91 (4H), 7.04-7.29 (5H), 7.31-7.48 (6H); 7.63-7.75 (5H) ppm.

EXAMPLE 12d (4S(4R,5S,6S,10RS))-4-(2,6-Dimethyl-10-[[(1,1-dimethylethyl)diphenylsilyl]oxy]-4-benzyl-3-oxo-5-(tetrahydropyran-2-yloxy)-undec-2-yl)-2,2-dimethyl-[1,3]dioxane Analogously to Example 1a, 2.90 g (4.4 mmol) of compound A that is presented according to Example 12c is reacted, and after working-up and purification, 3.18 g (4.2 mmol, 95%) of the title compound is isolated as a colorless oil.

EXAMPLE 12e (4S(4R,5S,6S,10RS))-4-(2,6-Dimethyl-4-benzyl-10-hydroxy-3-oxo-5-(tetrahydropyran-2-yloxy)-undec-2-yl)-2,2-dimethyl-[1,3]dioxane Analogously to Example 1i, 3.18 g (4.20 mmol) of the compound that is presented according to Example 12d is reacted, and after working-up and purification, 1.39 g (2.68 mmol, 64%) of the title compound is isolated as a colorless oil.

$^1$H-NMR (CDCl$_3$): δ=0.28+0.47+0.49 (3H), 0.92-1.14 (7H), 1.14-1.95 (24H), 2.79+2.99-3.13 (2H), 3.34-4.27 (8H), 4.45+4.56 (1H), 7.05-7.29 (5H) ppm.

EXAMPLE 12f (4S(4R,5S,6S))-4-(2,6-Dimethyl-4-benzyl-3,10-dioxo-5-(tetrahydropyran-2-yloxy)-undec-2-yl)-2,2-dimethyl-[1,3]dioxane Analogously to Example 1m, 1.39 g (2.68 mmol) of the compound that is presented according to Example 12e is reacted, and after working-up and purification, 1.18 g (2.28 mmol, 85%) of the title compound is isolated as a colorless oil.

$^1$H-NMR (CDCl$_3$): δ=0.26+0.47 (3H), 0.96-1.11 (7H), 1.27+1.31 (3H), 1.39+1.41 (3H), 1.20-1.90 (12H), 2.15 (3H), 2.45 (2H), 2.79+2.97-3.12 (2H), 3.36-4.07 (6H), 4.15+4.21 (1H), 4.43+4.54 (1H), 7.08-7.28 (5H) ppm.

EXAMPLE 12g (4S(4R,5S,6S,10E/Z,13S,14E))-4-(13-[[(1,1-Dimethylethyl)diphenylsilyl]oxy]-4-benzyl-15-(2-methyl-4-thiazolyl)-3-oxo-5-(tetrahydropyran-2-yloxy)-2,6,10,14-tetramethyl-pentadeca-10,14-dien-2-yl)-2,2-dimethyl-[1,3]dioxane Analogously to Example 1ao, 477 mg (923 µmol) of the compound that is presented according to Example 12f is reacted with use of n-butyllithium as a base, and after working-up and purification, 367 mg (393 µmol, 43%) of the title compound is isolated as a colorless oil.

$^1$H-NMR (CDCl$_3$): δ=0.23+0.46 (3H), 0.92-1.10 (19H), 1.10-1.92 (22H), 1.99 (3H), 2.13-2.40 (2H), 2.70 (3H), 2.80+2.94-3.14 (2H), 3.35-4.25 (6H), 4.47+4.53 (1H), 4.98 (1H), 6.22 (1H), 6.77 (1H), 7.07-7.24 (5H), 7.25-7.45 (6H), 7.60-7.73 (4H) ppm.

EXAMPLE 12h (4S(4R,5S,6S,10E/Z,13S,14E))-4-(4-Benzyl-13-hydroxy-15-(2-methyl-4-thiazolyl)-3-oxo-5-(tetrahydropyran-2-yloxy)-2,6,10,14-tetramethyl-pentadeca-10,14-dien-2-yl)-2,2-dimethyl-[1,3]dioxane Analogously to Example 1i, 548 mg (586 µmol) of the compound that is presented according to Example 12g is reacted, and after working-up and purification, 330 mg (474 µmol, 81%) of the title compound is isolated as a colorless oil.

$^1$H-NMR (CDCl$_3$): δ=0.25+0.46 (3H), 0.92-1.10 (6H), 1.10-1.90 (13H), 1.28+1.32 (3H), 1.39+1.41 (3H), 1.68+1.74 (3H), 1.99-2.13 (2H), 2.06 (3H), 2.36 (2H), 2.71 (3H), 2.81+3.00-3.14 (2H), 3.37-4.26 (9H), 4.48+4.57 (1H), 5.20 (1H), 6.58 (1H), 6.94 (1H), 7.08-7.26 (5H) ppm.

EXAMPLE 12i 3S,6R,7S,8S,12E/Z,15S,16E)-6-Benzyl-17-(2-methyl-4-thiazolyl)-5-oxo-4,4,8,12,16-pentamethyl-heptadeca-12,16-diene-1,3,7,15-tetraol Analogously to Example 1f, 330 mg (474 µmol) of the compound that is presented according to Example 12h is reacted, and after working-up and purification, 224 mg (392 µmol, 83%) of the title compound is isolated as a colorless oil.

$^1$H-NMR (CDCl$_3$): δ=0.40 (3H), 0.93-1.04 (6H), 1.08-1.87 (8H), 1.63+1.71 (3H), 1.92-2.11 (5H), 2.33 (2H), 2.67-3.06 (3H), 2.72 (3H), 3.11 (1H), 3.23-3.50 (2H), 3.54 (1H), 3.65-3.92 (3H), 4.13 (1H), 5.18 (1H), 6.53 (1H), 6.94 (1H), 7.06-7.29 (5H) ppm.

EXAMPLE 12k (3S,6R,7S,8S,12E/Z,15S,16E)-6-Benzyl-17-(2-methyl-4-thiazolyl)-4,4,8,12,16-pentamethyl-1,3,7,15-tetrakis-[[dimethyl(1,1-dimethylethyl)silyl]oxy]-heptadeca-12,16-dien-5-one Analogously to Example 1aq, 224 mg (392 µmol) of the compound that is presented according to Example 12i is reacted, and after working-up and purification, 323 mg (314 µmol, 80%) of the title compound is isolated as a colorless oil.

$^1$H-NMR (CDCl$_3$): δ=−0.03-0.12 (24H), 0.79-1.73 (53H), 1.61+1.69 (3H), 1.91-2.07 (2H), 2.00 (3H), 2.26 (2H), 2.71 (3H), 2.86 (1H), 2.98 (1H), 3.33-3.55 (2H), 3.66 (1H), 3.80 (1H), 4.10 (1H), 5.17 (1H), 6.47 (1H), 6.91 (1H), 7.06-7.29 (H) ppm.

EXAMPLE 12l (3S,6R,7S,8S,12E/Z,15S,16E)-6-Benzyl-1-hydroxy-17-(2-methyl-4-thiazolyl)-4,4,8,12,16-pentamethyl-3,7,15-tris-[[dimethyl(1,1-dimethylethyl)silyl]oxy]-heptadeca-12,16-dien-5-one Analogously to Example 1ar, 432 mg (420 µmol) of the compound that is presented according to Example 12 is reacted, and after working-up and purification, 264 mg (289 µmol, 69%) of the title compound is isolated as a colorless oil.

$^1$H-NMR (CDCl$_3$): δ=−0.03-0.12 (18H), 0.53 (1H), 0.78-1.40 (41H), 1.62+1.71 (3H), 1.42-1.81 (2H), 2.00 (3H), 1.92-2.10 (2H), 2.27 (2H), 2.70 (3H), 2.852 (1H), 3.09 (1H), 3.30 (2H), 3.40 (1H), 3.70 (1H), 3.81 (1H), 4.11 (1H), 5.17 (1H), 6.46 (1H), 6.91 (1H), 7.11-7.30 (5H) ppm.

EXAMPLE 12m (3S,6R,7S,8S,12E/Z,15S,16E)-6-Benzyl-3,7,15-tris-[[dimethyl(1,1-dimethylethyl)silyl]oxy]-4,4,8,12,16-pentamethyl-17-(2-methyl-4-thiazolyl)-5-oxo-heptadeca-12,16-dienoic Acid Analogously to Example 1k, 264 mg (289 µmol) of the compound that is presented according to Example 12l is reacted, and after working-up, 255 mg (279 µmol, 97%) of the title compound is isolated as a colorless oil, which is further reacted without purification.

EXAMPLE 12n (3S,6R,7S,8S,12Z,15S,16E)-6-Benzyl-17-(2-methyl-4-thiazolyl)-5-oxo-4,4,8,12,16-pentamethyl-3,7,15-tris-[[dimethyl(1,1-dimethylethyl)silyl]oxy]-heptadeca-12,16-dienoic acid (A) and (3S,6R,7S,8S,12E,15S,16E)-6-benzyl-17-(2-methyl-4-thiazolyl)-5-oxo-4,4,8,12,16-pentamethyl-3,7,15-tris-[[dimethyl(1,1-dimethylethyl)silyl]oxy]-heptadeca-12,16-dienoic acid (B)

Analogously to Example 1at, 255 mg (279 µmol) of the compound that is presented according to Example 12m is reacted, and after working-up and purification, 61 mg (66 µmol, 24%) of title compound A is isolated as a colorless solid, and 54 mg (58 µmol, 21%) of title compound B is isolated as a colorless oil.

$^1$H-NMR (CDCl$_3$) of A: δ=−0.07-0.18 (18H), 0.60 (3H), 0.78 (3H), 0.82 (9H), 0.89 (9H), 0.92 (9H), 1.07 (3H), 1.72 (3H), 1.95 (3H), 0.74-2.33 (12H), 2.69 (3H), 2.91 (1H), 3.03 (1H), 3.41 (1H), 3.62 (1H), 4.20 (1H), 4.30 (1H), 5.23 (1H), 6.72 (1H), 6.96 (11H), 7.05-7.29 (5H) ppm.

$^1$H-NMR (CDCl$_3$) of B: δ=−0.08-0.14 (18H), 0.72 (3H), 0.82 (3H), 0.85 (9H), 0.90 (9H), 0.93 (9H), 0.98 (3H), 1.60 (3H), 0.65-2.08 (9H), 1.96 (3H), 2.12 (1H), 2.29 (2H), 2.71 (3H), 2.92 (2H), 3.47 (1H), 3.69 (1H), 4.09 (1H), 4.21 (1H), 5.12 (1H), 6.49 (1H), 6.95 (1H), 7.06-7.30 (5H) ppm.

EXAMPLE 12o (3S,6R,7S,8S,12Z,15S,16E)-6-Benzyl-15-hydroxy-17-(2-methyl-4-thiazolyl)-5-oxo-4,4,8,12,16-pentamethyl-3,7-bis-[[dimethyl(1,1-dimethylethyl)silyl]oxy]-heptadeca-12,16-dienoic acid Analogously to Example 1i, 61 mg (66 µmol) of compound A that is presented according to Example 12n is reacted at 23° C., and after working-up and purification, 33 mg (41 µmol, 61%) of the title compound is isolated as a colorless oil.

$^1$H-NMR (CDCl$_3$): δ=−0.11 (3H), −0.08-0.05 (9H), 0.80 (9H), 0.88 (9H), 0.91 (3H), 0.94 (3H), 0.99 (3H), 1.72 (3H), 1.98 (3H), 0.77-2.22 (12H), 2.69 (3H), 2.70-2.91 (2H), 3.39 (1H), 3.62 (1H), 4.18 (1H), 4.33 (1H), 4.43-5.73 (1H), 5.13 (1H), 6.68 (1H), 6.91 (1H), 7.05-7.26 (5H) ppm.

EXAMPLE 12p (4S,7R,8S,9S,13Z,16S(E))-4,8-Bis-[[dimethyl(1,1-dimethylethyl)silyl]oxy]-7-benzyl-16-(1-methyl-2-(2-methyl-4-thiazolyl)ethenyl)-1-oxa-5,5,9,13-tetramethyl-cyclohexadec-13-ene-2,6-dione Analogously to Example 1aw, 33 mg (40 µmol) of the compound that is presented according to Example 12o is reacted, and after working-up and purification, 17 mg (21 µmol, 53%) of the title compound is isolated as a colorless oil.

$^1$H-NMR (CDCl$_3$): δ=−0.06 (3H), 0.00 (3H), 0.07 (3H), 0.09 (3H), 0.98 (3H), 1.71 (3H), 2.10 (3H), 0.70-2.48 (34H), 2.63 (1H), 2.71 (3H), 2.81 (2H), 3.23 (1H), 3.76 (1H), 4.17 (1H), 5.13 (2H), 6.56 (1H), 6.95 (1H), 7.06-7.32 (5H) ppm.

EXAMPLE 12

(4S,7R,8S,9S,13Z,16S(E))-4,8-Dihydroxy-7-benzyl-16-(1-methyl-2-(2-methyl-4-thiazolyl)ethenyl)-1-oxa-5,5,9,13-tetramethyl-cyclohexadec-13-ene-2,6-dione Analogously to Example 1, 12.2 mg (9.7 µmol) of the compound that is presented according to Example 12p is reacted, and after working-up and purification, 5.0 mg (8.8 µmol, 91%) of the title compound is isolated as a colorless oil.

$^1$H-NMR (CDCl$_3$): δ=0.61 (3H), 0.83 (3H), 1.11 (3H), 1.22-2.00 (5H), 1.71 (3H), 2.05 (3H), 2.19-2.49 (5H), 2.61 (1H), 2.66 (3H), 2.89 (1H), 3.03 (1H), 3.59 (1H), 3.67 (1H), 4.21 (1H), 5.10 (1H), 5.24 (1H), 6.53 (1H), 6.92 (1H), 7.07-7.31 (5H) ppm.

EXAMPLE 13

(4S,7R,8S,9S,13E,16S(E))-4,8-Dihydroxy-7-benzyl-16-(1-methyl-2-(2-methyl-4-thiazolyl)ethenyl)-1-oxa-5,5,9,13-tetramethyl-cyclohexadec-13-ene-2,6-dione

EXAMPLE 13a (3S,6R,7S,8S,12E,15S,16E)-6-Benzyl-15-hydroxy-17-(2-methyl-4-thiazolyl)-5-oxo-4,4,8,12,16-pentamethyl-3,7-bis-[[dimethyl(1,1-dimethylethyl)silyl]oxy]-heptadeca-12,16-dienoic acid Analogously to Example 1i, 47 mg (51 µmol) of compound B that is presented according to Example 12n is reacted at 23° C., and after working-up and purification, 22 mg (27 µmol, 53%) of the title compound is isolated as a colorless oil.

$^1$H-NMR (CDCl$_3$): δ=−0.08 (3H), −0.03-0.09 (9H), 0.82 (9H), 0.89 (12H), 0.97 (6H), 1.64 (3H), 2.02 (3H), 0.78-2.10 (9H), 2.27-2.46 (2H), 2.70 (3H), 2.82 (2H), 2.92-3.34 (2H), 3.42 (1H), 3.67 (1H), 4.19 (1H), 4.32 (1H), 5.28 (1H), 6.63 (1H), 6.92 (1H), 7.02-7.27 (5H) ppm.

EXAMPLE 13b (4S,7R,8S,9S,13E,16S(E))-4,8-Bis-[[dimethyl(1,1-dimethylethyl)silyl]oxy]-7-benzyl-16-(1-methyl-2-(2-methyl-4-thiazolyl)ethenyl)-1-oxa-5,5,9,13-tetramethyl-cyclohexadec-13-ene-2,6-dione Analogously to Example 1aw, 22 mg (27 µmol) of the compound that is presented according to Example 13a is reacted, and after working-up and purification, 12 mg (15 µmol, 56%) of the title compound is isolated as a colorless oil.

$^1$H-NMR (CDCl$_3$): δ=−0.04 (3H), 0.06 (6H), 0.12 (3H), 0.80 (3H), 0.88 (9H), 0.90 (9H), 0.96 (3H), 1.08 (3H), 1.64 (3H), 0.74-1.72 (4H), 1.80-2.27 (5H), 2.09 (3H), 2.33 (1H), 2.53-2.82 (2H), 2.70 (3H), 2.96 (1H), 3.20 (1H), 3.74 (1H), 4.15 (1H), 5.19-5.32 (2H), 6.47 (1H), 6.90 (1H), 7.07-7.31 (5H) ppm.

EXAMPLE 13

(4S,7R,8S,9S,13E,16S(E))-4,8-Dihydroxy-7-benzyl-16-(1-methyl-2-(2-methyl-4-thiazolyl)ethenyl)-1-oxa-5,5,9,13-tetramethyl-cyclohexadec-13-ene-2,6-dione Analogously to Example 1, 12 mg (15 µmol) of the compound that is presented according to Example 13b is reacted, and after working-up and purification, 6.0 mg (11 µmol, 69%) of the title compound is isolated as a colorless oil.

$^1$H-NMR (CDCl$_3$): δ=0.69 (3H), 0.72 (3H), 0.89 (1H), 1.08 (3H), 1.38-1.69 (3H), 1.61 (3H), 1.90-2.12 (2H), 2.02 (3H), 2.19 (1H), 2.25-2.44 (3H), 2.54 (1H), 2.69 (3H), 2.79 (1H), 2.99 (1H), 3.73 (2H), 4.25-4.39 (2H), 4.66 (1H), 5.03 (1H), 5.34 (1H), 6.52 (1H), 6.97 (1H), 7.04-7.29 (5H) ppm.

EXAMPLE 14

(1S,3S(E),7S,10R,11S,12S,16R)-10-Benzyl-7,11-dihydroxy-3-(1-methyl-2-(2-methyl-4-thiazolyl)ethenyl)-8,8,12,16-tetramethyl-4,17-dioxabicyclo[14.1.0]heptadecane-5,9-dione (A) and (1R,3S(E),7S,10R,11S,12S,16S)-10-benzyl-7,11-dihydroxy-3-(1-methyl-2-(2-methyl-4-thiazolyl)ethenyl)-8,8,12,16-tetramethyl-4,17-dioxabicyclor[14.1.0]heptadecane-5,9-dione (B)

The solution of 4.0 mg (7.0 µmol) of the compound, presented according to Example 12, in 0.1 ml of acetonitrile is mixed with 38 µl of a 1 M solution of sodium ethylenediamine tetraacetate, cooled to 0° C., and mixed with 67 µl of 1,1,1-trifluoroacetone as well as a mixture of 21 mg of oxone and 4.5 mg of sodium bicarbonate. It is allowed to react for 5 hours, poured onto sodium thiosulfate solution and extracted several times with ethyl acetate. The combined organic extracts are washed with saturated sodium chloride solution, and the residue that is obtained after filtration and removal of the solvent is purified by chromatography on an analytic thin-layer plate. As a mobile solvent, a mixture of n-hexane and ethyl acetate is used. 2.2 mg (3.8 µmol, 54%) of title compound A and 0.3 mg (0.5 µmol, 7%) of title compound B are isolated in each case as a colorless oil.

$^1$H-NMR (CDCl$_3$) of A: δ=0.67 (3H), 0.80 (3H), 1.07 (3H), 1.29 (3H), 1.35-2.06 (9H), 2.09 (3H), 2.33 (1H), 2.49 (1H), 2.68 (3H), 2.72-2.85 (2H), 3.04 (1H), 3.40 (1H), 3.62 (1H), 3.77 (1H), 4.22 (1H), 4.51 (1H), 5.47 (1H), 6.51 (1H), 6.95 (1H), 7.06-7.30 (5H) ppm.

$^1$H-NMR (CDCl$_3$) of B: δ=0.68 (3H), 0.76 (3H), 0.86 (1H), 1.07 (3H), 1.23-2.13 (7H), 1.30 (3H), 2.08 (3H), 2.30-2.49 (2H), 2.70 (3H), 2.87-3.11 (3H), 3.28 (2H), 3.57 (1H), 3.93 (1H), 4.21 (1H), 4.54-5.73 (1H), 5.58 (1H), 6.58 (1H), 6.97 (1H), 7.07-7.31 (5H) ppm.

EXAMPLE 15

(1S,3S(E),7S,10R,11S,12S,16S)-10-Benzyl-7,11-dihydroxy-3-(1-methyl-2-(2-methyl-4-thiazolyl)ethenyl)-8,8,12,16-tetramethyl-4,17-dioxabicyclor[14.1.0]heptadecane-5,9-dione (A) and (1R,3S(E),7S,10R,11S,12S,16R)-10-benzyl-7,11-dihydroxy-3-(1-methyl-2-(2-methyl-4-thiazolyl)ethenyl)-8,8,12,16-tetramethyl-4,17-dioxabicyclor[14.1.0]heptadecane-5,9-dione (B)

Analogously to Example 14, 3.1 mg (5.4 μmol) of the compound that is presented according to Example 13 is reacted, and after working-up and purification, 0.7 mg (1.2 μmol, 22%) of title compound A or B and 0.6 mg (1.0 μmol, 19%) of title compound B or A are isolated as colorless oils.

$^1$H-NMR (CDCl$_3$) of A or B: δ=0.76 (3H), 0.88 (3H), 1.02 (3H), 1.24 (1H), 1.30 (3H), 1.38-1.78 (5H), 1.92-2.13 (3H), 2.07 (3H), 2.44 (2H), 2.70 (3H), 2.78-2.87 (2H), 3.04 (1H), 3.60 (1H), 3.71-3.80 (2H), 4.01 (1H), 4.28 (1H), 5.45 (1H), 6.62 (1H), 6.99 (1H), 7.11-7.31 (5H) ppm.

$^1$H-NMR (CDCl$_3$) of B or A: δ=0.70 (3H), 0.76 (3H), 1.06 (3H), 1.19-1.64 (5H), 1.22 (3H), 1.80 (1H), 1.90-2.12 (3H), 2.07 (3H), 2.46 (2H), 2.69 (3H), 2.79 (1H), 2.92 (1H), 3.08 (1H), 3.32 (1H), 3.57 (1H), 3.62 (1H), 3.71 (1H), 4.12 (1H), 5.42 (1H), 6.54 (1H), 6.96 (1H), 7.06-7.31 (5H) ppm.

EXAMPLE 16

(4S,7S,8R,9S,13Z,16S(E))-4,8-Dihydroxy-7-benzyl-16-(1-methyl-2-(2-methyl-4-thiazolyl)ethenyl)-1-oxa-5,5,9,13-tetramethyl-cyclohexadec-13-ene-2,6-dione

EXAMPLE 16a (4S(4S,5R,6S,10RS))-4-(2,6-Dimethyl-10-[[(1,1-dimethylethyl)diphenylsilyl]oxy]-4-benzyl-3-oxo-5-(tetrahydropyran-2-yloxy)-undec-2-yl)-2,2-dimethyl-[1,3]dioxane Analogously to Example 1a, 1.71 g (2.59 mmol) of compound B that is presented according to Example 12c is reacted, and after working-up and purification, 1.51 g (1.99 mmol, 77%) of the title compound is isolated as a colorless oil.

EXAMPLE 16b (4S(4S,5R,6S,10RS))-4-(2,6-Dimethyl-4-benzyl-10-hydroxy-3-oxo-5-(tetrahydropyran-2-yloxy)-undec-2-yl)-2,2-dimethyl-[1,3]dioxane Analogously to Example 1i, 1.51 g (1.99 mmol) of the compound that is presented according to Example 16a is reacted, and after working-up and purification, 855 mg (1.65 mmol, 83%) of the title compound is isolated as a colorless oil.

$^1$H-NMR (CDCl$_3$): δ=0.88+0.92 (3H), 0.92-1.95 (32H), 2.82-3.10 (2H), 3.32-3.59 (2H), 3.71-3.98 (5H), 4.43-4.59 (1H), 7.11-7.31 (5H) ppm.

EXAMPLE 16c (4S(4S,5R,6S))-4-(2,6-Dimethyl-4-benzyl-3,10-dioxo-5-(tetrahydropyran-2-yloxy)-undec-2-yl)-2,2-dimethyl-[1,3]dioxane Analogously to Example 1m, 850 mg (1.64 mmol) of the compound that is presented according to Example 16b is reacted, and after working-up and purification, 741 mg (1.43 mmol, 88%) of the title compound is isolated as a colorless oil.

$^1$H-NMR (CDCl$_3$): δ=0.84+0.90 (3H), 0.95+1.05 (3H), 0.97 (3H), 1.8-1.88 (19H), 2.15 (3H), 2.42 (2H), 2.79-3.08 (2H), 3.31-3.57 (2H), 3.69-3.96 (5H), 4.43+4.52 (1H), 7.10-7.29 (5H) ppm.

EXAMPLE 16d (4S(4S,5R,6S,10E/Z,13S,14E))-4-(13-[[(1,1-Dimethylethyl)diphenylsilyl]oxy]-4-benzyl-15-(2-methyl-4-thiazolyl)-3-oxo-5-(tetrahydropyran-2-yloxy)-2,6,10,14-tetramethyl-pentadeca-10,14-dien-2-yl)-2,2-dimethyl-[1,3]dioxane Analogously to Example 1ao, 737 mg (1.43 mmol) of the compound that is presented according to Example 16c is reacted with use of n-butyllithium as a base, and after working-up and purification, 491 mg (525 μmol, 37%) of the title compound is isolated as a colorless oil.

EXAMPLE 16e (4S(4S,5R,6S,10E/Z,13S,14E))-4-(4-Benzyl-13-hydroxy-15-(2-methyl-4-thiazolyl)-3-oxo-5-(tetrahydropyran-2-yloxy)-2,6,10,14-tetramethyl-pentadeca-10,14-dien-2-yl)-2,2-dimethyl-[1,3]dioxane Analogously to Example 1i, 1.09 g (1.17 mmol) of the compound that is presented according to Example 16d is reacted, and after working-up and purification, 677 mg (973 μmol, 83%) of the title compound is isolated as a colorless oil.

$^1$H-NMR (CDCl$_3$): δ=0.78-2.12 (31H), 1.67+1.73 (3H), 2.06 (3H), 2.36 (2H), 2.71 (3H), 2.81-3.08 (2H), 3.30-3.52 (2H), 3.69-3.96 (5H), 4.14 (1H), 4.43+4.51 (1H), 5.20 (1H), 6.57 (1H), 6.95 (1H), 7.08-7.30 (5H) ppm.

EXAMPLE 16f (3S,6S,7R,8S,12E/Z,15S,16E)-6-Benzyl-17-(2-methyl-4-thiazolyl)-5-oxo-4,4,8,12,16-pentamethyl-heptadeca-12,16-diene-1,3,7,15-tetraol Analogously to Example 1f, 675 mg (970 μmol) of the compound that is presented according to Example 16e is reacted, and after working-up and purification, 495 mg (866 μmol, 89%) of the title compound is isolated as a colorless oil.

$^1$H-NMR (CDCl$_3$): δ=0.73-0.86 (6H), 0.96-1.10 (3H), 1.21-1.79 (7H), 1.67+1.76 (3H), 1.98-2.17 (5H), 2.28-2.50 (3H), 2.70 (3H), 2.85 (1H), 2.97 (1H), 3.09 (1H), 3.40-3.87 (7H), 4.16 (1H), 5.27 (1H), 6.51+6.57 (1H), 6.94 (1H), 7.07-7.30 (5H) ppm.

EXAMPLE 16g (3S,6S,7R,8S,12E/Z,15S,16E)-6-Benzyl-17-(2-methyl-4-thiazolyl)-4,4,8,12,16-pentamethyl-1,3,7,15-tetrakis-[[dimethyl(1,1-dimethylethyl)silyl]oxy]-heptadeca-12,16-dien-5-one Analogously to Example 1aq, 337 mg (589 μmol) of the compound that is presented according to Example 16f is reacted, and after working-up and purification, 444 mg (432 μmol, 73%) of the title compound is isolated as a colorless oil.

¹H-NMR (CDCl₃): δ=−0.08-0.13 (24H), 0.42 (3H), 0.79-1.03 (42H), 1.11-1.73 (8H), 1.60+1.67 (3H), 1.90-2.08 (4H), 2.26 (2H), 2.71 (3H), 2.91 (2H), 3.22 (1H), 3.50-3.72 (3H), 3.85 (1H), 4.09 (1H), 5.16 (1H), 6.46 (1H), 6.91 (1H), 7.07-7.27 (5H) ppm.

EXAMPLE 16h (3S,6S,7R,8S,12E/Z,15S,16E)-6-Benzyl-1-hydroxy-17-(2-methyl-4-thiazolyl)-4,4,8,12,16-pentamethyl-3,7,15-tris-[[dimethyl(1,1-dimethylethyl)silyl]oxy]-heptadeca-12,16-dien-5-one Analogously to Example 1ar, 444 mg (432 μmol) of the compound that is presented according to Example 16g is reacted, and after working-up and purification, 272 mg (297 μmol, 69%) of the title compound is isolated as a colorless oil.

¹H-NMR (CDCl₃): δ=−0.07-0.18 (18H), 0.48 (3H), 0.79-1.72 (40H), 1.61+1.68 (3H), 1.81 (1H), 1.90-2.09 (5H), 2.26 (2H), 2.70 (3H), 2.86-3.04 (2H), 3.23 (1H), 3.59 (2H), 3.70 (1H), 3.91 (1H), 4.10 (1H), 5.16 (1H), 6.44 (1H), 6.91 (1H), 7.08-7.29 (5H) ppm.

EXAMPLE 16i (3S,6S,7R,8S,12E/Z,15S,16E)-6-Benzyl-3,7,15-tris-[[dimethyl(1,1-dimethylethyl)silyl]oxy]-4,4,8,12,16-pentamethyl-17-(2-methyl-4-thiazolyl)-5-oxo-heptadeca-12,16-dienoic acid Analogously to Example 1k, 272 mg (297 μmol) of the compound that is presented according to Example 16h is reacted, and after working-up, 264 mg (289 μmol, 97%) of the title compound is isolated as a colorless oil, which is further reacted without purification.

EXAMPLE 16k (3S,6S,7R,8S,12Z,15S,16E)-6-Benzyl-17-(2-methyl-4-thiazolyl)-5-oxo-4,4,8,12,16-pentamethyl-3,7,15-tris-[[dimethyl(1,1-dimethylethyl)silyl]oxy]-heptadeca-12,16-dienoic acid (A) and (3S,6S,7R,8S,12E,15S,16E)-6-benzyl-17-(2-methyl-4-thiazolyl)-5-oxo-4,4,8,12,16-pentamethyl-3,7,15-tris-[[dimethyl(1,1-dimethylethyl)silyl]oxy]-heptadeca-12,16-dienoic acid (B)

Analogously to Example 1at, 264 mg (289 μmol) of the compound that is presented according to Example 16i is reacted, and after working-up and purification, 87 mg (94 μmol, 32%) of title compound A and 67 mg (73 μmol, 25%) of title compound B are isolated in each case as a colorless oil.

¹H-NMR (CDCl₃) of A: δ=−0.09 (3H), −0.02-0.13 (15H), 0.69 (3H), 0.80-1.48 (32H), 1.03 (3H), 1.63-1.79 (1H), 1.68 (3H), 2.00 (3H), 1.91-2.09 (4H), 2.12-2.33 (3H), 2.72 (3H), 2.77-3.20 (6H), 3.31 (1H), 3.70 (1H), 4.10 (1H), 4.43 (1H), 5.16 (1H), 6.47 (1H), 6.91 (1H), 7.08-7.29 (5H) ppm.

¹H-NMR (CDCl₃) of B: δ=−0.10 (3H), −0.03-0.17 (15H), 0.68 (3H), 0.80-1.50 (33H), 1.02 (3H), 1.61 (3H), 1.71 (2H), 1.88-2.07 (2H), 2.00 (3H), 2.11-2.68 (4H), 2.71 (3H), 2.86 (2H), 3.30 (1H), 3.69 (1H), 3.75-4.08 (1H), 4.11 (1H), 4.43 (1H), 5.16 (1H), 6.47 (1H), 6.91 (1H), 7.08-7.30 (5H) ppm.

EXAMPLE 16l (3S,6S,7R,8S,12Z,15S,16E)-6-Benzyl-15-hydroxy-17-(2-methyl-4-thiazolyl)-5-oxo-4,4,8,12,16-pentamethyl-3,7-bis-[[dimethyl(1,1-dimethylethyl)silyl]oxy]-heptadeca-12,16-dienoic acid Analogously to Example 1i, 87 mg (94 μmol) of compound A that is presented according to Example 16k is reacted at 23° C., and after working-up and purification, 76 mg (93 μmol, 99%) of the title compound is isolated as a colorless oil.

¹H-NMR (CDCl₃): δ=−0.03-0.13 (12H), 0.52 (3H), 0.78-1.80 (28H), 1.73 (3H), 1.91-2.17 (2H), 2.00 (3H), 2.21 (2H), 2.34 (2H), 2.69-3.01 (3H), 2.73 (3H), 3.19 (1H), 3.31 (1H), 3.74 (1H), 4.13 (1H), 4.28-5.68 (1H), 4.36 (1H), 5.18 (1H), 6.62 (1H), 6.97 (1H), 7.08-7.31 (5H) ppm.

EXAMPLE 16m (4S,7S,8R,9S,13Z,16S(E))-4,8-Bis-[[dimethyl(1,1-dimethylethyl)silyl]oxy]-7-benzyl-16-(1-methyl-2-(2-methyl-4-thiazolyl)ethenyl)-1-oxa-5,5,9,13-tetramethyl-cyclohexadec-13-ene-2,6-dione Analogously to Example 1aw, 76 mg (93 μmol) of the compound that is presented according to Example 16l is reacted, and after working-up and purification, 68 mg (85 μmol, 92%) of the title compound is isolated as a colorless oil.

¹H-NMR (CDCl₃): δ=−0.02 (3H), 0.01 (3H), 0.16 (3H), 0.30 (3H), 0.54 (3H), 0.64 (3H), 0.85 (9H), 0.97 (9H), 0.99 (3H), 0.80-1.75 (5H), 1.69 (3H), 1.89 (1H), 1.98-2.31 (3H), 2.13 (3H), 2.37 (1H), 2.52 (1H), 2.70 (1H), 2.72 (3H), 3.10 (1H), 3.46 (1H), 3.96 (1H), 4.05 (1H), 5.10 (1H), 5.15 (1H), 6.48 (1H), 7.02 (1H), 7.09-7.31 (5H) ppm.

EXAMPLE 16

(4S,7S,8R,9S,13Z,16S(E))-4,8-Dihydroxy-7-benzyl-16-(1-methyl-2-(2-methyl-4-thiazolyl)ethenyl)-1-oxa-5,5,9,13-tetramethyl-cyclohexadec-13-ene-2,6-dione Analogously to Example 1, 10 mg (13 μmol) of the compound that is presented according to Example 12p is reacted, and after working-up and purification, 6.3 mg (11 μmol, 89%) of the title compound is isolated as a colorless oil.

¹H-NMR (CDCl₃): δ=0.47 (3H), 0.84 (1H), 0.97 (3H), 1.04 (3H), 1.22-1.70 (4H), 1.76 (3H), 1.94 (1H), 1.93 (3H), 2.22-2.49 (4H), 2.61-2.77 (1H), 2.71 (3H), 2.83 (1H), 2.90 (1H), 3.02 (1H), 3.08 (1H), 3.59 (1H), 3.62 (1H), 4.18 (1H), 5.19 (1H), 5.53 (1H), 6.50 (1H), 6.96 (1H), 7.08-7.31 (5H) ppm.

EXAMPLE 17

(4S,7S,8R,9S,13E,16S(E))-4,8-Dihydroxy-7-benzyl-16-(1-methyl-2-(2-methyl-4-thiazolyl)ethenyl)-1-oxa-5,5,9,13-tetramethyl-cyclohexadec-13-ene-2,6-dione

EXAMPLE 17a (3S,6S,7R,8S,12E,15S,16E)-6-Benzyl-15-hydroxy-17-(2-methyl-4-thiazolyl)-5-oxo-4,4,8,12,16-pentamethyl-3,7-bis-[[dimethyl(1,1-dimethylethyl)silyl]oxy]-heptadeca-12,16-dienoic Acid Analogously to Example 1i, 67 mg (72 μmol) of compound B that is presented according to Example 16k is reacted at 23° C., and after working-up and purification, 57 mg (70 μmol, 97%) of the title compound is isolated as a colorless oil.

¹H-NMR (CDCl₃): δ=−0.06-0.13 (12H), 0.47 (3H), 0.77-1.76 (28H), 1.64 (3H), 1.90-2.07 (2H), 2.00 (3H), 2.28 (2H), 2.39 (2H), 2.66-2.89 (2H), 2.73 (2H), 2.91-3.05 (3H), 3.19 (1H), 3.29 (1H), 3.76 (1H), 4.20 (1H), 4.36 (1H), 5.16 (1H), 6.58 (1H), 6.94 (1H), 7.07-7.31 (5H) ppm.

EXAMPLE 17b (4S,7S,8R,9S,13E,16S(E))-4,8-Bis-[[dimethyl(1,1-dimethylethyl)silyl]oxy]-7-benzyl-16-(1-methyl-2-(2-methyl-4-thiazolyl)ethenyl)-1-oxa-5,5,9,13-tetramethyl-cyclohexadec-13-ene-2,6-dione Analogously to Example 1aw, 57 mg (70 µmol) of the compound that is presented according to Example 17a is reacted, and after working-up and purification, 32 mg (40 µmol, 57%) of the title compound is isolated as a colorless solid.

$^1$H-NMR (CDCl$_3$): δ=0.07 (9H), 0.23 (3H), 0.53 (3H), 0.72 (3H), 0.88 (9H), 0.93 (9H), 0.98 (3H), 1.08-1.30 (2H), 1.39 (1H), 1.48-1.86 (3H), 1.61 (3H), 2.10 (3H), 2.07-2.27 (2H), 2.31-2.58 (3H), 2.63-2.78 (1H), 2.71 (3H), 3.08 (1H), 3.41 (1H), 3.82 (1H), 4.19 (1H), 5.08 (1H), 5.15 (1H), 6.51 (1H), 7.02 (1H), 7.08-7.30 (5H) ppm.

EXAMPLE 17

(4S,7S,8R,9S,13E,16S(E))-4,8-Dihydroxy-7-benzyl-16-(1-methyl-2-(2-methyl-4-thiazolyl)ethenyl)-1-oxa-5,5,9,13-tetramethyl-cyclohexadec-13-ene-2,6-dione Analogously to Example 1, 32 mg (40 µmol) of the compound that is presented according to Example 17b is reacted, and after working-up and purification, 16.6 mg (29 µmol, 73%) of the title compound is isolated as a colorless oil.

$^1$H-NMR (CDCl$_3$): δ=0.35 (3H), 0.91 (3H), 0.93 (3H), 1.61 (3H), 0.83-1.72 (5H), 1.94-2.20 (2H), 2.09 (3H), 2.32 (1H), 2.46 (1H), 2.51 (2H), 2.69 (3H), 2.90-3.02 (3H), 3.13 (1H), 3.55-3.68 (2H), 4.23 (1H), 5.11 (1H), 5.43 (1H), 6.47 (1H), 6.92 (1H), 7.07-7.31 (5H) ppm.

EXAMPLE 18

(1S,3S(E),7S,10S,11R,12S,16R)-10-Benzyl-7,11-dihydroxy-3-(1-methyl-2-(2-methyl-4-thiazolyl)ethenyl)-8,8,12,16-tetramethyl-4,17-dioxabicyclo[14.1.0]heptadecane-5,9-dione (A) and (1R,3S(E),7S,10S,11R,12S,16S)-10-benzyl-7,11-dihydroxy-3-(1-methyl-2-(2-methyl-4-thiazolyl)ethenyl)-8,8,12,16-tetramethyl-4,17-dioxabicyclor[14.1.0]heptadecane-5,9-dione (B)

Analogously to Example 14, 1.4 mg (2.5 µmol) of the compound that is presented according to Example 16 is reacted, and after working-up and purification, 0.3 mg (0.5 µmol, 21%) of title compounds A and B is isolated as a colorless oil.

$^1$H-NMR (CDCl$_3$): δ=0.27 (3H), 0.98 (3H), 1.08 (3H), 1.23 (3H), 1.15-2.46 (10H), 2.19 (3H), 2.71 (3H), 2.82 (1H), 2.91 (1H), 2.95 (1H), 3.10 (1H), 3.47 (1H), 3.95 (1H), 4.12 (1H), 4.42 (1H), 4.70-5.30 (1H), 5.60 (1H), 6.65 (1H), 7.00 (1H), 7.12-7.32 (5H) ppm.

EXAMPLE 19

(1S,3S(E),7S,10S,11R,12S,16S)-10-Benzyl-7,11-dihydroxy-3-(1-methyl-2-(2-methyl-4-thiazolyl)ethenyl)-8,8,12,16-tetramethyl-4,17-dioxabicyclor[14.1.0]heptadecane-5,9-dione (A) and (1R,3S(E),7S,10S,11R,12S,16R)-10-benzyl-7,11-dihydroxy-3-(1-methyl-2-(2-methyl-4-thiazolyl)ethenyl)-8,8,12,16-tetramethyl-4,17-dioxabicyclor[14.1.0]heptadecane-5,9-dione (B)

Analogously to Example 14, 7.4 mg (13 µmol) of the compound that is presented according to Example 17 is reacted, and after working-up and purification, 1.9 mg (3.3 µmol, 25%) of title compound A and 1.7 mg (2.9 µmol, 22%) of title compound B are isolated in each case as a colorless oil.

$^1$H-NMR (CDCl$_3$) of A: δ=0.40 (3H), 0.89 (3H), 0.97 (3H), 1.08-1.77 (6H), 1.22 (3H), 1.90-2.07 (3H), 2.08 (3H), 2.38 (1H), 2.57 (1H), 2.70 (3H), 2.83 (1H), 2.92-3.06 (3H), 3.19 (1H), 3.54 (1H), 3.77 (1H), 4.19 (1H), 5.53 (1H), 6.52 (1H), 6.97 (1H), 7.08-7.31 (5H) ppm.

$^1$H-NMR (CDCl$_3$) of B: δ=0.17 (3H), 0.89 (3H), 1.00 (3H), 1.21-1.97 (8H), 1.28 (3H), 2.06 (1H), 2.10 (3H), 2.27-2.44 (3H), 2.71 (3H), 2.90 (1H), 2.99-3.11 (2H), 3.36 (1H), 3.96 (1H), 4.20 (1H), 4.29 (1H), 5.77 (1H), 6.57 (1H), 6.98 (1H), 7.08-7.31 (5H) ppm.

EXAMPLE 20

(4S,7R,8S,9S,13(Z),16S(E))-4,8-Dihydroxy-16-(1-methyl-2-(2-pyridyl)ethenyl)-1-oxa-5,5,7,9,13-pentamethyl-cyclohexadec-13-ene-2,6-dione

EXAMPLE 20a (5E,3S)-[3-[[(1,1-Dimethylethyl)diphenylsilyl]oxy]-4-methyl-5-(2-pyridyl)-pent-4-en-1-yl]-triphenylphosphonium iodide Analogously to Examples 7a to 7d, the title compound is obtained as a crystalline solid with use of diethyl(2-pyridyl)methanephosphonate.

$^1$H-NMR (CDCl$_3$): δ=1.08 (9H), 1.70-1.95 (2H), 1.99 (1H), 3.00 (1H), 3.31 (1H), 4.59 (1H), 6.68 (1H), 7.10 (1H), 7.18-7.46 (8H), 7.50-7.74 (18H), 7.74-7.87 (3H), 8.57 (1H) ppm.

EXAMPLE 20b (4S(4R,5S,6S,10E/Z,13S,14E))-4-(13-[[(1,1-Dimethylethyl)diphenylsilyl]oxy]-15-(2-pyridyl)-3-oxo-5-(tetrahydropyran-2-yloxy)-2,4,6,10,14-pentamethyl-pentadeca-10,14-dien-2-yl)-2,2-dimethyl-[1,3]dioxane Analogously to Example 1ao, 2.9 g (6.58 mmol) of the compound (4S(4R,5S,6S))-4-(3,10-dioxo-2,4,6-trimethyl-5-(tetrahydropyran-2-yloxy)-undec-2-yl)-2,2-dimethyl-[1,3]dioxane that is produced analogously to Examples 11 (reaction with ethylmagnesium bromide) to 1an is reacted with 8.0 g (9.95 mmol) of the compound that is described under Example 20a and 7.54 ml of a 1.6 M solution of n-butyllithium in n-hexane. In addition to starting material, 1.71 g (2.0 mmol, 31%) of the title compound is obtained.

$^1$H-NMR (CDCl$_3$): δ=0.84-0.98 (3H), 0.99-1.97 (42H), 2.01 (3H), 2.29 (2H), 3.22 (1H), 3.41 (1H), 3.58-4.01 (4H), 4.07-4.22 (2H), 4.47+4.51 (1H), 5.01 (1H), 6.24 (1H), 7.07 (1H), 7.22-7.46 (7H), 7.52-7.75 (5H), 8.57 (1H) ppm.

EXAMPLE 20c (4S(4R,5S,6S,10E/Z,13S,14E))-4-(13-Hydroxy-15-(2-pyridyl)-3-oxo-5-(tetrahydropyran-2-yloxy)-2,4,6,10,14-pentamethyl-pentadeca-10,14-dien-2-yl)-2,2-dimethyl-[1,3]dioxane Analogously to Example 1i, 1.76 g (2.11 mmol) of the compound that is presented according to Example 20b is reacted, and after working-up and purification, 1.17 g (1.95 mmol, 93%) of the title compound is isolated as a colorless oil.

¹H-NMR (CDCl₃): δ=0.88-2.13 (37H), 2.09 (3H), 2.39 (2H), 3.26 (1H), 3.44 (1H), 3.75-4.02 (3H), 4.08-4.22 (2H), 4.48+4.55 (1H), 5.21 (1H), 6.60 (1H), 7.10 (1H), 7.25 (1H), 7.64 (1H), 8.60 (1H) ppm.

EXAMPLE 20d (3S,6R,7S,8S,12E/Z,15S,16E)-1,3,7,15-Tetrahydroxy-4,4,6,8,12,16-hexamethyl-17-(2-pyridyl)-heptadeca-12,16-dien-5-one Analogously to Example 1f, 1.17 g (1.95 mmol) of the compound that is presented according to Example 20c is reacted with use of p-toluenesulfonic acid-monohydrate, and after working-up and purification, 852 mg (1.79 mmol, 92%) of the title compound is isolated as a colorless oil.

¹H-NMR (CDCl₃): δ=0.83+0.88 (3H), 1.06 (3H), 1.12 (3H), 1.22 (3H), 1.63+1.72 (3H), 0.98-1.82 (7H), 1.96-2.21 (3H), 2.07 (3H), 2.39 (2H), 2.90-3.80 (2H), 3.28 (1H), 3.32-3.48 (2H), 3.89 (2H), 4.06 (1H), 4.18 (1H), 5.20 (1H), 6.59 (1H), 7.11 (1H), 7.28 (1H), 7.64 (1H), 8.59 (1H) ppm.

EXAMPLE 20e (3S,6R,7S,8S,12E/Z,15S,16E)-1,3,7,15-Tetrakis-[[dimethyl(1,1-dimethylethyl)silyl]oxy]-4,4,6,8,12,16-hexamethyl-17-(2-pyridyl)-heptadeca-12,16-dien-5-one Analogously to Example 1aq, 847 mg (1.78 mmol) of the compound that is presented according to Example 20d is reacted, and after working-up and purification, 1.32 g (1.42 mmol, 80%) of the title compound is isolated as a colorless oil.

¹H-NMR (CDCl₃): δ=-0.02-0.13 (24H), 0.80-0.97 (39H), 1.02 (3H), 1.04 (3H), 1.21 (3H), 1.59+1.68 (3H), 1.08-1.70 (7H), 1.89-2.08 (2H), 2.06 (3H), 2.28 (2H), 3.13 (1H), 3.52-3.74 (2H), 3.77 (1H), 3.89 (1H), 4.11 (1H), 5.18 (1H), 6.48 (1H), 7.08 (1H), 7.21 (1H), 7.62 (1H), 8.60 (1H) ppm.

EXAMPLE 20f (3S,6R,7S,8S,12E/Z,15S,16E)-3,7,15-Tris-[[dimethyl(1,1-dimethylethyl)silyl]oxy]-4,4,6,8,12,16-hexamethyl-1-hydroxy-17-(2-pyridyl)-heptadeca-12,16-dien-5-one Analogously to Example 1ar, 1.32 g (1.42 mmol) of the compound that is presented according to Example 20e is reacted, and after working-up and purification, 1.06 g (1.29 mmol, 91%) of the title compound is isolated as a colorless oil.

¹H-NMR (CDCl₃): δ=0.00-0.13 (18H), 0.80-0.97 (30H), 1.06 (6H), 1.00-1.63 (7H), 1.21 (3H), 1.58+1.68 (3H), 1.89-2.08 (3H), 2.04 (3H), 2.28 (2H), 3.12 (1H), 3.63 (2H), 3.79 (1H), 4.02-4.16 (2H), 5.18 (1H), 6.48 (1H), 7.08 (1H), 7.21 (1H), 7.61 (1H), 8.60 (1H) ppm.

EXAMPLE 20g (3S,6R,7S,8S,12E/Z,15S,16E)-3,7,15-Tris-[[dimethyl(1,1-dimethylethyl)silyl]oxy]-4,4,6,8,12,16-hexamethyl-17-(2-pyridyl)-5-oxo-heptadeca-12,16-dienal Analogously to Example 1k, 1.14 g (1.39 mmol) of the compound that is presented according to Example 20f is reacted, and after working-up, 1.10 q (1.35 mmol, 97%) of the title compound is isolated as a colorless oil, which is further reacted without purification.

EXAMPLE 20h (3S,6R,7S,8S,12E,15S,16E)-3,7,15-Tris-[[dimethyl(1,1-dimethylethyl)silyl]oxy]-4,4,6,8,12,16-hexamethyl-17-(2-pyridyl)-5-oxo-heptadeca-12,16-dienoic acid (A) and (3S,6R,7S,8S,12Z,15S,16E)-3,7,15-tris-[[dimethyl(1,1-dimethylethyl)silyl]oxy]-4,4,6,8,12,16-hexamethyl-17-(2-pyridyl)-5-oxo-heptadeca-12,16-dienoic acid (B)

Analogously to Example 1at, 1.10 g (1.35 mmol) of the compound that is presented according to Example 20g is reacted, and after working-up and purification, 467 mg (0.56 mmol, 42%) of title compound B and 374 mg (0.45 mmol, 33%) of title compound A are isolated in each case as a colorless oil.

¹H-NMR (CDCl₃) of A: δ=0.00-0.19 (18H), 0.85 (3H), 0.90 (27H), 1.01-1.50 (6H), 1.07 (3H), 1.15 (3H), 1.21 (3H), 1.57 (3H), 1.81-2.08 (1H), 1.96 (3H), 2.24-2.41 (4H), 2.60 (1H), 3.18 (1H), 3.83 (1H), 4.13 (1H), 4.38 (1H), 5.13 (1H), 6.50 (1H), 7.16 (1H), 7.36 (1H), 7.71 (1H), 8.61 (1H) ppm.

¹H-NMR (CDCl₃) of B: δ=-0.02-0.17 (18H), 0.80-0.98 (30H), 1.00-1.59 (6H), 1.05 (3H), 1.13 (3H), 1.18 (3H), 1.69 (3H), 1.81-1.98 (1H), 1.91 (3H), 2.10-2.40 (4H), 2.49 (1H), 3.10 (1H), 3.79 (1H), 4.15 (1H), 4.42 (1H), 5.21 (1H), 6.63 (1H), 7.17 (1H), 7.31 (1H), 7.70 (1H), 8.58 (1H) ppm.

EXAMPLE 20i (3S,6R,7S,8S,12Z,15S,16E)-3,7-Bis-[[dimethyl(1,1-dimethylethyl)silyl]oxy]-4,4,6,8,12,16-hexamethyl-15-hydroxy-17-(2-pyridyl)-5-oxo-heptadeca-12,16-dienoic acid Analogously to Example 1i, 405 mg (0.49 mmol) of compound B that is presented according to Example 20h is reacted, and after working-up and purification, 338 mg (0.47 mmol, 96%) of the title compound is isolated as a colorless oil.

¹H-NMR (CDCl₃): δ=0.00-0.15 (12H), 0.80-0.99 (21H), 1.02-1.60 (6H), 1.07 (3H), 1.14 (3H), 1.19 (3H), 1.72 (3H), 1.90-2.08 (1H), 1.99 (3H), 2.17 (1H), 2.31 (1H), 2.38 (2H), 2.49 (1H), 3.00-4.00 (1H), 3.12 (1H), 3.81 (1H), 4.19 (1H), 4.43 (1H), 5.24 (1H), 6.73 (1H), 7.18 (1H), 7.32 (1H), 7.71 (1H), 8.60 (1H) ppm.

EXAMPLE 20j (4S,7R,8S,9S,13(Z),16S(E))-4,8-Bis-[[dimethyl(1,1-dimethylethyl)silyl]oxy]-16-(1-methyl-2-(2-pyridyl)ethenyl)-1-oxa-5,5,7,9,13-pentamethyl-cyclohexadec-13-ene-2,6-dione Analogously to Example 1aw, 287 mg (0.40 mmol) of the compound that is presented according to Example 20i is reacted, and after working-up and purification, 144 mg (0.21 mmol, 51%) of the title compound is isolated as a colorless oil.

¹H-NMR (CDCl₃): δ=-0.09 (3H), 0.01-0.18 (9H), 0.79-1.32 (4H), 0.85 (9H), 0.94 (9H), 0.98 (3H), 1.10 (3H), 1.14 (3H), 1.20 (3H), 1.46-1.82 (3H), 1.69 (3H), 2.03-2.21 (1H), 2.15 (3H), 2.49 (1H), 2.62-2.88 (2H), 3.03 (1H), 3.90 (1H), 4.05 (1H), 5.02 (1H), 5.19 (1H), 6.58 (1H), 7.11 (1H), 7.27 (1H), 7.65 (1H), 8.61 (1H) ppm.

EXAMPLE 20

(4S,7R,8S,9S,13(Z),16S(E))-4,8-Dihydroxy-16-(1-methyl-2-(2-pyridyl)ethenyl)-1-oxa-5,5,7,9,13-pentamethyl-cyclohexadec-13-ene-2,6-dione Analogously to Example 1, 144 mg (206 μmol) of the compound that is presented according to Example 20j is reacted, and after working-up and purification, 90 mg (191 μmol, 93%) of the title compound is isolated as a colorless oil.

$^1$H-NMR (CDCl$_3$): δ=1.02 (3H), 1.08 (3H), 1.20 (3H), 1.24-1.43 (4H), 1.38 (3H), 1.67 (3H), 1.60-1.98 (2H), 2.06 (3H), 2.23 (1H), 2.31 (2H), 2.45 (1H), 2.64 (1H), 3.11-3.27 (2H), 3.73 (1H), 4.41 (1H), 4.50-4.77 (1H), 5.09-5.23 (2H), 6.62 (1H), 7.14 (1H), 7.31 (1H), 7.69 (1H), 8.52 (1H) ppm.

EXAMPLE 21

(1S,3S(E),7S,10R,11S,12S,16R)-7,11-Dihydroxy-3-(1-methyl-2-(2-pyridyl)ethenyl)-8,8,10,12,16-pentamethyl-4,17-dioxabicyclo[14.1.0]heptadecane-5,9-dione (A) and (1R,3S(E),7S,10R,11S,12S,16S)-7,11-dihydroxy-3-(1-methyl-2-(2-pyridyl)ethenyl)-8,8,10,12,16-pentamethyl-4,17-dioxabicyclor[14.1.0]heptadecane-5,9-dione (B) and (4S,7R,8S,9S,13(Z),16S(E))-4,8-dihydroxy-16-(1-methyl-2-(2-N-oxypyridyl)ethenyl)-1-oxa-5,5,7,9,13-pentamethyl-cyclohexadec-13-ene-2,6-dione (C) and (1S,3S(E),7S,10R,11S,12S,16R)-7,11-dihydroxy-3-(1-methyl-2-(2-N-oxypyridyl)ethenyl)-8,8,10,12,16-pentamethyl-4,17-dioxabicyclo[14.1.0]heptadecane-5,9-dione (D) and (1R,3S(E),7S,10R,11S,12S,16S)-7,11-dihydroxy-3-(1-methyl-2-(2-N-oxypyridyl)ethenyl)-8,8,10,12,16-pentamethyl-4,17-dioxabicyclor[14.1.0]heptadecane-5,9-dione (E)

Analogously to Example 14, 40 mg (84 μmol) of the compound that is presented according to Example 20 is reacted, and after working-up and purification, 8.5 mg (17 μmol, 21%) of title compound A, 2.0 mg (4 μmol, 5%) of title compound B, 2.9 mg (6 μmol, 7%) of title compound C, 12.6 mg (25 μmol, 30%) of title compound D, and 2.5 mg (5 μmol, 6%) of title compound E are isolated.

$^1$H-NMR (CDCl$_3$) of A: δ=1.00 (3H), 1.08 (3H), 1.16 (3H), 1.21-1.98 (9H), 1.29 (3H), 1.38 (3H), 2.07 (3H), 2.19 (1H), 2.30 (1H), 2.53 (1H), 2.81 (1H), 2.89 (1H), 3.29 (1H), 3.76 (1H), 4.37 (1H), 5.40 (1H), 6.53 (1H), 7.16 (1H), 7.29 (1H), 7.70 (1H), 8.53 (1H) ppm.

$^1$H-NMR (CDCl$_3$) of B: δ=0.94 (3H), 1.03 (3H), 1.11 (3H), 1.28 (3H), 1.38 (3H), 1.00-1.95 (8H), 2.14 (3H), 2.08-2.20 (1H), 2.41 (1H), 2.49 (1H), 2.83 (1H), 3.09 (1H), 3.33 (1H), 3.95 (1H), 4.06 (1H), 4.17 (1H), 5.70 (1H), 6.64 (1H), 7.12 (1H), 7.25 (1H), 7.67 (1H), 8.59 (1H) ppm.

$^1$H-NMR (CDCl$_3$) of C: δ=1.01 (3H), 1.04 (3H), 1.20 (3H), 1.43 (3H), 1.68 (3H), 1.12-1.93 (6H), 2.02-2.64 (5H), 2.13 (3H), 3.22 (1H), 3.38 (1H), 3.69 (1H), 4.56 (1H), 5.11 (1H), 5.18 (1H), 6.28 (1H), 7.03 (1H), 7.21 (1H), 7.37 (1H), 7.48 (1H), 8.29 (1H) ppm.

$^1$H-NMR (CDCl$_3$) of D: δ=1.01 (3H), 1.06 (3H), 1.18 (3H), 1.30 (3H), 1.46 (3H), 1.13-1.89 (8H), 2.14 (3H), 2.09-2.30 (2H), 2.52 (1H), 2.78 (1H), 3.17 (1H), 3.29 (1H), 3.71 (1H), 4.54 (1H), 5.37 (1H), 6.24 (1H), 6.96 (1H), 7.22 (1H), 7.37 (1H), 7.42 (1H), 8.28 (1H) ppm.

$^1$H-NMR (CDCl$_3$) of E: δ=0.96 (3H), 1.06 (3H), 1.10 (3H), 1.29 (3H), 1.43 (3H), 1.22-1.77 (6H), 1.78-2.18 (3H), 2.11 (3H), 2.35-2.52 (2H), 2.96 (1H), 3.31 (1H), 3.43 (1H), 3.91 (1H), 4.49 (1H), 5.42 (1H), 5.49 (1H), 7.02 (1H), 7.19 (1H), 7.33 (1H), 7.45 (11H), 8.28 (1H) ppm.

EXAMPLE 22

(4S,7R,8S,9S,13(E),16S(E))-4,8-Dihydroxy-16-(1-methyl-2-(2-pyridyl)ethenyl)-1-oxa-5,5,7,9,13-pentamethyl-cyclohexadec-13-ene-2,6-dione EXAMPLE 22a (3S,6R,7S,8S,12E,15,16E)-3,7-Bis-[[dimethyl(1,1-dimethylethyl)silyl]oxy]-4,4,6,8,12,16-hexamethyl-15-hydroxy-17-(2-pyridyl)-5-oxo-heptadeca-12,16-dienoic acid Analogously to Example 1i, 370 mg (444 μmol) of compound A that is presented according to Example 20h is reacted, and after working up and purification, 309 mg (430 μmol, 97%) of the title compound is isolated as a colorless oil.

EXAMPLE 22b (4S,7R,8S,9S,13(E),16S(E))-4,8-Bis-[[dimethyl(1,1-dimethylethyl)silyl]oxy]-16-(1-methyl-2-(2-pyridyl)ethenyl)-1-oxa-5,5,7,9,13-pentamethyl-cyclohexadec-13-ene-2,6-dione Analogously to Example 1aw, 309 g (430 μmol) of the compound that is presented according to Example 22a is reacted, and after working-up and purification, 233 mg (333 μmol, 77%) of the title compound is isolated as a colorless oil.

$^1$H-NMR (CDCl$_3$): δ=0.02-0.17 (12H), 0.88 (18H), 0.93 (3H), 1.09 (3H), 1.12 (3H), 1.16-1.37 (2H), 1.19 (3H), 1.45-1.64 (3H), 1.59 (3H), 1.93 (1H), 2.08-2.21 (1H), 2.18 (3H), 2.50 (1H), 2.54-2.70 (3H), 3.07 (1H), 3.90 (1H), 4.51 (1H), 5.20 (1H), 5.30 (1H), 6.58 (1H), 7.10 (1H), 7.19 (1H), 7.63 (1H), 8.60 (1H) ppm.

EXAMPLE 22

(4S,7R,8S,9S,13(E),16S(E))-4,8-Dihydroxy-16-(1-methyl-2-(2-pyridyl)ethenyl)-1-oxa-5,5,7,9,13-pentamethyl-cyclohexadec-13-ene-2,6-dione Analogously to Example 1, 228 mg (326 μmol) of the compound that is presented according to Example 22b is reacted, and after working-up and purification, 131 mg (278 μmol, 85%) of the title compound is isolated as a colorless oil $^1$H-NMR (CDCl$_3$): δ=0.98 (3H), 1.07 (3H), 1.17 (3H), 1.31 (3H), 1.20-1.46 (3H), 1.52-1.83 (2H), 1.61 (3H), 1.98 (1H), 2.08 (3H), 2.17 (1H), 2.39 (1H), 2.41-2.66 (3H), 3.18-3.39 (2H), 3.66 (1H), 3.87 (1H), 4.38 (1H), 5.14 (1H), 5.42 (1H), 6.60 (1H), 7.13 (1H), 7.32 (1H), 7.69 (1H), 8.56 (1H) ppm.

EXAMPLE 23

(1R,3S(E),7S,10R,11S,12S,16R)-7,11-Dihydroxy-3-(1-methyl-2-(2-pyridyl)ethenyl)-8,8,10,12,16-pentamethyl-4,17-dioxabicyclor[14.1.0]pentadecane-5,9-dione (A) and (1S,3S(E),7S,10R,11S,12S,16S)-7,11-dihydroxy-3-(1-methyl-2-(2-pyridyl)ethenyl)-8,8,10,12,16-pentamethyl-4,17-dioxabicyclo[14.1.0]heptadecane-5,9-dione (B) (1R,3S(E),7S,10R,11S,12S,16R)-7,11-dihydroxy-3-(1-methyl-2-(2-N-oxidopyridyl)ethenyl)-8,8,10,12,16-pentamethyl-4,17-dioxabicyclor[14.1.0]heptadecane-5,9-dione (C) and (1S,3S(E),7S,10R,11S,12S,16S)-7,11-dihydroxy-3-(1-methyl-2-(2-N-oxidopyridyl)ethenyl)-8,8,10,12,16-pentamethyl-4,17-dioxabicyclor[14.1.0]heptadecane-5,9-dione (D)

Analogously to Example 14, 50 mg (106 μmol) of the compound that is presented according to Example 20 is reacted, and after working-up and purification, 5.3 mg (11 μmol, 10%) of title compound A (or B), 4.4 mg (9 μmol, 9%) of title compound B (or A), 9.6 mg (10 μmol, 9%) of title compound C (or D), and 11.1 mg (11 μmol, 11%) of title compound D (or C) are isolated.

$^1$H-NMR (CDCl$_3$) of A or B: δ=0.94 (3H), 1.04 (3H), 1.13 (3H), 1.28 (3H), 1.39 (3H), 2.11 (3H), 1.01-2.15 (9H), 2.44 (1H), 2.58 (1H), 2.74 (1H), 2.91 (1H), 3.31 (1H), 3.73 (1H), 4.21 (1H), 4.30 (1H), 5.53 (1H), 6.53 (1H), 7.13 (1H), 7.30 (1H), 7.67 (1H), 8.57 (1H) ppm.

$^1$H-NMR (CDCl$_3$) of B or A: δ=0.93 (3H), 1.09 (3H), 1.14 (3H), 1.28 (3H), 1.37 (3H), 1.22-2.16 (9H), 2.09 (3H), 2.46 (1H), 2.57 (1H), 2.96 (1H), 3.08 (1H), 3.26 (1H), 3.72 (1H), 3.89 (1H), 4.37 (1H), 5.47 (1H), 6.62 (1H), 7.13 (1H), 7.28 (1H), 7.68 (1H), 8.57 (1H), ppm.

$^1$H-NMR (CDCl$_3$) of C or D: δ=0.93 (3H), 1.06 (3H), 1.19 (3H), 1.21 (3H), 1.44 (3H), 1.15-2.01 (8H), 2.10 (3H), 2.12-2.26 (2H), 2.49 (1H), 2.89 (1H), 3.26 (1H), 3.48 (1H), 3.67 (1H), 4.63 (1H), 5.45 (1H), 5.76 (1H), 7.09 (1H), 7.21 (1H), 7.36 (1H), 7.45 (1H), 8.29 (1H) ppm.

$^1$H-NMR (CDCl$_3$) of D or C: δ=0.96 (3H), 1.06 (3H), 1.15 (3H), 1.24 (3H), 1.43 (3H), 1.02-2.19 (9H), 2.08 (3H), 2.23 (1H), 2.56 (1H), 2.96 (1H), 3.29 (1H), 3.68 (2H), 4.53 (1H), 5.60-5.72 (2H), 7.10 (1H), 7.21 (1H), 7.37 (1H), 7.52 (1H), 8.29 (1H) ppm.

EXAMPLE 24

(4S,7R,8S,9S,13(Z),16S(E))-4,8-Dihydroxy-7-ethyl-16-(1-methyl-2-(2-pyridyl)ethenyl)-1-oxa-5,5,9,13-tetramethyl-cyclohexadec-13-ene-2,6-dione

EXAMPLE 24h,

Variant I (3S,6R,7S,8S,12E/Z,15S,16E)-6-Ethyl-1,3,7,15-tetrakis-[[dimethyl(1,1-dimethylethyl)silyl]oxy]-4,4,8,12,16-pentamethyl-17-(2-pyridyl)-heptadeca-12,16-dien-5-one

EXAMPLE 24a/I (2S)-2-Methyl-1-(tetrahydropyran-2-yloxy)-heptan-6-one

Analogously to Example 1m, 9.0 g (39.1 mmol) of the compound that is presented according to Example 1v is reacted, and after working-up and purification, 8.05 g (35.3 mmol, 90%) of the title compound is isolated as a colorless oil.

$^1$H-NMR (CDCl$_3$): δ=0.93 (3H), 1.12 (1H), 1.32-1.89 (10H), 2.14 (3H), 2.42 (2H), 3.19 (1H), 3.45-3.63 (2H), 3.84 (1H), 4.56 (1H) ppm.

EXAMPLE 24b/I (2S,6E/Z,9S,10E)-9-[[(1,1-Dimethylethyl)diphenylsilyl]oxy]-11-(2-pyridyl)-1-(tetrahydropyran-2-yloxy)-2,6,10-trimethyl-undeca-6,10-diene Analogously to Example 7ao or 20b, 1.89 g (8.28 mmol) of the compound that is presented according to Example 24a/I is reacted with 10.0 g (12.4 mmol) of the compound that is presented according to Example 20a with use of n-butyllithium as a base, and after working-up and purification, 1.98 g (3.2 mmol, 38%) of the title compound is isolated as a colorless oil.

$^1$H-NMR (CDCl$_3$): δ=0.81-0.92 (3H), 1.08 (9H), 1.18-1.92 (16H), 2.02 (3H), 2.19-2.42 (2H), 3.02-3.62 (3H), 3.83 (1H), 4.20 (1H), 4.55 (1H), 5.00 (1H), 6.24 (1H), 6.98-7.10 (2H), 7.22-7.46 (6H), 7.57 (1H), 7.62-7.75 (4H), 8.58 (1H) ppm.

EXAMPLE 24c/I (2S,6E/Z,9S,10E)-11-(2-Pyridyl)-1-(tetrahydropyran-2-yloxy)-2,6,10-trimethyl-undeca-6,10-dien-9-ol Analogously to Example 1i, 1.98 g (3.2 mmol) of the compound that is presented according to Example 24b/I is reacted, and after working-up and purification, 1.16 g (3.0 mmol, 94%) of the title compound is isolated as a colorless oil.

$^1$H-NMR (CDCl$_3$): δ=0.87-1.00 (3H), 1.12 (1H), 1.32-1.95 (11H), 1.67+1.73 (3H), 1.98-2.18 (2H), 2.10 (3H), 2.40 (2H), 3.08-3.28 (1H), 3.42-3.65 (2H), 3.84 (1H), 4.19 (1H), 4.55 (1H), 5.19 (1H), 6.59 (1H), 7.10 (1H), 7.24 (1H), 7.63 (1H), 8.60 (1H) ppm.

EXAMPLE 24d/I (2S,6E/Z,9S,10E)-9-[[Dimethyl(1,1-dimethylethyl)silyl]oxy]-11-(2-pyridyl)-1-(tetrahydropyran-2-yloxy)-2,6,10-trimethyl-undeca-6,10-diene Analogously to Example 1n, 1.15 g (2.97 mmol) of the compound that is presented according to Example 24c/I is reacted, and after working-up and purification, 1.43 g (2.85 mmol, 96%) of the title compound is isolated as a colorless oil.

$^1$H-NMR (CDCl$_3$): δ=0.03 (3H), 0.08 (3H), 0.81-0.98 (12H), 1.11 (1H), 1.28-2.10 (12H), 1.60+1.69 (3H), 2.06 (3H), 2.28 (2H), 3.07-3.27 (1H), 3.42-3.63 (2H), 3.85 (1H), 4.12 (1H), 4.56 (1H), 5.18 (1H), 6.48 (1H), 7.08 (1H), 7.22 (1H), 7.62 (1H), 8.60 (1H) ppm.

EXAMPLE 24e/I (2S,6E/Z,9S,10E)-9-[[Dimethyl(1,1-dimethylethyl)silyl]oxy]-11-(2-pyridyl)-2,6,10-trimethyl-undeca-6,10-dien-1-ol Analogously to Example 1f, 1.43 g (2.85 mmol) of the compound that is presented according to Example 24d/I is reacted with use of p-toluenesulfonic acid-monohydrate at 23° C., and after working-up and purification, 1.11 g (2.66 mmol, 93%) of the title compound is isolated as a colorless oil.

$^1$H-NMR (CDCl$_3$): δ=0.03 (3H), 0.08 (3H), 0.82-0.96 (12H), 0.97-1.71 (6H), 1.59+1.69 (3H), 1.90-2.14 (2H), 2.04 (3H), 2.30 (2H), 3.35-3.56 (2H), 4.13 (1H), 5.13+5.21 (1H), 6.48 (1H), 7.10 (1H), 7.25 (1H), 7.63 (1H), 8.58 (1H) ppm.

EXAMPLE 24f/I (2S,6E/Z,9S,10E)-9-[[Dimethyl(1,1-dimethylethyl)silyl]oxy]-11-(2-pyridyl)-2,6,10-trimethyl-undeca-6,10-dienal Analogously to Example 1k, 1.01 g (2.42 mmol) of the compound that is presented according to Example 24e/I is reacted, and after working-up and purification, 921 mg (2.22 mmol, 92%) of the title compound is isolated as a colorless oil.

$^1$H-NMR (CDCl$_3$): δ=0.03 (3H), 0.08 (3H), 0.92 (9H), 1.05+1.09 (3H), 1.22-1.75 (4H), 1.60+1.68 (3H), 1.95-2.11 (2H), 2.07 (3H), 2.23-2.38 (3H), 4.12 (1H), 5.19 (1H), 6.48 (1H), 7.08 (1H), 7.22 (1H), 7.63 (1H), 8.60 (1H), 9.57+9.61 (1H) ppm.

EXAMPLE 24g/I (3S,6R,7S,8S,12E/Z,15S,16E)-6-Ethyl-7-hydroxy-1,3,15-tris-[[dimethyl(1,1-dimethylethyl)silyl]oxy]-4,4,8,12,16-pentamethyl-17-(2-pyridyl)-heptadeca-12,16-dien-5-one (A) and (3S,6S,7R,8S,12E/Z,15S,16E)-6-ethyl-7-hydroxy-1,3,15-tris-[[dimethyl(1,1-dimethylethyl)silyl]oxy]-4,4,8,12,16-pentamethyl-17-(2-pyridyl)-heptadeca-12,16-dien-5-one (B)

Analogously to Example 1ak, 1.0 g (2.41 mmol) of the compound that is presented according to Example 24f/I is reacted with 1.16 g (2.78 mmol) of the compound that is presented according to Example 1m, and after working-up and purification, 972 mg (1.17 mmol, 48%) of title compound A and 178 mg (0.21 mmol, 9%) of title compound B are isolated in each case as a colorless oil.

$^1$H-NMR (CDCl$_3$) of A: δ=0.00-0.14 (18H), 0.80-0.95 (33H), 1.00-1.81 (9H), 1.11 (3H), 1.17 (3H), 1.60+1.68 (3H), 1.90-2.11 (2H), 2.04 (3H), 2.29 (2H), 3.03 (1H), 3.18 (1H), 3.32 (1H), 3.54-3.77 (2H), 3.99 (1H), 4.12 (1H), 5.18 (1H), 6.48 (1H), 7.09 (1H), 7.23 (1H), 7.62 (1H), 8.60 (1H) ppm.

$^1$H-NMR (CDCl$_3$) of B: δ=−0.02-0.14 (18H), 0.83-1.01 (33H), 1.02-1.80 (9H), 1.10 (3H), 1.16 (3H), 1.62+1.70 (3H), 1.92-2.10 (2H), 2.06 (3H), 2.30 (2H), 3.02 (1H), 3.15 (1H), 3.42 (1H), 3.53-3.74 (2H), 4.02 (1H), 4.12 (1H), 5.19 (1H), 6.49 (1H), 7.09 (1H), 7.23 (1H), 7.63 (1H), 8.60 (1H) ppm.

EXAMPLE 24h/I (3S,6R,7S,8S,12E/Z,15S,16E)-6-Ethyl-1,3,7,15-tetrakis-[[dimethyl(1,1-dimethylethyl)silyl]oxy]-4,4,8,12,16-pentamethyl-17-(2-pyridyl)-heptadeca-12,16-dien-5-one Analogously to Example 1aq, 972 mg (1.17 mmol) of compound A that is presented according to Example 24g/I is reacted, and after working-up and purification, 1.02 g (1.08 mmol, 92%) of the title compound is isolated as a colorless oil.

$^1$H-NMR (CDCl$_3$): δ=0.00-0.12 (24H), 0.78-0.97 (42H), 1.00-1.80 (9H), 1.03 (3H), 0.21 (3H), 1.60+1.68 (3H), 1.90-2.10 (2H), 2.05 (3H), 2.28 (2H), 3.02 (1H), 3.52-3.73 (2H), 3.82 (1H), 3.91 (1H), 4.11 (1H), 5.19 (1H), 6.49 (1H), 7.08 (1H), 7.22 (1H), 7.61 (1H), 8.60 (1H) ppm.

EXAMPLE 24h,

Variant II (3S,6R,7S,8S,12E/Z,15S,16E)-6-Ethyl-1,3,7,15-tetrakis-[[dimethyl(1,1-dimethylethyl)silyl]oxy]-4,4,8,12,16-pentamethyl-17-(2-pyridyl)-heptadeca-12,16-dien-5-one EXAMPLE 24a/II (4S(4R,5S,6S,10E/Z,13S,14E))-4-(13-[[(1,1-Dimethylethyl)diphenylsilyl]oxy]-4-ethyl-15-(2-pyridyl)-3-oxo-5-(tetrahydropyran-2-yloxy)-2,6,10,14-tetramethyl-pentadeca-10,14-dien-2-yl)-2,2-dimethyl-[1,3]dioxane Analogously to Example 1ao or 20b, 724 mg (1.59 mmol) of the compound that is presented according to Example 1an is reacted with 1.93 g (2.40 mmol) of the compound that is presented according to Example 20a with use of n-butyllithium as a base, and after working-up and purification, 478 mg (0.56 mmol, 35%) of the title compound is isolated as a colorless oil.

$^1$H-NMR (CDCl$_3$): δ=0.72-1.96 (48H), 2.01 (3H), 2.16-2.41 (2H), 3.03+3.13 (1H), 3.41 (1H), 3.59-4.04 (3H), 4.12-4.32 (2H), 4.43+4.52 (1H), 5.01 (1H), 6.23 (1H), 6.97-7.10 (2H), 7.21-7.46 (6H), 7.58 (1H), 7.62-7.74 (4H), 8.57 (1H) ppm.

EXAMPLE 24b/II (4S(4R,5S,6S,10E/Z,13S,14E))-4-(4-Ethyl-13-hydroxy-15-(2-pyridyl)-3-oxo-5-(tetrahydropyran-2-yloxy)-2,6,10,14-tetramethyl-pentadeca-10,14-dien-2-yl)-2,2-dimethyl-[1,3]dioxane Analogously to Example 1i, 660 mg (0.77 mmol) of the compound that is presented according to Example 24a/II is reacted, and after working-up and purification, 475 mg (0.77 mmol, 100%) of the title compound is isolated as a colorless oil.

$^1$H-NMR (CDCl$_3$): δ=0.72-2.12 (39H), 2.09 (3H), 2.39 (2H), 3.07+3.17 (1H), 3.42 (1H), 3.62-4.32 (6H), 4.43+4.54 (1H), 5.20 (1H), 6.61 (1H), 7.10 (11H), 7.25 (1H), 7.63 (1H), 8.60 (1H) ppm.

EXAMPLE 24c/II (3S,6R,7S,8S,12E/Z,15S,16E)-6-Ethyl-1,3,7,15-tetrahydroxy-4,4,8,12,16-pentamethyl-17-(2-pyridyl)-heptadeca-12,16-dien-5-one Analogously to Example 1f, 472 mg (0.77 mmol) of the compound that is presented according to Example 24b/II is reacted with use of p-toluenesulfonic acid-monohydrate at 23° C., and after working-up and purification, 348 mg (0.71 mmol, 92%) of the title compound is isolated as a colorless oil.

$^1$H-NMR (CDCl$_3$): δ=0.75-0.92 (6H), 1.07 (3H), 1.11-2.47 (13H), 1.26 (3H), 1.63 (3H), 1.72 (3H), 2.04+2.05 (3H), 2.96 (1H), 3.18 (1H), 3.41+3.48 (1H), 3.86 (2H), 4.04-4.23 (2H), 5.18+5.23 (1H), 6.57 (1H), 7.12 (1H), 7.29 (1H), 7.67 (1H), 8.59 (1H) ppm.

EXAMPLE 24h/II (3S,6R,7S,8S,12E/Z,15S,16E)-6-Ethyl-1,3,7,15-tetrakis-[[dimethyl(1,1-dimethylethyl)silyl]oxy]-4,4,8,12,16-pentamethyl-17-(2-pyridyl)-heptadeca-12,16-dien-5-one Analogously to Example 1aq, 343 mg (0.70 mmol) of the compound that is presented according to Example 24c/II is reacted, and after working-up and purification, 497 mg (0.52 mmol, 75%) of the title compound is isolated as a colorless oil.

$^1$H-NMR (CDCl$_3$): coverage is identical to that described under Example 24h/I.

EXAMPLE 24i (3S,6R,7S,8S,12E/Z,15S,16E)-6-Ethyl-3,7,15-tris-[[dimethyl(1,1-dimethylethyl)silyl]-oxy]-4,4,8,12,16-pentamethyl-1-hydroxy-17-(2-pyridyl)-heptadeca-12,16-dien-5-one Analogously to Example 1ar, 1.71 g (1.81 mmol) of the compound that is presented according to Example 24h/I or Example 24h/II is reacted, and after working-up and purification, 1.38 g (1.66 mmol, 97%) of the title compound is isolated as a colorless oil.

$^1$H-NMR (CDCl$_3$): δ=0.00-0.15 (18H), 0.80-0.98 (33H), 1.02-2.10 (1H), 1.09 (3H), 1.21 (3H), 1.59+1.68 (3H), 2.05 (3H), 2.29 (2H), 3.01 (1H), 3.69 (2H), 3.84 (1H), 4.02-4.19 (3H), 5.18 (1H), 6.48 (1H), 7.09 (1H), 7.22 (1H), 7.62 (1H), 8.59 (1H) ppm.

EXAMPLE 24k (3S,6R,7S,8S,12E/Z,15S,16E)-6-Ethyl-3,7,15-tris-[[dimethyl(1,1-dimethlethyl)silyl]oxy]-4,4,8,12,16-pentamethyl-17-(2-pyridyl)-5-oxo-heptadeca-12,16-dienal Analogously to Example 1k, 1.38 g (1.66 mmol) of the compound that is presented according to Example 24i is reacted, and after working-up and purification, 1.34 g (1.61 mmol, 97%) of the title compound is isolated as a colorless oil.

$^1$H-NMR (CDCl$_3$): δ=0.01-0.13 (18H), 0.78-0.97 (35H), 1.09 (3H), 1.13-1.79 (5H), 1.21 (3H), 1.60+1.68 (3H), 1.91-2.10 (2H), 2.05 (3H), 2.28 (2H), 2.40 (1H), 2.57 (1H), 3.02 (1H), 3.82 (1H), 4.12 (1H), 4.48 (1H), 5.18 (1H), 6.48 (1H), 7.08 (1H), 7.22 (1H), 7.62 (1H), 8.60 (1H), 9.79 (1H) ppm.

EXAMPLE 24l (3S,6R,7S,8S,12E,15S,16E)-6-Ethyl-3,7,15-tris-[[dimethyl(1,1-dimethylethyl)silyl]oxy]-4,4,8,12,16-pentamethyl-17-(2-pyridyl)-5-oxo-heptadeca-12,16-dienoic acid (A) and (3S,6R,7S,8S,12Z,15S,16E)-6-ethyl-3,7,15-tris-[[dimethyl(1,1-dimethylethyl)silyl]oxy]-4,4,8,12,16-pentamethyl-17-(2-pyridyl)-5-oxo-heptadeca-12,16-dienoic acid (B)

Analogously to Example 1at, 1.34 g (1.61 mmol) of the compound that is presented according to Example 24k is reacted, and after working-up and purification, 433 mg (0.51 mmol, 32%) of title compound A and 662 mg (0.78 mmol, 49%) of title compound B are isolated in each case as a colorless oil.

$^1$H-NMR (CDCl$_3$) of A: δ=0.00-0.16 (18H), 0.78-0.93 (35H), 0.98-1.71 (6H), 1.12 (3H), 1.21 (3H), 1.56 (3H), 1.80-2.07 (2H), 1.93 (3H), 2.23-2.41 (3H), 2.67 (1H), 3.05 (1H), 3.86 (1H), 4.12 (1H), 4.33 (1H), 5.11 (1H), 6.48 (1H), 7.24 (1H), 7.33 (1H), 7.69 (1H), 8.61 (1H) ppm.

$^1$H-NMR (CDCl$_3$) of B: δ=–0.01-0.17 (18H), 0.81-0.96 (35H), 1.00-1.78 (6H), 1.15 (3H), 1.21 (3H), 1.70 (3H), 1.89 (1H), 1.96 (3H), 2.11-2.42 (4H), 2.59 (1H), 3.00 (1H), 3.82 (1H), 4.17 (1H), 4.41 (1H), 5.24 (1H), 6.63 (1H), 7.19 (1H), 7.33 (1H), 7.71 (1H), 8.64 (1H) ppm.

EXAMPLE 24m (3S,6R,7S,8S,12Z,15S,16E)-3,7-Bis-[[dimethyl(1,1-dimethylethyl)silyl]oxy]-6-ethyl-4,4,8,12,16-pentamethyl-15-hydroxy-17-(2-pyridyl)-5-oxo-heptadeca-12,16-dienoic Acid Analogously to Example 1i, 662 mg (0.78 mmol) of compound B that is presented according to Example 24 l is reacted at 23° C., and after working-up, 680 mg of the title compound is isolated as a crude product, which is further reacted without purification.

EXAMPLE 24n (4S,7R,8S,9S,13(Z),16S(E))-4,8-Bis-[[dimethyl(1,1-dimethylethyl)silyl]oxy]-16-(1-methyl-2-(2-pyridyl)ethenyl)-7-ethyl-1-oxa-5,5,9,13-tetramethyl-cyclohexadec-13-ene-2,6-dione Analogously to Example 1aw, 680 mg (max. 0.78 mmol) of the compound that is presented according to Example 24m is reacted, and after working-up and purification, 287 mg (402 μmol, 52%) of the title compound is isolated as a colorless oil.

$^1$H-NMR (CDCl$_3$): δ=–0.11 (3H), 0.03-0.15 (9H), 0.72 (3H), 0.80-1.78 (23H), 0.83 (3H), 0.92 (3H), 0.98 (3H), 1.11 (3H), 1.18 (3H), 1.68 (3H), 1.85 (1H), 2.09 (1H), 2.12 (3H), 2.46 (1H), 2.55-2.82 (3H), 3.05 (1H), 4.01 (1H), 4.03 (1H), 4.99 (1H), 5.16 (1H), 6.54 (1H), 7.08 (1H), 7.23 (1H), 7.61 (1H), 8.58 (1H) ppm.

EXAMPLE 24

(4S,7R,8S,9S,13(Z),16S(E))-4,8-Dihydroxy-7-ethyl-16-(1-methyl-2-(2-pyridyl)ethenyl)-1-oxa-5,5,9,13-tetramethyl-cyclohexadec-13-ene-2,6-dione Analogously to Example 1, 282 mg (395 μmol) of the compound that is presented according to Example 24n is reacted, and after working-up and purification, 115 mg (237 μmol, 60%) of the title compound is isolated as a colorless oil.

$^1$H-NMR (CDCl$_3$): δ=0.89 (3H), 1.04 (3H), 1.09 (3H), 1.22-2.11 (8H), 1.36 (3H), 1.70 (3H), 2.07 (3H), 2.20-2.39 (3H), 2.49 (1H), 2.65 (1H), 2.69 (1H), 3.23 (1H), 3.70 (1H), 4.35 (1H), 4.59 (1H), 5.12 (1H), 5.19 (1H), 6.61 (1H), 7.13 (1H), 7.29 (1H), 7.69 (1H), 8.53 (1H) ppm.

EXAMPLE 25

(1S,3S(E),7S,10R11S,12S,16R)-7,11-Dihydroxy-10-ethyl-3-(1-methyl-2-(2-pyridyl)ethenyl)-8,8,12,16-tetramethyl-4,17-dioxabicyclo[14.1.0]heptadecane-5,9-dione (A) and (1R,3S(E),7S,10R,11S,12S,16S)-7,11-dihydroxy-10-ethyl-3-(1-methyl-2-(2-pyridyl)ethenyl)-8,8,12,16-tetramethyl-4,17-dioxabicyclor[14.1.0]heptadecane-5,9-dione (B) and (4S,7R,8S,9S,13(Z),16S(E))-4,8-dihydroxy-9-ethyl-16-(1-methyl-2-(2-N-oxypyridyl)ethenyl)-1-oxa-5,5,7,13-tetramethyl-cyclohexadec-13-ene-2,6-dione (C) and (1S,3S(E),7S,10R,11S,12S,16R)-7,11-dihydroxy-10-ethyl-3-(1-methyl-2-(2-N-oxypyridyl)ethenyl)-8,8,12,16-tetramethyl-4,17-dioxabicyclor[14.1.0]heptadecane-5,9-dione (D) and (1R,3S(E),7S,10R,11S,12S,16S)-7,11-dihydroxy-10-ethyl-3-(1-methyl-2-(2-N-oxypyridyl)ethenyl)-8,8,12,16-tetramethyl-4,17-dioxabicyclo[14.1.0]heptadecane-5,9-dione (E)

Analogously to Example 14, 50 mg (103 µmol) of the compound that is presented according to Example 24 is reacted, and after working-up and purification, 15.3 mg (30 µmol, 30%) of title compound A, 2 mg (4 µmol, 4%) of title compound B, 2 mg (4 µmol, 4%) of title compound C, 21 mg (42 µmol, 41%) of title compound D and 3.3 mg (7 µmol, 6%) of title compound E are isolated in each case as a colorless solid.

$^1$H-NMR (CDCl$_3$) of A: δ=0.87 (3H), 0.99 (3H), 1.06 (3H), 1.21-2.03 (10H), 1.30 (3H), 1.39 (3H), 2.03 (3H), 2.15 (1H), 2.37 (1H), 2.56 (1H), 2.81 (1H), 2.83 (1H), 3.32 (1H), 3.66 (1H), 4.36 (1H), 5.24 (1H), 5.45 (1H), 6.61 (1H), 7.16 (1H), 7.29 (1H), 7.70 (1H), 8.53 (1H) ppm.

$^1$H-NMR (CDCl$_3$) of B: δ=0.85 (3H), 0.95 (3H), 1.04 (3H), 1.20-1.93 (10H), 1.30 (3H), 1.38 (3H), 2.08 (1H), 2.11 (3H), 2.42-2.61 (2H), 2.95 (1H), 2.98 (1H), 3.22 (1H), 3.63 (1H), 3.93 (1H), 4.33 (1H), 5.59 (1H), 6.66 (1H), 7.13 (1H), 7.28 (1H), 7.67 (1H), 8.58 (1H) ppm.

$^1$H-NMR (CDCl$_3$) of C: δ=0.80-1.92 (8H), 0.92 (3H), 1.03 (3H), 1.08 (3H), 1.44 (3H), 1.70 (3H), 2.08-2.64 (5H), 2.12 (3H), 2.82 (1H), 3.29 (1H), 3.67 (1H), 4.53 (1H), 5.09 (1H), 5.17 (1H), 6.19 (1H), 6.99 (1H), 7.19 (1H), 7.35 (1H), 7.44 (1H), 8.29 (1H) ppm.

$^1$H-NMR (CDCl$_3$) of D: δ=0.87 (3H), 1.00 (3H), 1.04 (3H), 1.09-2.03 (10H), 1.29 (3H), 1.42 (3H), 2.10 (3H), 2.18-2.32 (2H), 2.53 (1H), 2.67-2.82 (2H), 3.31 (1H), 3.62 (1H), 4.52 (1H), 5.41 (1H), 6.16 (1H), 6.93 (1H), 7.21 (1H), 7.37 (1H), 7.42 (1H), 8.28 (1H) ppm.

$^1$H-NMR (CDCl$_3$) of E: δ=0.83 (3H), 0.94 (3H), 1.08 (3H), 1.20-2.08 (11H), 1.29 (3H), 1.45 (3H), 2.12 (3H), 2.39-2.56 (2H), 2.87 (1H), 3.24 (1H), 3.29 (1H), 3.87 (1H), 4.52 (1H), 5.41 (1H), 5.56 (1H), 7.03 (1H), 7.19 (1H), 7.34 (1H), 7.46 (1H), 8.29 (1H) ppm.

EXAMPLE 26

(4S,7R,8S,9S,13(E),16S(E))-4,8-Dihydroxy-7-ethyl-16-(1-methyl-2-(2-pyridyl)ethenyl)-1-oxa-5,5,7,13-tetramethyl-cyclohexadec-13-ene-2,6-dione

EXAMPLE 26a (3S,6R,7S,8S,12E,15S,16E)-3,7-Bis-[[dimethyl(1,1-dimethylethyl)silyl]oxy]-6-ethyl-4,4,8,12,16-pentamethyl-15-hydroxy-17-(2-pyridyl)-5-oxo-heptadeca-12,16-dienoic Acid Analogously to Example 1i, 433 mg (0.51 mmol) of compound A that is presented according to Example 24l is reacted, and after working-up, 447 mg of the title compound is isolated as a crude product, which is further reacted without purification.

EXAMPLE 26b (4S,7R,8S,9S,13(E),16S(E))-4,8-Bis-[[dimethyl(1,1-dimethylethyl)silyl]oxy]-7-ethyl-16-(1-methyl-2-(2-pyridyl)ethenyl)-1-oxa-5,5,9,13-tetramethyl-cyclohexadec-13-ene-2,6-dione Analogously to Example 1aw, 447 mg (511 µmol) of the compound that is presented according to Example 26a is reacted, and after working-up and purification, 264 mg (370 µmol, 72%) of the title compound is isolated as a colorless oil.

$^1$H-NMR (CDCl$_3$): δ=0.06-0.15 (12H), 0.85 (3H), 0.89 (9H), 0.91 (9H), 0.94 (3H), 1.08-1.92 (11H), 1.12 (3H), 1.21 (3H), 2.10-2.23 (1H), 2.16 (3H), 2.40 (1H), 2.46-2.68 (3H), 2.98 (1H), 3.95 (1H), 4.41 (1H), 5.23 (1H), 5.30 (1H), 6.57 (1H), 7.10 (1H), 7.21 (1H), 7.63 (1H), 8.60 (1H) ppm.

EXAMPLE 26

(4S,7R,8S,9S,13(E),16S(E))-4,8-Dihydroxy-7-ethyl-16-(1-methyl-2-(2-pyridyl)ethenyl)-1-oxa-5,5,9,13-tetramethyl-cyclohexadec-13-ene-2,6-dione Analogously to Example 1, 260 mg (364 µmol) of the compound that is presented according to Example 26b is reacted, and after working-up and purification, 121 mg (249 µmol, 68%) of the title compound is isolated as a colorless oil.

$^1$H-NMR (CDCl$_3$): δ=0.83 (3H), 0.90 (1H), 0.98 (3H), 1.01 (3H), 1.31 (3H), 1.37-2.00 (7H), 1.61 (3H), 2.08 (3H), 2.18 (1H), 2.37-2.52 (3H), 2.60 (1H), 3.35 (1H), 3.70 (1H), 3.83-4.32 (2H), 4.45 (1H), 5.08 (1H), 5.39 (1H), 6.58 (1H), 7.13 (1H), 7.35 (1H), 7.68 (1H), 8.53 (1H) ppm.

EXAMPLE 27

(1R,3S(E),7S,10R,11S,12S,16R)-7,11-Dihydroxy-10-ethyl-3-(1-methyl-2-(2-pyridyl)ethenyl)-8,8,12,16-tetramethyl-4,17-dioxabicyclo[14.1.0]heptadecane-5,9-dione (A) and (1S,3S(E),7S,10R,11S,12S,16S)-7,11-dihydroxy-10-ethyl-3-(1-methyl-2-(2-pyridyl)ethenyl)-8,8,12,16-tetramethyl-4,17-dioxabicyclo[14.1.0]heptadecane-5,9-dione (B) (1R,3S(E),7S,10R,11S,12S,16R)-7,11-dihydroxy-10-ethyl-3-(1-methyl-2-(2-N-oxidopyridyl)ethenyl)-8,8,12,16-tetramethyl-4,17-dioxabicyclor[14.1.0]heptadecane-5,9-dione (C) and (1S,3S(E),7S,10R,11S,12S,16S)-7,11-dihydroxy-10-ethyl-3-(1-methyl-2-(2-N-oxidopyridyl)ethenyl)-8,8,12,16-pentamethyl-4,17-dioxabicyclo[14.1.0]heptadecane-5,9-dione (D)

Analogously to Example 14, 59 mg (121 µmol) of the compound that is presented according to Example 26 is reacted, and after working-up and purification, 5 mg (10 µmol, 8%) of title compound A or B, 2 mg (4 µmol, 3%) of title compound B or A, 14 mg (27 µmol, 22%) of title compound C or D and 6.9 mg (13 µmol, 11%) of title compound D or C are isolated in each case as a colorless solid.

$^1$H-NMR (CDCl$_3$) of A or B: δ=0.83 (3H), 0.92 (3H), 1.02 (3H), 1.09-2.19 (12H), 1.27 (3H), 1.37 (3H), 2.11 (3H), 2.43-2.61 (2H), 2.88 (1H), 3.31 (1H), 3.78 (1H), 4.26 (1H), 4.33 (1H), 5.48 (1H), 6.64 (1H), 7.12 (1H), 7.30 (1H), 7.67 (1H), 8.57 (1H) ppm.

¹H-NMR (CDCl₃) of B or A: δ=0.86 (3H), 0.93 (3H), 1.09 (3H), 1.19-2.19 (11H), 1.27 (3H), 1.38 (3H), 2.10 (3H), 2.50-2.63 (2H), 2.87 (1H), 2.98 (1H), 3.28 (1H), 3.71 (1H), 3.88 (1H), 4.31 (1H), 5.48 (1H), 6.62 (1H), 7.13 (1H), 7.28 (1H), 7.67 (1H), 8.85 (1H) ppm.

¹H-NMR (CDCl₃) of C or D: δ=0.84 (3H), 0.91 (3H), 1.06 (3H), 1.11-2.08 (10H), 1.26 (3H), 1.38 (3H), 2.02 (3H), 2.19 (1H), 2.37 (1H), 2.53 (1H), 2.92 (1H), 3.34 (1H), 3.56-3.72 (2H), 4.53 (1H), 5.05 (1H), 5.60 (1H), 6.99 (1H), 7.21 (1H), 7.33 (1H), 7.45 (1H), 8.28 (1H) ppm.

¹H-NMR (CDCl₃) of D or C: δ=0.84 (3H), 0.89 (3H), 1.07 (3H), 1.15-2.23 (11H), 1.22 (3H), 1.43 (3H), 2.09 (3H), 2.36 (1H), 2.53 (1H), 2.97 (1H), 3.02 (1H), 3.32 (1H), 3.58 (1H), 4.58 (1H), 5.44 (1H), 5.58 (1H), 7.06 (1H), 7.21 (1H), 7.36 (1H), 7.44 (1H), 8.29 (1H) ppm.

EXAMPLE 28

(4S,7R,8S,9S,13(Z),16S(E))-4,8-Dihydroxy-16-(1-methyl-2-(2-methyl-4-thiazolyl)ethenyl)-1-oxa-7,9,13-trimethyl-5,5-trimethylene-cyclohexadec-13-ene-2,6-dione

EXAMPLE 28a 1,1-Cyclobutanedimethanol 170 ml of a 1.2 molar solution of diisobutylaluminum hydride is added in drops to a solution of 20 g (99.9 mmol) of 1,1-cyclobutanedicarboxylic acid diethyl ester in 200 ml of absolute tetrahydrofuran at 0° C. It is allowed to stir for one more hour at 0° C., and then 30 ml of water is added. It is filtered on Celite. The filtrate is dried with sodium sulfate and concentrated by evaporation in a vacuum. The crude product that is obtained (9.9 g, 85.2 mmol, 85%) is used without purification in the next step.

EXAMPLE 28b

1-[[Dimethyl(1,1-dimethylethyl)silyl]oxy]methyl]-cyclobutanemethanol

A solution of 9.9 g (85 mmol) of the compound, presented according to Example 28a, in 100 ml of absolute tetrahydrofuran is added to a suspension of 3.4 g of sodium hydride (60% in oil) in 35 ml of absolute tetrahydrofuran at 0° C. It is allowed to stir for 30 more minutes, and then a solution of 12.8 g of tert-butyldimethylsilyl chloride in 50 ml of tetrahydrofuran is added. It is allowed to stir for one more hour at 25° C., and then the reaction mixture is poured onto saturated aqueous sodium bicarbonate solution. It is extracted with ethyl acetate. The organic phase is washed with saturated sodium chloride solution and dried on sodium sulfate. After the solvent is drawn off in a vacuum, the crude product that is obtained is purified by column chromatography on silica gel with a mixture of hexane/ethyl acetate. 13.5 g (58.6 mmol, 69%) of the title compound is obtained.

¹H-NMR (CDCl₃): δ=0.04 (6H), 0.90 (9H), 1.70-2.00 (6H), 3.70 (4H) ppm

EXAMPLE 28c

1-[[[Dimethyl(1,1-dimethylethyl)silyl]oxy]methyl]-cyclobutanecarbaldehyde

Analogously to Example 1k, after purification, 7.7 g (33.7 mmol, 58%) of the title compound is obtained from 13.5 g (58.6 mmol) of the compound that is described under 28b.

¹H-NMR (CDCl₃): δ=9.70 s ((1H), 3.83 s (2H), 2.20-2.30 m (2H), 1.85-2.00 m (4H), 0.90 s (9H), 0.03 s (6H) ppm.

EXAMPLE 28d

[1R-[1α(R*)2β]]-2-Phenylcyclohexyl 3-[1-[[[dimethyl(1,1-dimethylethyl)silyl]oxy]methyl]cyclobutyl]-3-hydroxypropanoate (A) and [1R-[1α(S*),2β]]-2-phenylcyclohexyl 3-[1-[[[dimethyl(1,1-dimethylethyl)silyl]oxy]methyl]cyclobutyl]-3-hydroxypropanoate (B)

Lithium diisopropylamide in absolute tetrahydrofuran is produced from 7.2 ml of diisopropylamine and butyllithium (32 ml of a 1.6 molar solution in hexane). Then, a solution of 11.2 g (1R-trans)-2-phenylcyclohexyl acetate in 100 ml of absolute tetrahydrofuran is added at −78° C., and it is allowed to stir for 30 more minutes at this temperature. Then, a solution of 7.7 g (33.7 mmol) of the compound, presented according to Example 28c, in 50 ml of tetrahydrofuran is added. It is allowed to stir for 1.5 more hours at −78° C., and then the reaction mixture is poured onto saturated aqueous ammonium chloride solution. It is extracted with ethyl acetate, the organic phase is washed with saturated sodium chloride solution, dried on sodium sulfate and concentrated by evaporation in a vacuum. After column chromatography of the crude product on silica gel with a mixture of hexane/ethyl acetate, 6.34 g (14.2 mmol, 42%) of title compound A and 4.22 g (9.4 mmol, 28%) of title compound B are obtained.

¹H-NMR (CDCl₃) of A: δ=0.04 (6H), 0.98 (9H), 2.69 (1H), 3.08 (1H), 3.60 (1H), 3.67 (1H), 3.78-3.84 (1H), 4.97 (1H), 7.15-7.30 (5H) ppm.

¹H-NMR (CDCl₃) of B: δ=0.03 (6H), 0.90 (9H), 2.68 (1H), 2.80 (1H), 3.56 (2H), 3.68-3.72 (1H), 4.99 (1H), 7.18-7.30 m (5H) ppm.

EXAMPLE 28e (S)-1-[1-[[[Dimethyl(1,1-dimethylethyl)silyl]oxy]methyl]-cyclobutyl]-1,3-propanediol 4 ml of a 1.2 molar solution of diisobutylaluminum hydride in toluene is added in drops to a solution of 1 g (2.24 mmol) of compound A, presented according to Example 28d, in 10 ml of absolute toluene at 0° C. It is allowed to stir for 1.5 more hours at 0° C., and then 5 ml of water is added. It is filtered on Celite. The filtrate is dried on sodium sulfate and concentrated by evaporation in a vacuum. After column chromatography of the crude product on silica gel with a mixture of hexane/ethyl acetate, 370 mg (1.35 mmol, 60%) of the title compound is obtained.

¹H-NMR (CDCl₃): δ=0.05 (6H), 0.90 (9H), 1.55-1.60 (2H), 1.80 (2H), 1.90 (3H), 2.10 (1H), 3.75 (1H), 3.85-3.95 (4H) ppm.

EXAMPLE 28f (S)-2,2-Dimethyl-4-[1-[[[dimethyl(1,1-dimethylethyl)silyl]oxy]methyl]cyclobutyl]-1,3-dioxane Analogously to Example 1h, after purification, 338 mg (1.07 mmol, 79%) of the title compound is obtained from 370 mg (1.35 mmol) of the compound that is described under 28e.

¹H-NMR (CDCl₃): δ=0.03 (6H), 0.88 (9H), 1.38 (3H), 1.42 (3H), 1.50-1.80 (4H), 2.00 (1H), 3.52 (1H), 3.62 (1H), 3.85-4.00 (3H) ppm.

EXAMPLE 28g

(S)-1-(2,2-Dimethyl-1,3-dioxan-4-yl)cyclobutane-methanol

Analogously to 1i, 1.27 g (4.04 mmol) of the compound that is produced according to Example 28f is reacted with 6 ml of a 1 molar solution of tetrabutylammonium chloride in tetrahydrofuran. After column chromatography, 794 mg (98%) of the title compound is obtained.

$^1$H-NMR (CDCl$_3$): δ=1.38 (3H), 1.46 (3H), 1.55-1.67 (2H), 1.75-2.05 (6H), 2.97 (1H), 3.62 (1H), 3.84-4.10 (4H) ppm.

EXAMPLE 28h

(S)-1-(2,2-Dimethyl-1,3-dioxan-4-yl)cyclobutanecarbaldehyde

Analogously to Example 1k, 794 mg (3.97 mmol) of 28g is reacted, and 786 mg (100%) of the title compound is isolated as a crude product, which is used without purification in the next step.

EXAMPLE 28i

(S)-1-(2,2-Dimethyl-1,3-dioxan-4-yl)-α-ethylcyclobutanemethanol

Analogously to Example 1l, 786 mg (3.97 mmol) of the compound that is described under 28h is reacted with a 2 molar solution of ethylmagnesium chloride in tetrahydrofuran. After purification, 835 mg (95%) of the title compound is obtained.

$^1$H-NMR (CDCl$_3$): δ=1.05 (3H), 1.38 (3H), 1.49 (3H), 1.60-2.10 (8H), 2.60 (1H), 2.83 (1H), 3.50 (1H), 3.85-4.15 (3H) ppm.

EXAMPLE 28k

(S)-1-[1-(2,2-Dimethyl-1,3-dioxan-4-yl)cyclobutyl]propan-1-one

Analogously to Example 1m, after purification, 689 mg (83%) of the title compound is obtained from 835 mg (3.67 mmol) of the compound that is described under 28i.

$^1$H-NMR (CDCl$_3$): δ=1.03 (3H), 1.35 (1H), 1.36 (3H), 1.45 (3H), 1.55 (1H), 1.65-1.90 (2H), 2.02 (1H), 2.14-2.30 (2H), 2.33 (1H), 2.45-2.60 (2H), 3.80-4.00 (2H), 4.10 (1H) ppm.

EXAMPLE 28l

(S)-1-[1-(1,3-Dihydroxypropyl)cyclobutyl]propan-1-one 680 mg (3 mmol) of the compound that is described under 28k is dissolved in 30 ml of tetrahydrofuran. 1 ml of water and 30 mg of p-toluenesulfonic acid are added, and it is allowed to stir for 30 more minutes at 50° C. After working-up and purification, 471 mg (84%) of the title compound is obtained.

$^1$H-NMR (CDCl$_3$): δ=1.05 (3H), 1.10 (1H), 1.53 (1H), 1.65 (1H), 1.80-2.00 (3H), 2.15 (1H), 2.40-2.70 (3H), 3.35 (1H), 3.55 (1H), 3.88 (1H), 4.10 (1H) ppm.

EXAMPLE 28m

(S)-1-(1,3-Bis[[dimethyl(1,1-dimethylethyl)silyl]oxy]cyclobutyl)propan-1-one Analogously to Example 1aq, after purification, 709 mg (68%) of the title compound is obtained from 470 mg (2.54 mmol) of the compound that is described under 28l.

$^1$H-NMR (CDCl$_3$): δ=0.02 (6H), 0.15 (3H), 0.17 (3H), 0.90 (9H), 0.94 (9H), 1.05 (3H), 1.30-1.53 (2H), 1.70-1.85 (2H), 1.98 (1H), 2.23 (3H), 2.45-2.53 (2H), 3.54 (2H), 4.11 (1H) ppm.

EXAMPLE 28n

(2S,6E/Z,9S,10E)-9-[[(1,1-Dimethylethyl)diphenylsilyl]oxy]-11-(2-methylthiazol-4-yl)-1-(tetrahydropyran-2-yloxy)-2,6,10-trimethyl-undeca-6,10-diene Analogously to Example 24b/I, after purification, 3.01 g (47%) of the title compound is obtained from 2.24 g (9.84 mmol) of the compound that is described under 24 a/I, and 12.2 g (14.81 mmol) of the compound that is described under 1ai, with use of butyllithium as a base.

$^1$H-NMR (CDCl$_3$): δ=0.86 (3H), 1.04 (9H), 1.55+1.60 (3H), 1.30 (2H), 1.99 (3H), 2.25 (2H), 2.70 (3H), 1.10-3.20 (1H), 3.45-3.60 (2H), 3.86 (1H), 4.14 (1H), 4.54 (1H), 4.97 (1H), 6.22 (1H), 6.78 (1H), 7.30-7.50 (6H), 7.60-7.70 (4H) ppm.

EXAMPLE 28o

(2S,6E/Z,9S,10E)-11-(2-Methylthiazolyl-4-yl)-1-(tetrahydropyran-2-yloxy)-2,6,10-trimethyl-undeca-6,10-dien-9-ol Analogously to Example 1i, after purification, 4.53 g (94%) of the title compound is obtained from 7.65 g (11.84 mmol) of the compound that is described under 28n.

$^1$H-NMR (CDCl$_3$): δ=0.91 (3H), 1.10 (1H), 1.65+1.71 (3H), 2.04 (3H), 2.39 (2H), 2.70 (3H), 3.12+3.21 (1H), 3.50+3.58 (2H), 3.85 (1H), 4.14 (1H), 4.55 (1H), 5.15 (1H), 6.56 (1H), 6.93 (1H) ppm.

EXAMPLE 28p

(2S,6E/Z,9S,10E)-9-[[Dimethyl(1,1-dimethylethyl)silyl]oxy]-11-(2-methylthiazol-4-yl)-1-(tetrahydropyran-2-yloxy)-2,6,10-trimethyl-undeca-6,10-diene Analogously to Example 1ad, after purification, 5.68 g (98%) of the title compound is obtained from 4.53 g of the compound that is described under 28o.

$^1$H-NMR (CDCl$_3$): δ=0.00 (3H), 0.03 (3H), 0.90 (12H), 1.56+1.64 (3H), 1.99 (3H), 2.21 (2H), 3.10+3.20 (1H), 3.45-3.60 (2H), 3.85 (1H), 4.10 (1H), 4.57 (1H), 5.12 (1H), 6.45 (1H), 6.90 (1H) ppm.

EXAMPLE 28q

(2S,6E/Z,9S,10E)-9-[[Dimethyl(1,1-dimethylethyl)silyl]Oxy]-11-(2-methylthiazol-4-1)-2,6,10-trimethyl-undeca-6,10-dien-1-ol Analogously to Example 1f, after purification, 4.02 g (84%) of the title compound is obtained (2 hours of reaction time at 50° C.) from 5.68 g (10.88 mmol) of the compound that is described under 28p.

¹H-NMR (CDCl₃): δ=0.00 (3H), 0.05 (3H), 0.90 (12H), 1.60+1.65 (3H), 2.00 (3H), 2.23 (2H), 2.71 (3H), 3.38-3.55 (2H), 4.10 (1H), 5.09+5.14 (1H), 6.45+6.48 (1H), 6.91+6.93 (1H) ppm.

EXAMPLE 28r (2S,6E/Z,9S,10E)-9-[[Dimethyl(1,1-dimethylethyl)silyl]oxy]-11-(2-methylthiazol-4-yl)-2,6,10-trimethyl-undeca-6,10-dien-1-al Analogously to Example 1k, after filtration on silica gel, 648 mg (98%) of the title compound is obtained from 667 mg (1.5 mmol) of the compound that is described under 28q.
¹H-NMR (CDCl₃): δ=0.01 (3H), 0.06 (3H), 0.90 (9H), 1.06+1.09 (3H), 1.58+1.66 (3H), 2.00 (3H), 4.10 (1H), 5.13 (1H), 6.46 (1H), 6.91+6.93 (1H) ppm.

EXAMPLE 28s (3S,6R,7S,8S,12Z,15S,16E)-7-Hydroxy-1,3,15-tris-[[dimethyl(1,1-dimethylethyl)silyl]oxy]-6,8,12,16-tetramethyl-4,4-trimethylene-17-(2-methylthiazol-4-yl)-heptadeca-12,16-dien-5-one (A) and (3S,6R,7S,8S,12E,15S,16E)-7-hydroxy-1,3,15-tris-[[dimethyl(1,1-dimethylethyl)silyl]oxy]-6,8,12,16-tetramethyl-4,4-trimethylene-17-(2-methylthiazol-4-yl)-heptadeca-12,16-dien-5-one (B)

Analogously to Example 1ak, after purification, 352 mg (27%) of title compound A and 227 mg (17%) of title compound B are obtained from 709 mg (1.71 mmol) of the compound that is described under 28 m and 667 mg (1.52 mmol) of the compound that is described under 28r.
¹H-NMR (CDCl₃) of compound A: δ=0.00 (3H), 0.04 (9H), 0.14 (3H), 0.16 (3H), 0.80 (3H), 0.88 (18H), 0.91 (9H), 1.03 (3H), 1.68 (3H), 2.00 (3H), 2.20-2.40 (3H), 2.72 (3H), 3.25 (1H), 3.44 (1H), 3.58 (3H), 4.10 (2H), 5.13 (1H), 6.42 (1H), 6.93 (1H) ppm.
¹H-NMR (CDCl₃) of compound B: δ=0.00 (3H), 0.04 (6H), 0.08 (3H), 0.15 (3H), 0.18 (3H), 0.80 (3H), 0.89 (18H), 0.92 (9H), 1.05 (3H), 1.60 (3H), 2.00 (3H), 2.20-2.40 (3H), 2.70 (3H), 3.25 (1H), 3.45 (1H), 3.60 (3H), 4.10 (2H), 5.15 (1H), 6.45 (1H), 6.91 (1H) ppm.

EXAMPLE 28t (3S,6R,7S,8S,12Z,15S,16E)-1,3,7,15-Tetrakis-[[dimethyl(1,1-dimethylethyl)silyl]oxy]-6,8,12,16-tetramethyl-4,4-trimethylene-17-(2-methylthiazol-4-yl)-heptadeca-12,16-dien-5-one Analogously to Example 1aq, 381 mg (95%) of the title compound is obtained from 352 mg (0.41 mmol) of compound A that is described under 28s.
¹H-NMR (CDCl₃): δ=0.00 (3H), 0.02 (6H), 0.04 (3H), 0.07 (3H), 0.09 (3H), 0.13 (3H), 0.16 (3H), 0.90 (18H), 0.94 (18H), 0.95 (3H), 1.09 (3H), 1.68 (3H), 2.20-2.40 (3H), 2.71 (3H), 3.10 (1H), 3.58 (2H), 3.78 (1H), 4.10 (2H), 5.13 (1H), 6.47 (1H), 6.90 (1H) ppm.

EXAMPLE 28u (3S,6R,7-S,8S,12Z,15S,16E)-3,7,15-Tris-[[dimethyl(1,1-dimethylethyl)silyl]oxy]-1-hydroxy-6,8,12,16-tetramethyl-4,4-trimethylene-17-(2-methylthiazol-4-yl)-heptadeca-12,16-dien-5-one Analogously to Example 1ar, 289 mg (86%) of the title compound is obtained from 381 mg (0.39 mmol) of the compound that is described under 28t.

¹H-NMR (CDCl₃): δ=0.01 (3H), 0.05 (3H), 0.08 (3H), 0.11 (3H), 0.16 (3H), 0.18 (3H), 0.90-1.00 (30H), 1.10 (3H), 1.67 (3H), 1.99 (3H), 2.20-2.40 (3H), 2.71 (3H), 3.14 (1H), 3.63 (2H), 3.82 (1H), 4.09 (2H), 5.12 (1H), 6.46 (1H), 6.92 (1H) ppm.

EXAMPLE 28v (3S,6R,7S,8S,12Z,15S,16E)-3,7,15-Tris-[[dimethyl(1,1-dimethylethyl)silyl]oxy]-6,8,12,16-tetramethyl-4,4-trimethylene-17-(2-methylthiazol-4-yl)-5-oxo-heptadeca-12,16-dien-1-al Analogously to Example 1k, after filtration on silica gel, 284 mg (100%) of the title compound is obtained from 285 mg (0.34 mmol) of the compound that is described under 28u.

EXAMPLE 28w (3S,6R,7S,8S,12Z,15S,16E)-3,7,15-Tris-[[dimethyl(1,1-dimethylethyl)silyl]oxy]-6,8,12,16-tetramethyl-4,4-trimethylene-17-(2-methylthiazol-4-yl)-5-oxo-heptadeca-12,16-dienoic acid Analogously to Example 1at, after purification, 235 mg (81%) of the title compound is obtained from 284 mg (0.34 mmol) of the compound that is described under 28v.
¹H-NMR (CDCl₃): δ=0.00 (3H), 0.02 (3H), 0.04 (3H), 0.09 (3H), 0.14 (3H), 0.19 (3H), 0.87-0.96 (30H), 1.13 (3H), 1.70 (3H), 1.95 (3H), 2.12-2.30 (3H), 2.70 (3H), 3.00 (1H), 3.80 (1H), 4.13 (1H), 4.49 (1H), 5.18 (1H), 6.63 (1H), 6.93 (1H) ppm.

EXAMPLE 28x (3S,6R,7S,8S,12Z,15S,16E)-3,7-Bis-[[dimethyl)1,1-dimethylethyl)silyl]oxy]-15-hydroxy-17-(2-methylthiazol-4-yl)-6,8,12,16-tetramethyl-4,4-trimethylen-5-oxo heptadeca-12,16-dienoic Acid Analogously to Example 1i, 200 mg (100%) of the title compound, which is used without purification in the next step, is obtained from 230 mg (0.27 mmol) of the compound that is described under 28w.
¹H-NMR (CDCl₃): δ=0.05 (3H), 0.10 (6H), 0.19 (3H), 0.90 (18H), 0.95 (3H), 1.12 (3H), 1.70 (3H), 2.00 (3H), 2.70 (3H), 3.00 (1H), 3.84 (1H), 4.15 (1H), 4.49 (1H), 5.15 (1H), 6.67 (1H), 6.91 (1H) ppm.

EXAMPLE 28y (4S,7R,8S,9S,13(Z),16S(E))-4,8-Bis-[[dimethyl(1,1-dimethylethyl)silyl]oxy]-16-(1-methyl-2-(2-methylthiazol-4-yl)-ethenyl)-1-oxa-7,9,13-trimethyl-5,5-trimethylene-cyclohexadec-13-ene-2,6-dione Analogously to Example 1aw, after working-up, 101 mg (52%) of the title compound is obtained from 200 mg (0.27 mmol) of the compound that is described under 28x.
¹H-NMR (CDCl₃): δ=−0.05 (3H), 0.12 (3H), 0.15 (6H), 0.82 (9H), 0.98 (9H), 1.00 (3H), 1.24 (3H), 1.68 (3H), 2.11 (3H), 2.28 (1H), 2.47 (1H), 2.60-2.70 (2H), 2.72 (3H), 2.98 (1H), 3.93 (1H), 4.41 (1H), 5.03 (1H), 5.17 (3H), 6.58 (1H), 6.98 (1H) ppm.

EXAMPLE 28

(4S,7R,8S,9S,13(Z),16S(E))-4,8-Dihydroxy-16-(1-methyl-2-(2-methyl-4-thiazolyl)ethenyl)-1-oxa-7,9,13-trimethyl-5,5-trimethylene-cyclohexadec-13-ene-2,6-dione Analogously to Example 1, 51 mg (73%) of the title compound is obtained from 101 mg (0.14 mmol) of the compound that is described under 28y.

$^1$H-NMR (CDCl$_3$): δ=1.01 (3H), 1.28 (3H), 1.67 (3H), 2.09 (3H), 2.70 (3H), 3.01 (1H), 3.73 (1H), 4.46 (1H), 5.14 (1H), 5.19 (1H), 6.60 (1H), 6.96 (1H) ppm.

EXAMPLE 29

(1S,3S(E),7S,10R,11S,12S,16R)-7,11-Dihydroxy-3-(1-methyl-2-(2-methyl-4-thiazolyl)ethenyl)-10,12,16-trimethyl-8,8-trimethylene-4,17-dioxabicyclo[14.1.0]heptadecane-5,9-dione (A) and (1R,3S(E),7S,10R,11S,12S,16S)-7,11-dihydroxy-3-(1-methyl-2-(2-methyl-4-thiazolyl)ethenyl)-10,12,16-trimethyl-8,8-trimethylene-4,17-dioxabicyclo[14.1.0]heptadecane-5,9-dione (B)

Analogously to Example 14, 29 mg (59%) of title compound A and 7 mg (14%) of title compound B are obtained after separation from 47 mg (0.09 mmol) of the compound that is described under 28.

$^1$H-NMR (CDCl$_3$) of compound A: δ=1.01 (3H), 1.24 (3H), 1.28 (3H), 2.09 (3H), 2.72 (3H), 2.78 (1H), 3.05 (1H), 3.72 (1H), 4.20 (1H), 4.45 (1H), 5.37 (1H), 6.59 (1H), 6.96 (1H) ppm.

$^1$H-NMR (CDCl$_3$) of compound B: δ=0.94 (3H), 1.20 (3H), 1.26 (3H), 2.12 (3H), 2.71 (3H), 2.99 (1H), 3.11 (1H), 4.41 (1H), 4.39 (1H), 5.60 (1H), 6.62 (1H), 6.99 (1H) ppm.

EXAMPLE 30

(4S,7R,8S,9S,13(E),16S(E))-4,8-Dihydroxy-16-(1-methyl-2-(2-methyl-4-thiazolyl)ethenyl)-1-oxa-7,9,13-trimethyl-5,5-trimethylene-cyclohexadec-13-ene-2,6-dione

EXAMPLE 30a (3S,6R,7S,8S,12E,15S,16E)-1,3,7,15-Tetrakis-[[dimethyl(1,1-dimethylethyl)silyl]oxy]-6,8,12,16-tetramethyl-4,4-trimethylene-17-(2-methylthiazol-4-yl)-heptadeca-12,16-dien-5-one Analogously to Example 1aq, 230 mg (90%) of the title compound is obtained from 227 mg (0.27 mmol) of compound B that is described under 28s.

$^1$H-NMR (CDCl$_3$): δ=0.01 (3H), 0.03 (3H), 0.04 (3H), 0.06 (3H), 0.08 (3H), 0.11 (3H), 0.15 (3H), 0.17 (3H), 0.87-0.98 (39H), 1.06 (3H), 1.57 (3H), 2.00 (3H), 2.20-2.39 (3H), 2.70 (3H), 3.09 (1H), 3.61 (2H), 3.78 (1H), 4.10 (2H), 5.14 (3H), 6.45 (1H), 6.91 (1H) ppm.

EXAMPLE 30b (3S,6R,7S,8S,12E,15S,16E)-3,7,15-Tris-[[dimethyl(1,1-dimethylethyl)silyl]oxy]-1-hydroxy-6,8,12,16-tetramethyl-4,4-trimethylene-17-(2-methylthiazol-4-yl)-heptadeca-12,16-dien-5-one Analogously to Example 1ar, 170 mg (84%) of the title compound is obtained from 230 mg (0.24 mmol) of the compound that is described under 30a.

$^1$H-NMR (CDCl$_3$): δ=0.01 (3H), 0.06 (3H), 0.08 (3H), 0.10 (3H), 0.17 (3H), 0.19 (3H), 0.85-1.00 (30H), 1.10 (3H), 1.62 (3H), 2.15-2.40 (3H), 2.71 (3H), 3.12 (1H), 3.63 (2H), 3.79 (1H), 4.09 (2H), 5.13 (1H), 6.42 (1H), 6.90 (1H) ppm.

EXAMPLE 30c (3S,6R,7S,8S,12E,15S,16E)-3,7,15-Tris-[[dimethyl(1,1-dimethylethyl)silyl]oxy]-6,8,12,16-tetramethyl-4,4-trimethylene-17-(2-methylthiazol-4-yl)-5-oxo-heptadeca-12,16-dien-1-al Analogously to Example 1k, after filtration on silica gel, 170 mg (100%) of the title compound is obtained from 170 mg (0.20 mmol) of the compound that is described under 30b.

EXAMPLE 30d (3S,6R,7S,8S,12E,15S,16E)-3,7,15-Tris-[[dimethyl(1,1-dimethylethyl)silyl]oxy]-4,4,6,8,12,16-tetramethyl-4,4-trimethylene-17-(2-methylthiazol-4-yl)-5-oxo-heptadeca-12,16-dienoic Acid Analogously to Example 1at, after purification, 144 mg (83%) of the title compound is obtained from 170 mg (0.20 mmol) of the compound that is described under 30c.

$^1$H-NMR (CDCl$_3$): δ=0.01 (3H), 0.05 (3H), 0.06 (3H), 0.09 (3H), 0.15 (3H), 0.20 (3H), 0.85-1.00 (30H), 1.12 (3H), 1.55 (3H), 1.97 (3H), 2.71 (3H), 3.09 (1H), 3.82 (1H), 4.10 (1H), 4.41 (1H), 5.11 (1H), 6.46 (1H), 6.95 (1H) ppm.

EXAMPLE 30e (3S,6R,7S,8S,12E,15S,16E)-3,7-Bis-[[dimethyl(1,1-dimethylethyl)silyl]oxy]-15-hydroxy-17-(2-methylthiazol-4-yl)-6,8,12,16-tetramethyl-4,4-trimethylen-5-oxo heptadeca-12,16-dienoic acid Analogously to Example 1i, 121 mg (100%) of the title compound, which is used without purification in the next step, is obtained from 140 mg (0.16 mmol) of the compound that is described under 30d.

$^1$H-NMR (CDCl$_3$): δ=0.05 (3H), 0.09 (6H), 0.18 (3H), 0.85-0.95 (18H), 0.98 (3H), 1.11 (3H), 1.61 (3H), 2.00 (3H), 2.69 (3H), 3.02 (1H), 3.82 (1H), 4.15 (1H), 4.40 (1H), 5.15 (1H), 6.54 (1H), 6.91 (1H) ppm.

EXAMPLE 30f (4S,7R,8S,9S,13(E),16S(E))-4,8-Bis-[[dimethyl(1,1-dimethylethyl)silyl]oxy]-16-(1-methyl-2-(2-methylthiazol-4-yl)ethenyl)-1-oxa-7,9,13-trimethyl-5,5-trimethylene-cyclohexadec-13-ene-2,6-dione Analogously to Example 1aw, after purification, 55 mg (48%) of the title compound is obtained from 121 mg (0.16 mmol) of the compound that is described under 30e.

¹H-NMR (CDCl₃): δ=0.01 (3H), 0.09 (3H), 0.15 (6H), 0.92 (9H), 0.96 (9H), 0.98 (3H), 1.26 (3H), 1.50 (3H), 2.19 (3H), 2.73 (3H), 2.91 (1H), 4.18 (1H), 4.63 (1H), 5.09 (1H), 5.31 (1H), 6.53 (1H), 6.93 (1H) ppm.

EXAMPLE 30

(4S,7R,8S,9S,13(E),16S(E))-4,8-Dihydroxy-16-(1-methyl-2-(2-methyl-4-thiazolyl)ethenyl)-1-oxa-7,9,13-trimethyl-5,5-trimethylene-cyclohexadec-13-ene-2,6-dione Analogously to Example 1, 27 mg (67%) of the title compound is obtained from 55 mg (0.08 mmol) of the compound that is described under 30f.

¹H-NMR (CDCl₃): δ=1.03 (3H), 1.23 (3H), 1.55 (3H), 2.07 (3H), 2.72 (3H), 3.04 (1H), 3.32 (1H), 3.51 (1H), 3.70 (1H), 4.46 (1H), 5.06 (1H), 5.49 (1H), 6.59 (1H), 7.02 (1H) ppm.

EXAMPLE 31

(1R,3S(E),7S,10R,11S,12S,16R)-7,11-Dihydroxy-3-(1-methyl-2-(2-methyl-4-thiazolyl)ethenyl)-10,12,16-trimethyl-8,8-trimethylene-4,17-dioxabicyclo[14.1.0]heptadecane-5,9-dione (A) and (1S,3S(E),7S,10R,11S,12S,16S)-7,11-dihydroXy-3-(1-methyl-2-(2-methyl-4-thiazolyl)ethenyl)-10,12,16-trimethyl-8,8-trimethylene-4,17-dioxabicyclo[14.1.0]heptadecane-5,9-dione (B)

Analogously to Example 14, 10 mg (39%) of title compound A and 8 mg (31%) of title compound B are obtained after separation from 25 mg (0.05 mmol) of the compound that is described under 30.

¹H-NMR (CDCl₃) of compound A: δ=1.02 (3H), 1.25 (3H), 1.27 (3H), 2.08 (3H), 2.71 (3H), 2.84 (1H), 3.13 (1H), 3.72 (1H), 4.93 (1H), 5.51 (1H), 6.68 (1H), 7.04 (1H) ppm.

¹H-NMR (CDCl₃) of compound B: δ=0.98 (3H), 1.27 (3H), 1.28 (3H), 2.11 (3H), 2.89 (1H), 3.08 (1H), 3.70 (1H), 4.48 (1H), 5.43 (1H), 6.58 (1H), 6.97 (1H) ppm.

EXAMPLE 32

(4S,7R,8S,9S,13(Z),16S(E))-4,8-Dihydroxy-9,13-dimethyl-7-ethyl-16-(1-methyl-2-(2-methyl-4-thiazolyl)ethenyl)-1-oxa-5,5-trimethylene-cyclohexadec-13-ene-2,6-dione EXAMPLE 32a 1-[[[Dimethyl(1,1-dimethylethyl)silyl]oxy]methyl]-α-propylcyclobutanemethanol Analogously to Example 1l, after purification, 20.81 g (72%) of the title compound is obtained from 24.15 g (105.8 mmol) of the compound that is described under 28c.

¹H-NMR (CDCl₃): δ=0.09 (6H), 0.93 (9H), 0.95 (3H), 1.36 (3H), 1.48-1.80 (3H), 1.87 (3H), 2.08 (1H), 3.18 (1H), 3.56 (1H), 3.72 (1H), 3.86 (1H) ppm.

EXAMPLE 32b

1-[1-[[[Dimethyl(1,1-dimethylethyl)silyl]oxy]methyl]cyclobut-1-yl]-1-butanone

Analogously to Example 1k, after filtration on silica gel, 20.7 g (100%) of the title compound is obtained from 20.81 g (76.34 mmol) of the compound that is described under 32a.

¹H-NMR (CDCl₃): δ=0.05 (6H), 0.88 (9H), 0.92 (3H), 1.59 (2H), 1.75-1.95 (4H), 2.23-2.34 (2H), 2.43 (2H), 3.81 (2H) ppm.

EXAMPLE 32c

1-[1-(Hydroxymethyl)cyclobut-1-yl]-1-butanone

Analogously to Example 1i, after purification, 11.57 g (97%) of the title compound is obtained from 20.7 g (76.34 mmol) of the compound that is described under 32b.

¹H-NMR (CDCl₃): δ=0.94 (3H), 1.64 (2H), 1.85-2.10 (4H), 2.29-2.43 (2H), 2.53 (2H), 3.87 (2H) ppm.

EXAMPLE 32d 1-(1-Oxobutyl)cyclobutanecarbaldehyde

Analogously to Example 1k, after filtration on silica gel, 2.31 g (100%) of the title compound is obtained from 2.34 g (15 mmol) of the compound that is described under 32c.

¹H-NMR (CDCl₃): δ=0.92 (3H), 1.62 (2H), 1.85-2.01 (4H), 2.38-2.55 (6H), 9.69 (1H) ppm.

EXAMPLE 32e (4S,5R)-3-(Bromoacetyl)-4-methyl-5-phenyloxazolidin-2-one 82 ml of a 2.5 molar solution of butyllithium in hexane is added to a solution of 33.06 g (186.6 mmol) of (4S,5R)-4-methyl-5-phenyloxazolidin-2-one in 500 ml of tetrahydrofuran within 30 minutes at −70° C. under argon. Then, a solution of 15.55 ml (187 mmol) of bromoacetyl chloride in 250 ml of tetrahydrofuran is added in drops in such a way that the internal temperature does not exceed −65° C. Then, it is stirred for one more hour at −70° C. Then, the reaction mixture is poured onto 50 ml of saturated aqueous ammonium chloride solution. 90 ml of saturated aqueous sodium bicarbonate solution is then added, allowed to come to 25° C., diluted with water and extracted with ethyl acetate. The organic phase is washed with saturated aqueous sodium chloride solution, dried on sodium sulfate and chromatographed on silica gel. 42.32 g (76%) of the title compound is obtained.

¹H-NMR (CDCl₃): δ=0.95 (3H), 4.57 (2H), 4.80 (1H), 5.76 (1H), 7.2-7.5 (5H) ppm.

EXAMPLE 32f

[4S-[3(R*),4α,5α]]-3-[3-Hydroxy-1-oxo-3-[1-(1-oxobutyl)cyclobut-1-yl]propyl]-4-methyl-5-phenyloxazolidin-2-one 200 mg (1.5 mmol) of anhydrous lithium iodide is added to a suspension of 5 g (40.68 mmol) of anhydrous chromium(II) chloride in 60 ml of tetrahydrofuran under argon. Then, a mixture of 5 g (16.77 mmol) of the compound that is described under 32e and 2.31 g (15 mmol) of the compound that is described under 32d is added to 10 ml of tetrahydrofuran (exothermal reaction, the internal temperature should not exceed 35° C.). It is allowed to stir for one more hour at 25° C., and then 50 ml of saturated aqueous sodium chloride solution is added with slight cooling. It is stirred for another 30 minutes at 25° C. Then, it is extracted with ethyl acetate. The organic phase is washed with saturated aqueous sodium chloride solution, dried on sodium sulfate and chromatographed on silica gel. 3.89 g (69%) of the title compound is obtained.

¹H-NMR (CDCl₃): δ=0.90-0.99 (6H), 1.58-1.73 (4H), 1.79-2.05 (2H), 2.10-2.69 (7H), 3.00-3.12 (2H), 3.44 (1H), 4.39 (1H), 4.78 (1H), 5.70 (1H), 7.27-7.33 (2H), 7.35-7.48 (3H) ppm.

EXAMPLE 32g

[4S-[3(R*),4α,5α]]-3-[3-[[Dimethyl(1,1-dimethylethyl)silyl]oxy]-1-oxo-3-[1-(1-oxobutyl)cyclobut-1-yl]propyl]-4-methyl-5-phenyloxazolidin-2-one Analogously to Example 1aq, after purification, 3.94 g (76%) of the title compound is obtained from 3.89 g (10.42 mol) of the compound that is described under Example 32f.

¹H-NMR (CDCl₃): δ=0.08 (3H), 0.20 (3H), 0.85-0.98 (15H), 1.55-1.93 (4H), 2.03 (1H), 2.20-2.38 (3H), 2.45-2.67 (2H), 2.91-3.13 (2H), 4.62-4.75 (2H), 5.67 (1H), 7.29-7.47 (5H) ppm.

EXAMPLE 32h (S)-3-[3-[[Dimethyl(1,1-dimethyl)silyl]oxy]-3-[1-(1-oxopropyl)cyclobut-1-yl]propanoic Acid 3.29 ml (32.3 mmol) of a 30% hydrogen peroxide solution (exothermal reaction, the internal temperature should not exceed 15° C.) is added to a solution of 3.94 g (8.08 mmol) of the compound, described under 32g, in 40 ml of a mixture of tetrahydrofuran and water (4:1) at 0° C. It is allowed to stir for 5 more minutes at 0° C., and then a solution of 309 mg (32.3 mmol) of lithium hydroxide in 16 ml of water is added. Then, it is stirred for 3 more hours at 0° C. Then, the reaction mixture is carefully poured onto ice-cold sodium thiosulfate solution. It is stirred for 5 more minutes at 0° C. and for 15 minutes at 25° C. Then, the tetrahydrofuran is drawn off in a vacuum, and the remaining solution is acidified with 5N hydrochloric acid to pH=1. It is extracted with dichloromethane. The organic phase is washed with saturated aqueous sodium chloride solution, dried on sodium sulfate and chromatographed on silica gel. 2.34 g (89%) of the title compound and 1.04 g (4S,5R)-4-methyl-5-phenyloxazolidin-2-one, which can be used again in Example 32e, is obtained.

¹H-NMR (CDCl₃): δ=0.09 (3H), 0.18 (3H), 0.86-0.97 (12H), 1.59 (2H), 1.56-1.94 (3H), 2.05-2.36 (4H), 2.40-2.57 (3H), 4.44 (1H) ppm.

EXAMPLE 32i (3S,6R,7S,8S,12Z,15S,16E)-3,7,15-Tris-[[dimethyl(1,1-dimethylethyl)silyl]oxy]-6-ethyl-8,12,16-trimethyl-4,4-trimethylene-17-(2-methylthiazol-4-yl)-5-oxo-heptadeca-12,16-dienoic acid (A) and (3S,6S,7R,8S,12E,15S,16E)-3,7,15-tris-[[dimethyl(1,1-dimethylethyl)silyl]oxy]-6-ethyl-8,12,16-trimethyl-4,4-trimethylene-17-(2-methylthiazol-4-yl)-5-oxo-heptadeca-12,16-dienoic acid (B) and (3S,6R,7R,8S,12Z,15S,16E)-3,7,15-tris-[[dimethyl(1,1-dimethylethyl)silyl]oxy]-6-ethyl-8,12,16-trimethyl-4,4-trimethylene-17-(2-methylthiazol-4-yl)-5-oxo-heptadeca-12,16-dienoic acid (C) and (3S,6S,7R,8S,12E,15S,16E)-3,7,15-tris-[[dimethyl(1,1-dimethylethyl)silyl]oxy]-6-ethyl-8,12,16-trimethyl-4,4-trimethylene-17-(2-methylthiazol-4-yl)-5-oxo-heptadeca-12,16-dienoic Acid (D)

Analogously to Example 1ak, lithium diisopropylamide is produced from 842 μl (5.99 mmol) of diisopropylamine and 3.74 ml (5.99 mmol) of a 1.6 molar solution of butyllithium in hexane in 5 ml of absolute tetrahydrofuran. A solution of 787 mg (2.4 mmol) of the compound, described under 32h, in 5 ml of absolute tetrahydrofuran is added to this solution at −78° C. It is stirred for one more hour at −40° C. Then, it is cooled again to −78° C., and a solution of 524 mg (1.2 mmol) of the compound, described under 28r, in 5 ml of absolute tetrahydrofuran is added. It is stirred for another hour at −78° C. Then, the reaction mixture is poured onto saturated aqueous ammonium chloride solution, 0.45 ml of glacial acetic acid is added and allowed to stir for one more hour. Then, it is extracted with ethyl acetate. The organic phase is washed with saturated aqueous sodium chloride solution, dried on sodium sulfate and concentrated by evaporation in a vacuum. The crude product that is obtained (max. 920 mg (100%)) is dissolved in 10 ml of dichloromethane and converted into the persilylated compound analogously to Example 1aq. The crude product that is thus obtained is dissolved in 30 ml of a 1:1 mixture of dichloromethane and methanol. 280 mg (1.2 mmol) of DL-camphorsulfonic acid is added at 0° C. and allowed to stir for 2.5 more hours at this temperature. Then, 2.5 ml of triethylamine is added. Then, it is concentrated by evaporation in a vacuum. The residue is taken up in dichloromethane. It is washed with 1N hydrochloric acid and saturated aqueous sodium chloride solution. It is dried on sodium sulfate and concentrated by evaporation in a vacuum. The crude product that is obtained is separated by repeated column chromatography on silica gel. Obtained are: 229 mg (22%) of compound A, 174 mg (17%) of compound B and 292 mg (28%) of a mixture of compounds C and D.

¹H-NMR (CDCl₃) of compound A: δ=0.00 (3H), 0.02 (3H), 0.04 (3H), 0.08 (3H), 0.13 (3H), 0.18 (3H), 0.85-0.99 (33H), 1.79 (3H), 1.94 (3H), 2.10-2.28 (5H), 2.30-2.45 (2H), 2.48 (H), 2.70 (3H), 2.90 (1H), 3.78 (1H), 4.17 (1H), 4.46 (1H), 5.19 (1H), 6.64 (1H), 6.95 (1H) ppm.

¹H-NMR (CDCl₃) of compound B: δ=0.00 (3H), 0.03 (3H), 0.06 (3H), 0.07 (3H), 0.14 (3H), 0.19 (3H), 0.78-0.98 (33H), 1.55 (3H), 1.92 (3H), 2.12-2.50 (10H), 2.69 (3H), 2.72 (1H), 3.00 (1H), 3.88 (1H), 4.08 (1H), 4.41 (1H), 5.10 (1H), 6.48 (1H), 6.94 (1H) ppm.

EXAMPLE 32k (3S,6R,7S,8S,12Z,15S,16E)-3,7-Bis-[[dimethyl(1,1-dimethylethyl)-silyl]oxy]-15-hydroxy-17-(2-methylthiazol-4-yl)-6-ethyl-8,12,16-trimethyl-4,4-trimethylen-5-oxo heptadeca-12,16-dienoic acid Analogously to Example 1i, 200 mg (100%) of the title compound, which is used without purification in the next step, is obtained from 229 mg (0.26 mmol) of compound A that is described under 32i.

EXAMPLE 32l (4S,7R,8S,9S,13(Z),16S(E))-4,8-Bis-[[dimethyl(1,1-dimethylethyl)-silyl]oxy]-16-(1-methyl-2-(2-methylthiazol-4-yl)ethenyl)-1-oxa-7-ethyl-9,13-trimethyl-5,5-trimethylene-cyclohexadec-13-ene-2,6-dione Analogously to Example 1aw, after purification, 100 mg (51%) of the title compound is obtained from 200 mg (0.26 mmol) of the compound that is described under 32k.

¹H-NMR (CDCl₃): δ=0.93 (3H), 0.11 (3H), 0.16 (6H), 0.83 (9H), 0.88 (9H), 0.96 (9H), 1.02 (3H), 1.68 (3H), 2.12 (3H), 2.30-2.70 (6H), 2.72 (3H), 3.03 (1H), 4.07 (1H), 4.43 (1H), 5.01 (1H), 5.17 (1H), 6.58 (1H), 6.98 (1H) ppm.

EXAMPLE 32

(4S,7R,8S,9S,13(Z),16S(E))-4,8-Dihydroxy-9,13-dimethyl-7-ethyl-16-(1-methyl-2-(2-methyl-4-thiazolyl)ethenyl)-1-oxa-5,5-trimethylene-cyclohexadec-13-ene-2,6-dione Analogously to Example 1, after purification, 63 mg (90%) of the title compound is obtained from 100 mg (0.13 mmol) of the compound that is described under 32l.
$^1$H-NMR (CDCl$_3$): δ=0.95 (3H), 1.00 (3H), 1.68 (3H), 2.05 (3H), 2.72 (3H), 2.97 (1H), 3.67 (1H), 4.46 (1H), 5.08 (1H), 5.23 (1H), 6.59 (1H), 6.98 (1H) ppm.

EXAMPLE 33

(1S,3S(E),7S,10R,11S,12S,16R)-7,11-Dihydroxy-3-(1-methyl-2-(2-methyl-4-thiazolyl)ethenyl)-12,16-dimethyl-10-ethyl-8,8-trimethylene-4,17-dioxabicyclo[14.1.0]heptadecane-5,9-dione (A) and (1R,3S(E),7S,10R,11S,12S,16S)-7,11-dihydroxy-3-(1-methyl-2-(2-methyl-4-thiazolyl)ethenyl)-12,16-dimethyl-10-ethyl-8,8-trimethylene-4,17-dioxabicyclo[14.1.0]heptadecane-5,9-dione (B)

Analogously to Example 14, 24 mg (47%) of title compound A and 6 mg (12%) of title compound B are obtained from 50 mg (0.10 mmol) of the compound that is described under 32.
$^1$H-NMR (CDCl$_3$) of compound A: δ=0.95 (3H), 0.98 (3H), 1.30 (3H), 2.07 (3H), 2.71 (3H), 2.76 (1H), 3.03 (1H), 3.69 (1H), 4.44 (1H), 5.40 (1H), 6.58 (1H), 6.97 (1H) ppm.
$^1$H-NMR (CDCl$_3$) of compound B: δ=0.92 (3H), 0.95 (3H), 2.10 (3H), 2.71 (3H), 2.88 (1H), 3.04 (1H), 3.78 (1H), 4.49 (1H), 5.53 (1H), 6.64 (1H), 6.99 (1H) ppm.

EXAMPLE 34

(4S,7R,8S,9S,13(E),16S(E))-4,8-Dihydroxy-9,13-dimethyl-7-ethyl-16-(1-methyl-2-(2-methyl-4-thiazolyl)ethenyl)-1-oxa-5,5-trimethylene-cyclohexadec-13-ene-2,6-dione

EXAMPLE 34a (3S,6R,7S,8S,12E,15S,16E)-3,7-Bis-[[dimethyl(1,1-dimethylethyl)silyl]oxy]-15-hydroxy-17-(2-methylthiazol-4-yl)-6-ethyl-8,12,16-trimethyl-4,4-trimethylen-5-oxo-heptadeca-12,16-dienoic acid Analogously to Example 1i, 151 mg (100%) of the title compound, which is used without purification in the next step, is obtained from 174 mg (0.20 mmol) of compound B that is described under Example 32i.

EXAMPLE 34b (4S,7R,8S,9S,13(E),16S(E))-4,8-Bis-[[dimethyl(1,1-dimethylethyl)silyl]oxy]-16-(1-methyl-2-(2-methylthiazol-4-yl)ethenyl)-1-oxa-7-ethyl-9,13-trimethyl-5,5-trimethylene-cyclohexadec-13-ene-2,6-dione Analogously to Example 1aw, after purification, 86 mg (58%) of the title compound is obtained from 151 mg (0.20 mmol) of the compound that is described under 34a.
$^1$H-NMR (CDCl$_3$): δ=0.04 (3H), 0.11 (6H), 0.13 (3H), 0.86 (3H), 0.88 (9H), 0.93 (9H), 1.01 (3H), 1.54 (3H), 2.17 (3H), 2.24-2.46 (3H), 2.72 (3H), 2.83 (1H), 3.03 (1H), 4.08 (1H), 4.53 (1H), 5.13 (1H), 5.27 (1H), 6.53 (1H), 6.96 (1H) ppm.

EXAMPLE 34

(4S,7R,8S,9S,13(E),16S(E))-4,8-Dihydroxy-9,13-dimethyl-7-ethyl-16-(1-methyl-2-(2-methyl-4-thiazolyl)ethenyl)-1-oxa-5,5-trimethylene-cyclohexadec-13-ene-2,6-dione Analogously to Example 1, 39 mg (65%) of the title compound is obtained from 86 mg (0.12 mmol) of the compound that is described under 34b.
$^1$H-NMR (CDCl$_3$): δ=0.93 (3H), 1.06 (3H), 1.53 (3H), 2.03 (3H), 2.69 (3H), 3.09 (1H), 3.82 (1H), 4.52 (1H), 5.03 (1H), 5.36 (1H), 6.60 (1H), 7.03 (1H) ppm.

EXAMPLE 35

(1R,3S(E),7S,10R,11S,12S,16R)-7,11-Dihydroxy-3-(1-methyl-2-(2-methyl-4-thiazolyl)ethenyl)-12,16-dimethyl-10-ethyl-8,8-trimethylene-4,17-dioxabicyclo[14.1.0]heptadecane-5,9-dione (A) and (1S,3S(E),7S,10R,11S,12S,16S)-7,11-dihydroxy-3-(1-methyl-2-(2-methyl-4-thiazolyl)ethenyl)-12,16-dimethyl-10-ethyl-8,8-trimethylene-4,17-dioxabicyclo[14.1.0]heptadecane-5,9-dione (B)

Analogously to Example 14, 10 mg (32%) of title compound A and 8 mg (26%) of title compound B are obtained from 30 mg (0.06 mmol) of the compound that is described under Example 34.
$^1$H-NMR (CDCl$_3$) of compound A: δ=0.95 (3H), 1.03 (3H), 1.23 (3H), 2.08 (3H), 2.71 (3H), 2.84 (1H), 3.16 (1H), 3.82 (1H), 4.52 (1H), 5.50 (1H), 6.72 (1H), 7.06 (1H) ppm.
$^1$H-NMR (CDCl$_3$) of compound B: δ=0.93 (3H), 0.98 (3H), 1.22 (3H), 2.06 (3H), 2.70 (3H), 2.88 (1H), 3.05 (1H), 3.62 (1H), 4.46 (1H), 5.41 (1H), 6.60 (1H), 6.96 (1H) ppm.

The invention claimed is:
1. A compound which is:
(4S,7R,8S,9S,13(Z),16S(E))-4,8-Dihydroxy-7-ethyl-16-(1-methyl-2-(2-methyl-4-thiazolyl)ethenyl)-1-oxa-5,5,9,13-tetramethyl-cyclohexadec-13-ene-2,6-dione,
(4S,7R,8S,9S,13E,16S(E))-4,8-dihydroxy-7-ethyl-16-(1-methyl-2-(2-methyl-4-thiazolyl)ethenyl)-1-oxa-5,5,9,13-tetramethyl-cyclohexadec-13-ene-2,6-dione (B),
(1S,3S(E),7S,10R,11S,12S,16R)-7,11-Dihydroxy-3-(1-methyl-2-(2-methyl-4-thiazolyl)ethenyl)-10-ethyl-8,8,12,16-tetramethyl-4,17-dioxabicyclo[14.1.0]heptadecane-5,9-dione,
(1R,3S(E),7S,10R,11S,12S,16S)-7,11-dihydroxy-3-(1-methyl-2-(2-methyl-4-thiazolyl)ethenyl)-10-ethyl-8,8,12,16-tetramethyl-4,17-dioxabicyclo[14.1.0]heptadecane-5,9-dione,
(1S,3S(E),7S,10R,11S,12S,16S)-7,11-Dihydroxy-3-(1-methyl-2-(2-methyl-4-thiazolyl)ethenyl)-10-ethyl-8,8,12,16-tetramethyl-4,17-dioxabicyclo[14.1.0]heptadecane-5,9-dione,
(1R,3S(E),7S,10R,11S,12S,16R)-7,11-dihydroxy-3-(1-methyl-2-(2-methyl-4-thiazolyl)ethenyl)-10-ethyl-8,8,12,16-tetramethyl-4,17-dioxabicyclo[14.1.0]heptadecane-5,9-dione,
(4S,7S,8R,9S,13Z,16S(E))-4,8-Dihydroxy-7-ethyl-16-(1-methyl-2-(2-methyl-4-thiazolyl)ethenyl)-1-oxa-5,5,9,13-tetramethyl-cyclohexadec-13-ene-2,6-dione,

(4S,7S,8R,9S,13E,16S(E))-4,8-dihydroxy-7-ethyl-16-(1-methyl-2-(2-methyl-4-thiazolyl)ethenyl)-1-oxa-5,5,9,13-tetramethyl-cyclohexadec-13-ene-2,6-dione, (1S,3S(E),7S,10S,11R,12S,16R)-7,11-Dihydroxy-3-(1-methyl-2-(2-methyl-4-thiazolyl)ethenyl)-10-ethyl-8,8,12,16-tetramethyl-4,17-dioxabicyclo[14.1.0]heptadecane-5,9-dione, (1R,3S(E),7S,10S,11R,12S,16S)-7,11-dihydroxy-3-(1-methyl-2-(2-methyl-4-thiazolyl)ethenyl)-10-ethyl-8,8,12,16-tetramethyl-4,17-dioxabicyclo[14.1.0]heptadecane-5,9-dione, (1S,3S(E),7S,10S,11R,12S,16R)-7,11-Dihydroxy-3-(1-methyl-2-(2-methyl-4-thiazolyl)ethenyl)-10-ethyl-8,8,12,16-tetramethyl-4,17-dioxabicyclo[14.1.0]heptadecane-5,9-dione, (1R,3S(E),7S,10S,11R,12S,16S)-7,11-dihydroxy-3-(1-methyl-2-(2-methyl-4-thiazolyl)ethenyl)-10-ethyl-8,8,12,16-tetramethyl-4,17-dioxabicyclo[14.1.0]heptadecane-5,9-dione, (4S,7R,8S,9S,13(E or Z),16S(E))-4,8-Dihydroxy-16-(1-methyl-2-(2-methyl-4-thiazolyl)ethenyl)-1-oxa-7-phenyl-5,5,9,13-tetramethyl-cyclohexadec-13-ene-2,6-dione, (1(S or R),3S(E),7S,10R,11S,12S,16R)-7,11-Dihydroxy-3-(1-methyl-2-(2-methyl-4-thiazolyl)ethenyl)-10-phenyl-8,8,12,16-tetramethyl-4,17-dioxabicyclo[14.1.0]heptadecane-5,9-dione, (1(R or S),3S(E),7S,10R,11S,12S,16S)-7,11-Dihydroxy-3-(1-methyl-2-(2-methyl-4-thiazolyl)ethenyl)-10-phenyl-8,8,12,16-tetramethyl-4,17-dioxabicyclo[14.1.0]heptadecane-5,9-dione, (4S,7R,8S,9S,13(E or Z),16S(E))-7-Benzyl-4,8-dihydroxy-16-(1-methyl-2-(2-methyl-4-thiazolyl)ethenyl)-1-oxa-5,5,9,13-tetramethyl-cyclohexadec-13-ene-2,6-dione, (4S,7R,8S,9S,13E,16S(E))-4,8-dihydroxy-7-ethyl-16(1-methyl-2-(2-thiazolyi)ethenyl)-1-oxa-5,5,9,13-tetramethyl-cyclohexadec-13-ene-2,6-dione, (1S,3S(E),7S,10S,11R,12S,16R)-7,11-Dihydroxy-3-(1-methyl-2-(2-methyl-4-thiazolyl)ethenyl)-10-ethyl-8,8,12,16-tetramethyl-4,17-dioxabicyclo[14.1.0]heptadecane-5,9-dione, (1R,3S(E),7S,10S,11R,12S,16S)-7,1 1-dihydroxy-3-(1-methyl-2-(2-methyl-4-thiazolyl)ethenyl)-10-ethyl-8,8,12,16-tetramethyl-4,17-dioxabicyclo[14.1.0]heptadecane-5,9-dione, (1S,3S(E),7S,10S,11R,12S,16R)-7,11-Dihydroxy-3-(1-methyl-2-(2-methyl-4-thiazolyl)ethenyl)-10-ethyl-8,8,12,16-tetramethyl-4,17-dioxabicyclo[14.1.0]heptadecane-5,9-dione, (1R,3S(E),7S,10S,11R,12S,16S)-7,11-dihydroxy-3-(1-methyl-2-(2-methyl-4-thiazolyl)ethenyl)-10-ethyl-8,8,12,16-tetramethyl-4,17-dioxabicyclo[14.1.0]heptadecane-5,9-dione, (4S,7R,8S,9S,13(E or Z),16S(E))-4,8-Dihydroxy-16-(1-methyl-2-(2-methyl-4-thiazolyl)ethenyl)-1-oxa-7-phenyl-5,5,9,13-tetramethyl-cyclohexadec-13-ene-2,6-dione, (1(S or R),3S(E),7S,10R,11S,12S,16R)-7,11-Dihydroxy-3-(1-methyl-2-(2-methyl-4-thiazolyl)ethenyl)-10-phenyl-8,8,12,16-tetramethyl-4,17-dioxabicyclo[14.1.0]heptadecane-5,9-dione, (1R or S),3S(E),7S,10R,11S,12S,16S)-7,11-Dihydroxy-3-(1-methyl-2-(2-methyl-4-thiazolyl)ethenyl)-10-phenyl-8,8,12,16-tetramethyl-4,17-dioxabicyclo[14.1.0]heptadecane-5,9-dione, (4S,7R,8S,9S,13(E or Z),16S(E))-7-Benzyl-4,8-dihydroxy-16-(1-methyl-2-(2-methyl-4-thiazolyl)ethenyl)-1-oxa-5,5,9,13-tetramethyl-cyclohexadec-13-ene-2,6-dione, (1(S or R),3S(E),7S,10R,11S,12S,16R)-10-Benzyl-7,11-dihydroxy-3-(1-methyl-2-(2-methyl-4-thiazolyl)ethenyl)-8,8,12,16-tetramethyl-4,17-dioxabicyclo[14.1.0]heptadecane-5,9-dione, (4S,7R,8S,9S,11E/Z,13(E or Z),16S(E))-4,8-Dihydroxy-13-ethyl-16-(1-methyl-2-(2-methyl-4-thiazolyl)ethenyl)-1-oxa-5,5,7,9-tetramethyl-cyclohexadec-11,13-diene-2,6-dione (1(S or R),3S(E),7S,10R,11S,12S,14E/Z,16R)-7,11-Dihydroxy-16-ethyl-3-(1-methyl-2-(2-methyl-4-thiazolyl)ethenyl)-8,8,10,12-tetramethyl-4,17-dioxabicyclo[14.1.0]heptadec-14-ene-5,9-dione, (1R or S),3S(E),7S,10R,11S,12S,14E/Z,16S)-7,11-Dihydroxy-16-ethyl-3-(1-methyl-2-(2-methyl-4-thiazolyl)ethenyl)-8,8,10,12-tetramethyl-4,17-dioxabicyclo[14.1.0]heptadec-14-ene-5,9-dione, (4S,7R,8S,9S,11E/Z,13(E or Z),16S(E))-4,8-Dihydroxy-16-(1-methyl-2-(2-methyl-4-thiazolyl)ethenyl)-1-oxa-13-propyl-5,5,7,9-tetramethyl-cyclohexadec-11,13-diene-2,6-dione, (1(S or R),3S(E),7S,10R,11S,12S,14E/Z,16R)-7,11-Dihydroxy-3-(1-methyl-2-(2-methyl-4-thiazolyl)ethenyl)-16-propyl-8,8,10,12-tetramethyl-4,17-dioxabicyclo[14.1.0]heptadec-14-ene-5,9-dione, (1R or S),3S(E),7S,10R,11S,12S,14E/Z,16S)-7,11-Dihydroxy-3-(1-methyl-2-(2-methyl-4-thiazolyl)ethenyl)-16-propyl-8,8,10,12-tetramethyl-4,17-dioxabicyclo[14.1.0]heptadec-14-ene-5,9-dione, (4S,7R,8S,9S,13(E or Z),16S(E))-4,8-Dihydroxy-16-(1-methyl-2-(2-methyl-4-thiazolyl)ethenyl)-1-oxa-5,5,7,13-tetramethyl-9-trifluoromethyl-cyclohexadec-13-ene-2,6-dione, (1(S orR),3S(E),7S,10R,11S,12S,16R)-7,11-Dihydroxy-3-(1-methyl-2-(2-methyl-4-thiazolyl)ethenyl)-8,8,10,16-tetramethyl-12-trifluoromethyl-4,17-dioxabicyclo[14.1.0]heptadecane-5,9-dione, (1R or S),3S(E),7S,10R,11S,12S,16S)-7,11-Dihydroxy-3-(1-methyl-2-(2-methyl-4-thiazolyl)ethenyl)-8,8,10,16-tetramethyl-12-trifluoromethyl-4,17-dioxabicyclo[14.1.0]heptadecane-5,9-dione, (4S,7R,8S,9S,13(E or Z),16S(E))-4,8-Dihydroxy-16-(1-methyl-2-(2-methyl-4-thiazolyl)ethenyl)-1-oxa-5,5,7,9-tetramethyl-13-trifluoromethyl-cyclohexadec-13-ene-2,6-dione, (1(S or R),3S(E),7S,10R,11S,12S,16R)-7,11-Dihydroxy-3-(1-methyl-2-(2-methyl-4-thiazolyl)ethenyl)-8,8,10,12-tetramethyl-16-trifluoromethyl-4,17-dioxabicyclo[14.1.0]heptadeca-5,9-dione, (1R or S),3S(E),7S,10R,11S,12S,16S)-7,11-Dihydroxy-3-(1-methyl-2-(2-methyl-4-thiazolyl)ethenyl)-8,8,10,12-tetramethyl-16-trifluoromethyl-4,17-dioxabicyclo[14.1.0]heptadeca-5,9-dione, (4S,7R,8S,9S,13(E or Z),16S(E))-4,8-Dihydroxy-16-(1-methyl-2-(2-methyl-4-thiazolyl)ethenyl)-1-oxa-13-pentafluoroethyl-5,5,7,9-tetramethyl-cyclohexadec-13-ene-2,6-dione, (1(S or R),3S(E),7S,10R,11S,12S,16R)-7,11-Dihydroxy-3-(1-methyl-2-(2-methyl-4-thiazolyl)ethenyl)-16-pentafluoroethyl-8,8,10,12-tetramethyl-4,17-dioxabicyclo[14.1.0]heptadeca-5,9-dione, (1R or S),3S(E),7S,10R,11S,12S,16S)-7,11-Dihydroxy-3-(1-methyl-2-(2-methyl-4-thiazolyl)ethenyl)-16-pentafluoroethyl-8,8,10,12-tetramethyl-4,17-dioxabicyclo[14.1.0]heptadeca-5,9-dione.

* * * * *